United States Patent
Protopopova et al.

(12) 
(10) Patent No.: US 6,951,961 B2
(45) Date of Patent: Oct. 4, 2005

(54) METHODS OF USE AND COMPOSITIONS FOR THE DIAGNOSIS AND TREATMENT OF INFECTIOUS DISEASE

(76) Inventors: Marina Nikolaevna Protopopova, 1425 Crestridge Dr., Silver Spring, MD (US) 20910; Richard Edward Lee, 8233 Byre Hollow Cove, Cordova, TN (US) 38018; Richard Allan Slayden, 3007 Rockborough Ct., Ft. Collins, CO (US) 80525; Clifton E. Barry, III, 200 Congressional La. #T2, Rockville, MD (US) 20852

( * ) Notice: Subject to any disclaimer, the term of this patent is extended or adjusted under 35 U.S.C. 154(b) by 90 days.

(21) Appl. No.: 10/147,587

(22) Filed: May 17, 2002

(65) Prior Publication Data

US 2003/0236225 A1 Dec. 25, 2003

(51) Int. Cl.[7] ........................ C07C 215/00; A01N 25/00
(52) U.S. Cl. ........................................ 564/506; 514/924
(58) Field of Search ........................... 564/506; 514/924

(56) References Cited

U.S. PATENT DOCUMENTS 3,176,040 A * 3/1965 Wilkinson .................. 564/506

OTHER PUBLICATIONS

Sterling, T.R., Chemical Abstracts 131:281083, abstract of AIDS, vol 13(14), pp 1899–1904, 1999.*

* cited by examiner

Primary Examiner—D. Margaret Seaman
(74) Attorney, Agent, or Firm—Kilpatrick Stockton LLP

(57) ABSTRACT

Methods and compositions for treating disease caused by microorganisms, particularly tuberculosis. In particular, methods and compositions comprising substituted ethylene diamines for the treatment of infectious diseases are provided. In one embodiment, these methods and compositions are used for the treatment of mycobacterial infections, including, but not limited to, tuberculosis.

79 Claims, 61 Drawing Sheets

Primary Amines 1. 4-Methylbenzylamine
2. Cyclopentylamine
3. 2-(Aminomethylo)pyridine
6. Furfurylamine
7. 3,4,5-Trimethoxybenzylamine
8. 1-Methyl-3-phenylproplyamine
9. Cyclobutylamine
10. 1,2,3,4-Trimethoxybenzylamine

| | | |
|---|---|---|
| 11. | 2,3-Dimethylcyclohexylamine |  |
| 12. | Tyramine |  |
| 13. | 2-Fluorobenzylamine |  |
| 16. | (R)-2-Amino-1-butanol |  |
| 17. | 3,4-Dimethoxyphenethylamine |  |
| 18. | 3,3-Diphenylpropylamine |  |
| 19. | Propylamine |  |
| 21. | 1-(2-Aminoethyl)piperidine |  |

| | |
|---|---|
| 22. | Phenethylamine |
| 23. | 4-(2-Aminoethyl)morpholine |
| 24. | (S)-Phenylglycinol |
| 25. | Tryptamine |
| 27. | Cyclohexylamine |
| 28a. | (+)-Isopinocampheylamine |
| 29. | Benzylamine |
| 30. | 3-Amino-1-propanol |
| 31. | 2-Fluorophenethylamine |

42a. (+)-Bornylamine 43. tert-Octylamine 44. 1-Adamantanemethylamine 45. 2-Amino-1-propanol, d,l 46. 3-Phenyl-1-propylamine 47. 2,2-Diphenylamine 48. 1-(3-Aminopropyl)-2-pyrrolidinone (tech)

| | | |
|---|---|---|
| 49. | 4-(Trifluoromethyl)benzylamine |  |
| 50. | 1-(2-Aminoehtyl)-pyrrolidine |  |
| 51. | Veratryl amine |  |
| 52. | 5-Amino-1-pentanol |  |
| 53. | 2-(1-Cylcohexenyl)ethylamine |  |
| 54. | 5-Aminoquinoline |  |
| 55. | 1-Aminomethyl-1-cylcohexanol, HCl |  |
| 56. | 1-Aminopiperidine |  |

| | |
|---|---|
| 57. | 3-Fluorobenzylamine |
| 59. | (1S,2R)-cis-1-Amino-2-indanol |
| 61. | 4-Amino-1-butanol |
| 63. | (S)-2-Amino-1-butanol |
| 66. | 2,4-Dimethoxybenzylamine |
| 68. | 1-(1-Naphthyl)ethylamine |
| 69. | 2-(2-Aminoethyoxy)ethanol |
| 70. | 3-Amino-1,2,4-triazine |

71. 2-Ethoxybenzylamine 72. 4-(3-Aminopropyl)morpholine 73. 2-Amino-1-methoxypropane 74a. cis-(-)-Myrtanylamine 77a. Cyclooctylamine 78a. 2-Adamantamine, HCl 79. trans-2-Aminocyclohexanol, HCl 80. 3,Amino-5-phenyl pyrazole 82. 2,3-Dimethoxybenzylamine 83a. Noradamantamine, HCl 84. 4-Amino-1-benzylpiperidine 85. 4-Methylcyclohexylamine 86. (1R,2S)-1-Amino-2-indanol 87. 3-Aminopyrazole 88. 4-Fluorobenzylamine 90a. trans-2-Phenylcyclopropylamine, HCl 91. 1-(3-Aminopropyl)pipecoline
92. 2-Amino-1,3-propanediol
93. Thiomicamine
94. (R)-1-Amino-2-propanol
95. (S)-2-Amino-3-cyclohexyl-1-propanol, HCl
97. 1-Amino-1-cyclopentane methanol
98. (S)-Isoleucinol
99. 4-Clorophenyl alaniol 100. l-Leucinol
101. (1S,2S)-(+)-2-Amino-1-phenyl-1,3-propanediol
102. (S)-(+)-1-Amino-2-propanol
103. 2-Amino-2-methyl-1,3-propanediol
104. d,l-Serine methyl ester, HCl
105a. (-)-Isopinocampheylamine
107. Histidinol 108. 2-Amino-5-cyclopropyl-1,3,4-thiadiazol 109. 2-Amino-2-methyl-1-propanol 111. Allylamine 112. 3-Amino-1,2-propanediol 115. Hexamethyleimine 117. 3-Aminorhodamine 119. (R)-(-)-2-Phenylglycinol 126. Methyl-3-aminocrotonate 129. d,1-Homocysteine, thiolactone, HCl 137. 2-Amino-5trifluoromethyl-1,3,4-thiadiazol

138. Racemic; "test" well

138. d,1-2-Amino-1-butanol (test, making EMB)

140. 3-Etoxypropylamine 141. sec-Butylamine 142. 2-Aminoheptane 143. 2-Amino-2-methyl-1-propanol**

144. (S)-1-Amino-2-(Methoxymethyl)pyrrolidine 145a. trans-1,2-Diaminocyclohexane 147. 3-Amino-2-methoxydibenzofuran 148. 2-Amino-4-methoxybenzothiazole 149. 1-Aminohomopiperidine 150. 2-Amino-3-hydroxypyridine 151. 1-Aminopyrrolidine, HCl 152. d,1-2-Amino-1-pentanol 154. Ethanolamine 155. 3-Methylbenzylamine 156. 3-(Dibutylamino)propylamine 157. Norephedrine, HCl 158. Piperonylamine 159. 2-Methoxyethylamine 160. 1-Ethylpropylamine 161. 1-(3-Aminopropyl)imidazol 162. 1-Aminoadamantamine 164. Dimethyl aminomalonate, HCl

| | |
|---|---|
| 166. | Isopropylamine |
| 167. | 3-(Dimethylamino)propylamine |
| 169. | 4-Fluorophenethylamine |
| 170. | 2-(4-Aminophenyl)ethylamine |
| 171. | 3-Aminoisoxazole |
| 172. | 1,2-Diaminopropane |
| 173. | d,l-Tryptophan methyl ester, HCl |
| 174. | d-Aspartic acid, dimethyl ester, HCl |
| 175. | l-Leucine ethyl ester, HCl |

176. l-Methionine ethyl ester, HCl 177. d,l-a-Amino-n-butyric acid methyl ester, HCl 178. 3-Mnitro-l-tyrosine ethyl ester, HCl 179. l-3,4-Dihydroxyphenylalanine methyl ester, HCl 180. l-Lysine methyl ester, HCl 181. (S)-Benzyl-l-cysteine ethyle ester, HCl

| | | |
|---|---|---|
| 182. | l-Isoleucine methyl ester, HCl |  |
| 183. | l-Arginine methyl ester, HCl |  |
| 184. | d,l-Norleucine methyl ester, HCl |  |
| 185. | b-Alanine ethyle ester, HCl |  |
| 186. | l-Glutamic acid ethyl ester, HCl |  |
| 187. | l-Phenylalanine ethyl ester, HCl |  |
| 188. | d,l-Phenylalanin methyl ester, HCl |  |

189. l-Histidine methyl ester, HCl 190. d,l-Alanine ethyl ester, HCl

191. Tyrosine ethyl ester, HCl 192. l-Valine ethyl ester, HCl 193. tert-Amylamine 194. tert-Butylamine 197. S-Benzyl-L-cysteinol 198. N-Phenylethyldiamine 201. N,N,2,2-Tetramethyl-1,3-propanediamine 202. Isonipecotamide 203. Isobutylamine 204. Hexetidine (mixture of stereosiomers)

206. exo-Aminonorbornane

207. Ehtyl 4-amino-1-piperidinecarboxylate

211. D-Glucosamine, HCl

| | | |
|---|---|---|
| 214. | Aminodiphenylmethane |  |
| 215. | alpha-Methyltryptamine |  |
| 216. | 9-Aminofluorene, HCl |  |
| 219. | 4-Phenylbutylamine |  |
| 221. | 4-Chloroamphetamine, HCl |  |
| 222. | 4-Amino-2,2,6,6-tetramethylpiperidine |  |
| 223. | 4-(Hexacylamino)benzylamine | |

225. 3-o-Methyldopamine, HCl 226. 3-Fluorophenethylamine 227. 3-Aminopyrrolidine, diHCl 229. 2-Thiopheneethylamine 230. 2-Methylcyclohexylamine 231. 2-Methoxyphenethylamine 232. 2-Fluoroethylamine, HCl 233. 2-Chlorobenzylamine 234. 2-Aminoindan, HCl 235. 2-Amino-4-phenyl-5-tetradecylthiazole 236. 2-Amino-1-phenylethanol 238. 2,5-Dimethoxyphenethylamine 240. 2,4-Dichlorophenethylamine 241. 2,2,2-Trifluoroethylamine 242. 2-(2-Chlorophenyl)ethylamine 243. 2-(2-Aminomethyl)phenylthio)benzyl alcohol 245. 1-Aminoindan 246. 1-Amino-4-(2-hydroxyethyl)piperazine 247. 1,3-Dimethylbutylamine 249. 1,2-Dimethylbutylamine 253. 1-(1-Adamantyl)ethylamine, HCl 254. (S)-(+)-2-(Aminomethyl)pyrrolidine 255. (S)-(-)-2-Cyclohexylethylamine 256. (S)-(-)-2-Amino-3-phenyl-1-propanol 257. (R)-(-)-Cyclohexylethylamine 259. (1S,2S)-(+)-2-Amino-3-methoxy-1-phenyl-1-propanol 260. (1R,2S)-(-)-2-Amino-1,2-diphenylethanol 261. (-)-3,4-Dihydroxynorephedrine 262. (1S,2R)-(+)-2-Amino-1,2-diphenylethanol 263. Octadecylamine

263. H₃C—(CH₂)17—NH₂

264. 3-Aminoquinonuclidine, diHCl 265. (R)-Cycloserine

266. Undecylamine

266. H₃C—(CH₂)10—NH₂

| | | |
|---|---|---|
| 267. | 3,4-Dihydroxynorephedrine |  |
| 268. | 3-Hydroxytyramine |  |
| 269. | 4-(Trifluoromethoxy)benzylamine |  |
| 272. | Geranylamine |  |
| 275. | 5-Methoxytryptamine |  |
| 276. | 6-Amino-2-methyl-2-heptanol, HCl |  |
| 277. | 6-Amino-1-hexanol |  |

278. Dehydroabietylamine 279. 1-(1-Naphthyl)ethylamine 281. 2-(2-Aminoethyl)-1-methylpyrrolidine 282. d,l-Valinol 283. d,l-2-Amino-1-hexanol 284. trans-2-Aminocyclohexanol, HCl 285. S-Benzylcysteamine, HCl 288. 4-Fluoro-a-methylbenzylamine

Acyclic Secondary Amines

4. N-Propylcyclopropanemethylamine 15. 2-(Ethylamino)ethanol

20. N-Methyl-iso-propylamine

60. N-Methylpropylamine 62. 2-Methylaminomethyl 1,3-dioxolane

64. Dibenzylamine

65. N-Butylbenzylamine

| | | |
|---|---|---|
| 67. | N-Benzylethylamine |  |
| 76. | (Methylaminomethyl)benzyl alcohol |  |
| 81. | N-Benzyl-2-phenethylamine |  |
| 89. | Pseudoephedrine |  |
| 110. | (1R,2S)-(-)-Ephedrine |  |
| 113. | Diethanolamine |  |
| 118. | N-Benzylethanolamine |  |

120. 2-(Propylamine)-ethanol

121. N-methylbutylamine

127. N-Benzyl-n,N-dimethylethylenediamine

131. N-Methylphenethylamine

132. N-Ethylcyclohexylamine 136. 4-(Ethylaminomethyl)pyridine

163. Bis(2-methoxyethyl)amiane 183. l-Arginine methyl ester, HCl

196. Synephrine

198. N-Phenylethyldiamine

199. N-Methylhomoveratrylamine

200. N-Allylcyclopentylamine

208. Epinephrine

209. Di-sec-butylamine (mix of (+), (-) and meso)

210. Diisopropylamine 212. cis-(1S,2R)-(-)-2-(Benzylamino)cyclohexanemethanol 213. cis-(1R,2S)—(+)-2-(Benzylamino)cyclohexanemethanol 223. 4-(Hexacylamino)benzylamine 258. (3S(3a,4Ab),8A b)-N-t-butyl-D-ecahydro-3-isoquinolinecarboxamide 274. Allylcyclohexyamine

Cyclic Secondary Amines 5. 4-Benzylpiperidine 14. 3-Piperidinemethanol

25. Tryptamine

26. Morpholine 32. 4-Piperidinopiperidine

40. Ethyl 1-piperazine carboxylate 41. 1-(2-Aminoethyl)piperazine

58. Decahydroquinoline 75. 1,2,3,4-Tetrahydropyridoindole 80. 3-Amino-5-phenyl pyrazole 87. 3-Aminopyrazole 96a. 1-(2-Fluorophenyl)piperazine 106. 1-Proline methyl ester 107. Histidinol 114. 1-Piperonylpiperazine 115. Hexamethyleimine 122. 4-Hydroxypiperidine 123. 2-Piperidinemethanol 124. 1,3,3-Trimethyl-6-azabicyclo[3.2.1]octane 125. 3-Pyrrolidinol 128. 1-Methylpiperazine 130. (S)-(+)-(2-Pyrolidinylmethyl)pyrrolidine 133. 1-Methylhomopiperazine 135. Methyl pipecolinate, HCl 139. 2-Ethylpiperidine 153. 1,2,3,4-Tetrahydroisoquinoline 165. Piperidine 168. 1-(4-Fluorophenyl)piperazine 173. d,l-Tryptophan methyl ester, HCl 189. l-Histidine methyl ester, HCl 195. tert-Butyl (1S,4S)-(-)-2,5-diazabicyclo[2.2.1]heptane-2-carboxylate 202. Isonipecotamide 205. Heptamethyleneimine 215. alpha-Methyltryptamine 217. 6-Fluoro-1,2,3,4-tetrahydro-2-methylquinoline 218. 6,7-Dimethoxy 1,2,3,4-tetrahydroisoquinoline, HCl 222. 4-Amino-2,2,6,6-tetramethylpiperidine 224. 4-(-4-Chlorophenyl)-4-hydroxypiperidine 227. 3-Aminopyrrolidine, diHCl 228. 3,5-Dimethylpiperidine (cis-and trans-)

237. 2,6-Dimethylmorpholine 239. 1,4-Dioxo-8-azaspiro[4.5]decane 244. 1-Methyl-6,7-dihydroxy-1,2,3,4-tetrahydroisoquinoline, HBr 248. 1,3,4,6,7,8-Hexahydro-2H-pyrido(1,2-A)pyrimidine 250. 1,2,3,4-Tetrahydroquinoline 251. 1-(2-Methoxyphenyl)piperazine 252. 1-(2-(2-Hydroxyethoxy)ethyl)piperazine 254. (S)-(+)-2-(Aminomethyl)pyrrolidine 258. (3S(3a,4Ab),8A b)-N-t-butyl-D-ecahydro-3-isoquinolinecarboxamide 265. 3-Aminoquinonuclidine, diHCl 270. Homopiperazine 271. 2,6-Dimethylpiperazine 273. Iminodibenzyl 275. 5-Methoxytryptamine 280. 4,4'-Bipiperidine, HCl 286. 1-(2-Hydroxyethyl)piperazine 287. 4-Methylpiperidine

METHODS OF USE AND COMPOSITIONS FOR THE DIAGNOSIS AND TREATMENT OF INFECTIOUS DISEASE

STATEMENT OF GOVERNMENT LICENSE RIGHTS

This invention was made through the support of the National Institute of Health (Grant No. 1UC1 AI49514-01). The Federal Government may retain certain license rights in this invention.

FIELD OF INVENTION

The present invention relates to methods and compositions for treating disease caused by microorganisms, particularly tuberculosis. The present invention also relates to methods and compositions having improved anti-mycobacterial activity, namely compositions comprising novel substituted ethylene diamine compounds.

BACKGROUND OF THE INVENTION

Mycobacterial infections often manifest as diseases such as tuberculosis. Human infections caused by mycobacteria have been widespread since ancient times, and tuberculosis remains a leading cause of death today. Although the incidence of the disease declined, in parallel with advancing standards of living, since the mid-nineteenth century, mycobacterial diseases still constitute a leading cause of morbidity and mortality in countries with limited medical resources. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent. Nearly one third of the world's population is infected with *mycobacterium tuberculosis* complex, commonly referred to as tuberculosis (TB), with approximately 8 million new cases, and two to three million deaths attributable to TB yearly. Tuberculosis (TB) is the cause of the largest number of human deaths attributable to a single etiologic agent (see Dye et al., J. Am. Med. Association, 282, 677–686, (1999); and 2000 WHO/OMS Press Release).

After decades of decline, TB is now on the rise. In the United States, up to 10 million individuals are believed to be infected. Almost 28,000 new cases were reported in 1990, constituting a 9.4 percent increase over 1989. A sixteen percent increase in TB cases was observed from 1985 to 1990. Overcrowded living conditions and shared air spaces are especially conducive to the spread of TB, contributing to the increase in instances that have been observed among prison inmates, and among the homeless in larger U.S. cities. Approximately half of all patients with "Acquired Immune Deficiency Syndrome" (AIDS) will acquire a mycobacterial infection, with TB being an especially devastating complication. AIDS patients are at higher risks of developing clinical TB, and anti-TB treatment seems to be less effective than in non-AIDS patients. Consequently, the infection often progresses to a fatal disseminated disease.

Mycobacteria other than *M. tuberculosis* are increasingly found in opportunistic infections that plague the AIDS patient. Organisms from the *M. avium-intracellulare* complex (MAC), especially serotypes four and eight, account for 68% of the mycobacterial isolates from AIDS patients. Enormous numbers of MAC are found (up to $10^{10}$ acid-fast bacilli per gram of tissue), and consequently, the prognosis for the infected AIDS patient is poor.

The World Health Organization (WHO) continues to encourage the battle against TB, recommending prevention initiatives such as the "Expanded Program on Immunization" (EPI), and therapeutic compliance initiatives such as "Directly Observed Treatment Short-Course" (DOTS). For the eradication of TB, diagnosis, treatment, and prevention are equally important. Rapid detection of active TB patients will lead to early treatment by which about 90% cure is expected. Therefore, early diagnosis is critical for the battle against TB. In addition, therapeutic compliance will ensure not only elimination of infection, but also reduction in the emergence of drug-resistance strains.

The emergence of drug-resistant *M. tuberculosis* is an extremely disturbing phenomenon. The rate of new TB cases proven resistant to at least one standard drug increased from 10 percent in the early 1980's to 23 percent in 1991. Compliance with therapeutic regimens, therefore, is also a crucial component in efforts to eliminate TB and prevent the emergence of drug resistant strains. Equally important is the development of new therapeutic agents that are effective as vaccines, and as treatments, for disease caused by drug resistant strains of mycobacteria.

Although over 37 species of mycobacteria have been identified, more than 95% of all human infections are caused by six species of mycobacteria: *M. tuberculosis, M. avium intracellulare, M. kansasii, M. fortuitum, M. chelonae,* and *M. leprae.* The most prevalent mycobacterial disease in humans is tuberculosis (TB) which is predominantly caused by mycobacterial species comprising *M. tuberculosis, M. bovis,* or *M. africanum* (Merck Manual 1992). Infection is typically initiated by the inhalation of infectious particles which are able to reach the terminal pathways in lungs. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately eliminated. The disease is further disseminated during the initial stages by the infected macrophages which travel to local lymph nodes, as well as into the blood stream and other tissues such as the bone marrow, spleen, kidneys, bone and central nervous system. (See Murray et al. *Medical Microbiology,* The C. V. Mosby Company 219–230 (1990)).

There is still no clear understanding of the factors which contribute to the virulence of mycobacteria. Many investigators have implicated lipids of the cell wall and bacterial surface as contributors to colony morphology and virulence. Evidence suggests that C-mycosides, on the surface of certain mycobacterial cells, are important in facilitating survival of the organism within macrophages. Trehalose 6,6' dimycolate, a cord factor, has been implicated for other mycobacteria.

The interrelationship of colony morphology and virulence is particularly pronounced in *M. avium. M. avium* bacilli occur in several distinct colony forms. Bacilli which grow as transparent, or rough, colonies on conventional laboratory media are multiplicable within macrophages in tissue culture, are virulent when injected into susceptible mice, and are resistant to antibiotics. Rough or transparent bacilli, which are maintained on laboratory culture media, often spontaneously assume an opaque R colony morphology, at which time they are not multiplicable in macrophages, are avirulent in mice, and are highly susceptible to antibiotics. The differences in colony morphology between the transparent, rough and opaque strains of *M. avium* are almost certainly due to the presence of a glycolipid coating on the surface of transparent and rough organisms which acts as a protective capsule. This capsule, or coating, is composed primarily of C-mycosides which apparently shield the virulent *M. avium* organisms from lysosomal enzymes and antibiotics. By contrast, the non-virulent opaque forms of *M. avium* have very little C-mycoside on their surface. Both the resistance to antibiotics and the resistance to killing by macrophages have been attributed to the glycolipid barrier on the surface of *M. avium*.

Diagnosis of mycobacterial infection is confirmed by the isolation and identification of the pathogen, although conventional diagnosis is based on sputum smears, chest X-ray examination (CXR), and clinical symptoms. Isolation of mycobacteria on a medium takes as long as four to eight weeks. Species identification takes a further two weeks. There are several other techniques for detecting mycobacteria such as the polymerase chain reaction (PCR), mycobacterium tuberculosis direct test, or amplified mycobacterium tuberculosis direct test (MTD), and detection assays that utilize radioactive labels.

One diagnostic test that is widely used for detecting infections caused by *M. tuberculosis* is the tuberculin skin test. Although numerous versions of the skin test are available, typically one of two preparations of tuberculin antigens are used: old tuberculin (OT), or purified protein derivative (PPD). The antigen preparation is either injected into the skin intradermally, or is topically applied and is then invasively transported into the skin with the use of a multiprong inoculator (Tine test). Several problems exist with the skin test diagnosis method. For example, the Tine test is not generally recommended because the amount of antigen injected into the intradermal layer cannot be accurately controlled. (See Murray et al. *Medical Microbiology*, The C. V. Mosby Company 219–230 (1990)).

Although the tuberculin skin tests are widely used, they typically require two to three days to generate results, and many times, the results are inaccurate since false positives are sometimes seen in subjects who have been exposed to mycobacteria, but are healthy. In addition, instances of mis-diagnosis are frequent since a positive result is observed not only in active TB patients, but also in persons vaccinated with Bacille Calmette-Guerin (BCG), and those who had been infected with mycobacteria, but have not developed the disease. It is hard therefore, to distinguish active TB patients from the others, such as household TB contacts, by the tuberculin skin test. Additionally, the tuberculin test often produces a cross-reaction in those individuals who were infected with mycobacteria other than *M. tuberculosis* (MOTT). Therefore, diagnosis using the skin tests currently available is frequently subject to error and inaccuracies.

The standard treatment for tuberculosis caused by drug-sensitive organisms is a six-month regimen consisting of four drugs given for two months, followed by two drugs given for four months. The two most important drugs, given throughout the six-month course of therapy, are isoniazid and rifampin. Although the regimen is relatively simple, its administration is quite complicated. Daily ingestion of eight or nine pills is often required during the first phase of therapy; a daunting and confusing prospect. Even severely ill patients are often symptom free within a few weeks, and nearly all appear to be cured within a few months. If the treatment is not continued to completion, however, the patient may experience a relapse, and the relapse rate for patients who do not continue treatment to completion is high. A variety of forms of patient-centered care are used to promote adherence with therapy. The most effective way of ensuring that patients are taking their medication is to use directly observed therapy, which involves having a member of the health care team observe the patient take each dose of each drug. Directly observed therapy can be provided in the clinic, the patient's residence, or any mutually agreed upon site. Nearly all patients who have tuberculosis caused by drug-sensitive organisms, and who complete therapy will be cured, and the risk of relapse is very low ("Ending Neglect: The Elimination of Tuberculosis in the United States" ed. L. Geiter Committee on the Elimination of Tuberculosis in the United States Division of Health Promotion and Disease Prevention, Institute of Medicine. Unpublished.)

What is needed are effective therapeutic regimens that include improved vaccination and treatment protocols. Currently available therapeutics are no longer consistently effective as a result of the problems with treatment compliance, and these compliance problems contribute to the development of drug resistant mycobacterial strains.

Ethambutol (EMB) is a widely used antibiotic for the treatment of TB, with over 300 million doses delivered for tuberculosis therapy in 1988.

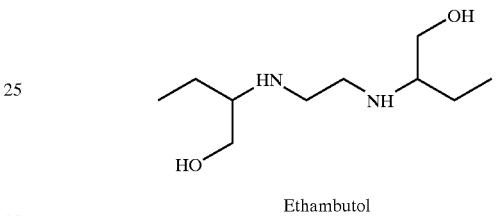

Ethambutol

Ethambutol, developed by Lederle Laboratories in the 1950s, has low toxicity and is a good pharmacokinetic. However, ethambutol has a relatively high Minimum Inhibition Concentration (MIC) of about 5 μg/ml, and can cause optic neuritis. Thus, there is an increasing need for new, and more effective, therapeutic compositions (See for example, U.S. Pat. Nos. 3,176,040, 4,262,122; 4,006,234; 3,931,157; 3,931,152; U.S. Re. No. 29,358; and Häusler et al., Bioorganic & Medicinal Chemistry Letters 11 (2001) 1679–1681). In the decoder years since the discovery of the beneficial effects of ethambutol, few pharmacological advances in TB treatment have been developed. Moreover, with the combined emergence of drug resistant strains, and the more prevalent spread of mycobacterial disease, it is becoming seriously apparent that new therapeutic compositions are crucial in the fight against tuberculosis.

Clearly effective therapeutic regimens that include improved vaccination and treatment protocols are needed. A therapeutic vaccine that would prevent the onset of tuberculosis, and therefore eliminate the need for therapy is desirable. Although currently available therapeutics such as ethambutol are effective, the emergence of drug resistant strains has necessitated new formulations and compositions that are more versatile than ethambutol. Currently available therapeutics are no longer consistently effective as a result of the problems with treatment compliance, lending to the development of drug resistant mycobacterial strains. What is needed are new anti-tubercular drugs that provide highly effective treatment, and shortens or simplifies tuberculosis chemotherapy.

SUMMARY OF THE INVENTION

The present invention comprises methods and compositions for the treatment of microorganisms, particularly methods and compositions comprising ethylene diamine compounds effective in the treatment of infectious organisms.

The present invention also provides methods and compositions comprising substituted ethylene diamines having improved anti-mycobacterial activity, including substituted ethylene diamines having improved anti-tuberculosis activity.

The present invention contemplates substituted ethylene diamines, which can derive from a variety of amine compounds. In the present invention, the substituted ethylene diamines are based on the following structure.

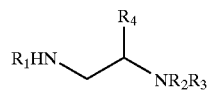

Substituted Ethylene Diamine

The substituted ethylene diamine compounds described herein are synthesized and screened for activity as follows. A chemical library of substituted ethylene diamines is prepared on a solid polystyrene support using split and pool technologies. This technique allows for the synthesis of a diverse set of substituted ethylene diamines. These diamines are screened for anti-TB activity using in vitro, biological assays, including a High-Throughput Screening (HTS) assay, based on the recently completed genomic sequence of *M. tuberculosis*, and a Minimum Inhibition Concentration (MIC) assay.

The methods and compositions described herein comprise substituted ethylene diamines that are effective against disease caused by microorganisms, but not limited to bacterial infection. One embodiment of the invention provides methods and compositions comprising substituted ethylene diamines that are effective against mycobacterial disease. Another embodiment of the invention provides methods and compositions comprising substituted ethylene diamines that have MIC of 50 $\mu$M or lower for mycobacterial disease. Another embodiment of the present invention comprises substituted ethylene diamines that have an MIC of 25 $\mu$M or lower for mycobacterial disease. Yet another embodiment of the present invention comprises substituted ethylene diamines that have an MIC of 12.5 $\mu$M or lower for mycobacterial disease. Another embodiment of the present invention comprises substituted ethylene diamines that have an MIC of 5 $\mu$M or lower for mycobacterial disease In another embodiment of the present invention, the methods and compositions comprise substituted ethylene diamines with HTS Luc activity of 10% or greater. In yet another embodiment of the present invention, the methods and compositions comprise substituted ethylene diamines, wherein one amine group is derived from a primary amine, and wherein the other amine group is derived from a primary or secondary amine. In another embodiment of the present invention, the methods and compositions comprise substituted ethylene diamines, wherein one amine is derived from cis-(−)myrtanylamine, cyclooctylamine, 2,2-diphenylethylamine, 3,3-diphenylpropylamine, (+)-bornylamine, 1-adamantanemethylamine, (+)-isopinocampheylamine; or (−)-isopinocampheylamine.

The present invention contemplates various salt complexes and other substituted derivatives of the substituted ethylene diamines. The present invention also contemplates enantiomers and other stereoisomers of the substituted ethylene diamines and their substituted derivatives. The present invention further contemplates treatment for animals, including, but not limited to, humans.

Accordingly, it is an object of the present invention to provide methods and compositions for the treatment and prevention of diseases caused by microorganisms.

Accordingly, it is an object of the present invention to provide methods and compositions for the treatment and prevention of infectious diseases.

Another object of the present invention is to provide methods and compositions for the treatment and prevention of mycobacterial disease, including but not limited to, tuberculosis.

Yet another object of the present invention is to provide methods and compositions for the treatment and prevention of infectious diseases using compositions comprising substituted ethylene diamines.

Another object of the present invention is to provide methods and compositions for the treatment and prevention of mycobacterial disease using compositions comprising substituted ethylene diamines.

Still another object of the present invention is to provide methods and compositions for the treatment and prevention of tuberculosis using compositions comprising substituted ethylene diamines.

Another object of the present invention is to provide methods and compositions for the treatment and prevention of tuberculosis using compositions comprising substituted ethylene diamines, wherein the diamine has an MIC of 50 $\mu$M, or less.

Another object of the present invention is to provide methods and compositions for the treatment and prevention of tuberculosis using compositions comprising substituted ethylene diamines, wherein the diamine has an MIC of 25 $\mu$M, or less.

Another object of the present invention is to provide methods and compositions for the treatment and prevention of tuberculosis using compositions comprising substituted ethylene diamines, wherein the diamine has an MIC of 12.5 $\mu$M, or less.

Yet another object of the present invention is to provide methods and compositions for the treatment and prevention of tuberculosis using compositions comprising substituted ethylene diamines, wherein the diamine has an MIC of 5 $\mu$M, or less.

Yet another object of the present invention is to provide methods and compositions for the treatment and prevention of tuberculosis using compositions comprising substituted ethylene diamines, wherein the diamine has HTS/Luc activity of 10% or greater.

Another object of the present invention is to provide methods and compositions for the treatment and prevention of tuberculosis using compositions comprising substituted ethylene diamines, wherein one amine group is derived from a primary amine, and the other amine group is derived from a primary or secondary amine.

Yet another object of the present invention is to provide methods and compositions for the treatment and/or prevention of tuberculosis using compositions comprising substituted ethylene diamines, wherein one amine is derived from cis-(−)myrtanylamine, cyclooctylamine, 2,2-diphenylethylamine, 3,3-diphenylpropylamine, (+)-bornylamine, 1-adamantanemethylamine, (+)-isopinocampheylamine; or (−)-isopinocampheylamine.

Yet another object of the present invention is to provide composition for the therapeutic formulation for the treatment and prevention of mycobacterial disease.

Another object of the present invention is to provide compositions for therapeutic formulations for the treatment and prevention of mycobacterial disease caused by mycobacterial species comprising *M. tuberculosis* complex, *M.*

*avium intracellulare, M. kansarii, M. fortuitum, M. chelonoe, M. leprae, M. africanum, M. microti,* or *M. bovis.*

These and other objects, features and advantages of the present invention will become apparent after a review of the following detailed description of the disclosed embodiments and the appended claims.

DETAILED DESCRIPTION

Figure 1:
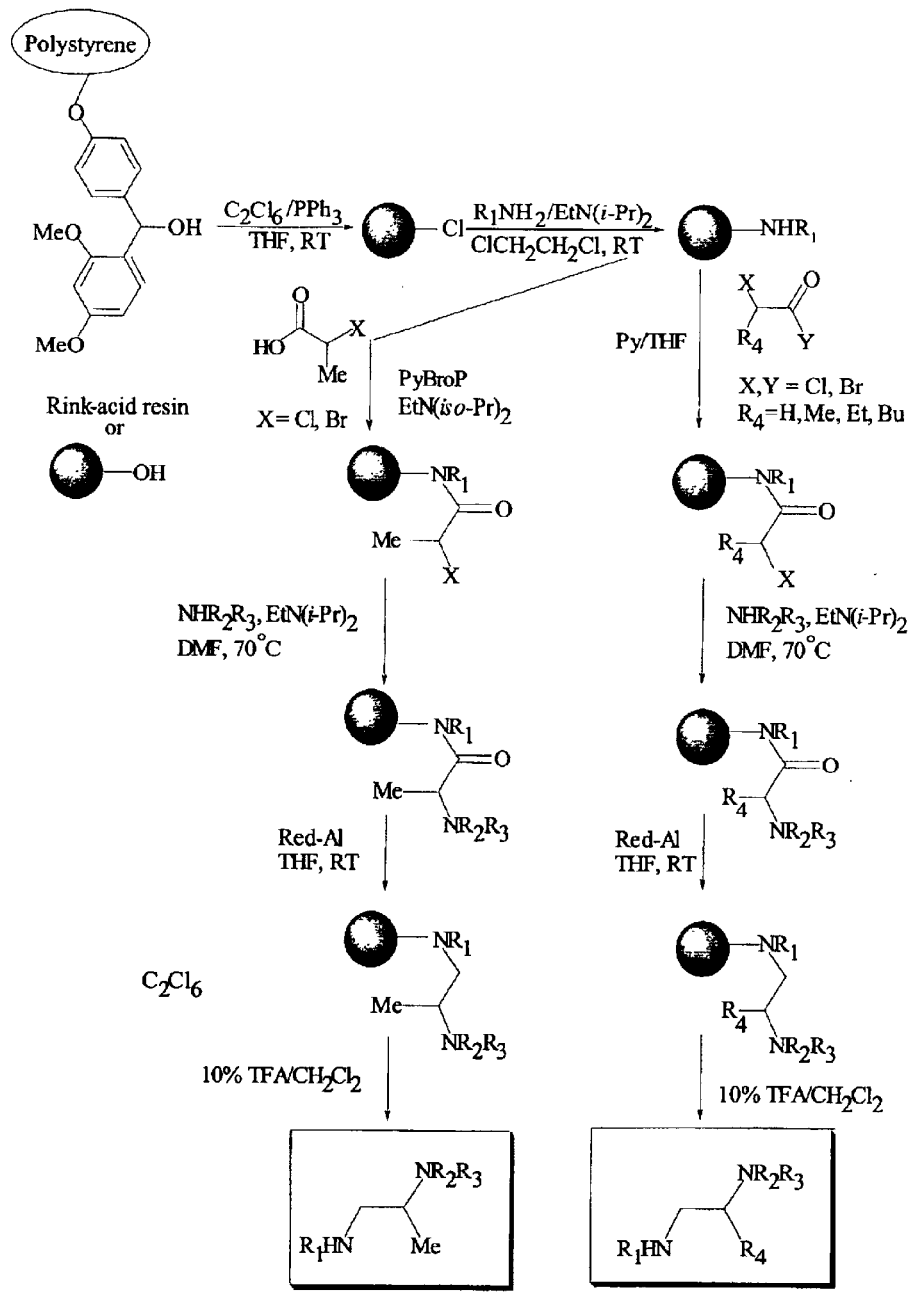
FIG. 1 represents a flow schematic showing various solid support syntheses used to prepare substituted ethylene diamines.

The present invention may be understood more readily by reference to the following detailed description of the specific embodiments included herein. However, although the present invention has been described with reference to specific details of certain embodiments thereof, it is not intended that such details should be regarded as limitations upon the scope of the invention.

Mycobacterial infections, such as those causing tuberculosis, once thought to be declining in occurrence, have rebounded, and again constitute a serious health threat. Tuberculosis (TB) is the cause of the largest number of human deaths attributed to a single etiologic agent with two to three million people infected with tuberculosis dying each year. Areas where humans are crowded together, or living in substandard housing, are increasingly found to have persons affected with mycobacteria. Individuals who are immunocompromised are at great risk of being infected with mycobacteria and dying from such infection. In addition, the emergence of drug-resistant strains of mycobacteria has led to treatment problems of such infected persons.

Many people who are infected with mycobacteria are poor, or live in areas with inadequate healthcare facilities. As a result of various obstacles (economical, education levels, etc.), many of these individuals are unable to comply with the prescribed therapeutic regimens. Ultimately, persistent non-compliance by these and other individuals results in the prevalence of disease. This noncompliance is frequently compounded by the emergence of drug-resistant strains of mycobacteria. Effective compositions and vaccines that target various strains of mycobacteria are necessary to bring the increasing number of tuberculosis cases under control.

Chemotherapy is a standard treatment for tuberculosis. Some current chemotherapy treatments require the use of three or four drugs, in combination, administered daily for two months, or administered biweekly for four to twelve months. Table 1 lists several treatment schedules for standard tuberculosis drug regimens.

TABLE 1

Treatment Schedules for Standard TB Drug Regimens.

| STANDARD DRUG REGIMEN | INDUCTION PHASE Dosing Schedule | DURATION | DRUG | CONTINUATION PHASE Dosing Schedule | DURATION |
|---|---|---|---|---|---|
| Isoniazid | Daily, DOT | 8 weeks | Isoniazid | 2/week, DOT | 16 weeks |
| Rifampicin | Daily, DOT | 8 weeks | Rifampicn | 2/week, DOT | 16 weeks |
| Pyrazinamide | Daily, DOT | 8 weeks | | | |

TABLE 1-continued

Treatment Schedules for Standard TB Drug Regimens.

| STANDARD<br>DRUG<br>REGIMEN | INDUCTION<br>PHASE<br>Dosing<br>Schedule | DURATION | DRUG | CONTINUATION<br>PHASE<br>Dosing Schedule | DURATION |
|---|---|---|---|---|---|
| Ethambutol or<br>Streptomycin | Daily, DOT | 8 weeks | | | |

Decades of misuse of existing antibiotics and poor compliance with prolong and complex therapeutic regimens has led to mutations of the mycobacterium tuberculosis and has created an epidemic of drug resistance that threatens tuberculosis control world wide. The vast majority of currently prescribed drugs, including the front line drugs, such as isoniazid, rifampin, pyrazinamide, ethambutol and streptomycin were developed from the 1950s to the 1970s. Thus, this earlier development of tuberculosis chemotherapy did not have at its disposal the implications of the genome sequence of *Mycobacterium tuberculosis*, the revolution in pharmaceutical drug discovery of the last decades, and the use of national drug testing and combinational chemistry.

Consequently, the treatments of drug-resistant *M. tuberculosis* strains, and latent tuberculosis infections, require new anti-tuberculosis drugs that provide highly effective treatments, and shortened and simplified tuberculosis chemotherapies. Moreover, it is desirable that these drugs be prepared by a low-cost synthesis, since the demographics of the disease dictate that cost is a significant factor.

The present invention provides methods and compositions comprising a class of substituted ethylene diamine compounds effective in treatment and prevention of disease caused by microorganisms including, but not limited to, bacteria. In particular, the methods and compositions of the present invention are effective in inhibiting the growth of the microorganism, *M. tuberculosis*. The methods and compositions of the present invention are intended for the treatment of mycobacteria infections in human, as well as other animals. For example, the present invention may be particularly useful for the treatment of cows infected by *M. bovis*.

As used herein, the term "tuberculosis" comprises disease states usually associated with infections caused by mycobacteria species comprising *M. tuberculosis* complex. The term "tuberculosis" is also associated with mycobacterial infections caused by mycobacteria other than *M. tuberculosis* (MOTT). Other mycobacterial species include *M. avium-intracellulare, M. kansarii, M. fortuitum, M. chelonae, M. leprae, M. africanum,* or *M. microti.*

The anti-infective methods and compositions of the present invention contain one or more substituted ethylene diamine compounds. In particular, these compounds encompass a wide range of substituted ethylene diamine compounds having the following general formula:

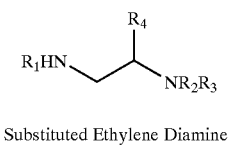

Figure 2A:
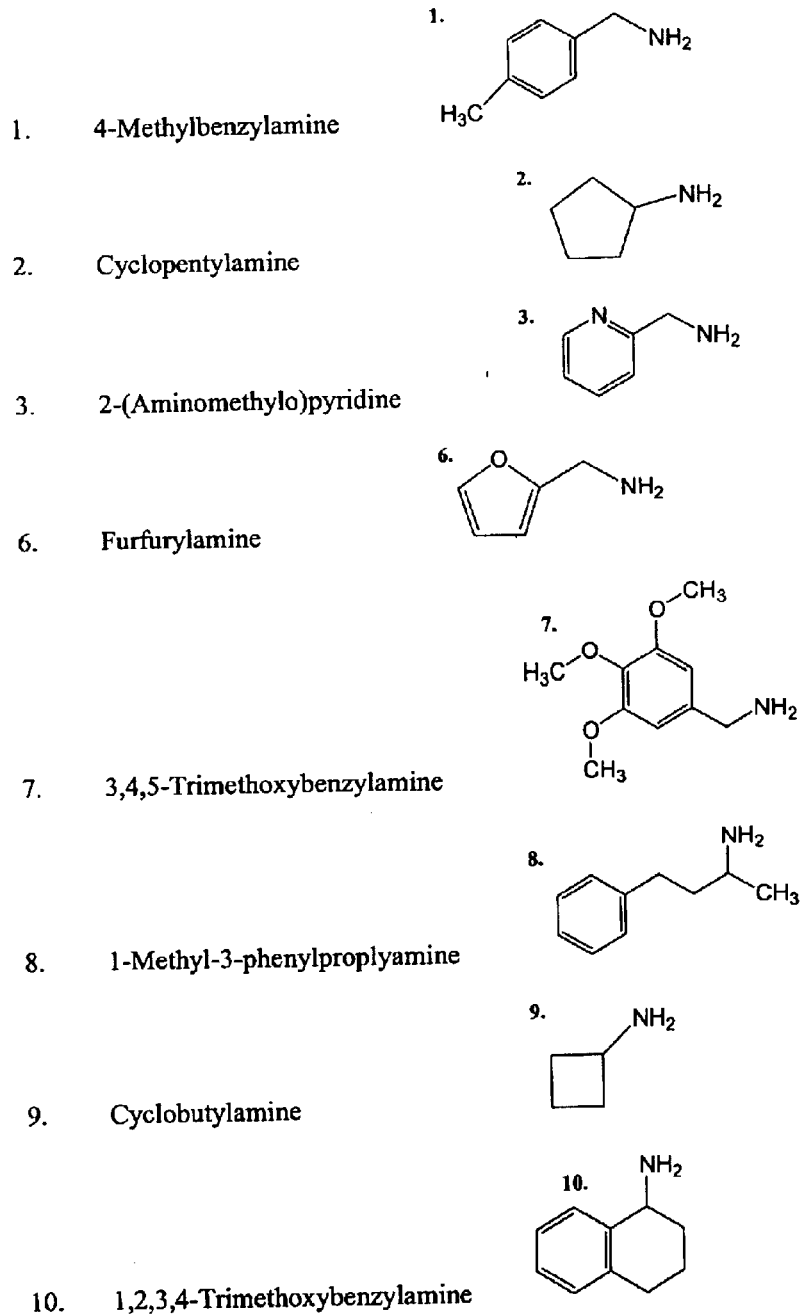
FIG. 2 provides chemical structures of a variety of primary amines.
Figure 2B:
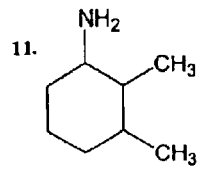
Figure 2B:
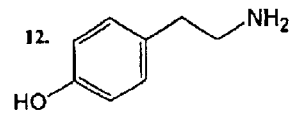
Figure 2B:
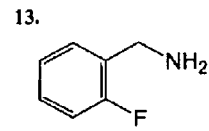
Figure 2B:
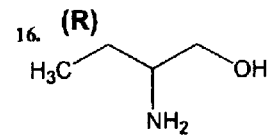
Figure 2B:
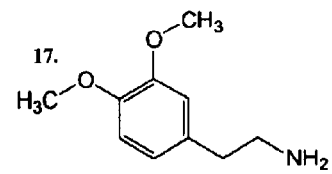
Figure 2B:
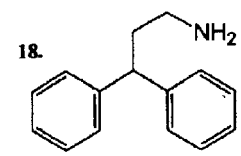
Figure 2B:
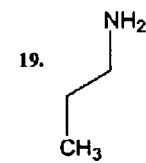
Figure 2B:
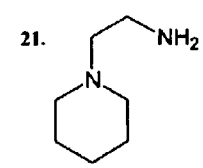
Figure 2C:
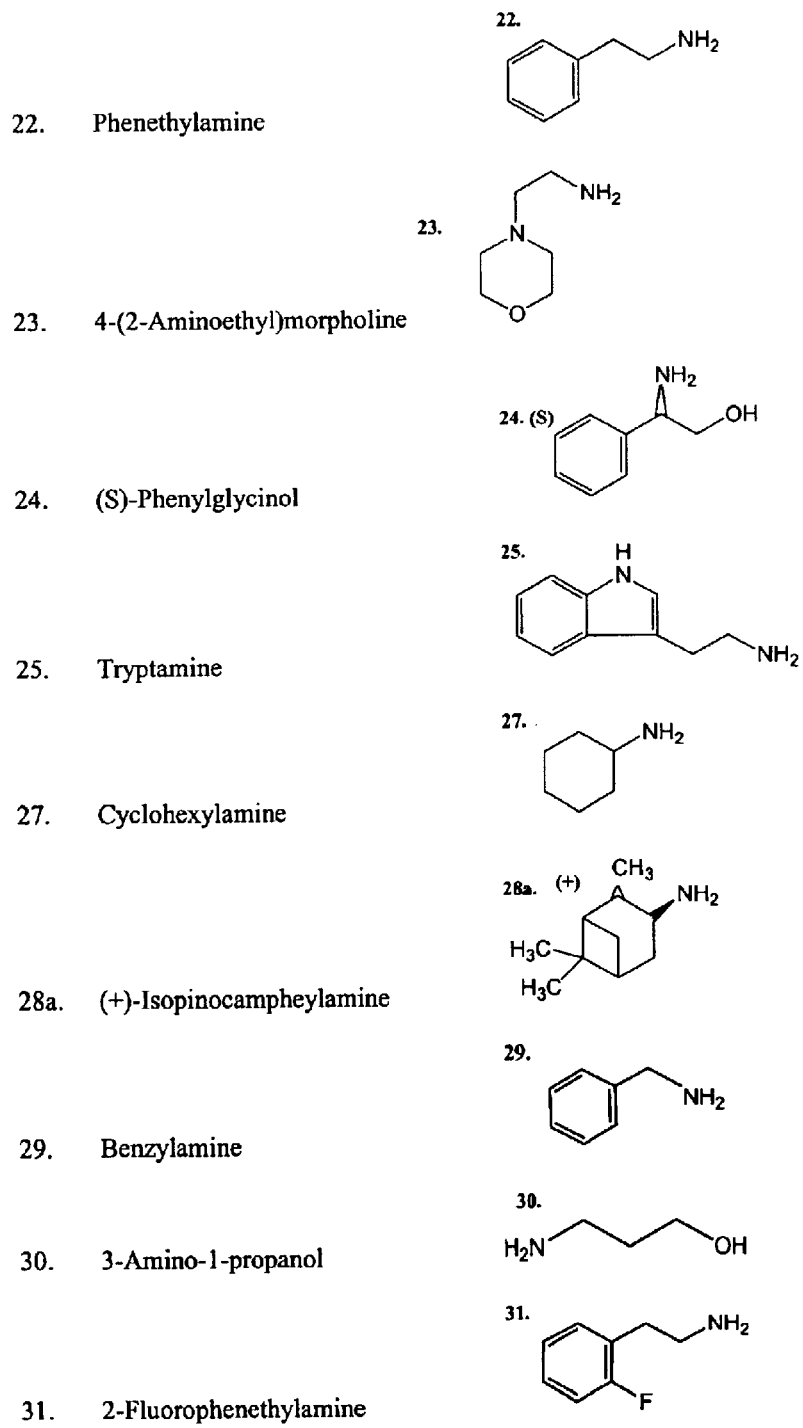
Figure 2D:
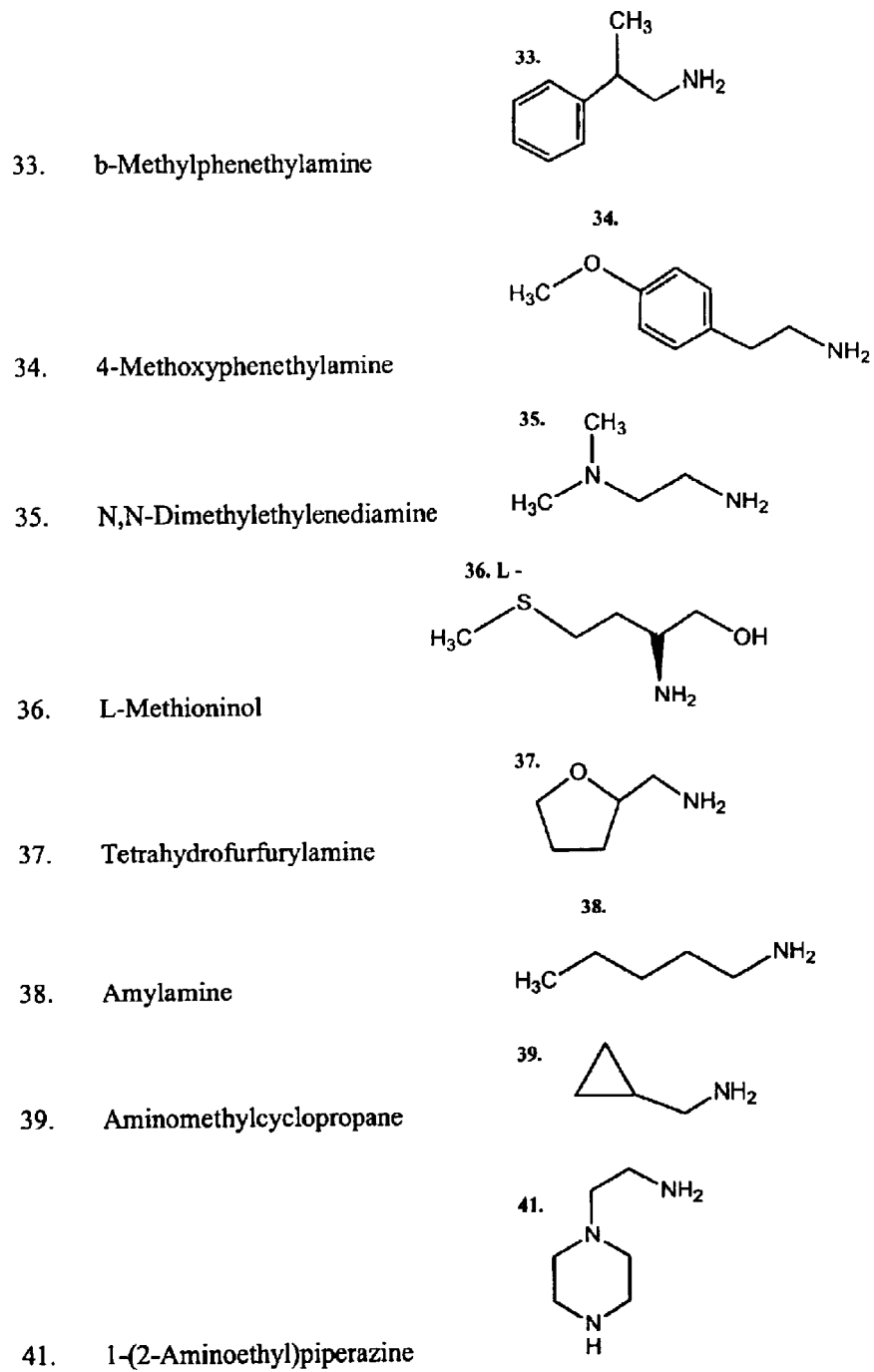
Figure 2E:
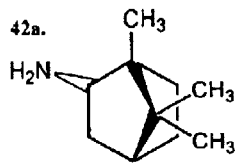
Figure 2E:
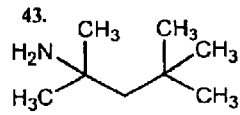
Figure 2E:
Figure 2E:
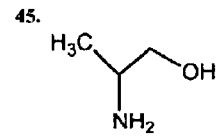
Figure 2E:
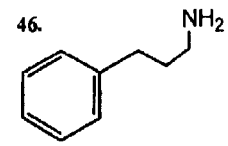
Figure 2E:
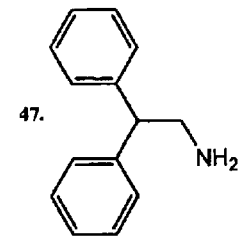
Figure 2E:
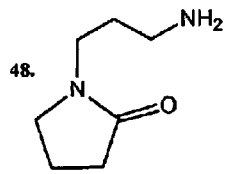
Figure 2F:
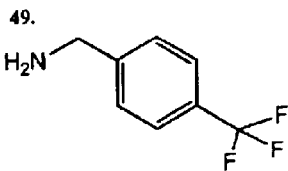
Figure 2F:
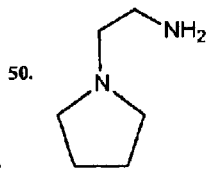
Figure 2F:
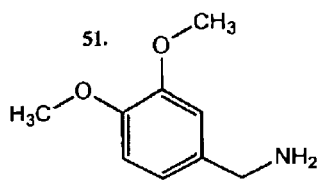
Figure 2F:
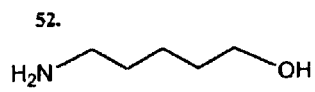
Figure 2F:
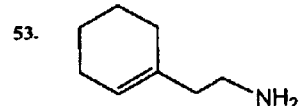
Figure 2F:
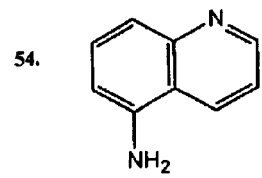
Figure 2F:
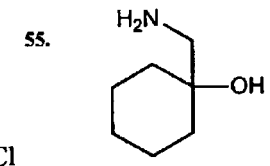
Figure 2F:
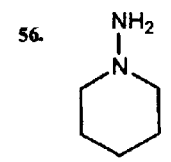
Figure 2G:
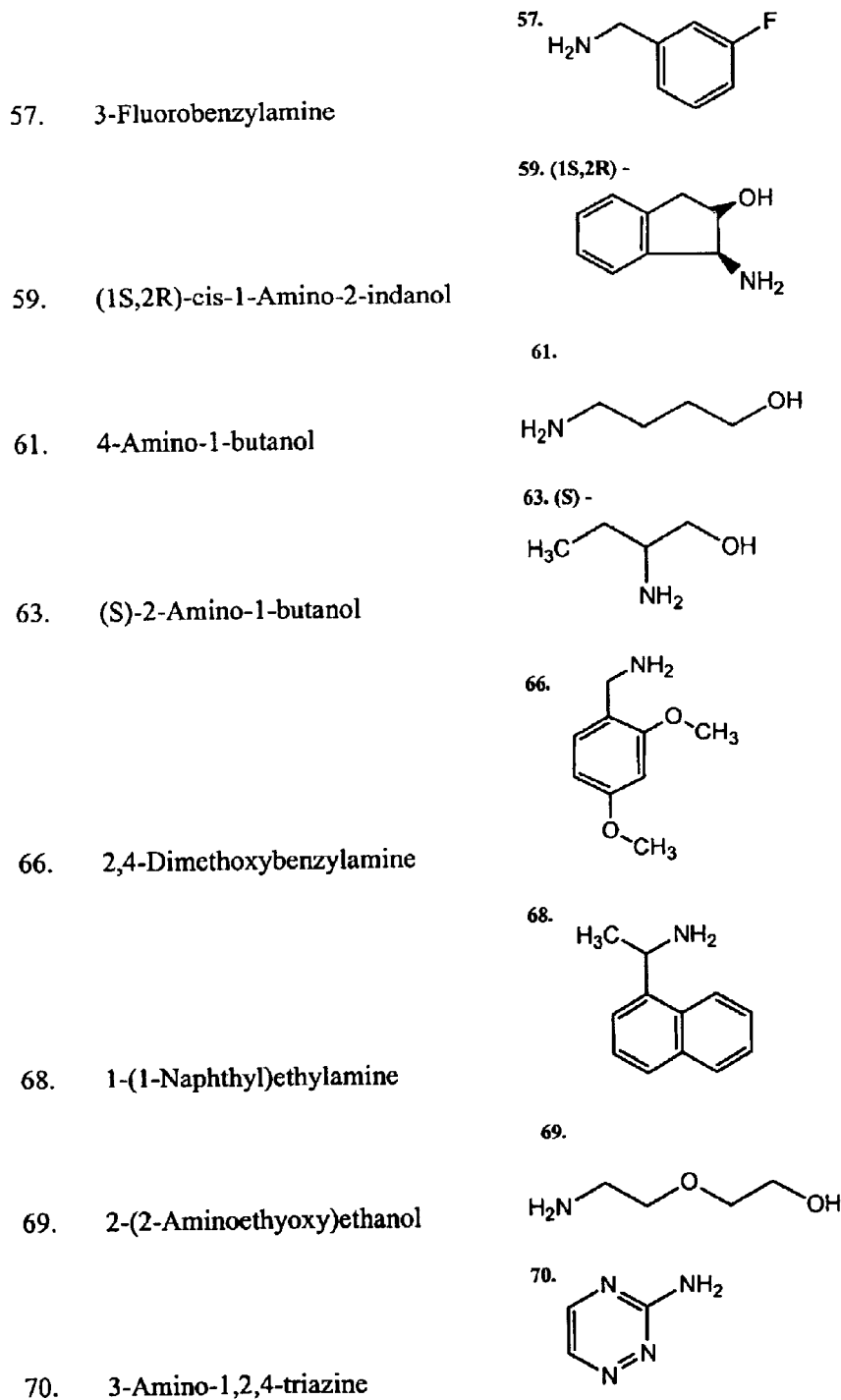
Figure 2H:
Figure 2H:
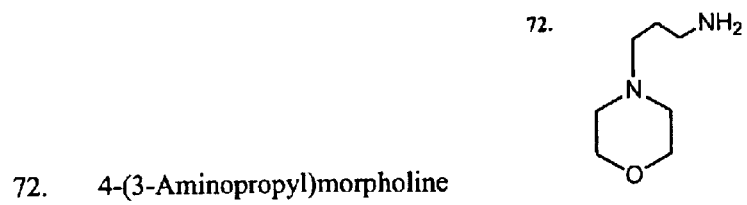
Figure 2H:
Figure 2H:
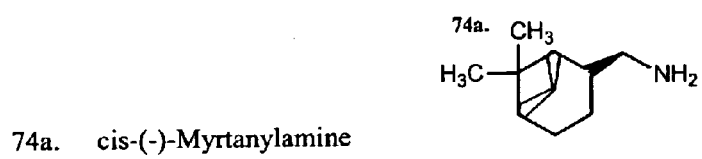
Figure 2H:
Figure 2H:
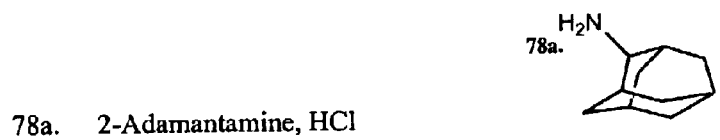
Figure 2H:
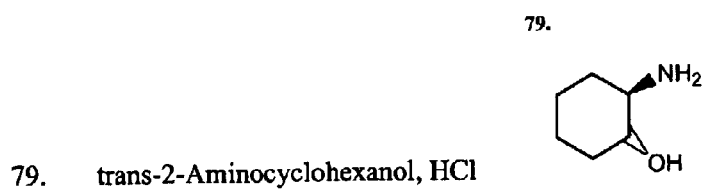
Figure 2H:
Figure 2I:
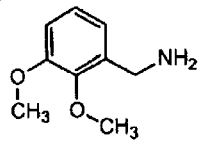
Figure 2I:
Figure 2I:
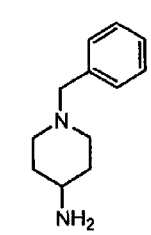
Figure 2I:
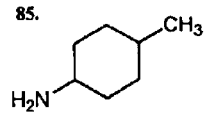
Figure 2I:
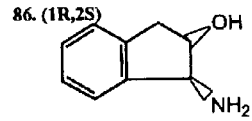
Figure 2I:
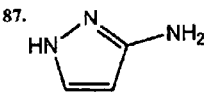
Figure 2I:
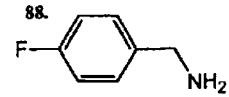
Figure 2I:
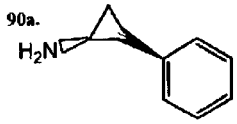
Figure 2J:
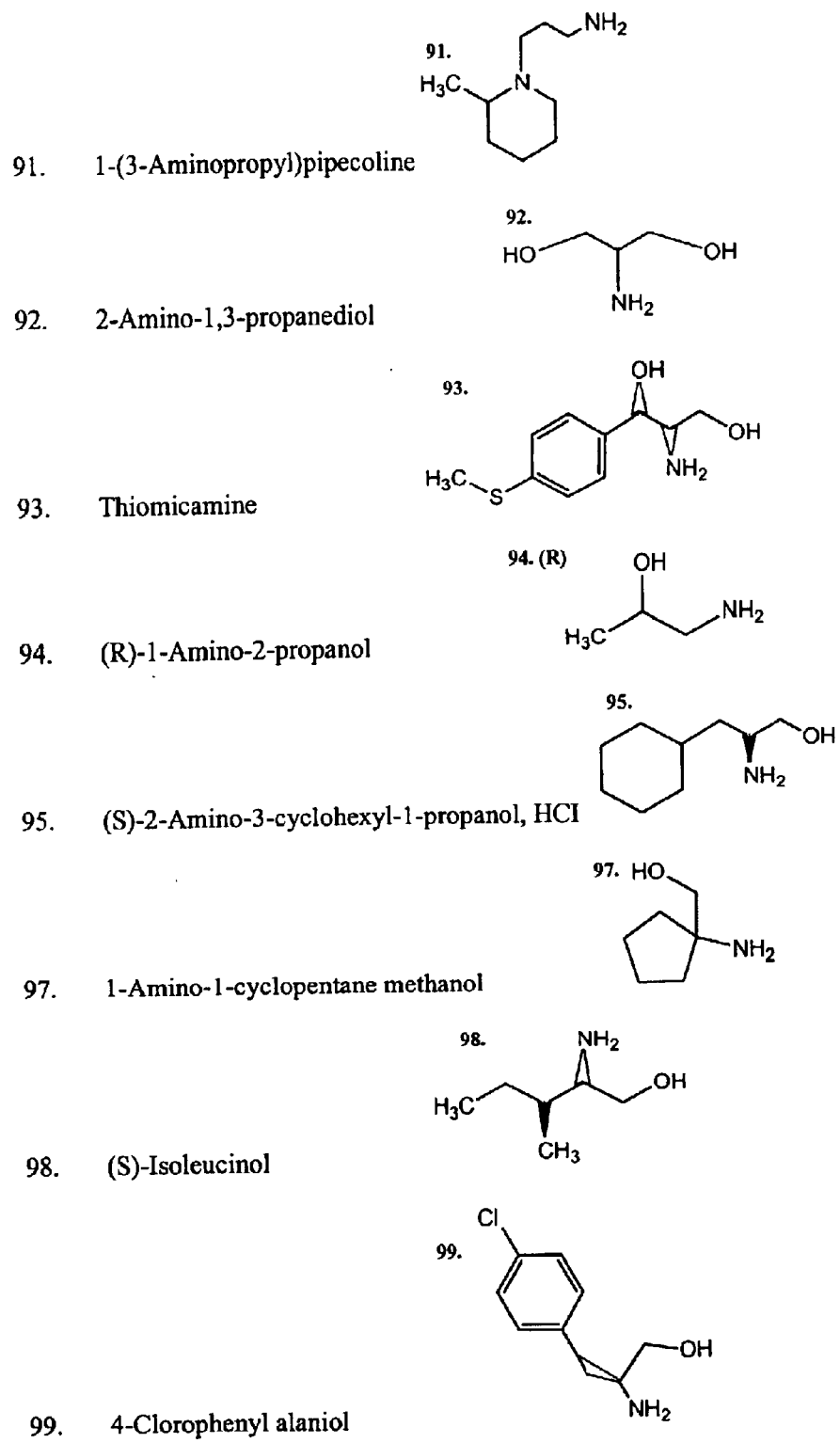
Figure 2K:
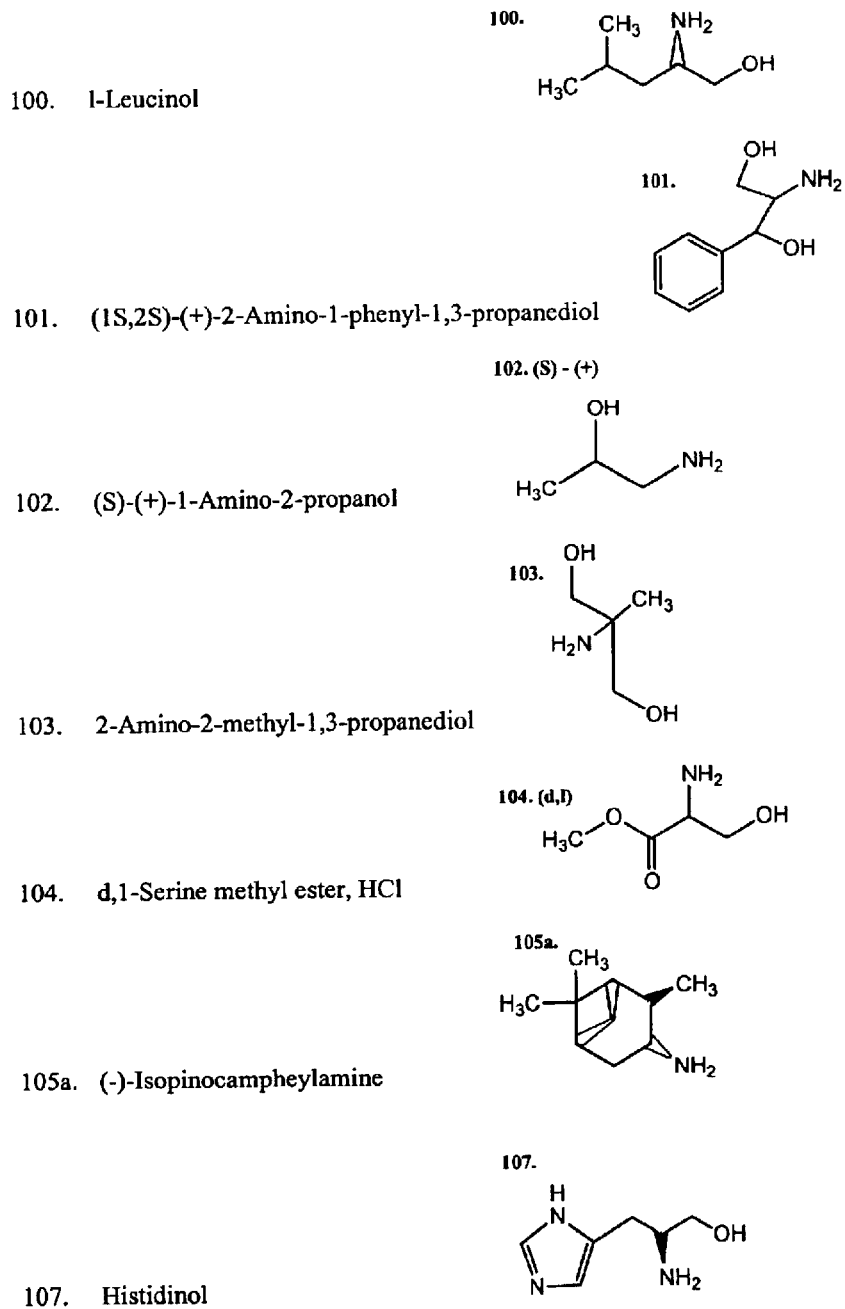
Figure 2L:
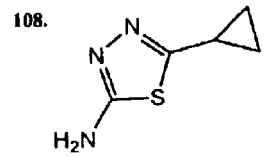
Figure 2L:
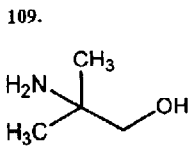
Figure 2L:
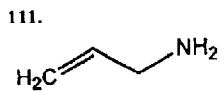
Figure 2L:
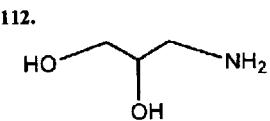
Figure 2L:
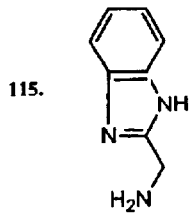
Figure 2L:
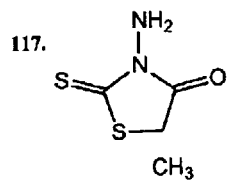
Figure 2L:
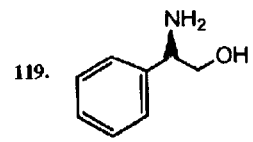
Figure 2L:
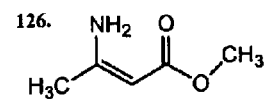
Figure 2M:
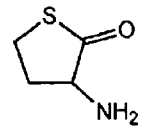
Figure 2M:
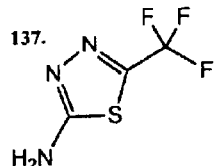
Figure 2M:
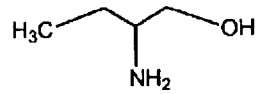
Figure 2M:
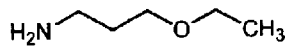
Figure 2M:
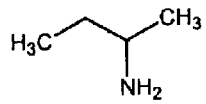
Figure 2M:
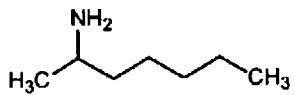
Figure 2M:
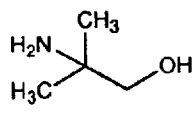
Figure 2M:
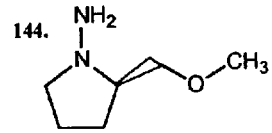
Figure 2N:
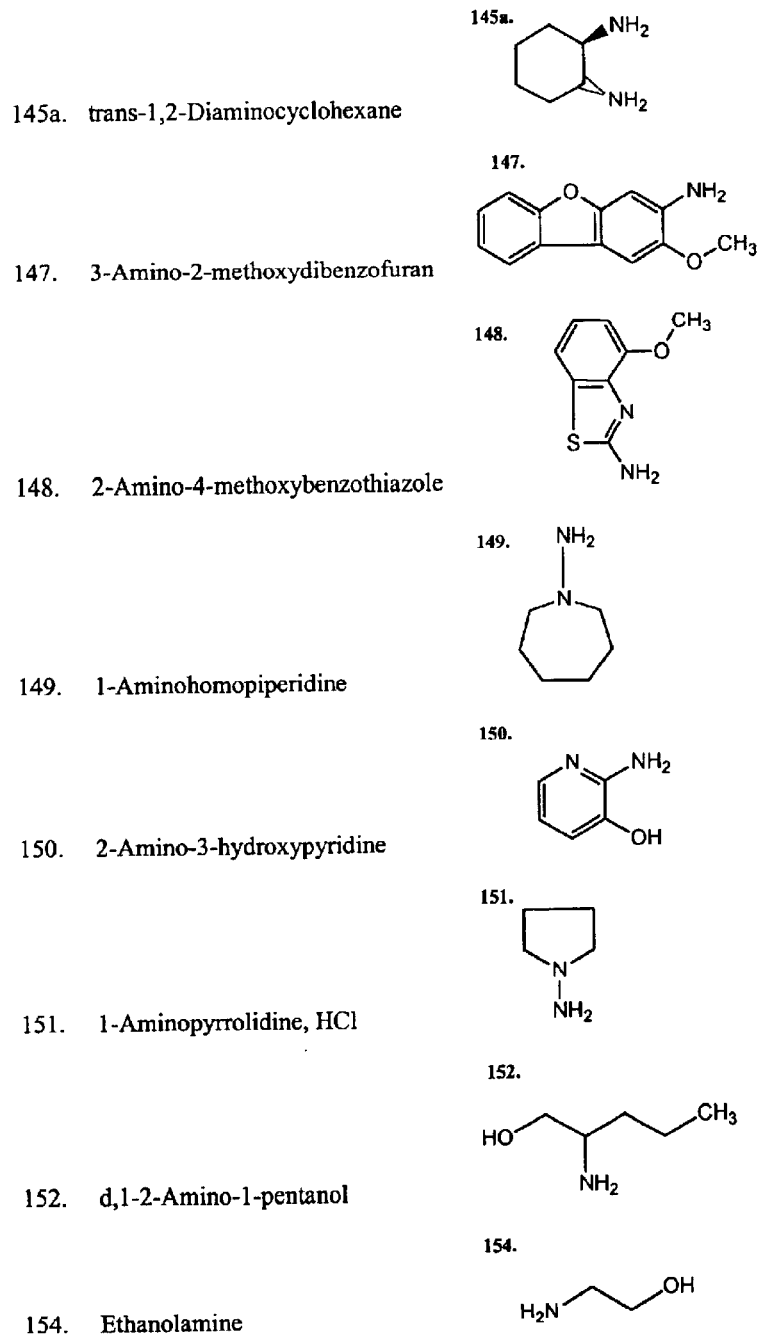
Figure 2O:
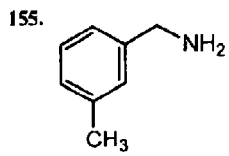
Figure 2O:
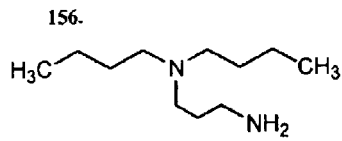
Figure 2O:
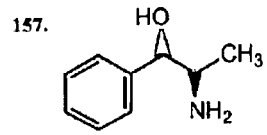
Figure 2O:
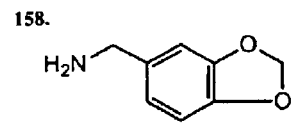
Figure 2O:
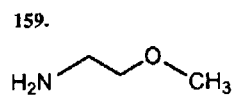
Figure 2O:
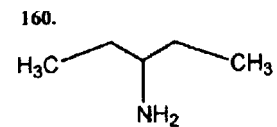
Figure 2O:
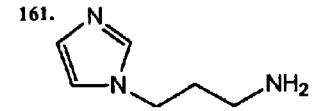
Figure 2O:
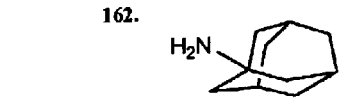
Figure 2O:
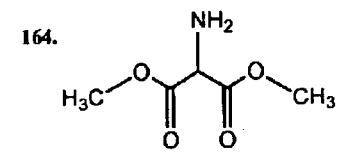
Figure 2P:
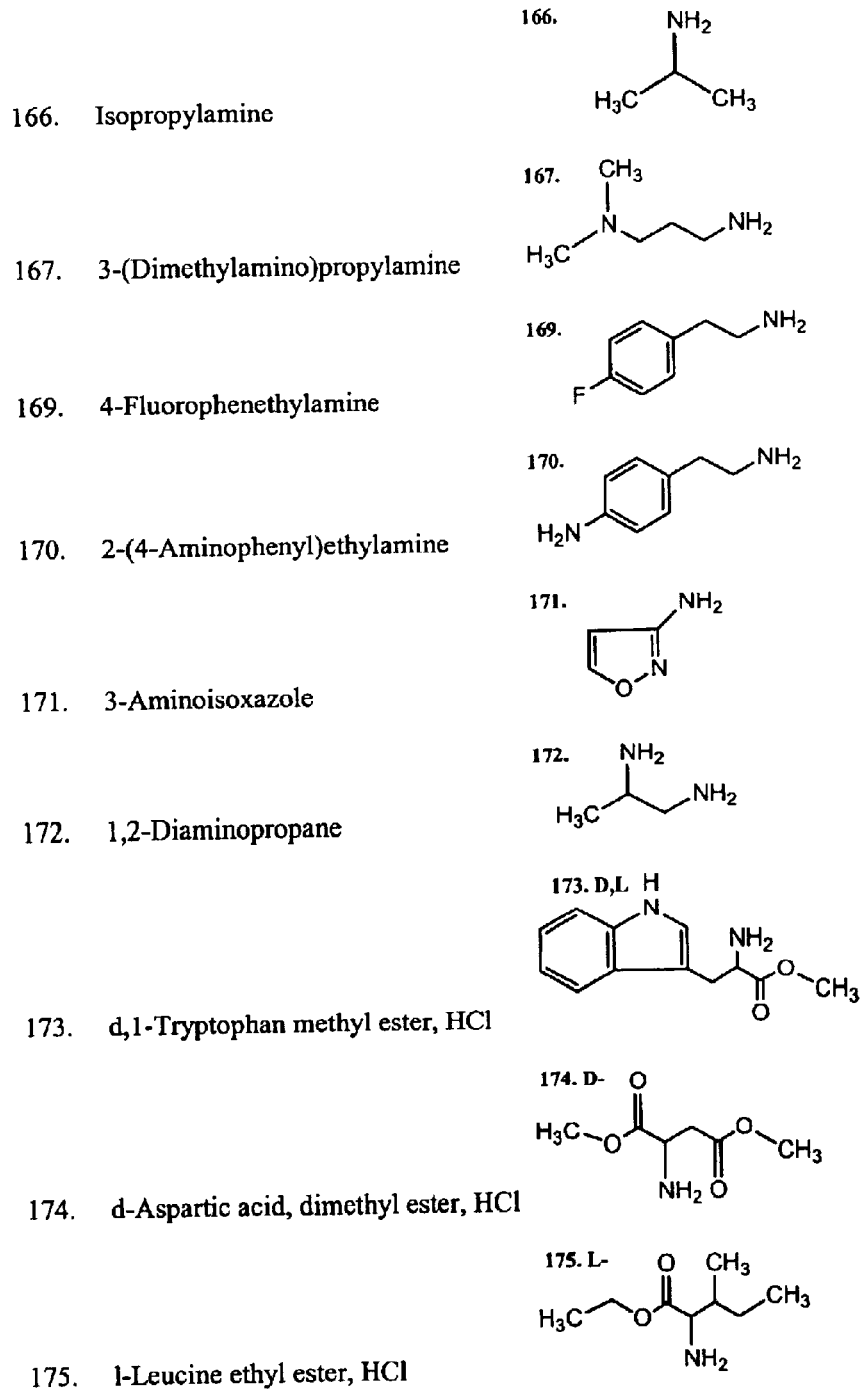
Figure 2Q:
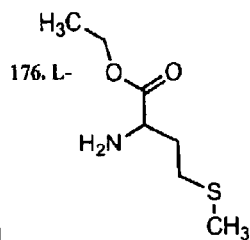
Figure 2Q:
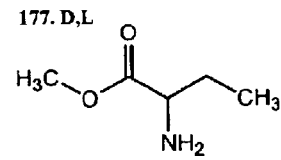
Figure 2Q:
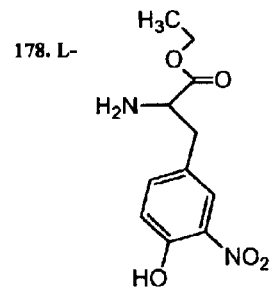
Figure 2Q:
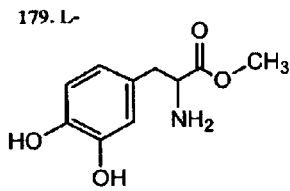
Figure 2Q:
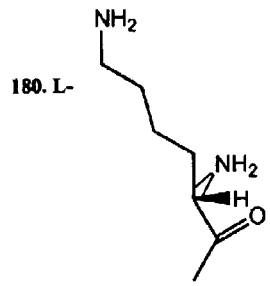
Figure 2Q:
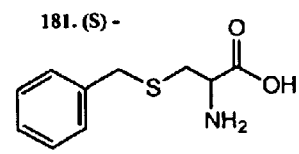
Figure 2R:
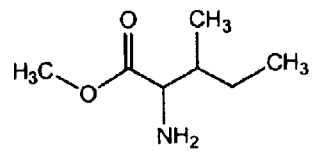
Figure 2R:
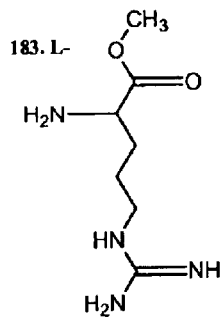
Figure 2R:
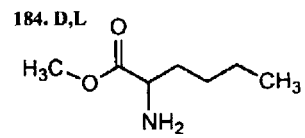
Figure 2R:
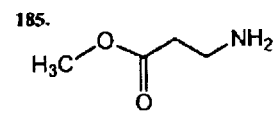
Figure 2R:
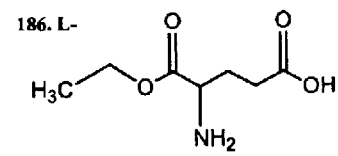
Figure 2R:
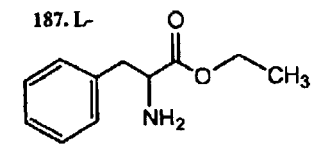
Figure 2R:
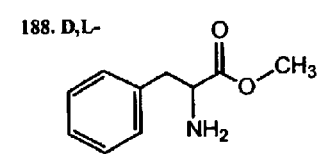
Figure 2S:
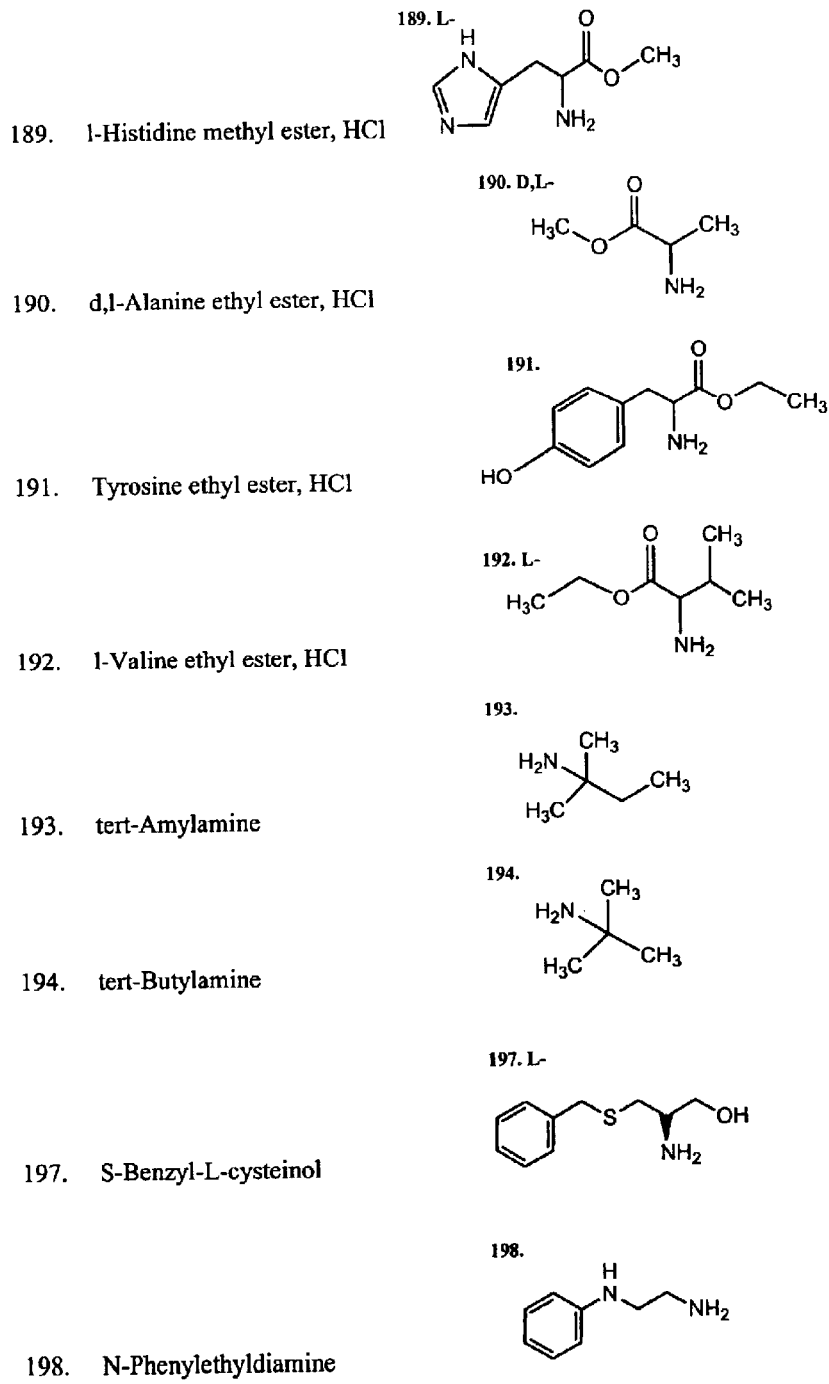
Figure 2T:
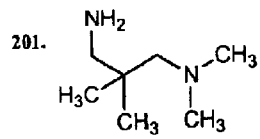
Figure 2T:
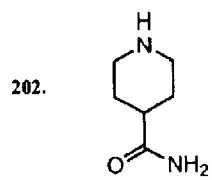
Figure 2T:
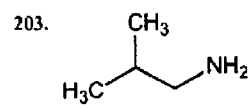
Figure 2T:
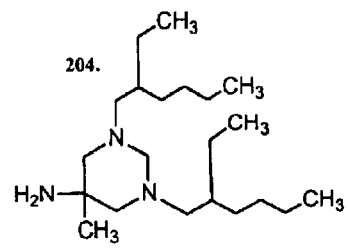
Figure 2T:
Figure 2T:
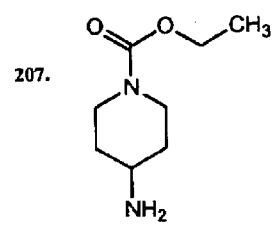
Figure 2T:
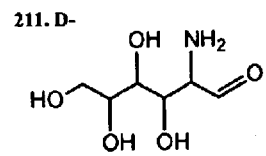
Figure 2U:
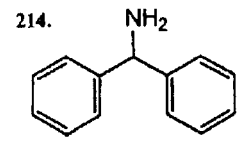
Figure 2U:
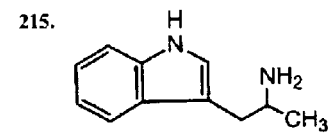
Figure 2U:
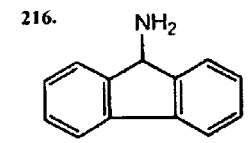
Figure 2U:
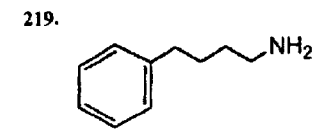
Figure 2U:
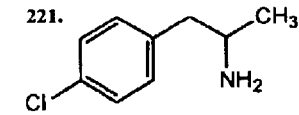
Figure 2U:
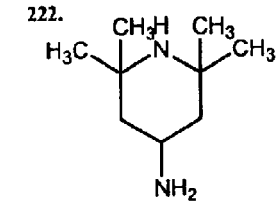
Figure 2U:
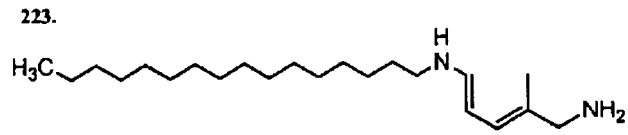
Figure 2V:
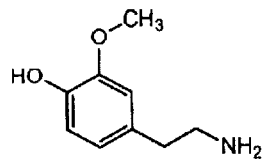
Figure 2V:
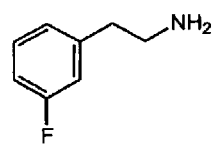
Figure 2V:
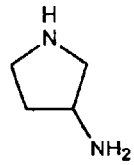
Figure 2V:
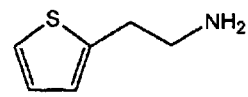
Figure 2V:
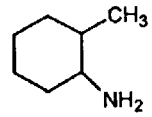
Figure 2V:
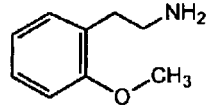
Figure 2V:
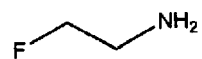
Figure 2W:
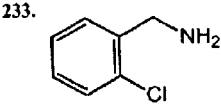
Figure 2W:
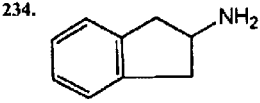
Figure 2W:
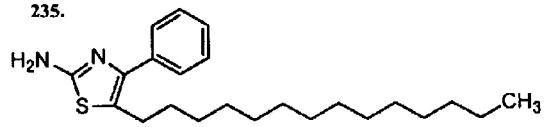
Figure 2W:
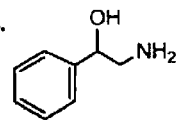
Figure 2W:
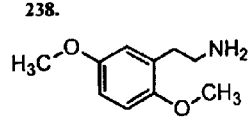
Figure 2W:
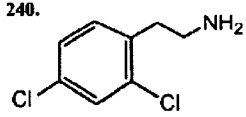
Figure 2W:
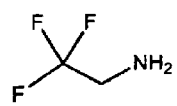
Figure 2X:
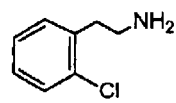
Figure 2X:
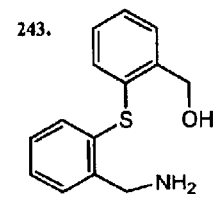
Figure 2X:
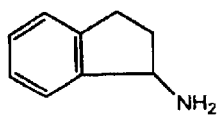
Figure 2X:
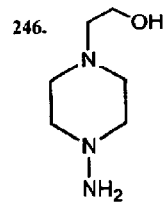
Figure 2X:
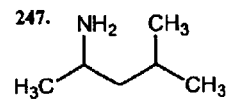
Figure 2X:
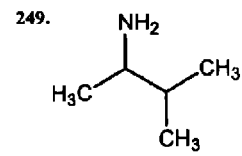
Figure 2Y:
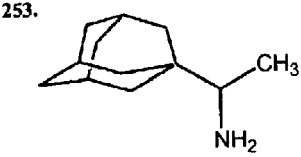
Figure 2Y:
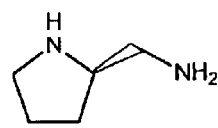
Figure 2Y:
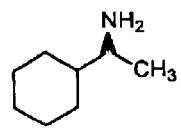
Figure 2Y:
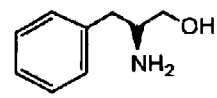
Figure 2Y:
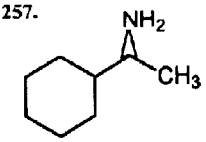
Figure 2Y:
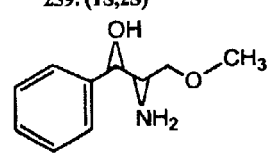
Figure 2Z:
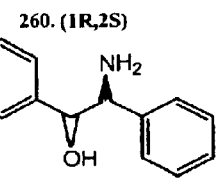
Figure 2Z:
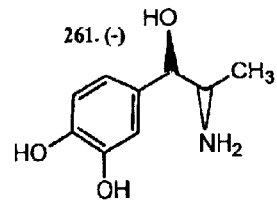
Figure 2Z:
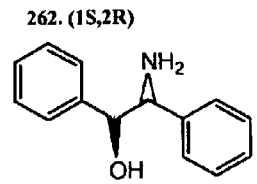
Figure 2Z:
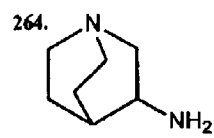
Figure 2Z:
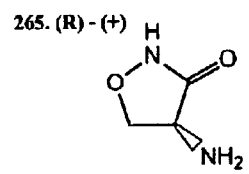
Figure 2:
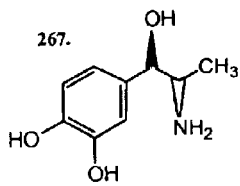
Figure 2:
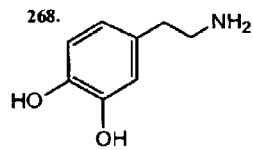
Figure 2:
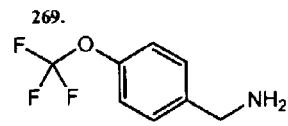
Figure 2:
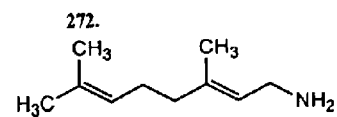
Figure 2:
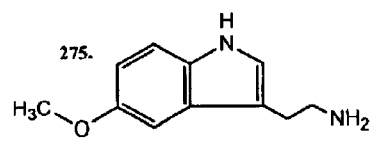
Figure 2:
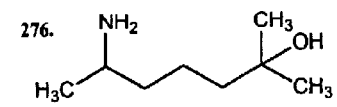
Figure 2:
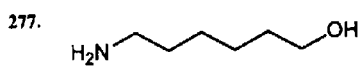
Figure 2:
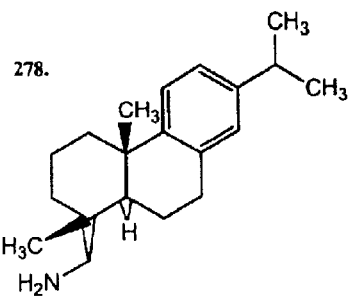
Figure 2:
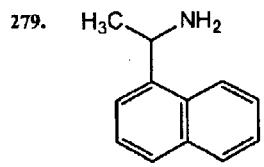
Figure 2:
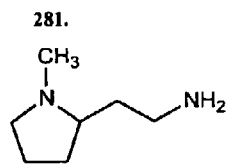
Figure 2:
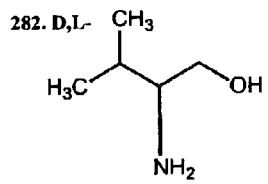
Figure 2:
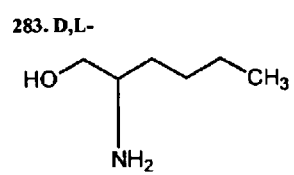
Figure 2:
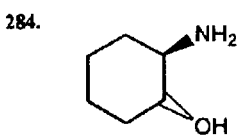
Figure 2:
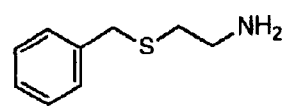
Figure 2:
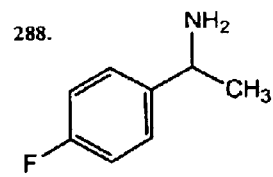
Figure 3A:
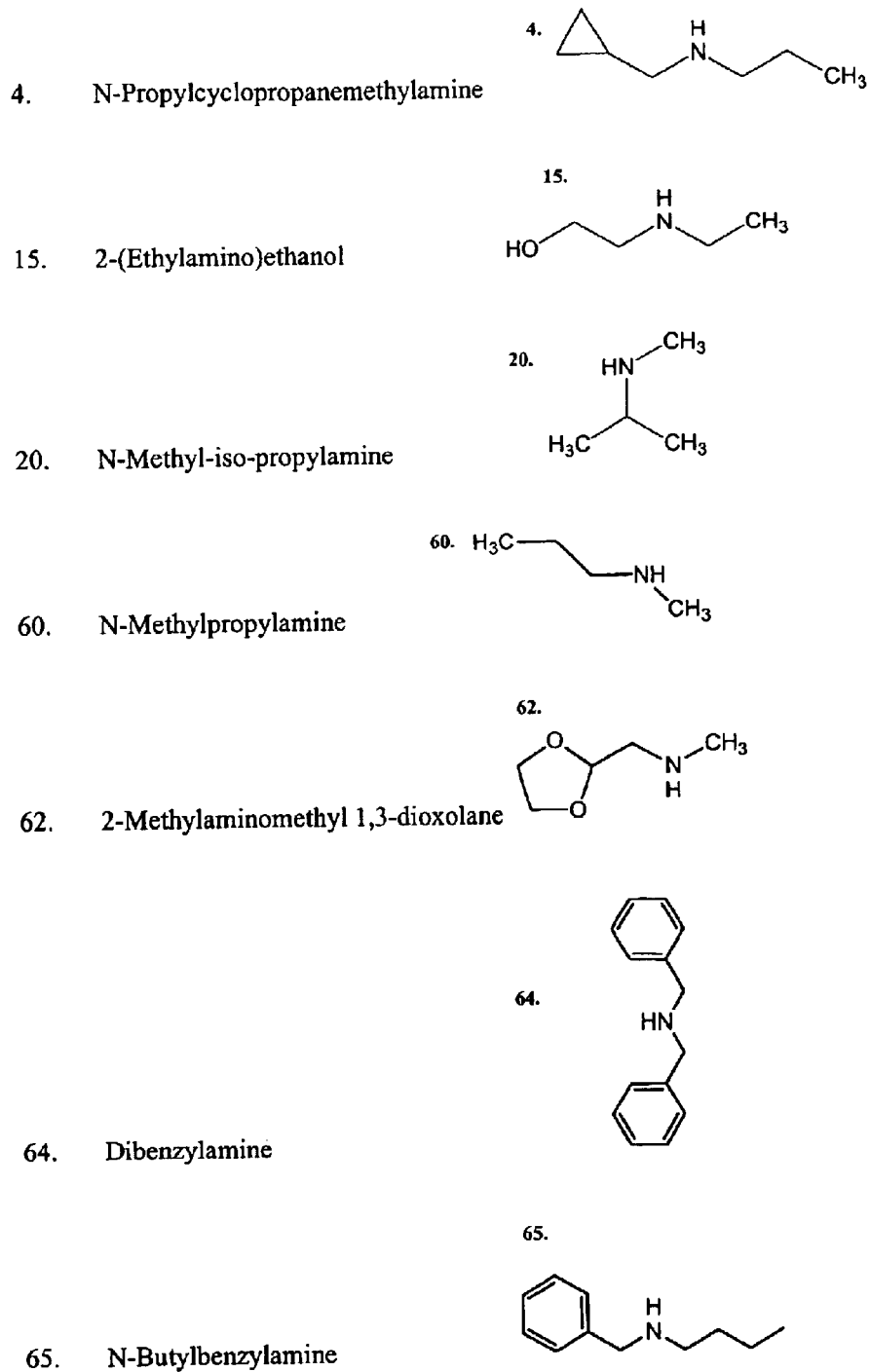
FIG. 3 provides chemical structures of a variety of acyclic secondary amines.
Figure 3B:
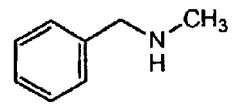
Figure 3B:
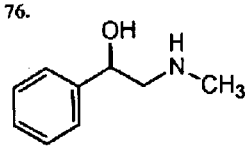
Figure 3B:
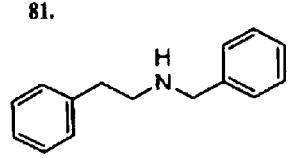
Figure 3B:
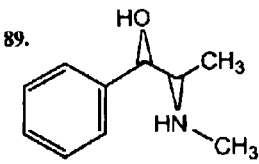
Figure 3B:
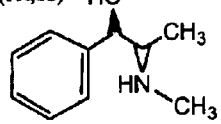
Figure 3B:
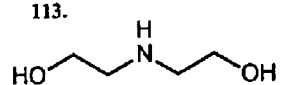
Figure 3B:
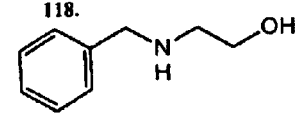
Figure 3C:
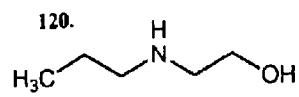
Figure 3C:
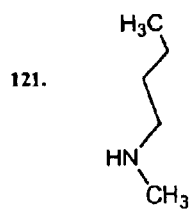
Figure 3C:
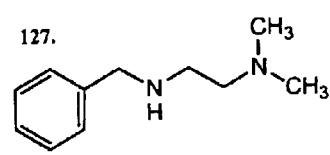
Figure 3C:
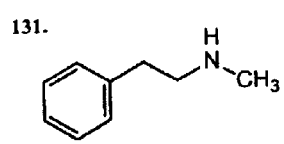
Figure 3C:
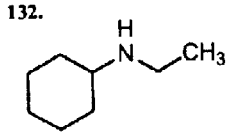
Figure 3C:
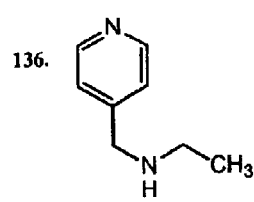
Figure 3C:
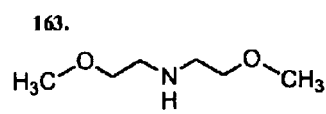
Figure 3D:
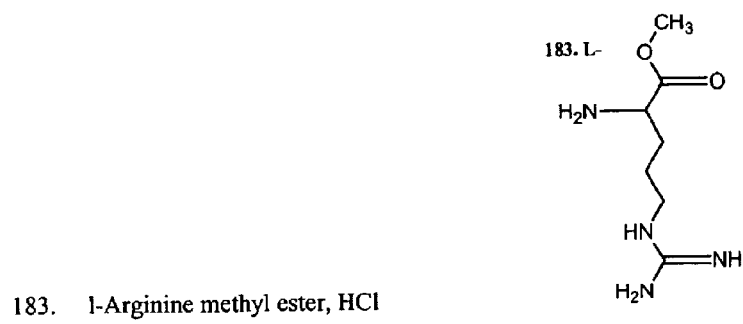
Figure 3D:
Figure 3D:
Figure 3D:
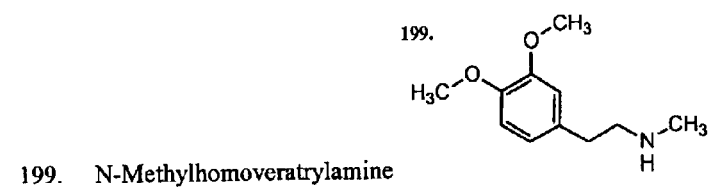
Figure 3D:
Figure 3D:
Figure 3E:
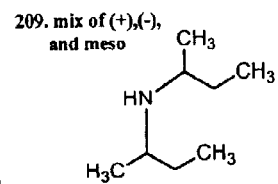
Figure 3E:
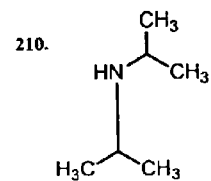
Figure 3E:
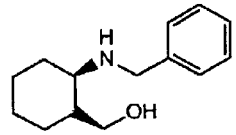
Figure 3E:
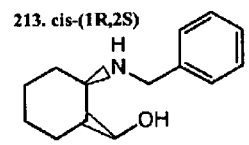
Figure 3E:
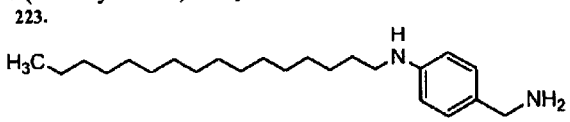
Figure 3E:
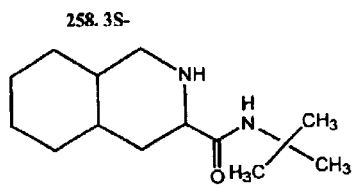
Figure 3F:
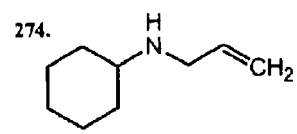
Figure 4A:
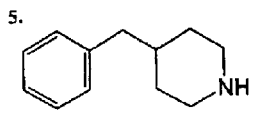
FIG. 4 provides chemical structures of a variety of cyclic secondary amines.
Figure 4A:
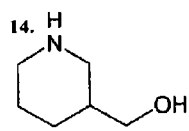
Figure 4A:
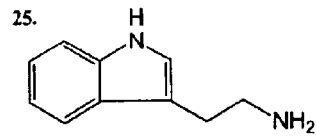
Figure 4A:
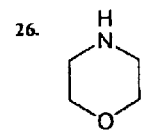
Figure 4A:
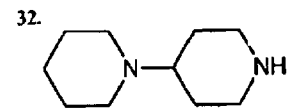
Figure 4A:
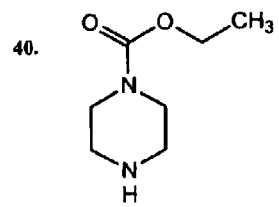
Figure 4B:
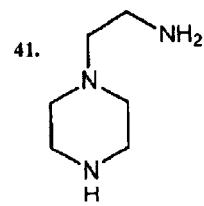
Figure 4B:
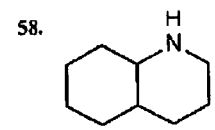
Figure 4B:
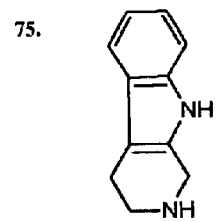
Figure 4B:
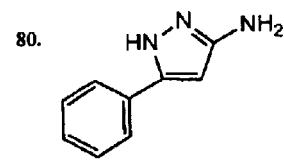
Figure 4B:
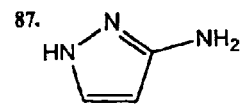
Figure 4B:
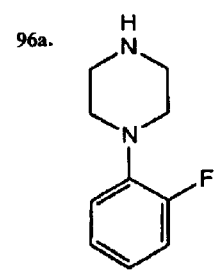
Figure 4C:
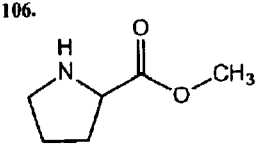
Figure 4C:
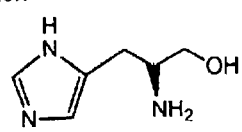
Figure 4C:
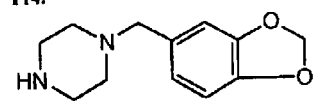
Figure 4C:
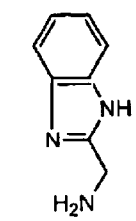
Figure 4C:
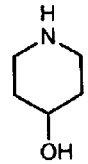
Figure 4C:
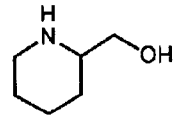
Figure 4D:
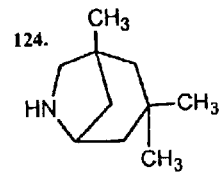
Figure 4D:
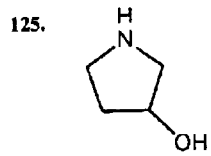
Figure 4D:
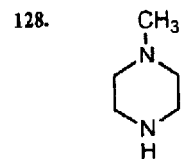
Figure 4D:
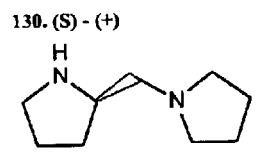
Figure 4D:
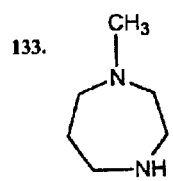
Figure 4D:
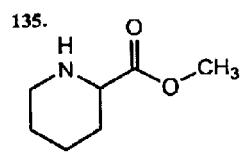
Figure 4D:
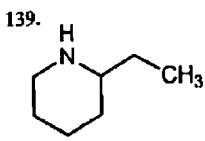
Figure 4E:
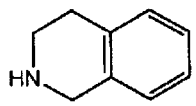
Figure 4E:
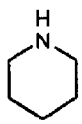
Figure 4E:
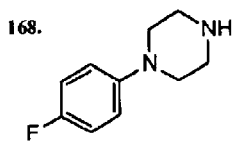
Figure 4E:
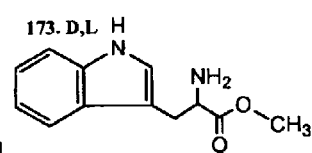
Figure 4E:
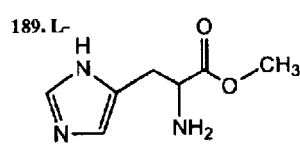
Figure 4E:
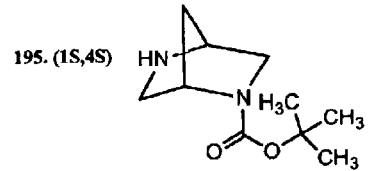
Figure 4E:
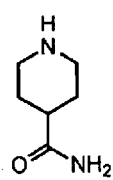
Figure 4F:
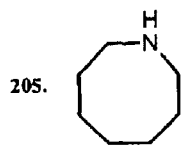
Figure 4F:
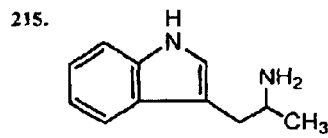
Figure 4F:
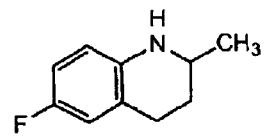
Figure 4F:
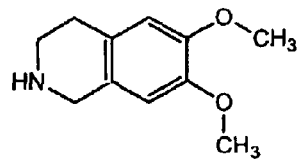
Figure 4F:
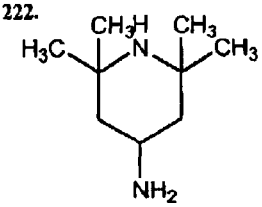
Figure 4F:
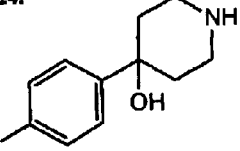
Figure 4G:
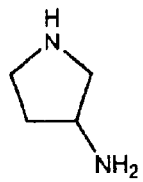
Figure 4G:
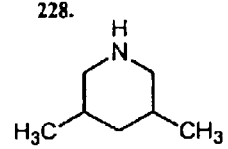
Figure 4G:
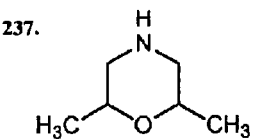
Figure 4G:
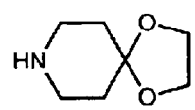
Figure 4G:
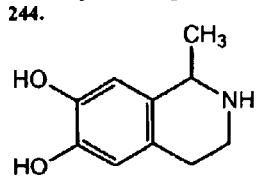
Figure 4G:
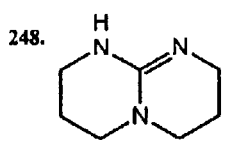
Figure 4G:
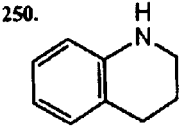
Figure 4H:
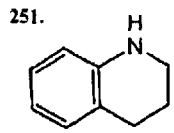
Figure 4H:
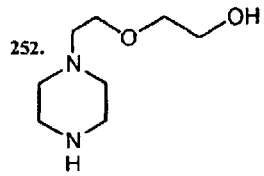
Figure 4H:
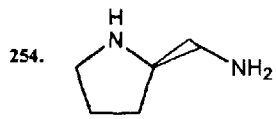
Figure 4H:
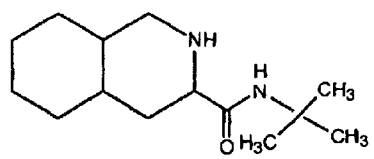
Figure 4H:
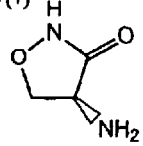
Figure 4H:
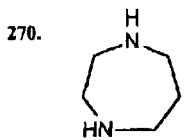
Figure 4I:
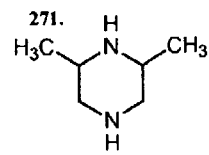
Figure 4I:
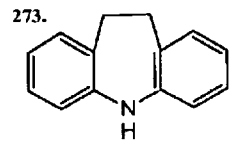
Figure 4I:
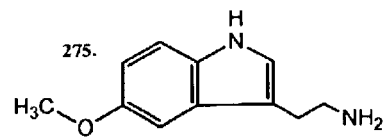
Figure 4I:
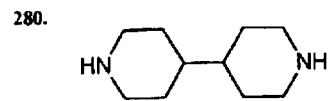
Figure 4I:
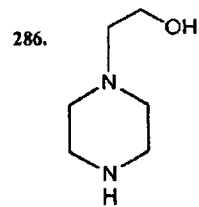
Figure 4I:
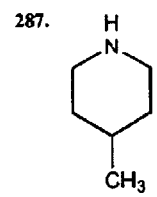

Substituted Ethylene Diamine where "$R_1NH$" is typically derived from a primary amine, and "$R_2R_3N$" is typically derived from a primary or secondary amine. The ethylene diamines of the present invention are prepared by a modular approach using primary and secondary amines as building blocks, and coupling the amine moieties with an ethylene linker building block. Representative primary amines, acyclic secondary amines, and cyclic secondary amines are shown in FIGS. 2, 3, and 4, respectively.

Generally, chemical moieties $R_1$, $R_2$, and $R_3$ of the ethylene diamine compounds of the present invention are independently selected from H, alkyl; aryl; alkenyl; alkynyl; aralkyl; aralkenyl; aralkynyl; cycloalkyl; cycloalkenyl; heteroalkyl; heteroaryl; halide; alkoxy; aryloxy; alkylthio; arylthio; silyl; siloxy; a disulfide group; a urea group; amino; and the like, including straight or branched chain derivatives thereof, cyclic derivatives thereof, substituted derivatives thereof, heteroatom derivatives thereof, heterocyclic derivatives thereof, functionalized derivatives thereof, salts thereof, such salts including, but not limited to hydrochlorides and acetates, isomers thereof, or combinations thereof. For example, nitrogen-containing heterocyclic moieties include, but are not limited to, groups such as pyridinyl (derived from pyridine, and bonded through a ring carbon), piperidinyl (derived from piperidine and bonded through the ring nitrogen atom or a ring carbon), and pyrrolidinyl (derived from pyrrolidine and bonded through the ring nitrogen atom or a ring carbon). Examples of substituted, or functionalized, derivatives of $R_1$, $R_2$, and $R_3$ include, but are not limited to, moieties containing substituents such as acyl, formyl, hydroxy, acyl halide, amide, amino, azido, acid, alkoxy, aryloxy, halide, carbonyl, ether, ester, thioether, thioester, nitrile, alkylthio, arythio, sulfonic acid and salts thereof, thiol, alkenyl, alkynyl, nitro, imine, imide, alkyl, aryl, combinations thereof, and the like. Moreover, in the case of alkylated derivatives of the recited moieties, the alkyl substituent may be pendant to the recited chemical moiety, or used for bonding to the amine nitrogen through the alkyl substituent.

Examples of chemical moieties $R_1$, $R_2$, and $R_3$ of the present invention include, but are not limited to: H; methyl; ethyl; propyl; butyl; pentyl; hexyl; heptyl; octyl; ethenyl; propenyl; butenyl; ethynyl; propynyl; butynyl; cyclopropyl; cyclobutyl; cyclopentyl; cyclohexyl; cyclooctyl cyclobutenyl; cyclopentenyl; cyclohexenyl; phenyl; tolyl; xylyl; benzyl; naphthyl; pyridinyl; furanyl; tetrahydro-1-napthyl; piperidinyl; indolyl; indolinyl; pyrrolidinyl; 2-(methoxymethyl) pyrrolidinyl; piperazinyl; quinolinyl; quinolyl; alkylated-1,3-dioxolane; triazinyl; morpholinyl; phenyl pyrazolyl; indanyl; indonyl; pyrazolyl; thiadiazolyl; rhodaninyl; thiolactonyl; dibenzofuranyl; benzothiazolyl; homopiperidinyl; thiazolyl; quinonuclidinyl; isoxazolidinonyl; any isomers, derivatives, or substituted analogs thereof; or any substituted or unsubstituted chemical species such as alcohol, ether, thiol, thioether, tertiary amine, secondary amine, primary amine, ester, thioester, carboxylic acid, diol, diester, acrylic acid, acrylic ester, methionine ethyl ester, benzyl-1-cysteine ethyl ester, imine, aldehyde, ketone, amide, or diene. Further examples of chemical moieties $R_1$, $R_2$, and $R_3$ of the present invention include, but are not limited to, the following species or substituted or alkylated derivatives of the following species, covalently bonded to the amine nitrogen: furan; tetrahydrofuran; indole; piperazine; pyrrolidine; pyrrolidinone; pyridine; quinoline; anthracene; tetrahydroquinoline; naphthalene; pyrazole; imidazole; thiophene; pyrrolidine; morpholine; and the like. One feature of the recited species or substituted or alkylated derivatives of these species, is that they may be covalently bonded to the amine nitrogen in any fashion, including through the pendant substituent or alkyl group, through the heteroatom as appropriate, or through a ring atom as appropriate, as understood by one of ordinary skill in the art.

The chemical moieties $R_1$, $R_2$, and $R_3$ of the present invention also include, but are not limited to, cyclic alkanes and cyclic alkenes, and include bridged and non-bridged rings. Examples of bridged rings include, but are not limited to, the following groups: isopinocamphenyl; bornyl; norbornyl; adamantanetetyl; cis-(−)myrtanyl; adamantyl; noradamantyl; 6-azabicyclo[3.2.1]octane; exo-norbornane; and the like.

In one embodiment of the present invention, $NR_2R_3$ is derived from a cyclic secondary amine. Examples of a cyclic chemical moiety, $NR_2R_3$, of the present invention include, but are not limited to, 4-benzyl-piperidine; 3-piperidinemethanol; piperidine; tryptamine; moropholine; 4-piperidinopiperidine; ethyl 1-piperazine carboxylate; 1-(2-amino-ethyl)piperazine; decahydroquinoline; 1,2,3,4-tetrahydro-pyridoindole (reaction at either amine); 3-amino-5-phenyl pyrazole; 3-aminopyrazole; 1-(2-fluorophenyl) piperazine; 1-proline methyl ester; histidinol; 1-piperonyl-piperazine; hexamethyleimine; 4-hydroxypiperidine; 2-piperidinemethanol; 1,3,3-trimethyl-6-azabicyclo[3.2.1] octane; 3-pyrrolidinol; 1-methylpiperazine; (S)-(+)-(2-pyrolidinylmethyl)pyrrolidine; 1-methylhomopiperazine; 2-ethyl-piperidine; 1,2,3,4-tetrahydroisoquinoline; 1-(4-fluorophenyl)piperazine; d,1-tryptophan methyl ester; tert-butyl (1S,4S)-(−)-2,5-diazabiclyclo[2.2.1]heptane-2-carboxylate; isonipecotamide; heptamethyleneimine; alpha-methyltryptamine; 6,7-dimethoxy-1,2,3,4-tetrahydroisoquinoline; 3-aminopyrrolidine; 3,5-dimethylpiperidine; 2,6-dimethylmorpholine; 1,4-dioxo-8-azaspiro[4.5]decane; 1-methol-6,7-dihydroxy-1,2,3,4-tetrahydroisoquinoline; 1,3,4,6,7,8-hexahydro-2H-pyrido (1,2-A)pyrimidine; 1,2,3,4-tetrahydroquinoline; 1-(2-methoxyphenyl)piperazine; 1-(2-(2-hydroxyethoxy)ethyl) piperazine; (S)-(+)-2-(aminomethyl)pyrroli-dine; (3S(3a, 4Ab),8Ab)-N-t-butyl-D-ecahydro-3-isoquino-linecarboxamide; (R)-cycloserine; homopiperazine; 2,6-dimethylpiperazine (reaction at either amine); iminodibenzyl; 5-methoxytryptamine; 4,4'-bipiperidine; 1-(2-hydroxyethyl) piperazine; 4-methylpiperidine; 1-histidine methyl ester; or methyl pipecoliate.

The $R_1HN$ substituent is derived from a primary amine. The $R_2R_3N$ substituent is typically derived from a primary or secondary amine, but may also arise from an amino acid, or an amino acid precursor. The amino acid can transform into an amino alcohol. When an amino acid is employed as the source of the $R_2R_3N$ moiety, the precursor compound may be selected from, among others, the following compounds and their derivatives: d,1-tryptophan methyl ester; 1-methionine ethyl ester; 1-lysine methyl ester (via reaction at either primary amine); (S)-benzyl-1-cysteine ethyl ester; 1-arginine methyl ester (via reaction at either primary amine); 1-glutamic acid ethyl ester; 1-histidine methyl ester; or (3S(3a,4Ab),8Ab)-N-t-butyl-D-ecahydro-3-iso-quino linecarboxamide.

The $R_4$ moiety of the substituted ethylene diamine compounds of the present invention is typically selected from H, alkyl or aryl, but $R_4$ can also constitute alkenyl, alkynyl, aralkyl, aralkenyl, aralkynyl, cycloalkyl, cycloalkenyl, and the like. Examples of the $R_4$ chemical moiety include, but are not limited to: H; methyl; ethyl; propyl; butyl; pentyl; hexyl; heptyl; octyl; ethenyl; propenyl; butenyl; ethynyl; propynyl; butynyl; cyclobutyl; cyclopentyl; cyclohexyl; cyclobutenyl; cyclopentenyl; cyclohexenyl; phenyl; tolyl; xylyl; benzyl; naphthyl; straight or branched chain derivatives thereof; cyclic derivatives thereof; substituted, functionalized, and heteroatom derivatives thereof; and heterocyclic derivatives thereof, and the like. Typically, $R_4$ is selected from H, methyl, ethyl, butyl or phenyl. However, when $R_4$ is "H" the ethylene diamine does not contain ethambutol.

A majority of the ethylene diamine compounds described hrein are preferably prepared using a solid support synthesis, as set forth in one of the representative reaction schemes shown in FIG. 1. However, when $R_4$ is H, the reaction does not proceed well when sterically hindered amines are used for $R_1NH_2$, or when diamines, such as amino alkylenemorpholine, or aminoalkylene-piperidines, are used for $R_1NH_2$. When $R_4$ is methyl, or phenyl, sterically hindered amines used for $R_3R_2NH$ do not work well due to steric hindrance at the reaction site. In this case, a competing hydrolysis reaction producing the corresponding amino alcohols, and incomplete reduction of the amidoethyleneamines, interfere with the reaction scheme. As a result, the desired diamine products form in low yields.

The preparation of the ethylene diamines is preferably accomplished in six steps, using a rink-acid resin. The first step of the synthesis is converting the rink-acid resin to rink-chloride by treatment with triphenylphosphine and hexachloroethane in tetrahydrofuran (THF). This step is followed by addition of the primary amine in the presence of Hunig's base (EtN(i-Pr)$_2$) in dichloroethane. The third step is the acylation of the resin-attached amine using either one of the two acylation routes shown in FIG. 1. The acylation step is preferably accomplished using either chloroacetyl chloride, α-bromo-α-methyl acetylbromide, α-bromo-α-ethylacetyl bromide, α-bromo-α-butyl acetylbromide, or α-chloro-α-phenyl-acetylchloride, each in the presence of pyridine in THF. Other acylation reagents known to those skilled in the art may also be used, however, the α-bromoacetyl halides result in low product yields, which may be attributed to HBr elimination. The acylation may also be accomplished via a peptide coupling mechanism using α-bromo-α-methylacetic acid, or α-chloro-α-methylacetic acid, in the presence of benzotriazole-1-yl-oxy-tris-pyrrolidino-phosphonium hexafluorophosphate (PyBrop) and N$_1$N-diisopropylethyl amine (EtN(i-Pr)$_2$) in dichloromethane (DCM) and dimethylformamide (DMF). Again, other acylation reagents known to those skilled in the art may also be used. The acylation step is preferably performed twice to achieve better acylated product yields.

Introduction of the second nitrogen moiety is preferably achieved in the presence of Hunig's base in dimethylformamide (DMF). Reduction of the intermediate amine-amide is carried out using Red-Al (3.4M solution of sodium bis (2-methoxyethoxy) aluminum hydride in toluene). The final product is cleaved from the resin support using a 10% solution (by volume) of trifluoroacetic acid (TFA) in dichloromethane (DCM). The solvent is evaporated, and the TFA salts of the final diamine products are analyzed by mass spec, and screened against *M. tuberculosis* for effectiveness.

Some of the substituted ethylene diamines, prepared using the above-described solid-support synthesis, are also prepared using a solution phase synthesis described below.

Formation of the Substituted Ethylene Diamine Library

The solid support syntheses, shown in FIG. 1, are preferably used to prepare a substituted ethylene diamine library. Solid phase synthesis offers at least three principal advantages: (i) a reduced need for chromatographic procedures, (ii) the use of excess reagents to drive a reaction forward in high yields, and (iii) the use of split and pool technologies for the synthesis of a large number of compounds. Solid support syntheses of 1,2-diamine libraries have previously been accomplished by the reduction of short peptides (Cuervo et al., Peptides 1994: Proceedings of the European Peptide Symposium; Maia HSL Ed., Esom: Leiden, 1995, 465–466). However, as described herein, an ethylene diamine library is created using amines, rather than simple amino acids, to allow for greater diversity in the building-block monomers. The first three steps of each support synthesis: the activation of the Rink-acid resin, the addition of the first amine, and the acylation step are carried out in 10 ml tubes on a QUEST® 210 Synthesizer manufactured by ARGONAUT TECHNOLOGIES®, Inc., Foster City, Calif. The synthesizer handles up to twenty simultaneous reactions in 5 ml or 10 ml reaction vessels to allow for rapid synthesis of target compounds. The synthesizer provides programmable temperature control and agitation, and the automated delivery of solvents into the reaction vessels. The addition of the second amine, the reduction with Red-Al, and the cleavage from the solid support are carried out in 2 ml wells in a 96-well, chemically resistant plate.

Figure 5:
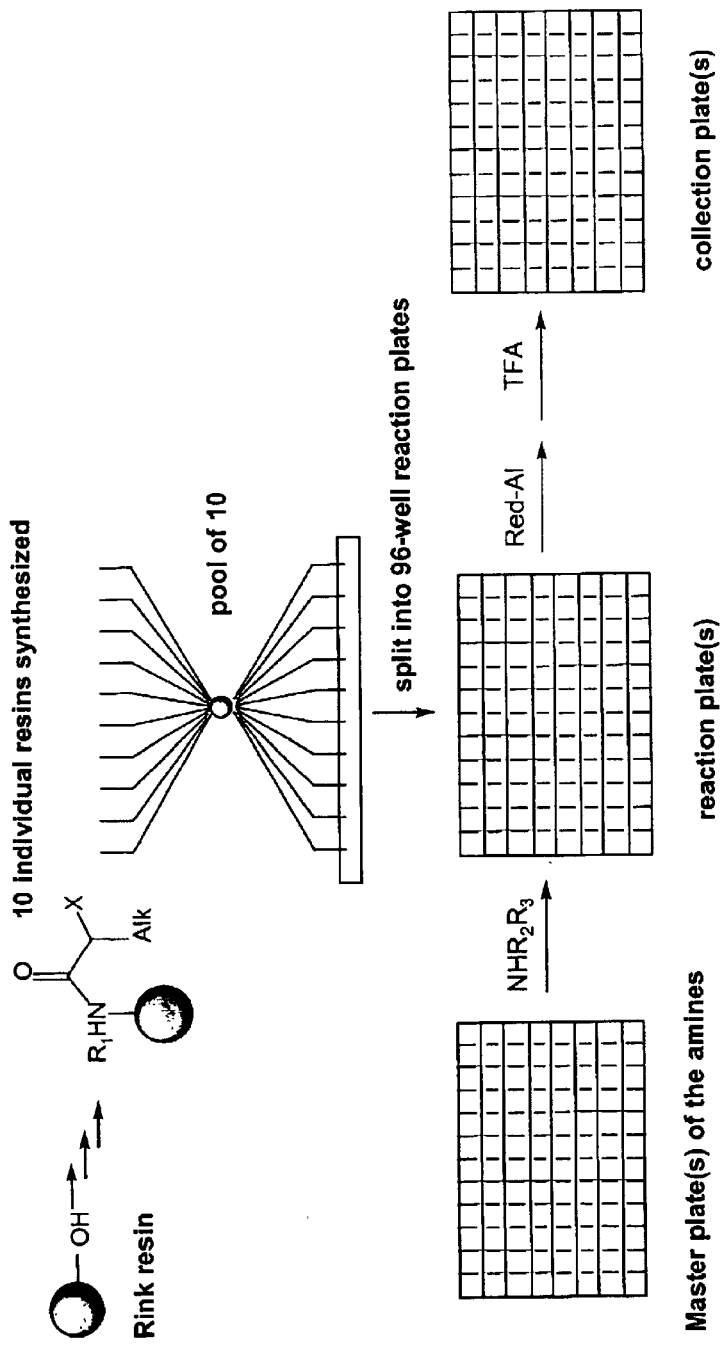
FIG. 5 represents a flow schematic for a representative reaction pool of ten substituted ethylene diamines.

Prior to the solid support synthesis, each amine, within numbers 1 to 288, as shown in FIGS. 2, 3, and 4, is dissolved in DMF as a one molar solution, and organized in three, 96-well plates (one amine per well), to yield three master plates of these amines. An individual haloacetyl amide from each primary amine and a particular $R_4$ group, is formed in the first three steps of the support synthesis. Individual haloacetyl amides are then pooled into groups of ten or thirty. A suspension of the pooled resins in a 2:1 mixture of DCM/THF is evenly distributed into one, two or three reaction plates to assure 15–20 mg of the suspension per well. The number of reaction plates used is based on the amount of suspension available. Each well of pooled resins is reacted with a corresponding amine from the master plates. FIG. 5 provides a flow schematic for a representative pool. Each reaction occurs in a separate well, in the presence of Hunig's base in DMF at 70–75° C. for 16–20 hours. Each resulting amine-amide is reduced using 65+w % Red-Al at room temperature. The reduction is followed by cleavage with 10% vol. TFA in DCM. The solvents in each reaction well are evaporated, and the TFA salts of the diamines analyzed (mass spec), and screened against M. tuberculosis. One plate of pooled diamines are screened against M. smegmatis. Two randomly selected rows in each plate; i.e., 24 samples per 96-well plate, or 25% of the library, are examined by mass spectroscopy. Specific protocols and detailed methods are provided below in the Examples.

Screening Against M. tuberculosis

An entire library of synthesized substituted ethylene diamines (targeted number of compounds about 100,000), prepared as described above, was screened, in vitro, against M. tuberculosis in ethambutol (EMB) sensitive Luc-assay. The MIC (Minimum Inhibition Concentration) was also determined. The MIC is the concentration of a growth inhibitor, here the substituted ethylene diamine, in which there is no multiplication of the microorganism under examination. Screening was done using a High-Throughout Screening (HTS) Luc assay with recombinant mycobacteria containing a promoter fusion of a luciferase to the EB-inducible gene (Luc assay). The Luc-assay and MIC assay are described in detail below. These assays are well known to those skilled in the art. Based on this initial screening, 300+ compound mixtures showed anti-TB activity. FIG. 6 represents typical assay data in a luciferase reporter strain containing an Rv0341 EMB-inducible promoter. FIG. 6 represents percent maximum Luminescense Count per Second (% Max. LCPS) for pooled compound mixtures in one row (row D) in one of the 96-well plates.

Deconvolution of the Reactive Wells

The *M. tuberculosis* screening revealed approximately 300 active compounds mixtures that were selected for deconvolution. In particular, wells possessing activity of approximately <12.5 $\mu$M in the HTS Luc assay, and/or an MIC of approximately <12.5 $\mu$M, were selected for a total of 336 wells.

Deconvolutions were performed by discrete re-synthesis of each substituted ethylene diamine compound in each active compound pool. The pooled compounds in each active well were individually synthesized, and screened. Syntheses of the targeted diamine compounds in each active pool were done in the 96-well plates using stored archived $\alpha$-haloacetyl amides (resin attached haloacetyl amides), according to the previously described reaction steps (the addition of the second amine, the reduction with Red-Al, and the cleavage from the solid support). The archived resins were stored as individual compounds at 4° C. The 96-well plates were used for the remaining synthesis steps as previously described.

The same screening tests, MIC and HTS Luc assay, were performed on each deconvoluted compound. Representative Luminescence data for deconvoluted compounds are shown in FIGS. 7 and 8. FIGS. 7 and 8 represent the Luminescence Count per Second (LCPS) for individual compounds.

Summary of Screening Results

Overall, the deconvolution screening results (revealed about 2,000 ethylene diamine compounds with inhibitory activity against *M. tuberculosis*. More than 150 of these compounds exhibited MICs equal to or lower than approximately 12.5 $\mu$M. FIG. 9 summarizes the MIC data for all synthesized discrete compounds with an MIC of 50 $\mu$M or less. FIG. 10 summarizes Luc assay data for all compounds that exhibit at least 10% activity at each concentration (the results are not cumulative). The MIC and Luc activities were obtained for non-purified samples, with chemical yields of approximately 20%, based on an assumed 80% yield at each reaction step. In the Luc assay, 32 compounds exhibited activity at 1.56 $\mu$M, and in the MIC assay, at least 11 compounds had an MIC of 3.13 $\mu$M.

The total frequency of the top thirteen amines that contributed to the activity of the substituted ethylene diamines are shown in FIG. 11, with each amine represented by its numerical designation. These amines include the following:

11 2,3-Dimethylcylochexy amines
18 3,3-Diphenylpropylamine
44 1-Adamantanemethylamine
47 2,2-Diphenylethylamine
63 (S)-2-Amino-1-butanol
74.1 (–)-cis-Myrtanylamine
77.1 Cyclooctylamine
78.1 2-Adamantamine
105a (1R,2R,3R,5S)-(–)-Isopinocampheylamine
231 2-Methoxyphenethylamine

255 (S)-Cylcohexylethylamine

266 Undecylamine

272 Geranylamine

Other amines that contributed to the activity of the substituted ethylene diamines are shown in Table 2. The compounds in Table 2 are sorted by their MIC results. Some compounds, synthesized in larger quantities (2–60 mg) on the Quest® Synthesizer, and purified by HPLC using semi-preparative C18-column, are shown in Table 3. Generally, the final purity of each compound in Table 3 was at least 90%.

TABLE 2

Synthetic Substituted Diethylene Diamines Sorted by Minimum Inhibition Concentration

| N1 | N2 | R4 | MIC (uM) | % Induction |
|---|---|---|---|---|
| 3,3-Diphenylpropylamine | exo-Aminonorbornane | Hydrogen | 3.13 | 53.70 |
| 2,2-Diphenylamine | (+)-Isopinocampheylamine | Hydrogen | 3.13 | 93.94 |
| 2,2-Diphenylamine | cis-(−)-Myrtanylamine | Hydrogen | 3.13 | 64.49 |
| 2,2-Diphenylamine | Cyclooctylamine | Hydrogen | 3.13 | 63.44 |
| 2,2-Diphenylamine | 3,4-Dihydroxynorephedrine | Hydrogen | 3.13 | 42.80 |
| 5-Aminoquinoline | Cyclohexylamine | Hydrogen | 3.13 | 18.33 |
| 5-Aminoquinoline | tert-Octylamine | Hydrogen | 3.13 | 20.85 |
| 5-Aminoquinoline | 4-Methylcyclohexylamine | Hydrogen | 3.13 | 26.33 |
| cis-(−)-Myrtanylamine | (+)-Bornylamine | Hydrogen | 3.13 | 100.00 |
| cis-(−)-Myrtanylamine | 1-Adamantanemethylamine | Hydrogen | 3.13 | 85.20 |
| cis-(−)-Myrtanylamine | (−)-Isopinocampheylamine | Hydrogen | 3.13 | 60.94 |
| 1-Adamantanemethylamine | tert-Octylamine | Hydrogen | 4.7 | 9.81 |
| 3,4-Dimethoxyphenethylamine | 1-Adamantanemethylamine | Hydrogen | 6.25 | 11.45 |
| 3,4-Dimethoxyphenethylamine | Hexetidine (mixture of isomers) | Hydrogen | 6.25 | 0 |
| 3,4-Dimethoxyphenethylamine | Dehydroabietylamine | Hydrogen | 6.25 | 0 |
| 3,3-Diphenylpropylamine | 1-Adamantanemethylamine | Hydrogen | 6.25 | 9.53 |
| 3,3-Diphenylpropylamine | 2-Methylcyclohexylamine (mix of cis and trans) | Hydrogen | 6.25 | 50.08 |
| 3,3-Diphenylpropylamine | 1,3-Dimethylbutylamine | Hydrogen | 6.25 | 39.40 |
| 3,3-Diphenylpropylamine | 1-(1-Adamantyl)ethylamine, HCl | Hydrogen | 6.25 | 45.14 |
| 3,3-Diphenylpropylamine | (S)-(−)-Cyclohexylethylamine | Hydrogen | 6.25 | 43.49 |
| 3,3-Diphenylpropylamine | (R)-(−)-Cyclohexylethylamine | Hydrogen | 6.25 | 34.54 |
| 3,3-Diphenylpropylamine | 1-Adamantanemethylamine | Methyl | 6.25 | 16.14 |
| Propylamine | Hexetidine (mixture of isomers) | Hydrogen | 6.25 | 0 |
| Phenethylamine | Hexetidine (mixture of isomers) | Hydrogen | 6.25 | 0 |
| b-Methylphenethylamine | Hexetidine (mixture of isomers) | Hydrogen | 6.25 | 0 |
| b-Methylphenethylamine | Undecylamine | Hydrogen | 6.25 | 0 |
| 2,2-Diphenylamine | (+)-Bornylamine | Hydrogen | 6.25 | 87.86 |
| 2,2-Diphenylamine | (−)-Isopinocampheylamine | Hydrogen | 6.25 | 77.80 |
| 2,2-Diphenylamine | alpha-Methyltryptamine | Hydrogen | 6.25 | 55.07 |
| 2,2-Diphenylamine | alpha-Methyltryptamine | Hydrogen | 6.25 | 23.08 |
| 2,2-Diphenylamine | 4-Phenylbutylamine | Hydrogen | 6.25 | |
| 2,2-Diphenylamine | 2,5-Dimethoxyphenethylamine | Hydrogen | 6.25 | |
| 2,2-Diphenylamine | 2,4-Dichlorophenethylamine | Hydrogen | 6.25 | |
| 2,2-Diphenylamine | 2-(2-Aminomethyl) phenylthio)benzyl alcohol | Hydrogen | 6.25 | |
| 2,2-Diphenylamine | 1-(1-Naphthyl)ethylamine | Hydrogen | 6.25 | 7.20 |
| Veratryl amine | 2,5-Dimethoxyphenethylamine | Hydrogen | 6.25 | |
| Veratryl amine | 2-(2-Aminomethyl) phenylthio)benzyl alcohol | Hydrogen | 6.25 | |
| 5-Aminoquinoline | 2-Aminoheptane | Hydrogen | 6.25 | 26.22 |
| 5-Aminoquinoline | 1-Adamantanamine | Hydrogen | 6.25 | 18.91 |
| 1-Aminomethyl-1-cyclohexanol, HCl | Hexetidine (mixture of isomers) | Hydrogen | 6.25 | |
| cis-(−)-Myrtanylamine | 2,3-Dimethylcyclohexylamine | Hydrogen | 6.25 | 100.00 |
| cis-(−)-Myrtanylamine | 3,3-Diphenylpropylamine | Hydrogen | 6.25 | 87.78 |
| cis-(−)-Myrtanylamine | (+)-Isopinocampheylamine | Hydrogen | 6.25 | 93.10 |
| cis-(−)-Myrtanylamine | 2,2-Diphenylamine | Hydrogen | 6.25 | 81.84 |
| cis-(−)-Myrtanylamine | cis-(−)-Myrtanylamine | Hydrogen | 6.25 | 68.24 |
| cis-(−)-Myrtanylamine | 1,3,3-Trimethyl-6-azabicyclo[3.2.1]octane | Hydrogen | 6.25 | 68.18 |
| cis-(−)-Myrtanylamine | 1-Adamantanemethylamine | Methyl | 6.25 | 24.22 |
| cis-(−)-Myrtanylamine | cis-(−)-Myrtanylamine | Methyl | 6.25 | 44.14 |
| Cyclooctylamine | 3,3-Diphenylpropylamine | Hydrogen | 6.25 | 100.00 |
| Cyclooctylamine | (−)-Isopinocampheylamine | Hydrogen | 6.25 | 59.13 |
| sec-Butylamine | Hexetidine (mixture of isomers) | Hydrogen | 6.25 | |
| 3-Methylbenzylamine | Hexetidine (mixture of isomers) | Hydrogen | 6.25 | |
| 3-Methylbenzylamine | Undecylamine | Hydrogen | 6.25 | |
| 2-Methoxyethylamine | Hexetidine (mixture of isomers) | Hydrogen | 6.25 | |
| Geranylamine | 2-Adamantanamine, HCl | Hydrogen | 6.25 | 25.66 |
| 1-Adamantanemethylamine | 4-Benzylpiperidine | Hydrogen | 9.4 | 0 |
| 1-Adamantanemethylamine | 2,3-Dimethylcyclohexylamine | Hydrogen | 9.4 | 0 |
| 1-Adamantanemethylamine | 3,3-Diphenylpropylamine | Hydrogen | 9.4 | 40.06 |
| 1-Adamantanemethylamine | 1-Adamantanemethylamine | Hydrogen | 9.4 | 15.25 |

TABLE 2-continued

Synthetic Substituted Diethylene Diamines Sorted by Minimum Inhibition Concentration

| N1 | N2 | R4 | MIC (uM) | % Induction |
|---|---|---|---|---|
| 1-Adamantanemethylamine | 2,2-Diphenylamine | Hydrogen | 9.4 | 0 |
| 1-Adamantanemethylamine | 1,3,3-Trimethyl-6-azabicyclo[3.2.1]octane | Hydrogen | 9.4 | 0 |
| 1-Adamantanemethylamine | 138 | Hydrogen | 9.4 | 0 |
| 3-Phenyl-1-propylamine | 138 | Hydrogen | 9.4 | |
| 2,2-Diphenylamine | 1-Adamantanemethylamine | Hydrogen | 9.4 | 65.89 |
| 2,2-Diphenylamine | 138 | Hydrogen | 9.4 | |
| Furfurylamine | Hexetidine (mixture of isomers) | Hydrogen | 12.5 | 0 |
| 3,4,5-Trimethoxybenzylamine | Hexetidine (mixture of isomers) | Hydrogen | 12.5 | 0 |
| 1-Methyl-3-phenylpropylamine | Dehydroabietylamine | Hydrogen | 12.5 | 0 |
| Cyclobutylamine | Hexetidine (mixture of isomers) | Hydrogen | 12.5 | 0 |
| 2-Fluorobenzylamine | Hexetidine (mixture of isomers) | Hydrogen | 12.5 | 0 |
| 2-Fluorobenzylamine | Dehydroabietylamine | Hydrogen | 12.5 | 0 |
| 3,4-Dimethoxyphenethylamine | Undecylamine | Hydrogen | 12.5 | 0 |
| 3,3-Diphenylpropylamine | exo-Aminonorbornane | Hydrogen | 12.5 | 14.38 |
| 3,3-Diphenylpropylamine | Decahydroquinoline | Hydrogen | 12.5 | 22.52 |
| 3,3-Diphenylpropylamine | Hexetidine (mixture of isomers) | Hydrogen | 12.5 | 0 |
| 3,3-Diphenylpropylamine | 4-Phenylbutylamine | Hydrogen | 12.5 | 0 |
| 3,3-Diphenylpropylamine | 2-Methoxyphenethylamine | Hydrogen | 12.5 | 6.82 |
| 3,3-Diphenylpropylamine | 2,4-Dichlorophenethylamine | Hydrogen | 12.5 | 0 |
| 3,3-Diphenylpropylamine | 1-Aminoindan | Hydrogen | 12.5 | 18.05 |
| 3,3-Diphenylpropylamine | Undecylamine | Hydrogen | 12.5 | 0 |
| 3,3-Diphenylpropylamine | Dehydroabietylamine | Hydrogen | 12.5 | 0 |
| 3,3-Diphenylpropylamine | 2-(1-Cyclohexenyl)ethylamine | Methyl | 12.5 | 9.5 |
| 3,3-Diphenylpropylamine | cis-(−)-Myrtanylamine | Methyl | 12.5 | 18.41 |
| 3,3-Diphenylpropylamine | Cyclooctylamine | Methyl | 12.5 | 20.84 |
| Propylamine | Dehydroabietylamine | Hydrogen | 12.5 | 0 |
| Phenethylamine | Dehydroabietylamine | Hydrogen | 12.5 | 0 |
| Cyclohexylamine | Hexetidine (mixture of isomers) | Hydrogen | 12.5 | 0 |
| 3-Amino-1-propanol | Hexetidine (mixture of isomers) | Hydrogen | 12.5 | 0 |
| b-Methylphenethylamine | Dehydroabietylamine | Hydrogen | 12.5 | 0 |
| 4-Methoxyphenethylamine | 2-Fluorophenethylamine | Hydrogen | 12.5 | 0 |
| 4-Methoxyphenethylamine | 2-(1-Cyclohexenyl)ethylamine | Hydrogen | 12.5 | 0 |
| 4-Methoxyphenethylamine | 2,4-Dimethoxybenzylamine | Hydrogen | 12.5 | 0 |
| 4-Methoxyphenethylamine | 4-Fluorophenethylamine | Hydrogen | 12.5 | 16.78 |
| 4-Methoxyphenethylamine | Hexetidine (mixture of isomers) | Hydrogen | 12.5 | 0 |
| Tetrahydrofurfurylamine | Hexetidine (mixture of isomers) | Hydrogen | 12.5 | 0 |
| Amylamine | 4-Fluorophenethylamine | Hydrogen | 12.5 | |
| 3-Phenyl-1-propylamine | 2-(1-Cyclohexenyl)ethylamine | Hydrogen | 12.5 | |
| 3-Phenyl-1-propylamine | 4-Fluorophenethylamine | Hydrogen | 12.5 | 12.94 |
| 2,2-Diphenylamine | tert-Amylamine | Hydrogen | 12.5 | 9.05 |
| 2,2-Diphenylamine | Undecylamine | Hydrogen | 12.5 | |
| 2,2-Diphenylamine | Dehydroabietylamine | Hydrogen | 12.5 | |
| 2,2-Diphenylamine | cis-(−)-Myrtanylamine | Methyl | 12.5 | 45.18 |
| 1-(3-Aminopropyl)-2-pyrrolidinone (tech) | 2,5-Dimethoxyphenethylamine | Hydrogen | 12.5 | |
| 1-(3-Aminopropyl)-2-pyrrolidinone (tech) | 2-(2-Aminomethyl)phenylthio)benzyl alcohol | Hydrogen | 12.5 | |
| 4-(Trifluoromethyl)benzylamine | 2,5-Dimethoxyphenethylamine | Hydrogen | 12.5 | |
| 4-(Trifluoromethyl)benzylamine | 1-(1-Naphthyl)ethylamine | Hydrogen | 12.5 | |
| Veratryl amine | 4-Phenylbutylamine | Hydrogen | 12.5 | |
| 5-Amino-1-pentanol | 2,5-Dimethoxyphenethylamine | Hydrogen | 12.5 | |
| 5-Amino-1-pentanol | 2-(2-Aminomethyl)phenylthio)benzyl alcohol | Hydrogen | 12.5 | |
| 2-(1-Cyclohexenyl)ethylamine | 2-(1-Cyclohexenyl)ethylamine | Hydrogen | 12.5 | |
| 2-(1-Cyclohexenyl)ethylamine | 4-Fluorophenethylamine | Hydrogen | 12.5 | |
| 2-(1-Cyclohexenyl)ethylamine | 4-Phenylbutylamine | Hydrogen | 12.5 | |
| 2-(1-Cyclohexenyl)ethylamine | 2,5-Dimethoxyphenethylamine | Hydrogen | 12.5 | |
| 2-(1-Cyclohexenyl)ethylamine | 2-(2-Aminomethyl)phenylthio)benzyl alcohol | Hydrogen | 12.5 | |
| 1-Aminomethyl-1-cyclohexanol, HCl | 2,5-Dimethoxyphenethylamine | Hydrogen | 12.5 | |
| 3-Fluorobenzylamine | 2,5-Dimethoxyphenethylamine | Hydrogen | 12.5 | |
| 4-Amino-1-butanol | Hexetidine (mixture of isomers) | Hydrogen | 12.5 | |
| 2-Ethoxybenzylamine | Hexetidine (mixture of isomers) | Hydrogen | 12.5 | |
| cis-(−)-Myrtanylamine | Cyclooctylamine | Hydrogen | 12.5 | 67.73 |
| cis-(−)-Myrtanylamine | 4-Methylcyclohexylamine | Hydrogen | 12.5 | 18.39 |
| cis-(−)-Myrtanylamine | 1-Adamantanamine | Hydrogen | 12.5 | 60.16 |
| cis-(−)-Myrtanylamine | 3,3-Diphenylpropylamine | Methyl | 12.5 | 22.32 |
| Cyclooctylamine | (+)-Isopinocampheylamine | Hydrogen | 12.5 | 57.83 |
| Cyclooctylamine | (+)-Bornylamine | Hydrogen | 12.5 | 100.00 |
| Cyclooctylamine | 1-Adamantanemethylamine | Hydrogen | 12.5 | 52.95 |

TABLE 2-continued

Synthetic Substituted Diethylene Diamines Sorted by Minimum Inhibition Concentration

| N1 | N2 | R4 | MIC (uM) | % Induction |
|---|---|---|---|---|
| Cyclooctylamine | 2,2-Diphenylamine | Hydrogen | 12.5 | 71.43 |
| Cyclooctylamine | cis-(−)-Myrtanylamine | Hydrogen | 12.5 | 84.56 |
| Cyclooctylamine | Cyclooctylamine | Hydrogen | 12.5 | 59.21 |
| Cyclooctylamine | Hexetidine (mixture of isomers) | Hydrogen | 12.5 | |
| Cyclooctylamine | Aminodiphenylmethane | Hydrogen | 12.5 | |
| Cyclooctylamine | Undecylamine | Hydrogen | 12.5 | 5.61 |
| Cyclooctylamine | 3,3-Diphenylpropylamine | Methyl | 12.5 | 53.92 |
| Cyclooctylamine | (+)-Isopinocampheylamine | Methyl | 12.5 | |
| Cyclooctylamine | cis-(−)-Myrtanylamine | Methyl | 12.5 | 33.89 |
| 4-Chlorophenylalaninol | Hexetidine (mixture of isomers) | Hydrogen | 12.5 | |
| (−)-Isopinocampheylamine | 3,3-Diphenylpropylamine | Hydrogen | 12.5 | 23.68 |
| (−)-Isopinocampheylamine | (+)-Bornylamine | Hydrogen | 12.5 | 44.85 |
| (−)-Isopinocampheylamine | 2-Amino-1-propanol, d,l | Hydrogen | 12.5 | 46.19 |
| (−)-Isopinocampheylamine | cis-(−)-Myrtanylamine | Hydrogen | 12.5 | 33.87 |
| (−)-Isopinocampheylamine | 2-Adamantanamine, HCl | Hydrogen | 12.5 | 24.29 |
| (−)-Isopinocampheylamine | Aminodiphenylmethane | Hydrogen | 12.5 | 48.35 |
| Allylamine | Hexetidine (mixture of isomers) | Hydrogen | 12.5 | |
| 3-Ethoxypropylamine | Hexetidine (mixture of isomers) | Hydrogen | 12.5 | |
| sec-Butylamine | Dehydroabietylamine | Hydrogen | 12.5 | |
| 2-Aminoheptane | Dehydroabietylamine | Hydrogen | 12.5 | |
| Ethanolamine | Hexetidine (mixture of isomers) | Hydrogen | 12.5 | |
| 3-Methylbenzylamine | 4-Phenylbutylamine | Hydrogen | 12.5 | |
| 3-Methylbenzylamine | 2,4-Dichlorophenethylamine | Hydrogen | 12.5 | |
| 3-Methylbenzylamine | Dehydroabietylamine | Hydrogen | 12.5 | |
| Piperonylamine | Hexetidine (mixture of isomers) | Hydrogen | 12.5 | |
| Piperonylamine | Dehydroabietylamine | Hydrogen | 12.5 | |
| 2-Methoxyethylamine | Dehydroabietylamine | Hydrogen | 12.5 | |
| 4-Fluorophenethylamine | Hexetidine (mixture of isomers) | Hydrogen | 12.5 | |
| 3-o-Methyldopamine, HCl | Hexetidine (mixture of isomers) | Hydrogen | 12.5 | |
| 3-o-Methyldopamine, HCl | Undecylamine | Hydrogen | 12.5 | |
| 3-o-Methyldopamine, HCl | Dehydroabietylamine | Hydrogen | 12.5 | |
| 3-Fluorophenethylamine | Hexetidine (mixture of isomers) | Hydrogen | 12.5 | |
| 3-Fluorophenethylamine | Dehydroabietylamine | Hydrogen | 12.5 | |
| 2-Methoxyphenethylamine | Hexetidine (mixture of isomers) | Hydrogen | 12.5 | |
| 2-Methoxyphenethylamine | Aminodiphenylmethane | Hydrogen | 12.5 | 34.67 |
| 2-Fluoroethylamine, HCl | Hexetidine (mixture of isomers) | Hydrogen | 12.5 | |
| 2-Amino-1-phenylethanol | Hexetidine (mixture of isomers) | Hydrogen | 12.5 | |
| 2-Amino-1-phenylethanol | Dehydroabietylamine | Hydrogen | 12.5 | |
| 2,5-Dimethoxyphenethylamine | 2-Adamantanamine, HCl | Hydrogen | 12.5 | 22.18 |
| 2-(2-Chlorophenyl)ethylamine | N-Allylcyclopentylamine | Hydrogen | 12.5 | 62.31 |
| 2-(2-Chlorophenyl)ethylamine | Hexetidine (mixture of isomers) | Hydrogen | 12.5 | |
| 3-Hydroxytyramine | Hexetidine (mixture of isomers) | Hydrogen | 12.5 | |
| 4-(Trifluoromethoxy)benzylamine | 2-Adamantanamine, HCl | Hydrogen | 12.5 | 28.34 |
| Geranylamine | (+)-Bornylamine | Hydrogen | 12.5 | |
| Geranylamine | 1,3,3-Trimethyl-6-azabicyclo[3.2.1]octane | Hydrogen | 12.5 | 37.42 |
| Geranylamine | 2-Ethylpiperidine | Hydrogen | 12.5 | 29.81 |
| Geranylamine | 1-Adamantanamine | Hydrogen | 12.5 | 16.63 |
| Geranylamine | N-Allylcyclopentylamine | Hydrogen | 12.5 | 74.86 |
| Geranylamine | Aminodiphenylmethane | Hydrogen | 12.5 | 57.93 |
| Geranylamine | Dehydroabietylamine | Hydrogen | 12.5 | |
| 1-Adamantanemethylamine | Decahydroquinoline | Hydrogen | 18.8 | 0 |
| 1-Adamantanemethylamine | 1-Adamantanamine | Hydrogen | 18.8 | 0 |
| 2,2-Diphenylamine | 2,3-Dimethylcyclohexylamine | Hydrogen | 18.8 | 23.60 |
| 2,2-Diphenylamine | tert-Octylamine | Hydrogen | 18.8 | 19.29 |
| 2,2-Diphenylamine | Decahydroquinoline | Hydrogen | 18.8 | 8.96 |
| 4-Methylbenzylamine | Furfurylamine | Hydrogen | 25 | 13.46 |
| 4-Methylbenzylamine | Benzylamine | Hydrogen | 25 | 17.07 |
| 4-Methylbenzylamine | Hexetidine (mixture of isomers) | Hydrogen | 25 | 0 |
| 4-Methylbenzylamine | Dehydroabietylamine | Hydrogen | 25 | 0 |
| Cyclopentylamine | Hexetidine (mixture of isomers) | Hydrogen | 25 | 0 |
| Cyclopentylamine | Dehydroabietylamine | Hydrogen | 25 | 0 |
| Furfurylamine | Furfurylamine | Hydrogen | 25 | 0 |
| 1-Methyl-3-phenylpropylamine | Hexetidine (mixture of isomers) | Hydrogen | 25 | 0 |
| 1-Methyl-3-phenylpropylamine | Undecylamine | Hydrogen | 25 | 0 |
| 1,2,3,4-Tetrahydro-1-naphthylamine | Undecylamine | Hydrogen | 25 | 6.24 |
| 1,2,3,4-Tetrahydro-1-naphthylamine | Dehydroabietylamine | Hydrogen | 25 | 0 |
| 2,3-Dimethylcyclohexylamine | Undecylamine | Hydrogen | 25 | 0 |
| 2,3-Dimethylcyclohexylamine | Dehydroabietylamine | Hydrogen | 25 | 0 |
| Tyramine | Hexetidine (mixture of isomers) | Hydrogen | 25 | 0 |
| Tyramine | Undecylamine | Hydrogen | 25 | 0 |

TABLE 2-continued

Synthetic Substituted Diethylene Diamines Sorted by Minimum Inhibition Concentration

| N1 | N2 | R4 | MIC (uM) | % Induction |
|---|---|---|---|---|
| Tyramine | Dehydroabietylamine | Hydrogen | 25 | 0 |
| Tyramine | cis-(−)-Myrtanylamine | Methyl | 25 | 0 |
| 2-Fluorobenzylamine | Undecylamine | Hydrogen | 25 | 0 |
| (R)-2-Amino-1-butanol | Hexetidine (mixture of isomers) | Hydrogen | 25 | 0 |
| 3,3-Diphenylpropylamine | (S)-(+)-1-Amino-2-propanol | Hydrogen | 25 | 0 |
| 3,3-Diphenylpropylamine | 2-Ethylpiperidine | Hydrogen | 25 | 11.32 |
| 3,3-Diphenylpropylamine | N-Allylcyclopentylamine | Hydrogen | 25 | 11.63 |
| 3,3-Diphenylpropylanime | Aminodiphenylmethane | Hydrogen | 25 | 0 |
| 3,3-Diphenylpropylamine | 3,5-Dimethylpiperidine (cis- and trans-) | Hydrogen | 25 | 30.28 |
| 3,3-Diphenylpropylamine | Allylcyclohexylamine | Hydrogen | 25 | 9.10 |
| Propylamine | Undecylamine | Hydrogen | 25 | 0 |
| Phenethylamine | Undecylamine | Hydrogen | 25 | 0 |
| Tryptamine | (S)-(+)-1-Amino-2-propanol | Hydrogen | 25 | 0 |
| Tryptamine | 2-Amino-2-methyl-1-propanol | Hydrogen | 25 | 0 |
| Cyclohexylamine | Undecylamine | Hydrogen | 25 | 0 |
| Cyclohexylamine | Dehydroabietylamine | Hydrogen | 25 | 0 |
| (+)-Isopinocampheylamine | Dehydroabietylamine | Hydrogen | 25 | 0 |
| Benzylamine | Hexetidine (mixture of isomers) | Hydrogen | 25 | |
| Benzylamine | Undecylamine | Hydrogen | 25 | |
| 3-Amino-1-propanol | Dehydroabietylamine | Hydrogen | 25 | 0 |
| 2-Fluorophenethylamine | 2-Fluorophenethylamine | Hydrogen | 25 | 0 |
| 2-Fluorophenethylamine | Veratryl amine | Hydrogen | 25 | 0 |
| 2-Fluorophenethylamine | 2,4-Dimethoxybenzylamine | Hydrogen | 25 | 0 |
| 2-Fluorophenethylamine | 2-Amino-2-methyl-1-propanol | Hydrogen | 25 | 0 |
| 2-Fluorophenethylamine | 4-Fluorophenethylamine | Hydrogen | 25 | 0 |
| 2-Fluorophenethylamine | Hexetidine (mixture of isomers) | Hydrogen | 25 | 0 |
| 2-Fluorophenethylamine | 1-(1-Naphthyl)ethylamine | Hydrogen | 25 | 0 |
| 2-Fluorophenethylamine | 1-Adamantanemethylamine | Methyl | 25 | 3.21 |
| 2-Fluorophenethylamine | cis-(−)-Myrtanylamine | Methyl | 25 | 4.89 |
| b-Methylphenethylamine | 4-Phenylbutylamine | Hydrogen | 25 | 0 |
| b-Methylphenethylamine | 2,4-Dichlorophenethylamine | Hydrogen | 25 | 0 |
| b-Methylphenethylamine | 1-(1-Naphthyl)ethylamine | Hydrogen | 25 | 0 |
| 4-Methoxyphenethylamine | 1-Adamantanemethylamine | Hydrogen | 25 | 0 |
| 4-Methoxyphenethylamine | 1-(3-Aminopropyl)-2-pyrrolidinone (tech) | Hydrogen | 25 | 0 |
| 4-Methoxyphenethylamine | Veratryl amine | Hydrogen | 25 | 0 |
| 4-Methoxyphenethylamine | Undecylamine | Hydrogen | 25 | 0 |
| 4-Methoxyphenethylamine | Dehydroabietylamine | Hydrogen | 25 | 0 |
| Tetrahydrofurfurylamine | Dehydroabietylamine | Hydrogen | 25 | 0 |
| Amylamine | 2-Fluorophenethylamine | Hydrogen | 25 | 0 |
| Amylamine | 2-(1-Cyclohexenyl)ethylamine | Hydrogen | 25 | 0 |
| Amylamine | 2,4-Dimethoxybenzylamine | Hydrogen | 25 | 0 |
| 3-Phenyl-1-propylamine | 2-Fluorophenethylamine | Hydrogen | 25 | |
| 3-Phenyl-1-propylamine | 1-Adamantanemethylamine | Hydrogen | 25 | |
| 3-Phenyl-1-propylamine | 2,4-Dimethoxybenzylamine | Hydrogen | 25 | |
| 3-Phenyl-1-propylamine | Hexetidine (mixture of isomers) | Hydrogen | 25 | |
| 3-Phenyl-1-propylamine | 4-Phenylbutylamine | Hydrogen | 25 | |
| 3-Phenyl-1-propylamine | 2,4-Dichlorophenethylamine | Hydrogen | 25 | |
| 3-Phenyl-1-propylamine | Undecylamine | Hydrogen | 25 | |
| 3-Phenyl-1-propylamine | Dehydroabietylamine | Hydrogen | 25 | |
| 2,2-Diphenylamine | 4-(2-Aminoethyl)morpholine | Hydrogen | 25 | |
| 2,2-Diphenylamine | 1-(3-Aminopropyl)-2-pyrrolidinone (tech) | Hydrogen | 25 | |
| 2,2-Diphenylamine | 2-(1-Cyclohexenyl)ethylamine | Hydrogen | 25 | |
| 2,2-Diphenylamine | 2,4-Dimethoxybenzylamine | Hydrogen | 25 | |
| 2,2-Diphenylamine | 4-(3-Aminopropyl)morpholine | Hydrogen | 25 | |
| 2,2-Diphenylamine | 4-Fluorophenethylamine | Hydrogen | 25 | |
| 2,2-Diphenylamine | Hexetidine (mixture of isomers) | Hydrogen | 25 | |
| 2,2-Diphenylamine | (S)-(−)-Cyclohexylethylamine | Hydrogen | 25 | |
| 2,2-Diphenylamine | 1-Adamantanemethylamine | Methyl | 25 | 5.84 |
| 1-(3-Aminopropyl)-2-pyrrolidinone (tech) | 4-Phenylbutylamine | Hydrogen | 25 | |
| 4-(Trifluoromethyl)benzylamine | 1-Adamantanemethylamine | Hydrogen | 25 | |
| 4-(Trifluoromethyl)benzylamine | tert-Amylamine | Hydrogen | 25 | |
| 4-(Trifluoromethyl)benzylamine | alpha-Methyltryptamine | Hydrogen | 25 | 6.06 |
| 4-(Trifluoromethyl)benzylamine | 4-Phenylbutylamine | Hydrogen | 25 | |
| 4-(Trifluoromethyl)benzylamine | 2-(2-Aminomethyl) phenylthio)benzyl alcohol | Hydrogen | 25 | 5.13 |
| 4-(Trifluoromethyl)benzylamine | Undecylamine | Hydrogen | 25 | |
| 4-(Trifluoromethyl)benzylamine | (−)-3,4-Dihydroxynorephedrine | Hydrogen | 25 | |
| 4-(Trifluoromethyl)benzylamine | Dehydroabietylamine | Hydrogen | 25 | |
| Veratryl amine | tert-Amylamine | Hydrogen | 25 | |
| 5-Amino-1-pentanol | 4-Phenylbutylamine | Hydrogen | 25 | |

TABLE 2-continued

Synthetic Substituted Diethylene Diamines Sorted by Minimum Inhibition Concentration

| N1 | N2 | R4 | MIC (uM) | % Induction |
|---|---|---|---|---|
| 2-(1-Cyclohexenyl)ethylamine | 2-Fluorophenethylamine | Hydrogen | 25 | |
| 2-(1-Cyclohexenyl)ethylamine | 1-Adamantanemethylamine | Hydrogen | 25 | |
| 1-Aminomethyl-1-cyclohexanol, HCl | 4-Phenylbutylamine | Hydrogen | 25 | |
| 3-Fluorobenzylamine | 4-Phenylbutylamine | Hydrogen | 25 | |
| 3-Fluorobenzylamine | 2-(2-Aminomethyl)phenylthio)benzyl alcohol | Hydrogen | 25 | |
| 2,4-Dimethoxybenzylamine | 1-Adamantanamine | Hydrogen | 25 | |
| 2,4-Dimethoxybenzylamine | Hexetidine (mixture of isomers) | Hydrogen | 25 | |
| 2,4-Dimethoxybenzylamine | Undecylamine | Hydrogen | 25 | |
| 2,4-Dimethoxybenzylamine | Dehydroabietylamine | Hydrogen | 25 | |
| 2-Ethoxybenzylamine | 1-Adamantanamine | Hydrogen | 25 | |
| 2-Ethoxybenzylamine | N-Phenylethyldiamine | Hydrogen | 25 | |
| 2-Ethoxybenzylamine | 2,4-Dichlorophenethylamine | Hydrogen | 25 | |
| 2-Ethoxybenzylamine | 2-(2-Chlorophenyl)ethylamine | Hydrogen | 25 | 3.89 |
| 2-Ethoxybenzylamine | Undecylamine | Hydrogen | 25 | |
| 2-Ethoxybenzylamine | Dehydroabietylamine | Hydrogen | 25 | |
| cis-(−)-Myrtanylamine | 2-(1-Cyclohexenyl)ethylamine | Hydrogen | 25 | |
| cis-(−)-Myrtanylamine | Hexetidine (mixture of isomers) | Hydrogen | 25 | |
| cis-(−)-Myrtanylamine | Aminodiphenylmethane | Hydrogen | 25 | |
| cis-(−)-Myrtanylamine | 2,4-Dichlorophenethylamine | Hydrogen | 25 | |
| cis-(−)-Myrtanylamine | (S)-(−)-Cyclohexylethylamine | Hydrogen | 25 | 28.94 |
| cis-(−)-Myrtanylamine | Undecylamine | Hydrogen | 25 | |
| cis-(−)-Myrtanylamine | (+)-Isopinocampheylamine | Methyl | 25 | |
| cis-(−)-Myrtanylamine | Cyclooctylamine | Methyl | 25 | 24.92 |
| Cyclooctylamine | 2,3-Dimethylcyclohexylamine | Hydrogen | 25 | 50.55 |
| Cyclooctylamine | (S)-2-Amino-1-butanol | Hydrogen | 25 | 100.00 |
| Cyclooctylamine | 2-Adamantanamine, HCl | Hydrogen | 25 | 29.61 |
| Cyclooctylamine | 4-Phenylbutylamine | Hydrogen | 25 | |
| Cyclooctylamine | 2-Chlorobenzylamine | Hydrogen | 25 | |
| Cyclooctylamine | 2-Aminoindan, HCl | Hydrogen | 25 | |
| Cyclooctylamine | Dehydroabietylamine | Hydrogen | 25 | |
| Cyclooctylamine | 1-(1-Naphthyl)ethylamine | Hydrogen | 25 | 4.62 |
| Cyclooctylamine | 1-Adamantanemethylamine | Methyl | 25 | 14.20 |
| 2,3-Dimethoxybenzylamine | Hexetidine (mixture of isomers) | Hydrogen | 25 | |
| 2,3-Dimethoxybenzylamine | Undecylamine | Hydrogen | 25 | |
| 2,3-Dimethoxybenzylamine | Dehydroabietylamine | Hydrogen | 25 | |
| 4-Methylcyclohexylamine | Hexetidine (mixture of isomers) | Hydrogen | 25 | |
| 4-Methylcyclohexylamine | Undecylamine | Hydrogen | 25 | |
| 4-Methylcyclohexylamine | Dehydroabietylamine | Hydrogen | 25 | |
| 4-Fluorobenzylamine | Dibenzylamine | Hydrogen | 25 | 27.98 |
| trans-2-Phenylcyclopropylamine, HCl | Cyclooctylamine | Hydrogen | 25 | 32.80 |
| trans-2-Phenylcyclopropylamine, HCl | 2-Adamantanamine, HCl | Hydrogen | 25 | 18.99 |
| trans-2-Phenylcyclopropylamine, HCl | 1-Adamantanamine | Hydrogen | 25 | 18.84 |
| Thiomicamine | Hexetidine (mixture of isomers) | Hydrogen | 25 | |
| (R)-1-Amino-2-propanol | Hexetidine (mixture of isomers) | Hydrogen | 25 | |
| 4-Chlorophenylalaninol | 2,4-Dichlorophenethylamine | Hydrogen | 25 | |
| 4-Chlorophenylalaninol | Undecylamine | Hydrogen | 25 | |
| 4-Chlorophenylalaninol | Dehydroabietylamine | Hydrogen | 25 | |
| l-Leucinol | Hexetidine (mixture of isomers) | Hydrogen | 25 | |
| l-Leucinol | 2,4-Dichlorophenethylamine | Hydrogen | 25 | |
| l-Leucinol | Dehydroabietylamine | Hydrogen | 25 | |
| (−)-Isopinocampheylamine | 2-Methoxyphenethylamine | Hydrogen | 25 | 29.59 |
| (−)-Isopinocampheylamine | Undecylamine | Hydrogen | 25 | |
| Allylamine | Dehydroabietylamine | Hydrogen | 25 | |
| 3-Amino-1,2-propanediol | Hexetidine (mixture of isomers) | Hydrogen | 25 | |
| 3-Ethoxypropylamine | 3,3-Diphenylpropylamine | Hydrogen | 25 | |
| 3-Ethoxypropylamine | Undecylamine | Hydrogen | 25 | |
| 3-Ethoxypropylamine | Dehydroabietylamine | Hydrogen | 25 | |
| sec-Butylamine | 2,4-Dichlorophenethylamine | Hydrogen | 25 | |
| sec-Butylamine | Undecylamine | Hydrogen | 25 | |
| 2-Aminoheptane | Hexetidine (mixture of isomers) | Hydrogen | 25 | |
| 2-Aminoheptane | 4-Phenylbutylamine | Hydrogen | 25 | |
| 2-Aminoheptane | 2,4-Dichlorophenethylamine | Hydrogen | 25 | |
| 1-Naphthalenemethylamine | Hexetidine (mixture of isomers) | Hydrogen | 25 | |
| 1-Naphthalenemethylamine | 4-Phenylbutylamine | Hydrogen | 25 | |
| 1-Naphthalenemethylamine | 2,4-Dichlorophenethylamine | Hydrogen | 25 | |
| 1-Naphthalenemethylamine | Undecylamine | Hydrogen | 25 | |
| Ethanolamine | Dehydroabietylamine | Hydrogen | 25 | |
| Piperonylamine | 4-Phenylbutylamine | Hydrogen | 25 | |

TABLE 2-continued

Synthetic Substituted Diethylene Diamines Sorted by Minimum Inhibition Concentration

| N1 | N2 | R4 | MIC (uM) | % Induction |
|---|---|---|---|---|
| 1-Ethylpropylamine | Hexetidine (mixture of isomers) | Hydrogen | 25 | |
| 1-Ethylpropylamine | Dehydroabietylamine | Hydrogen | 25 | |
| Isopropylamine | Hexetidine (mixture of isomers) | Hydrogen | 25 | |
| 4-Fluorophenethylamine | 4-Phenylbutylamine | Hydrogen | 25 | |
| 4-Fluorophenethylamine | 2,4-Dichlorophenethylamine | Hydrogen | 25 | |
| 4-Fluorophenethylamine | Dehydroabietylamine | Hydrogen | 25 | |
| 3-Fluorophenethylamine | Undecylamine | Hydrogen | 25 | |
| 2-Thiopheneethylamine | 2-Adamantanamine, HCl | Hydrogen | 25 | 19.09 |
| 2-Methylcyclohexylamine (mix of cis and trans) | Hexetidine (mixture of isomers) | Hydrogen | 25 | |
| 2-Methylcyclohexylamine (mix of cis and trans) | Dehydroabietylamine | Hydrogen | 25 | |
| 2-Methoxyphenethylamine | 2-Adamantanamine, HCl | Hydrogen | 25 | 26.77 |
| 2-Methoxyphenethylamine | (−)-Isopinocampheylamine | Hydrogen | 25 | 31.95 |
| 2-Methoxyphenethylamine | 1-Adamantanamine | Hydrogen | 25 | 24.38 |
| 2-Methoxyphenethylamine | N-Allylcyclopentylamine | Hydrogen | 25 | 14.56 |
| 2-Methoxyphenethylamine | 4-Phenylbutylamine | Hydrogen | 25 | |
| 2-Methoxyphenethylamine | Undecylamine | Hydrogen | 25 | |
| 2-Methoxyphenethylamine | Dehydroabietylamine | Hydrogen | 25 | |
| 2-Fluoroethylamine, HCl | Undecylamine | Hydrogen | 25 | |
| 2-Fluoroethylamine, HCl | Dehydroabietylamine | Hydrogen | 25 | |
| 2-Aminoindan, HCl | 2-Adamantanamine, HCl | Hydrogen | 25 | 17.72 |
| 2-Amino-1-phenylethanol | Undecylamine | Hydrogen | 25 | |
| 2,5-Dimethoxyphenethylamine | (+)-Bornylamine | Hydrogen | 25 | 25.78 |
| 2,5-Dimethoxyphenethylamine | Noradamantamine, HCl | Hydrogen | 25 | 11.73 |
| 2,5-Dimethoxyphenethylamine | 1-Adamantanamine | Hydrogen | 25 | 12.57 |
| 2-(2-Chlorophenyl)ethylamine | 4-Phenylbutylamine | Hydrogen | 25 | |
| 2-(2-Chlorophenyl)ethylamine | Undecylamine | Hydrogen | 25 | |
| 2-(2-Chlorophenyl)ethylamine | 1-(1-Naphthyl)ethylamine | Hydrogen | 25 | |
| 2-(2-Aminomethyl)phenylthio)benzyl alcohol | Hexetidine (mixture of isomers) | Hydrogen | 25 | |
| 2-(2-Aminomethyl)phenylthio)benzyl alcohol | 4-Phenylbutylamine | Hydrogen | 25 | |
| 2-(2-Aminomethyl)phenylthio)benzyl alcohol | Undecylamine | Hydrogen | 25 | |
| 1-Aminoindan | Hexetidine (mixture of isomers) | Hydrogen | 25 | |
| 1-Aminoindan | Undecylamine | Hydrogen | 25 | |
| 1-Aminoindan | Dehydroabietylamine | Hydrogen | 25 | |
| 1,3-Dimethylbutylamine | Hexetidine (mixture of isomers) | Hydrogen | 25 | |
| 1,3-Dimethylbutylamine | Undecylamine | Hydrogen | 25 | 5.92 |
| 1,3-Dimethylbutylamine | Dehydroabietylamine | Hydrogen | 25 | |
| (S)-(−)-Cyclohexylethylamine | (−)-Isopinocampheylamine | Hydrogen | 25 | 19.31 |
| (S)-(−)-Cyclohexylethylamine | Hexetidine (mixture of isomers) | Hydrogen | 25 | |
| (S)-(−)-Cyclohexylethylamine | Undecylamine | Hydrogen | 25 | 10.88 |
| (S)-(−)-Cyclohexylethylamine | Dehydroabietylamine | Hydrogen | 25 | |
| (S)-(−)-2-Amino-3-phenyl-1-propanol | Hexetidine (mixture of isomers) | Hydrogen | 25 | |
| (S)-(−)-2-Amino-3-phenyl-1-propanol | Undecylamine | Hydrogen | 25 | |
| (S)-(−)-2-Amino-3-phenyl-1-propanol | Dehydroabietylamine | Hydrogen | 25 | |
| (1S,2S)-(+)-2-Amino-3-methoxy-1-phenyl-1-propanol | Hexetidine (mixture of isomers) | Hydrogen | 25 | |
| Octadecylamine | (+)-Bornylamine | Hydrogen | 25 | |
| Octadecylamine | 1-Adamantanamine | Hydrogen | 25 | |
| Geranylamine | 2,3-Dimethylcyclohexylamine | Hydrogen | 25 | 14.53 |
| Geranylamine | tert-Octylamine | Hydrogen | 25 | 15.22 |
| Geranylamine | 1-Adamantanemethylamine | Hydrogen | 25 | 4.37 |
| Geranylamine | Decahydroquinoline | Hydrogen | 25 | 31.79 |
| Geranylamine | Dibenzylamine | Hydrogen | 25 | 6.48 |
| Geranylamine | N-Butylbenzylamine | Hydrogen | 25 | 16.44 |
| Geranylamine | Cyclooctylamine | Hydrogen | 25 | 12.37 |
| Geranylamine | (−)-Isopinocampheylamine | Hydrogen | 25 | 8.95 |
| Geranylamine | 1-(1-Adamantyl)ethylamine, HCl | Hydrogen | 25 | 32.95 |
| Geranylamine | Undecylamine | Hydrogen | 25 | |
| Geranylamine | 1-(1-Naphthyl)ethylamine | Hydrogen | 25 | |
| Amylamine | 1-Adamantanamine | Hydrogen | 37.5 | 0 |
| 3-Phenyl-1-propylamine | 3,3-Diphenylpropylamine | Hydrogen | 37.5 | |
| 3-Phenyl-1-propylamine | 2,2-Diphenylamine | Hydrogen | 37.5 | |
| 3-Phenyl-1-propylamine | 1-Adamantanamine | Hydrogen | 37.5 | 18.65 |

TABLE 2-continued

Synthetic Substituted Diethylene Diamines Sorted by Minimum Inhibition Concentration

| N1 | N2 | R4 | MIC (uM) | % Induction |
|---|---|---|---|---|
| 2,2-Diphenylamine | 3,3-Diphenylpropylamine | Hydrogen | 37.5 | |
| 2,2-Diphenylamine | 2,2-Diphenylamine | Hydrogen | 37.5 | 5.56 |
| 2,2-Diphenylamine | 1,3,3-Trimethyl-6-azabicyclo[3.2.1]octane | Hydrogen | 37.5 | 8.67 |
| 2,2-Diphenylamine | 1-Adamantanamine | Hydrogen | 37.5 | 58.10 |
| 4-(Trifluoromethyl)benzylamine | tert-Octylamine | Hydrogen | 37.5 | 7.47 |
| 4-(Trifluoromethyl)benzylamine | 138 | Hydrogen | 37.5 | |
| 4-Methylbenzylamine | 2-Fluorobenzylamine | Hydrogen | 50 | 22.10 |
| 4-Methylbenzylamine | 4-Fluorobenzylamine | Hydrogen | 50 | 14.62 |
| 4-Methylbenzylamine | alpha-Methyltryptamine | Hydrogen | 50 | 0 |
| 4-Methylbenzylamine | Undecylamine | Hydrogen | 50 | 0 |
| Cyclopentylamine | Undecylamine | Hydrogen | 50 | 0 |
| Furfurylamine | 2-Fluorobenzylamine | Hydrogen | 50 | 0 |
| Furfurylamine | Benzylamine | Hydrogen | 50 | 0 |
| Furfurylamine | 4-Fluorobenzylamine | Hydrogen | 50 | 0 |
| Furfurylamine | alpha-Methyltryptamine | Hydrogen | 50 | 0 |
| Furfurylamine | Undecylamine | Hydrogen | 50 | 0 |
| Furfurylamine | Dehydroabietylamine | Hydrogen | 50 | 0 |
| Furfurylamine | Furfurylamine | Hydrogen | 50 | 0 |
| 3,4,5-Trimethoxybenzylamine | 2-Fluorobenzylamine | Hydrogen | 50 | 0 |
| 3,4,5-Trimethoxybenzylamine | Benzylamine | Hydrogen | 50 | 0 |
| 3,4,5-Trimethoxybenzylamine | alpha-Methyltryptamine | Hydrogen | 50 | 0 |
| 3,4,5-Trimethoxybenzylamine | Undecylamine | Hydrogen | 50 | 0 |
| 3,4,5-Trimethoxybenzylamine | Dehydroabietylamine | Hydrogen | 50 | 0 |
| 1-Methyl-3-phenylpropylamine | alpha-Methyltryptamine | Hydrogen | 50 | 0 |
| 1-Methyl-3-phenylpropylamine | Octadecylamine | Hydrogen | 50 | 0 |
| Cyclobutylamine | Octadecylamine | Hydrogen | 50 | 0 |
| Cyclobutylamine | Undecylamine | Hydrogen | 50 | 0 |
| Cyclobutylamine | Dehydroabietylamine | Hydrogen | 50 | 0 |
| 1,2,3,4-Tetrahydro-1-naphthylamine | Hexetidine (mixture of isomers) | Hydrogen | 50 | 0 |
| 1,2,3,4-Tetrahydro-1-naphthylamine | Aminodiphenylmethane | Hydrogen | 50 | 4.31 |
| 1,2,3,4-Tetrahydro-1-naphthylamine | alpha-Methyltryptamine | Hydrogen | 50 | 0 |
| 1,2,3,4-Tetrahydro-1-naphthylamine | 2-Methoxyphenethylamine | Hydrogen | 50 | 0 |
| 2,3-Dimethylcyclohexylamine | Hexetidine (mixture of isomers) | Hydrogen | 50 | 0 |
| 2,3-Dimethylcyclohexylamine | Aminodiphenylmethane | Hydrogen | 50 | 3.64 |
| 2,3-Dimethylcyclohexylamine | alpha-Methyltryptamine | Hydrogen | 50 | 0 |
| Tyramine | Furfurylamine | Hydrogen | 50 | 0 |
| Tyramine | 2-Fluorobenzylamine | Hydrogen | 50 | 4.07 |
| Tyramine | Benzylamine | Hydrogen | 50 | 0 |
| Tyramine | 2,4-Dichlorophenethylamine | Hydrogen | 50 | 0 |
| 2-Fluorobenzylamine | Aminodiphenylmethane | Hydrogen | 50 | 0 |
| 2-Fluorobenzylamine | 4-Phenylbutylamine | Hydrogen | 50 | 0 |
| 2-Fluorobenzylamine | 2-Methoxyphenethylamine | Hydrogen | 50 | 0 |
| 2-Fluorobenzylamine | 2,4-Dichlorophenethylamine | Hydrogen | 50 | 0 |
| 2-Fluorobenzylamine | 1,3-Dimethylbutylamine | Hydrogen | 50 | 0 |
| 2-Fluorobenzylamine | 1-(1-Adamantyl)ethylamine, HCl | Hydrogen | 50 | 0 |
| (R)-2-Amino-1-butanol | Dehydroabietylamine | Hydrogen | 50 | 0 |
| 3,4-Dimethoxyphenethylamine | Aminodiphenylmethane | Hydrogen | 50 | 0 |
| 3,4-Dimethoxyphenethylamine | 4-Phenylbutylamine | Hydrogen | 50 | 0 |
| 3,4-Dimethoxyphenethylamine | 2-Methoxyphenethylamine | Hydrogen | 50 | 0 |
| 3,4-Dimethoxyphenethylamine | 2,4-Dichlorophenethylamine | Hydrogen | 50 | 0 |
| 3,4-Dimethoxyphenethylamine | 1,3-Dimethylbutylamine | Hydrogen | 50 | 0 |
| 3,3-Diphenylpropylamine | Piperidine | Hydrogen | 50 | 0 |
| 3,3-Diphenylpropylamine | 2,3-Dimethylcyclohexylamine | Methyl | 50 | 7.81 |
| 3,3-Diphenylpropylamine | (−)-Isopinocamphenylamine | Methyl | 50 | 13.06 |
| Propylamine | (S)-(+)-1-Amino-2-propanol | Hydrogen | 50 | 0 |
| Phenethylamine | (S)-(+)-1-Amino-2-propanol | Hydrogen | 50 | 0 |
| Phenethylamine | 4-Phenylbutylamine | Hydrogen | 50 | 0 |
| Phenethylamine | 2,4-Dichlorophenethylamine | Hydrogen | 50 | 0 |
| Phenethylamine | 1,3-Dimethylbutylamine | Hydrogen | 50 | 0 |
| Phenethylamine | 1-(1-Adamantyl)ethylamine HCl | Hydrogen | 50 | 0 |
| Phenethylamine | 1-(1-Naphthyl)ethylamine | Hydrogen | 50 | 0 |
| 4-(2-Aminoethyl)morpholine | 2-Amino-2-methyl-1-propanol | Hydrogen | 50 | 0 |
| Cyclohexylamine | 2,4-Dichlorophenethylamine | Hydrogen | 50 | 0 |
| exo-Aminonorbornane | Benzylamine | Hydrogen | 50 | 0 |
| (+)-Isopinocampheylamine | Hexetidine (mixture of isomers) | Hydrogen | 50 | 0 |
| (+)-Isopinocampheylamine | Aminodiphenylmethane | Hydrogen | 50 | 5.07 |
| (+)-Isopinocampheylamine | 4-Phenylbutylamine | Hydrogen | 50 | 0 |

TABLE 2-continued

Synthetic Substituted Diethylene Diamines Sorted by Minimum Inhibition Concentration

| N1 | N2 | R4 | MIC (uM) | % Induction |
|---|---|---|---|---|
| (+)-Isopinocampheylamine | 2,4-Dichlorophenethylamine | Hydrogen | 50 | 0 |
| (+)-Isopinocampheylamine | Undecylamine | Hydrogen | 50 | 0 |
| Benzylamine | 3,3-Diphenylpropylamine | Hydrogen | 50 | |
| Benzylamine | 2-Amino-2-methyl-1-propanol | Hydrogen | 50 | |
| Benzylamine | 1-(1-Naphthyl)ethylamine | Hydrogen | 50 | |
| Benzylamine | 2,4-Dichlorophenethylamine | Hydrogen | 50 | |
| 3-Amino-1-propanol | Undecylamine | Hydrogen | 50 | 0 |
| 2-Fluorophenethylamine | 3,3-Diphenylpropylamine | Hydrogen | 50 | 0 |
| 2-Fluorophenethylamine | 1-Adamantanemethylamine | Hydrogen | 50 | 0 |
| 2-Fluorophenethylamine | 1-(3-Aminopropyl)-2-pyrrolidinone (tech) | Hydrogen | 50 | 0 |
| 2-Fluorophenethylamine | Decahydroquinoline | Hydrogen | 50 | 0 |
| 2-Fluorophenethylamine | 1-Adamantanamine | Hydrogen | 50 | 24.34 |
| 2-Fluorophenethylamine | 2,4-Dichlorophenethylamine | Hydrogen | 50 | 0 |
| 2-Fluorophenethylamine | Undecylamine | Hydrogen | 50 | 0 |
| 2-Fluorophenethylamine | Dehydroabietylamine | Hydrogen | 50 | 0 |
| 2-Fluorophenethylamine | 2-(1-Cyclohexenyl)ethylamine | Methyl | 50 | 0 |
| 2-Fluorophenethylamine | Cyclooctylamine | Methyl | 50 | 5.81 |
| b-Methylphenethylamine | 3,3-Diphenylpropylamine | Hydrogen | 50 | 0 |
| b-Methylphenethylamine | tert-Octylamine | Hydrogen | 50 | 0 |
| b-Methylphenethylamine | 2-(1-Cyclohexenyl)ethylamine | Hydrogen | 50 | 0 |
| b-Methylphenethylamine | 2-Amino-2-methyl-1-propanol | Hydrogen | 50 | 0 |
| b-Methylphenethylamine | 4-Fluorophenethylamine | Hydrogen | 50 | 0 |
| b-Methylphenethylamine | Geranylamine | Hydrogen | 50 | 0 |
| b-Methylphenethylamine | 5-Methoxytryptamine | Hydrogen | 50 | 0 |
| 4-Methoxyphenethylamine | 3,3-Diphenylpropylamine | Hydrogen | 50 | 0 |
| 4-Methoxyphenethylamine | 2-Amino-2-methyl-1-propanol | Hydrogen | 50 | 0 |
| 4-Methoxyphenethylamine | 2,4-Dichlorophenethylamine | Hydrogen | 50 | 0 |
| 4-Methoxyphenethylamine | 1-(1-Naphthyl)ethylamine | Hydrogen | 50 | 0 |
| L-Methioninol | Hexetidine (mixture of isomers) | Hydrogen | 50 | 0 |
| Tetrahydrofurfurylamine | 1-Adamantanemethylamine | Hydrogen | 50 | 0 |
| Tetrahydrofurfurylamine | 2-(1-Cyclohexenyl)ethylamine | Hydrogen | 50 | 0 |
| Tetrahydrofurfurylamine | 4-Fluorophenethylamine | Hydrogen | 50 | 0 |
| Tetrahydrofurfurylamine | Undecylamine | Hydrogen | 50 | 0 |
| Amylamine | 1-Adamantanemethylamine | Hydrogen | 50 | 0 |
| Amylamine | Hexetidine (mixture of isomers) | Hydrogen | 50 | 0 |
| Amylamine | Undecylamine | Hydrogen | 50 | 0 |
| Amylamine | Dehydroabietylamine | Hydrogen | 50 | 0 |
| 1-Adamantanemethylamine | cis-(−)-Myrtanylamine | Methyl | 50 | 0 |
| 3-Phenyl-1-propylamine | 4-(2-Aminoethyl)morpholine | Hydrogen | 50 | |
| 3-Phenyl-1-propylamine | 1-(3-Aminopropyl)-2-pyrrolidinone (tech) | Hydrogen | 50 | |
| 3-Phenyl-1-propylamine | Veratryl amine | Hydrogen | 50 | |
| 3-Phenyl-1-propylamine | Aminodiphenylmethane | Hydrogen | 50 | |
| 3-Phenyl-1-propylamine | 2-(2-Aminomethyl)phenylthio)benzyl alcohol | Hydrogen | 50 | |
| 2,2-Diphenylamine | 2-Fluorophenethylamine | Hydrogen | 50 | |
| 2,2-Diphenylamine | 3,3-Diphenylpropylamine | Methyl | 50 | |
| 2,2-Diphenylamine | (+)-Isopinocampheylamine | Methyl | 50 | |
| 2,2-Diphenylamine | (+)-Bornylamine | Methyl | 50 | |
| 2,2-Diphenylamine | Cyclooctylamine | Methyl | 50 | |
| 2,2-Diphenylamine | (−)-Isopinocampheylamine | Methyl | 50 | 3.81 |
| 4-(Trifluoromethyl)benzylamine | 4-(2-Aminoethyl)morpholine | Hydrogen | 50 | |
| 4-(Trifluoromethyl)benzylamine | 2-(1-Cyclohexenyl)ethylamine | Hydrogen | 50 | |
| 4-(Trifluoromethyl)benzylamine | Hexetidine (mixture of isomers) | Hydrogen | 50 | |
| 4-(Trifluoromethyl)benzylamine | 2,4-Dichlorophenethylamine | Hydrogen | 50 | |
| 4-(Trifluoromethyl)benzylamine | (S)-(−)-Cyclohexylethylamine | Hydrogen | 50 | |
| Veratryl amine | 1-Adamantanemethylamine | Hydrogen | 50 | |
| Veratryl amine | 2-(1-Cyclohexenyl)ethylamine | Hydrogen | 50 | |
| Veratryl amine | 4-Fluorophenethylamine | Hydrogen | 50 | |
| Veratryl amine | Hexetidine (mixture of isomers) | Hydrogen | 50 | |
| Veratryl amine | 2,4-Dichlorophenethylamine | Hydrogen | 50 | |
| Veratryl amine | (S)-(−)-Cyclohexylethylamine | Hydrogen | 50 | |
| Veratryl amine | Undecylamine | Hydrogen | 50 | |
| Veratryl amine | Dehydroabietylamine | Hydrogen | 50 | |
| Veratryl amine | 1-(1-Naphthyl)ethylamine | Hydrogen | 50 | |
| 5-Amino-1-pentanol | 1-Adamantanemethylamine | Hydrogen | 50 | |
| 5-Amino-1-pentanol | Dibenzylamine | Hydrogen | 50 | |
| 5-Amino-1-pentanol | cis-(−)-Myrtanylamine | Hydrogen | 50 | 12.97 |
| 2-(1-Cyclohexenyl)ethylamine | 2,4-Dimethoxybenzylamine | Hydrogen | 50 | |
| 1-Aminomethyl-1-cyclohexanol, HCl | tert-Amylamine | Hydrogen | 50 | |
| 1-Aminomethyl-1- | 2-(2- | Hydrogen | 50 | |

TABLE 2-continued

Synthetic Substituted Diethylene Diamines Sorted by Minimum Inhibition Concentration

| N1 | N2 | R4 | MIC (uM) | % Induction |
|---|---|---|---|---|
| cyclohexanol, HCl | Aminomethyl)phenylthio)benzyl alcohol | | | |
| 1-Aminomethyl-1-cyclohexanol, HCl | Undecylamine | Hydrogen | 50 | |
| 1-Aminomethyl-1-cyclohexanol, HCl | 1-(1-Naphthyl)ethylamine | Hydrogen | 50 | |
| 3-Fluorobenzylamine | tert-Amylamine | Hydrogen | 50 | |
| 3-Fluorobenzylamine | Hexetidine (mixture of isomers) | Hydrogen | 50 | |
| 3-Fluorobenzylamine | Undecylamine | Hydrogen | 50 | |
| 4-Amino-1-butanol | Undecylamine | Hydrogen | 50 | |
| 4-Amino-1-butanol | Dehydroabietylamine | Hydrogen | 50 | |
| 2,4-Dimethoxybenzylamine | N-Phenylethyldiamine | Hydrogen | 50 | |
| 2,4-Dimethoxybenzylamine | Aminodiphenylmethane | Hydrogen | 50 | |
| 2,4-Dimethoxybenzylamine | 4-Phenylbutylamine | Hydrogen | 50 | |
| 2,4-Dimethoxybenzylamine | 2-Chlorobenzylamine | Hydrogen | 50 | |
| 2,4-Dimethoxybenzylamine | 2,4-Dichlorophenethylamine | Hydrogen | 50 | |
| 2,4-Dimethoxybenzylamine | 2-(2-Chlorophenyl)ethylamine | Hydrogen | 50 | |
| 2,4-Dimethoxybenzylamine | 4-(Trifluoromethoxy)benzylamine | Hydrogen | 50 | |
| 2-Ethoxybenzylamine | Aminodiphenylmethane | Hydrogen | 50 | |
| 2-Ethoxybenzylamine | 4-Phenylbutylamine | Hydrogen | 50 | |
| 2-Ethoxybenzylamine | 2-Chlorobenzylamine | Hydrogen | 50 | |
| 2-Ethoxybenzylamine | 2-Aminoindan, HCl | Hydrogen | 50 | |
| 2-Ethoxybenzylamine | 2,5-Dimethoxyphenethylamine | Hydrogen | 50 | |
| 2-Ethoxybenzylamine | 4-(Trifluoromethoxy)benzylamine | Hydrogen | 50 | |
| 2-Ethoxybenzylamine | 1-(1-Naphthyl)ethylamine | Hydrogen | 50 | |
| cis-(−)-Myrtanylamine | 4-(2-Aminoethyl)morpholine | Hydrogen | 50 | |
| cis-(−)-Myrtanylamine | 2-Fluorophenethylamine | Hydrogen | 50 | |
| cis-(−)-Myrtanylamine | 1-(3-Aminopropyl)-2-pyrrolidinone (tech) | Hydrogen | 50 | |
| cis-(−)-Myrtanylamine | Veratryl amine | Hydrogen | 50 | |
| cis-(−)-Myrtanylamine | N-Butylbenzylamine | Hydrogen | 50 | |
| cis-(−)-Myrtanylamine | 2,4-Dimethoxybenzylamine | Hydrogen | 50 | |
| cis-(−)-Myrtanylamine | 1,2,3,4-Tetrahydropyridoindole | Hydrogen | 50 | |
| cis-(−)-Myrtanylamine | 4-Phenylbutylamine | Hydrogen | 50 | |
| cis-(−)-Myrtanylamine | 2-(2-Chlorophenyl)ethylamine | Hydrogen | 50 | 3.91 |
| cis-(−)-Myrtanylamine | 1-(1-Adamantyl)ethylamine, HCl | Hydrogen | 50 | 10.85 |
| cis-(−)-Myrtanylamine | (R)-(−)-Cyclohexylethylamine | Hydrogen | 50 | 5.89 |
| cis-(−)-Myrtanylamine | Dehydroabietylamine | Hydrogen | 50 | |
| cis-(−)-Myrtanylamine | 1-(1-Naphthyl)ethylamine | Hydrogen | 50 | |
| cis-(−)-Myrtanylamine | (+)-Bornylamine | Methyl | 50 | 4.04 |
| Cyclooctylamine | 4-Methylcyclohexylamine | Hydrogen | 50 | 4.55 |
| Cyclooctylamine | N-Phenylethyldiamine | Hydrogen | 50 | |
| Cyclooctylamine | 4-(Hexacylamino)benzylamine | Hydrogen | 50 | |
| Cyclooctylamine | 2,5-Dimethoxyphenethylamine | Hydrogen | 50 | |
| Cyclooctylamine | 2,4-Dichlorophenethylamine | Hydrogen | 50 | 3.36 |
| Cyclooctylamine | 2-(2-Chlorophenyl)ethylamine | Hydrogen | 50 | 9.15 |
| Cyclooctylamine | 1-(1-Adamantyl)ethylamine, HCl | Hydrogen | 50 | 10.62 |
| Cyclooctylamine | (S)-(−)-Cyclohexylethylamine | Hydrogen | 50 | 5.85 |
| Cyclooctylamine | (R)-(−)-Cyclohexylethylamine | Hydrogen | 50 | |
| Cyclooctylamine | 4-(Trifluoromethoxy)benzylamine | Hydrogen | 50 | 4.54 |
| 2-Adamantanamine, HCl | cis-(−)-Myrtanylamine | Hydrogen | 50 | 49.73 |
| 4-Methylcyclohexylamine | N-Phenylethyldiamine | Hydrogen | 50 | |
| 4-Methylcyclohexylamine | 4-Phenylbutylamine | Hydrogen | 50 | |
| 4-Fluorobenzylamine | N-Benzyl-2-phenethylamine | Hydrogen | 50 | |
| 4-Fluorobenzylamine | Hexetidine (mixture of isomers) | Hydrogen | 50 | |
| 4-Fluorobenzylamine | Undecylamine | Hydrogen | 50 | |
| 4-Fluorobenzylamine | Dehydroabietylamine | Hydrogen | 50 | |
| trans-2-Phenylcyclopropylamine, HCl | Hexetidine (mixture of isomers) | Hydrogen | 50 | |
| trans-2-Phenylcyclopropylamine, HCl | Undecylamine | Hydrogen | 50 | |
| trans-2-Phenylcyclopropylamine, HCl | Dehydroabietylamine | Hydrogen | 50 | |
| (R)-1-Amino-2-propanol | 4-(Hexacylamino)benzylamine | Hydrogen | 50 | |
| (R)-1-Amino-2-propanol | Undecylamine | Hydrogen | 50 | |
| (R)-1-Amino-2-propanol | Dehydroabietylamine | Hydrogen | 50 | |
| l-Leucinol | Undecylamine | Hydrogen | 50 | |
| (−)-Isopinocampheylamine | 2-Ethoxybenzylamine | Hydrogen | 50 | 27.27 |
| (−)-Isopinocampheylamine | Hexetidine (mixture of isomers) | Hydrogen | 50 | |

TABLE 2-continued

Synthetic Substituted Diethylene Diamines Sorted by Minimum Inhibition Concentration

| N1 | N2 | R4 | MIC (uM) | % Induction |
|---|---|---|---|---|
| (−)-Isopinocampheylamine | 4-Phenylbutylamine | Hydrogen | 50 | |
| (−)-Isopinocampheylamine | Dehydroabietylamine | Hydrogen | 50 | |
| (−)-Isopinocampheylamine | 1-(1-Naphthyl)ethylamine | Hydrogen | 50 | |
| Allylamine | 3,3-Diphenylpropylamine | Hydrogen | 50 | |
| Allylamine | 2-Amino-1-propanol, d,1 | Hydrogen | 50 | |
| Allylamine | Undecylamine | Hydrogen | 50 | |
| 3-Amino-1,2-propanediol | Dehydroabietylamine | Hydrogen | 50 | |
| 3-Ethoxypropylamine | 2,2-Diphenylamine | Hydrogen | 50 | 95.81 |
| 3-Ethoxypropylamine | cis-(−)-Myrtanylamine | Hydrogen | 50 | |
| 2-Aminoheptane | 2-(2-Aminomethyl)phenylthio)benzyl alcohol | Hydrogen | 50 | |
| 1-Naphthalenemethylamine | Geranylamine | Hydrogen | 50 | |
| 1-Naphthalenemethylamine | Dehydroabietylamine | Hydrogen | 50 | |
| 1-Aminopyrrolidine, HCl | Hexetidine (mixture of isomers) | Hydrogen | 50 | |
| 1-Aminopyrrolidine, HCl | Undecylamine | Hydrogen | 50 | |
| 1-Aminopyrrolidine, HCl | Dehydroabietylamine | Hydrogen | 50 | |
| Ethanolamine | 3,3-Diphenylpropylamine | Hydrogen | 50 | |
| 3-Methylbenzylamine | Geranylamine | Hydrogen | 50 | |
| 3-Methylbenzylamine | 5-Methoxytryptamine | Hydrogen | 50 | |
| Piperonylamine | Aminodiphenylmethane | Hydrogen | 50 | |
| Piperonylamine | 2,4-Dichlorophenethylamine | Hydrogen | 50 | |
| Piperonylamine | 2-(2-Aminomethyl)phenylthio)benzyl alcohol | Hydrogen | 50 | |
| Isopropylamine | Dehydroabietylamine | Hydrogen | 50 | |
| 4-Fluorophenethylamine | 2,4-Dimethoxybenzylamine | Hydrogen | 50 | |
| 4-Fluorophenethylamine | Aminodiphenylmethane | Hydrogen | 50 | |
| 4-Fluorophenethylamine | 2-(2-Aminomethyl)phenylthio)benzyl alcohol | Hydrogen | 50 | |
| 4-Chloroamphetamine, HCl | N-Allylcyclopentylamine | Hydrogen | 50 | 10.25 |
| 4-Chloroamphetamine, HCl | Hexetidine (mixture of isomers) | Hydrogen | 50 | |
| 4-Chloroamphetamine, HCl | 4-Phenylbutylamine | Hydrogen | 50 | |
| 4-Chloroamphetamine, HCl | 2-Methoxyphenethylamine | Hydrogen | 50 | |
| 4-Chloroamphetamine, HCl | Undecylamine | Hydrogen | 50 | |
| 4-Chloroamphetamine, HCl | Dehydroabietylamine | Hydrogen | 50 | |
| 3-Fluorophenethylamine | (−)-Isopinocampheylamine | Hydrogen | 50 | |
| 3-Fluorophenethylamine | 1-Adamantamine | Hydrogen | 50 | 8.59 |
| 3-Fluorophenethylamine | 4-Phenylbutylamine | Hydrogen | 50 | |
| 2-Methylcyclohexylamine (mix of cis and trans) | Undecylamine | Hydrogen | 50 | |
| 2-Methoxyphenethylamine | 3,3-Diphenylpropylamine | Hydrogen | 50 | |
| 2-Methoxyphenethylamine | (+)-Bornylamine | Hydrogen | 50 | |
| 2-Methoxyphenethylamine | tert-Octylamine | Hydrogen | 50 | 20.46 |
| 2-Methoxyphenethylamine | 1-Adamantanemethylamine | Hydrogen | 50 | |
| 2-Methoxyphenethylamine | Dibenzylamine | Hydrogen | 50 | |
| 2-Methoxyphenethylamine | N-Butylbenzylamine | Hydrogen | 50 | 5.20 |
| 2-Methoxyphenethylamine | 1,3,3-Trimethyl-6-azabicyclo[3.2.1]octane | Hydrogen | 50 | 8.59 |
| 2-Methoxyphenethylamine | N-Phenylethyldiamine | Hydrogen | 50 | |
| 2-Methoxyphenethylamine | 2,4-Dichlorophenethylamine | Hydrogen | 50 | |
| 2-Methoxyphenethylamine | 2-(2-Chlorophenyl)ethylamine | Hydrogen | 50 | |
| 2-Methoxyphenethylamine | 1-(1-Adamantyl)ethylamine, HCl | Hydrogen | 50 | 3.61 |
| 2-Aminoindan, HCl | (+)-Bornylamine | Hydrogen | 50 | |
| 2-Aminoindan, HCl | Noradamantamine, HCl | Hydrogen | 50 | 7.43 |
| 2-(2-Chlorophenyl)ethylamine | N-Phenylethyldiamine | Hydrogen | 50 | |
| 2-(2-Chlorophenyl)ethylamine | Aminodiphenylmethane | Hydrogen | 50 | |
| 2-(2-Chlorophenyl)ethylamine | 2,4-Dichlorophenethylamine | Hydrogen | 50 | |
| 2-(2-Chlorophenyl)ethylamine | 1-(1-Adamantyl)ethylamine, HCl | Hydrogen | 50 | |
| 2-(2-Chlorophenyl)ethylamine | Dehydroabietylamine | Hydrogen | 50 | |
| 2-(2-Aminomethyl)phenylthio)benzyl alcohol | 2-Methoxyphenethylamine | Hydrogen | 50 | |
| 2-(2-Aminomethyl)phenylthio)benzyl alcohol | 2,5-Dimethoxyphenethylamine | Hydrogen | 50 | |
| 2-(2-Aminomethyl)phenylthio)benzyl alcohol | 2-(2-Chlorophenyl)ethylamine | Hydrogen | 50 | |
| 2-(2- | 1-(1-Adamantyl)ethylamine, | Hydrogen | 50 | |

TABLE 2-continued

Synthetic Substituted Diethylene Diamines Sorted by Minimum Inhibition Concentration

| N1 | N2 | R4 | MIC (uM) | % Induction |
|---|---|---|---|---|
| Aminomethyl)phenylthio)benzyl alcohol | HCl | | | |
| 2-(2-Aminomethyl)phenylthio)benzyl alcohol | Dehydroabietylamine | Hydrogen | 50 | |
| 1-Aminoindan | 4-Phenylbutylamine | Hydrogen | 50 | |
| 1-Aminoindan | 2,4-Dichlorophenethylamine | Hydrogen | 50 | |
| 1,3-Dimethylbutylamine | 4-Phenylbutylamine | Hydrogen | 50 | |
| (S)-(−)-Cyclohexylethylamine | Aminodiphenylmethane | Hydrogen | 50 | |
| (S)-(−)-Cyclohexylethylamine | 4-Phenylbutylamine | Hydrogen | 50 | |
| (S)-(−)-Cyclohexylethylamine | 2,4-Dichlorophenethylamine | Hydrogen | 50 | |
| (S)-(−)-Cyclohexylethylamine | 1-(1-Adamantyl)ethylamine, HCl | Hydrogen | 50 | |
| (1S,2S)-(+)-2-Amino-3-methoxy-1-phenyl-1-propanol | Dehydroabietylamine | Hydrogen | 50 | |
| Octadecylamine | 2-Adamantanamine, HCl | Hydrogen | 50 | |
| 3-Hydroxytyramine | (1R,2S)-(−)-2-Amino-1,2-diphenylethanol | Hydrogen | 50 | |
| 3-Hydroxytyramine | Dehydroabietylamine | Hydrogen | 50 | |
| Geranylamine | 3,3-Diphenylpropylamine | Hydrogen | 50 | |
| Geranylamine | N-Phenylethyldiamine | Hydrogen | 50 | |
| Geranylamine | Hexetidine (mixture of isomers) | Hydrogen | 50 | |
| Geranylamine | 2-Thiopheneethylamine | Hydrogen | 50 | |
| Geranylamine | 2-Methoxyphenethylamine | Hydrogen | 50 | |
| Geranylamine | 2,5-Dimethoxyphenethylamine | Hydrogen | 50 | |
| Geranylamine | 2,4-Dichlorophenethylamine | Hydrogen | 50 | |
| Geranylamine | 2-(2-Chlorophenyl)ethylamine | Hydrogen | 50 | |
| 2-Fluorophenethylamine | 2,3-Dimethylcyclohexylamine | Methyl | >50 | 2.07 |
| 4-(Trifluoromethyl)benzylamine | 2,3-Dimethylcyclohexylamine | Hydrogen | >50 | 8.20 |
| 4-(Trifluoromethyl)benzylamine | 1-Adamantanamine | Hydrogen | >50 | 32.02 |
| 5-Aminoquinoline | exo-Aminonorbornane | Hydrogen | >50 | 17.87 |

TABLE 3

Compounds Synthesized in Larger Quantities for Further in vitro Evaluations

| Cmpd # | Name | Structure | Amount, mg | Yields, % |
|---|---|---|---|---|
| 1 | N-(4-Methylphenyl)-N'-(furfuryl)ethane-1,2-diamine | 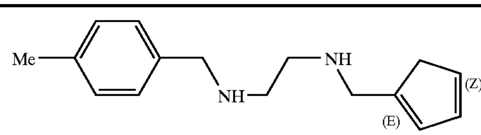 | 23 | 25 |
| 2 | N-(4-Methylphenyl)-N'-(benzyl)ethane-1,2-diamine | 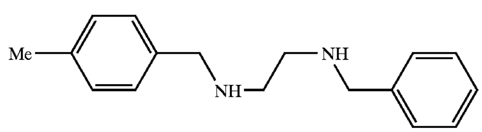 | 27 | 29 |
| 3 | N-[1-(1,2,3,4-Tetrahydro-naphthalene)-N'-(undecenyl)-ethane-1,2-diamine | 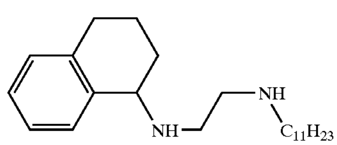 | 11 | 10 |
| 4 | N-[2-(3,4-Dimethoxy-phenyl)-ethyl-N'-(1-methyladamantyl)-ethane-1,2-diamine | 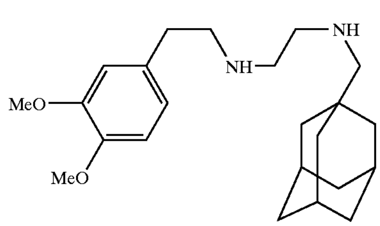 | 13 | 11 |

TABLE 3-continued

Compounds Synthesized in Larger Quantities for Further in vitro Evaluations

| Cmpd # | Name | Structure | Amount, mg | Yields, % |
|---|---|---|---|---|
| 5 | N-[2-(3,4-Dimethoxy-phenyl)ethyl-N'-(norbornyl)-ethane-1,2-diamine | 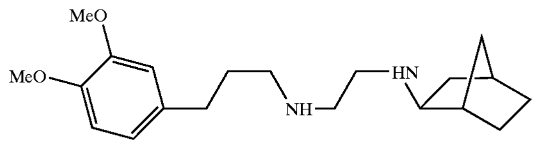 | 9 | 8 |
| 6 | N-(1-Adamantylmethyl)-N'-(3,3-diphenylpropyl)propane-1,2-diamine | 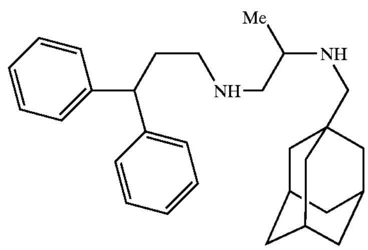 | 55 | 36 |
| 7 | N-(1-Adamantylmethyl)-N'-(3,3-diphenylpropyl)ethane-1,2-diamine | 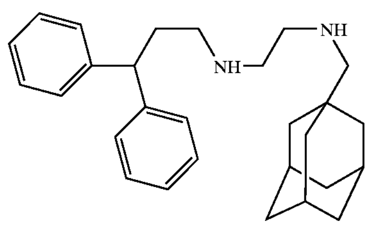 | 28 | 22 |
| 8 | N-[2-(Cyclohexen-1-yl)ethyl]-N'-(3,3-diphenylpropyl)-propane-1,2-diamine | 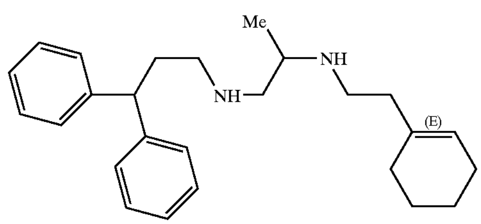 | 46 | 37 |
| 10 | N-(−)-cis-Myrtanyl-N'-(3,3-diphenylpropyl)ethane-1,2-diamine | 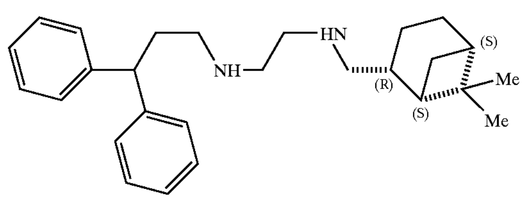 | 14 | 11 |
| 11 | N-Cyclooctyl-N'-(3,3-diphenylpropyl)ethane-1,2-diamine | 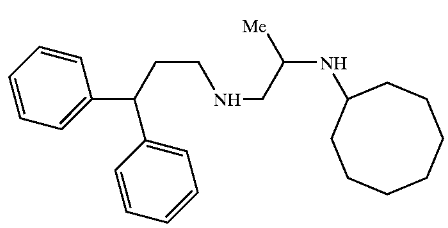 | 22 | 18 |
| 13 | N-Allyl-N-cyclopentyl-N-(3,3-diphenylpropyl)ethane-1,2-diamine | 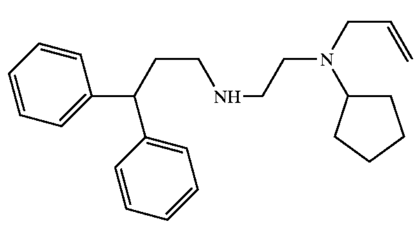 | 33 | 27 |

TABLE 3-continued

Compounds Synthesized in Larger Quantities for Further
in vitro Evaluations

| Cmpd # | Name | Structure | Amount, mg | Yields, % |
|---|---|---|---|---|
| 14 | N-(3,3-Diphenylpropyl)-N'-exo-(2-norborny)ethane-1,2-diamine | 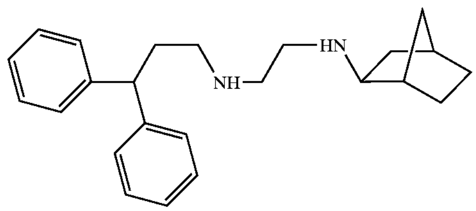 | 17 | 16 |
| 15 | 1-{2-[N-(3,3-Diphenylpropyl)]-aminoethyl}-3,5-dimethyl-piperidine | 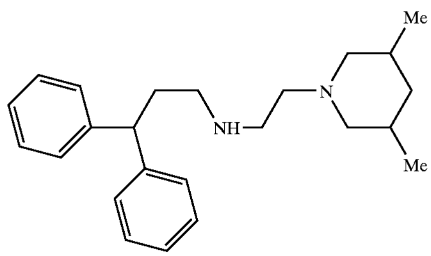 | 6.2 | 5 |
| 17 | N-2-(2-Methoxyphenyl)ethyl-N'-(3,3-diphenylethyl)ethane-1,2-diamine | 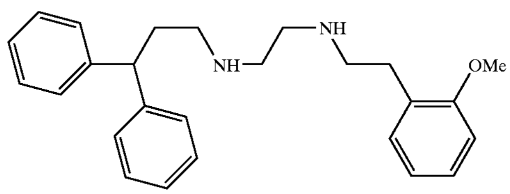 | 50 | 40 |
| 21 | N-(3,3-Diphenylpropyl)-N'-(1S)-(1-ethylcyclohexane)-ethane-1,2-diamine | 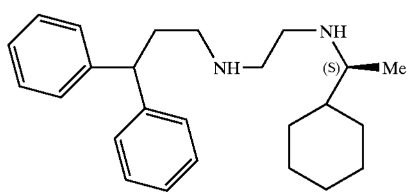 | 5 | 4 |
| 22 | N-(3,3-Diphenylpropyl)-N'-(1R)-(1-ethylcyclohexane)-ethane-1,2-diamine | 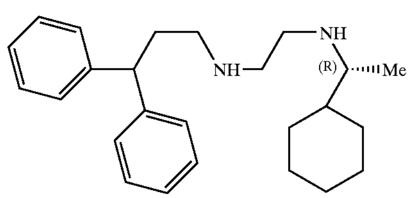 | 21 | 17 |
| 23 | N-Allyl-N-cyclohexyl-N-(3,3-diphenylpropyl)ethane-1,2-diamine | 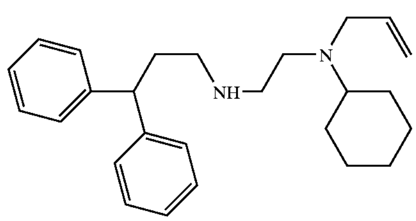 | 6 | 5 |

TABLE 3-continued

Compounds Synthesized in Larger Quantities for Further in vitro Evaluations

| Cmpd # | Name | Structure | Amount, mg | Yields, % |
|---|---|---|---|---|
| 24 | N-2-(2-Methoxyphenyl)ethyl-N'-(4-fluorophenylethyl)-ethane-1,2-diamine | 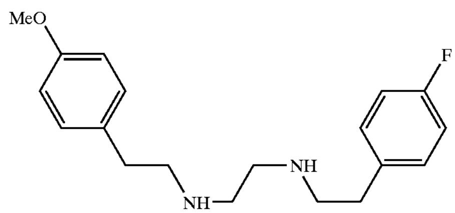 | 10 | 9 |
| 27 | N-(3-Phenylpropyl)-N'-(1-adamantyl)ethane-1,2-diamine | 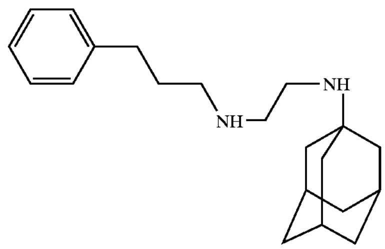 | 11 | 10 |
| 28 | N-(3-Phenylpropyl)-N'-(4-fluorophenyl)ethane-1,2-diamine | 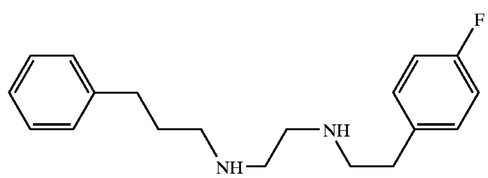 | 11 | 10 |
| 29 | N-(2,2-Diphenylethyl)-N'-(2,3-dimethylcylcohexyl)ethane-1,2-diamine | 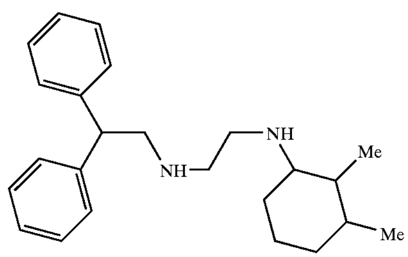 | 4.5 | 4 |
| 31 | N-(2,2-Diphenylethyl)-N'-(1S)-(1-ethylcyclohexane)-ethane-1,2-diamine | 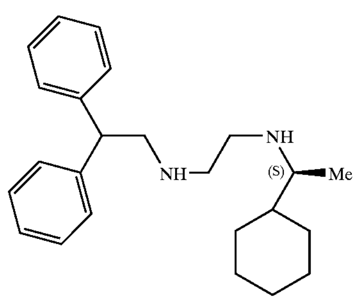 | 24 | 20 |
| 32 | N-(2,2-Diphenylethyl)-N'-(R)-(+)- | 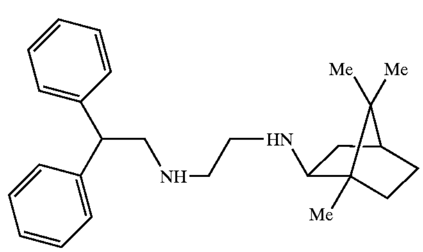 | 58 | 48 |

TABLE 3-continued

Compounds Synthesized in Larger Quantities for Further in vitro Evaluations

| Cmpd # | Name | Structure | Amount, mg | Yields, % |
|---|---|---|---|---|
| 33 | N-(2,2-Diphenylethyl)-N'-(1,1,3,3-tetramethylbutyl)-ethane-1,2-diamine | 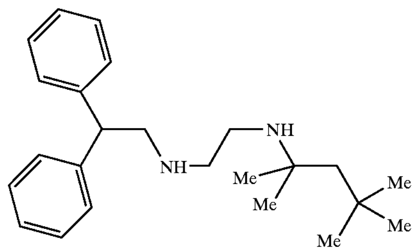 | 11 | 9 |
| 34 | N-(2,2-Diphenylethyl)-N'-(1-methyladamantyl)ethane-1,2-diamine | 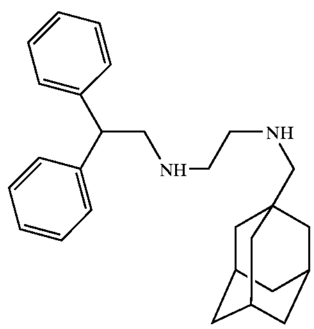 | 6.8 | 6 |
| 35 | N-(2,2-Diphenylethyl)-N'-{1,1,3-trimethyl-6-azabicyclo-[3.2.1]octyl}ethane-1,2-diamine | 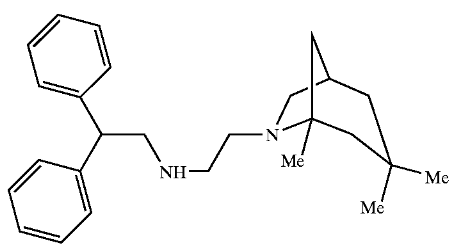 | 38 | 30 |
| 36 | N-{2-[N'-(2,2-Diphenylethyl)]-aminoethyl}-decahydroquinoline | 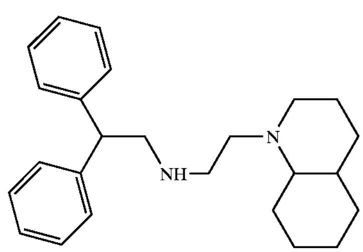 | 28 | 24 |
| 37 | N-(2,2-Diphenylethyl)-N'-(−)-cis-(myrtanyl)ethane-1,2-diamine | 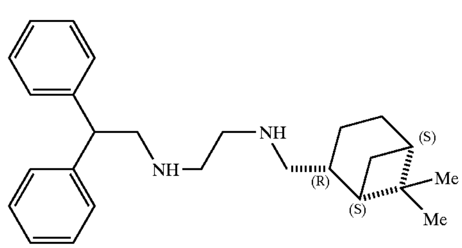 | 54 | 38 |

TABLE 3-continued

Compounds Synthesized in Larger Quantities for Further in vitro Evaluations

| Cmpd # | Name | Structure | Amount, mg | Yields, % |
|---|---|---|---|---|
| 38 | N-(−)-cis-(Myrtanyl)-N'-(2,2-diphenylethyl)propyl-1,2-diamine | 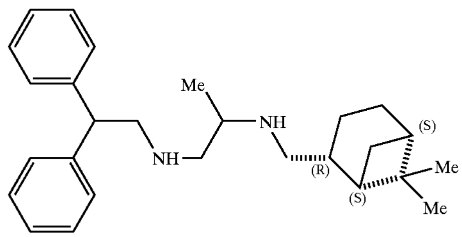 | 39 | 30 |
| 40 | N-(2,2-Diphenylethyl)-N'-(1R, 2R, 3R, 5S)-(−)-isopinocampheylethane-1,2-diamine | 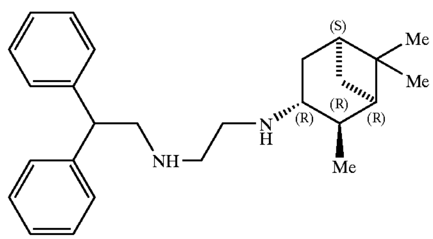 | 33 | 23 |
| 41 | N-(−)-cis-(Myrtanyl)-N'-(2,3-dimethylcyclohexyl)ethane-1,2-diamine | 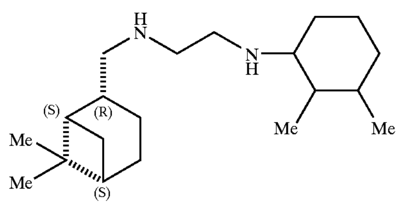 | 66 | 62 |
| 42 | N-(3,3-Diphenylpropyl)-N'(−)-cis-myrtanylethane-1,2-diamine | 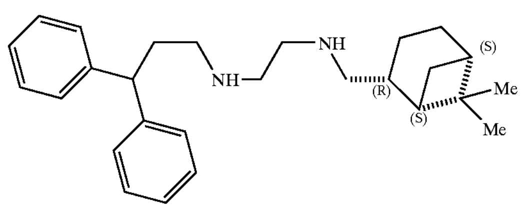 | 11 | 9 |
| 43 | N-(−)-cis-Myrtanyl-N'-(1S,2S, 3S,5R)-(+)-isopinocampheylethane-1,2-diamine | 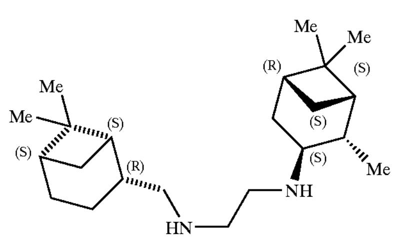 | 31 | 27 |
| 47 | N-(−)-cis-Myrtanyl-N'-(1R,2R, 3R,5S)-(−)-isopinocampheylethane-1,2-diamine | 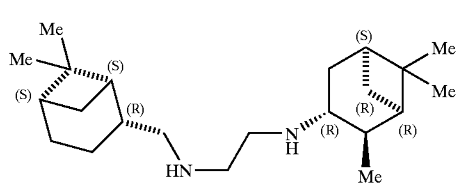 | 42 | 33 |

TABLE 3-continued

Compounds Synthesized in Larger Quantities for Further in vitro Evaluations

| Cmpd # | Name | Structure | Amount, mg | Yields, % |
|---|---|---|---|---|
| 51 | N-(Cyclooctyl)-N'-(2,3-dimethylcyclohexyl)ethane-1,2-diamine | 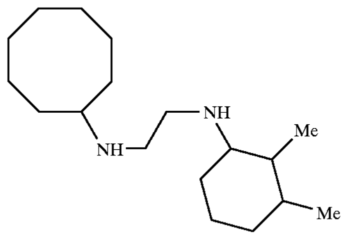 | 5.1 | 2 |
| 52 | N-(Cyclooctyl)-N'-(3,3-diphenylpropyl)ethane-1,2-diamine | 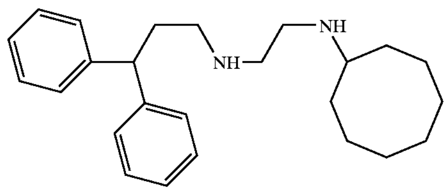 | 20 | 18 |
| 53 | N-Cyclooctyl-N'-(1S,2S,3S,5R)-(+)-isopinocampheyl-ethane-1,2-diamine | 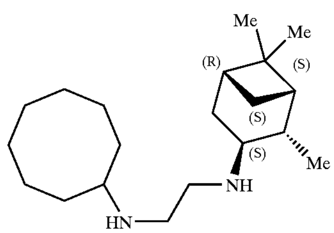 | 7.4 | 7 |
| 54 | N-Cyclooctyl-N'-(R)-(+)-bornylethane-1,2-diamine | 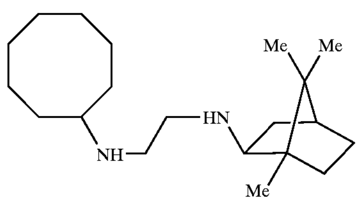 | 17 | 16 |
| 55 | N-(Cyclooctyl)-N'-(1-methyladamantyl)ethane-1,2-diamine | 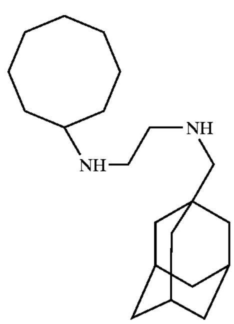 | 7 | 6 |
| 56 | N-(Cyclooctyl)-N'-(2S)-[2-(1-hydroxybutyl)]ethane-1,2-diamine | 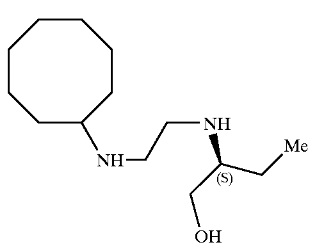 | 1.1 | 1 |

TABLE 3-continued

Compounds Synthesized in Larger Quantities for Further in vitro Evaluations

| Cmpd # | Name | Structure | Amount, mg | Yields, % |
|---|---|---|---|---|
| 57 | N-(−)-cis-Myrtanyl-N'-(cyclooctyl)ethane-1,2-diamine | 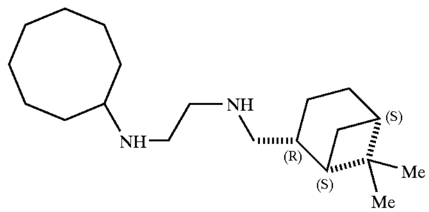 | 18 | 18 |
| 58 | N-(Cyclooctyl)-N'-(2-adamantyl)ethane-1,2-diamine | 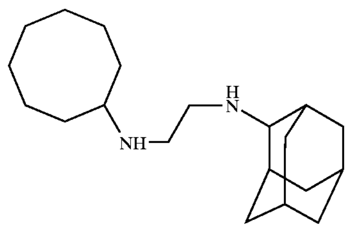 | 25 | 23 |
| 59 | N-(Cyclooctyl)-N'-(1R,2R,3R,5S)-(−)-isopinocampheylethane-1,2-diamine | 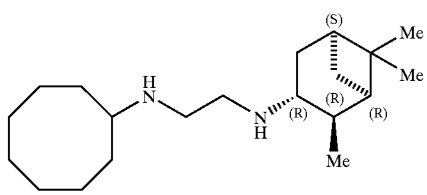 | 15 | 14 |
| 61 | N-(Cyclooctyl)-N'-[1-ethyl-(1-naphthyl)]ethane-1,2-diamine | 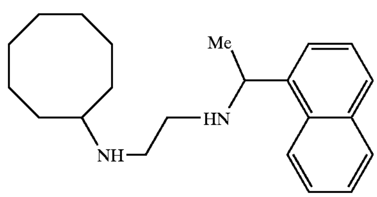 | 16 | 14 |
| 62 | N-(−)-cis-Myrtanyl-N'-(1S)-(1-ethylcyclohexane)ethane-1,2-diamine | 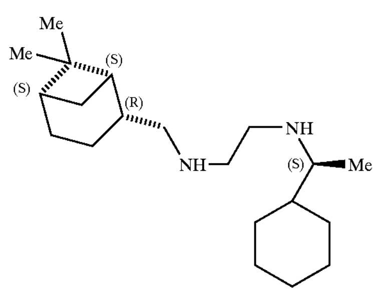 | 48 | 46 |
| 63 | N-(Cyclooctyl)-N'-trans-(2-phenylcyclopropyl)ethane-1,2-diamine | 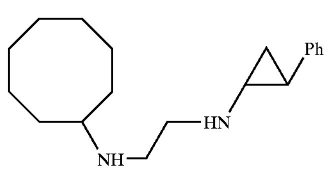 | 47 | 46 |

TABLE 3-continued

Compounds Synthesized in Larger Quantities for Further in vitro Evaluations

| Cmpd # | Name | Structure | Amount, mg | Yields, % |
|---|---|---|---|---|
| 64 | N-(2-Adamantyl)-N'-trans-(2-phenylcyclopropyl)ethane-1,2-diamine | 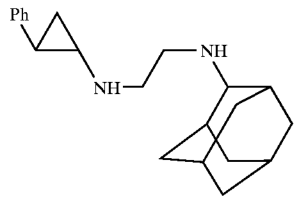 | 49 | 46 |
| 65 | N-(1-Adamantyl)-N'-trans-(2-phenylcyclopropyl)ethane-1,2-diamine | 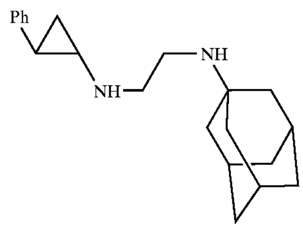 | 18 | 16 |
| 66 | N-(3,3-Diphenylpropyl)-N'-(1R,2R,3R,5S)-(−)-isopinocampheylethane-1,2-diamine | 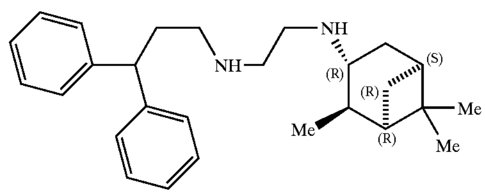 | 2.3 | 2 |
| 68 | N-(+/−)-[2-(1-Hydroxybutyl)]-N'-(1R,2R,3R,5S)-(−)-isopinocampheylethane-1,2-diamine | 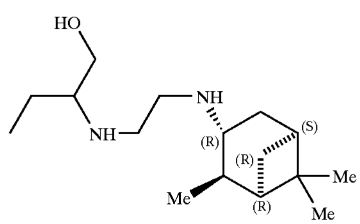 | 0.8 | 1 |
| 71 | N-(1,1-Diphenylmethyl)-N'-(1R,2R,3R,5S)-(−)-isopinocampheylethane-1,2-diamine | 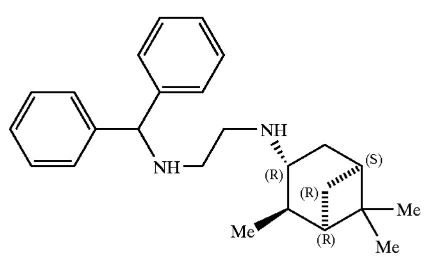 | 2.9 | 2 |
| 73 | N-(2-Adamantyl)-N'-[2-(2-methoxyphenyl)ethyl]ethane-1,2-diamine | 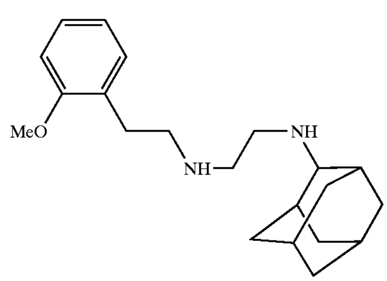 | 21 | 19 |

TABLE 3-continued

Compounds Synthesized in Larger Quantities for Further in vitro Evaluations

| Cmpd # | Name | Structure | Amount, mg | Yields, % |
|---|---|---|---|---|
| 76 | N-Allyl-N-cyclopentyl-N'-[2-(2-methoxyphenyl)ethyl]ethane-1,2-diamine | 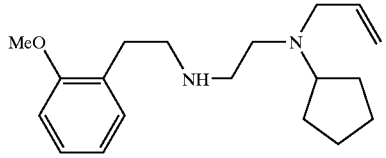 | 8 | 7 |
| 77 | N-(1,1-Diphenylmethyl)-N'-[2-(2-methoxyphenyl)-ethyl]ethane-1,2-diamine | 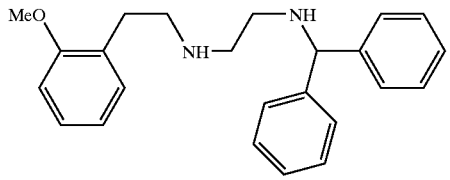 | 32 | 27 |
| 78 | N-2-Adamantyl-N'-2,3-dihydro-1H-inden-2-yl-ethane-1,2-diamine | 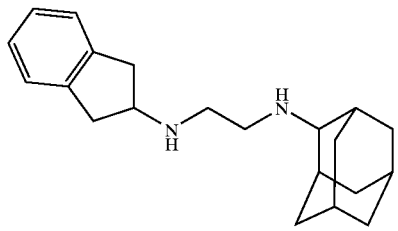 | 4.3 | 3 |
| 79 | N-[2-(2,5-Dimethoxyphenyl)-ethyl]-N'-(R)-(+)-bornylethane-1,2-diamine | 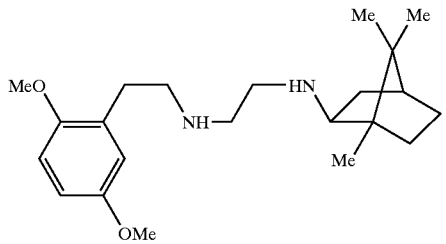 | 59 | 49 |
| 103 | N,N'-Bis(cyclooctyl)ethane-1,2-diamine | 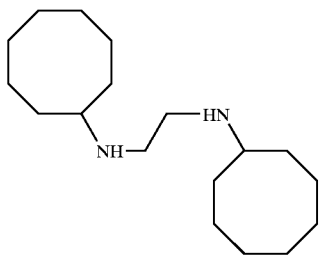 | 6.3 | 4 |
| 107 | N-(2,2-Diphenylethyl)-N-(3-ethoxypropyl)ethane-1,2-diamine | 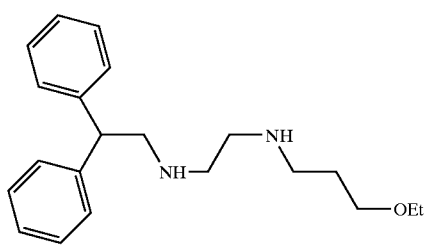 | 58 | 52 |

TABLE 3-continued

Compounds Synthesized in Larger Quantities for Further in vitro Evaluations

| Cmpd # | Name | Structure | Amount, mg | Yields, % |
|---|---|---|---|---|
| 109 | N-Geranyl-N'-(2-adamanthyl)ethane-1,2-diamine | | 27 | 24 |
| 111 | N-[2-(N'-Geranyl)aminoethyl]-2-ethylpiperidine | | 24 | 24 |
| 116 | N-Geranyl-N'-allyl-N'-(cyclopentyl)ethane-1,2-diamine | | 45 | 42 |
| 117 | N-Geranyl-N'-(1,1-diphenyl-methyl)ethane-1,2-diamine | | 24 | 20 |
| 118 | N-2-(2-Chlorophenyl)ethyl-N'-allyl-N'-(cyclopentyl)ethane-1,2-diamine | | 6.4 | 6 |
| 119 | N-2-(2-Chlorophenyl)ethyl-N'-[2-(3-fluorophenyl)-ethyl]ethane-1,2-diamine | | 30 | 27 |
| 125 | N,N'-bis-(−)-cis-Myrtanylpropane-1,2-diamine | | 41 | 35 |

TABLE 3-continued

Compounds Synthesized in Larger Quantities for Further in vitro Evaluations

| Cmpd # | Name | Structure | Amount, mg | Yields, % |
|---|---|---|---|---|
| 134 | N-[2-(N'-2,2-Diphenylethyl)-aminoethyl]-(−)-3,4-dihydroxynorephedrine | 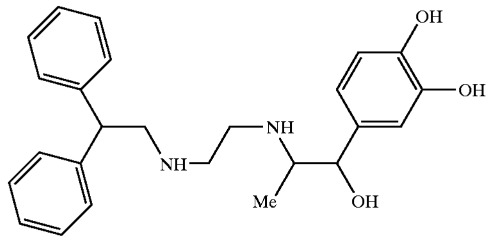 | 20 | 15 |
| 151 | N-[2-(2-Methoxy)phenylethyl]-N'-(1R,2R,3R,5S)-(−)-isopinocampheyl-ethane-1,2-diamine | 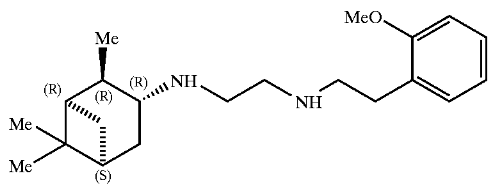 | 67 | 60 |
| 164 | $N^1$-[2-(4-fluorophenyl)ethyl]-$N^2$-[2-(4-Methoxy)phenylethyl]-1-phenylethane-1,2-diamine | 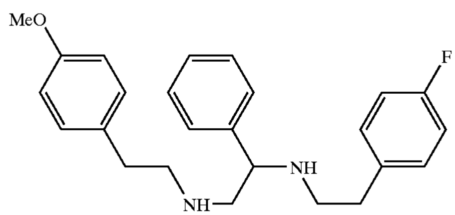 | 94 | 73 |
| 165 | N1-[2-(4-fluorophenyl)ethyl]-N2-(3-Phenylpropyl)-1-phenylethane-1,2-diamine | 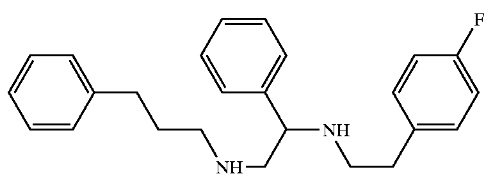 | 23 | 19 |

Formulations

Therapeutics, including compositions containing the substituted ethylene diamine compounds of the present invention, can be prepared in physiologically acceptable formulations, such as in pharmaceutically acceptable carriers, using known techniques. For example, a substituted ethylene diamine compound is combined with a pharmaceutically acceptable excipient to form a therapeutic composition.

The compositions of the present invention may be administered in the form of a solid, liquid or aerosol. Examples of solid compositions include pills, creams, soaps and implantable dosage units. Pills may be administered orally. Therapeutic creams and anti-mycobacteria soaps may be administered topically. Implantable dosage units may be administered locally, for example, in the lungs, or may be implanted for systematic release of the therapeutic composition, for example, subcutaneously. Examples of liquid compositions include formulations adapted for injection intramuscularly, subcutaneously, intravenously, intraarterially, and formulations for topical and intraocular administration. Examples of aerosol formulations include inhaler formulations for administration to the lungs.

A sustained release matrix, as used herein, is a matrix made of materials, usually polymers, which are degradable by enzymatic or acid/base hydrolysis, or by dissolution. Once inserted into the body, the matrix is acted upon by enzymes and body fluids. The sustained release matrix is chosen desirably from biocompatible materials, including, but not limited to, liposomes, polylactides, polyglycolide (polymer of glycolic acid), polylactide co-glycolide (coplymers of lactic acid and glycolic acid), polyanhydrides, poly(ortho)esters, polypeptides, hyaluronic acid, collagen, chondroitin sulfate, carboxylic acids, fatty acids, phospholipds, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide.

The dosage of the composition will depend on the condition being treated, the particular composition used, and other clinical factors, such as weight and condition of the patient, and the route of administration. A suitable dosage may range from 100 to 0.1 mg/kg. A more preferred dosage may range from 50 to 0.2 mg/kg. A more preferred dosage may range from 25 to 0.5 mg/kg. Tablets or other forms of media may contain from 1 to 1000 mg of the substituted ethylene diamine. Dosage ranges and schedules of administration similar to ethambutol or other anti-tuberculosis drugs may be used.

The composition may be administered in combination with other compositions and procedures for the treatment of other disorders occurring in combination with mycobacterial disease. For example, tuberculosis frequently occurs as a secondary complication associated with acquired immunodeficiency syndrome (AIDS). Patients undergoing AIDS treatment, which includes procedures such as surgery, radiation or chemotherapy, may benefit from the therapeutic methods and compositions described herein.

The following specific examples will illustrate the invention as it applies to the particular synthesis of the substituted ethylene diamine compounds, and the in vitro and in vivo suppression of the growth of colonies of M. tuberculosis. It will be appreciated that other examples, including minor variations in chemical procedures, will be apparent to those skilled in the art, and that the invention is not limited to these specific illustrated examples.

EXAMPLE I

Generating the Ethylene Diamine Library

The Rink-acid resin was obtained from NOVABIOCHEM® Inc., San Diego, Calif. Solvents: acetonitrile, dichloromethane, dimethylformamide, ethylenedichloride, methanol and tetrahydrofuran were purchased from ALDRICH®, Milwaukee, Wis., and used as received. All other reagents were purchased from SIGMA-ALDRICH®, West Monroe Highland, Ill. Solid phase syntheses were performed on a QUEST® 210 Synthesizer, from ARGONAUT TECHNOLOGIES®, Foster City, Calif., with the aid of combinatorial chemistry equipment, from WHATMAN® POLYFILTRONICS® (Kent, England; Rockland, Mass.) and ROBBINS SCIENTIFIC®, Sunnyvale, Calif. Evaporation of solvents was done using SPEEDVAC® AES, from SAVANT®, Holbrook, N.Y. All necessary chromatographic separations were performed on a WATERS' ALLIANCE HT SYSTEM®, Milford, Mass. Analytical thin-layer chromatography was performed on MERCK® silica gel $60F_{254}$ plates, purchased from SIGMA-ALDRICH®, West Monroe Highland, Ill.

The activation of the Rink-acid resin, the addition of the first amine, and the acylation step were carried out in 10 ml tubes using the QUEST® 210 Synthesizer. The addition of the second amine, the reduction with Red-AL, and the cleavage from the solid support were carried out in 96-deep (2 ml) well, chemically resistant plates.

A. Activation of the Rink-acid Resin

The Rink-acid resin had a coverage of 0.43–0.63 mmol of linker per gram resin. Four to five grams of this resin were suspended in 80 ml of a 2:1 mixture of dichloromethane and tetrahydrofuran (THF), and distributed into ten, 10 ml tubes, with 8 ml of resin suspension per tube. Each suspension was filtered and washed twice with THF. A solution of triphenylphosphine (3.80 g, 14.5 mmol) in 30 ml of THF was prepared, and 3 ml of this solution was added to each tube, followed by the addition of 3 ml of a solution of hexachloroethane in THF (3.39 g/14.3 mmol hexachloroethane in 30 ml THF). After agitation for six hours at room temperature, each activated resin was washed twice with THF and twice with dichloromethane.

B. Addition of the First Amine

Each tube, containing the activated rink resin, was charged with 3 ml of dichloroethane, 0.3 ml (1.74 mmol) $N_1N$-diisopropylethylamine ($EtN(iPr)_2$) and the corresponding amine (around 1 mmol). If the selected amine was a solid at room temperature, it was added as a solution, or a suspension in DMF. Enough dichloroethane was added to each tube for a final volume of 8 ml. The reaction mixture was heated at 45° C. for 6–8 hours. The resins were filtered, washed with a 2:1 mixture of dichloromethane and methanol (1×8 ml), then with methanol (2×8 ml), and then dried under argon for 10 minutes.

C. Acylation with the Halo-acylchloride a. Acylation with Chloroacetyl Chloride. Each resin was prewashed with THF (2×8 ml), and then charged with THF (8 ml), pyridine (0.3 ml, 3.67 mmole) and chloroacetyl chloride (0.25 ml, 2.5 mmole). The reaction mixture was stirred for 8 hours at 45° C., and then for 6–8 hours at room temperature. Each resin was filtered, washed with a 2:1 mixture of dichloromethane/methanol (1×8 ml), methanol (2×8 ml) and THF (2×8 ml). The acylation was repeated using the same loading of reagents, but a shorter reaction time of 4 hours at 45° C., and 2 hours at room temperature. Each resin was then filtered, washed with a 2:1 mixture of dichloromethane and methanol (1×8 ml), and then with methanol (3×8 ml). Each resin was dried under argon for 10 minutes. Each resin was then transferred into a vial and dried in a desiccator under vacuum for 1 hour.

b. Acylation with α-Phenyl-α-Chloroacetyl Chloride. The same procedure set out for the acylation with chloroacetyl chloride was used. A 2.5 mmol excess of α-phenyl-α-chloroacetyl chloride, relative to mmol amount of linker in the rink-acid resin, was used.

c. Acylation with α-Halo-α-Methyl; α-Halo-α-Ethyl and α-Halo-α-Butylacetyl Bromide. A 1:1:1 mixture (by volume) of the α-bromoproponyl bromide ($R_4$=Me), α-bromobutyryl bromide ($R_4$=Et), and α-bromohexanoyl bromide ($R_4$=Bu) was used to give a molar ratio of 0.52:0.56:0.42 (in mmols). This resulted in a molar excess of 1.65, 1.75 and 1.31, respectively, if the original coverage of the resin was 0.63 mmol/g (0.5 g resin per tube), and 2.4, 2.6 and 1.9 if the original coverage of the resins was 0.43 mmol/g (0.5 g resin per tube).

d. Acylation with α-Chloro-α-Methyl Acetic acid. Each resin was prewashed with dichloromethane. Each tube was charged with 3 ml of a solution of PyBrop (0.29 g, 0.62 mmole) in dichloromethane, a solution of the α-chloro-α-methylacetic acid (0.095 g, 0.62 mmole) in 3 ml of DMF, and $EtN(iPr)_2$ (0.2 ml, 1.2 mmole). Each reaction mixture was allowed to react for 16–18 hours at room temperature. Each resin was then filtered, washed with dichcloromethane (2×8 ml) and methanol (2×8 ml), and the acylation was repeated. Each resin was then filtered, washed with dichloromethane (2×8 ml), methanol (3×8 ml), and dried under argon for about 10 minutes. Each resin was transferred into a vial, and dried in a desiccator under vacuum for one hour.

D. Addition of the Second Amine

Ten, or thirty prepared α-haloacetyl amide resins from the first three steps were pooled together, leaving 0.05–0.10 gram of each individual resin for necessary deconvolutions. A suspension of the pooled resin mixture in 100 ml of a 2:1 mixture of dichloromethane and THF was distributed into one, two or three, 96-well reaction plates. For one reaction plate, 1.7 to 2.0 grams of resin were used. For two reaction plates, 3.0 to 3.3 grams of resin were used, and for three reaction plates, 4.7 to 5.0 grams of resin were used. The distributed suspension was then filtered using a filtration manifold, a small lightweight manifold that is generally used for drawing solvents and reagents from the chambers of the 96-well reaction plates. The reaction plates were transferred into COMBICLAMPS® (Huntington, W. Va.), and 10% $EtN(iPr)_2$ in DMF was added at 0.2 ml per well (0.21 mmole of EtN(iPr)$_2$ per well), followed by the addition of a 11.0M solution of the appropriate amine from the corresponding master plate, 0.1 ml per well (0.1 mmole amine per well). The COMBICLAMPS® are used to accommodate 96-well reaction plates during synthesis, allowing for the addition of reagents into the plates, and a proper sealing that maintains reagents and solvents for hours at elevated temperatures. These clamps consist of a top and bottom cover provided with changeable, chemically resistant sealing gaskets. They are designed to accommodate 96-well reaction plates between the top and bottom covers. The reaction plates were sealed and kept in an oven at 70–75° C. for 16 hours. After cooling to room temperature, the resins were filtered, washed with a 1:1 mixture of DCM/methanol (1×1 ml), methanol (2×1 ml), and then dried in a desiccator under vacuum for 2 hours.

E. Reduction with Red-Al

The reaction plates were placed into COMBICLAMPS®. A 1:6 mixture of Red-Al (65+w % in toluene) and THF was added, at 0.6 ml per well (0.28 mmole of Red-Al per well), and allowed to react for 4 hours. Each resin was then filtered, washed with THF (2×1 ml), and methanol (3×1 ml). The addition of methanol should proceed with caution. Each resin was then dried under vacuum.

F. Cleavage of Final Ethylene Diamine Compound

This step was carried out using a cleavage manifold, a Teflon coated aluminum, filter/collection vacuum manifold, designed for recovering cleavage products from the reaction plates into collection plates. The manifold is designed to ensure that the filtrate from each well is directed to a corresponding well in a receiving 96-well collection plate. The reaction plates (placed on the top of the collection plates in this manifold) were charged with a 10:85:5 mixture of TFA, dichloromethane, and methanol (0.5 ml of mixture per well). After fifteen minutes, the solutions were filtered and collected into proper wells on the collection plates. The procedure was repeated. Solvents were evaporated on a SPEED VAC®, Holbrook, N.Y., and the residual samples (TFA salts) were tested without further purification.

EXAMPLE II

Deconvolution Example

Deconvolution of the active wells was performed by re-synthesis of discrete compounds, from the archived α-haloacetyl amide resins (10 resins, 0.05–0.10 g each), which were set aside at the end of the acylation step before the pooling. Each resin was assigned a discrete column (1, or 2, or 3, etc., see the template) in a 96 well filterplate, and was divided between X rows (A, B, C, etc), where X is the number of hits discovered in the original screening plate. To each well, in a row, a selected N2 (R$_3$R$_2$NH) hit amine (0.1 mmol), DMF (180 ml) and EtNiPr$_2$ (20 ml) were added: the first selected amine was added to the resins in the row "A", the second amine—to the resins in the row "B", the third amine—to the resins in the row "C", etc. A lay-out of a representative 96-well filter plate is shown in Table 4.

The reaction plates were sealed and kept in an oven at 70–75° C. for 16 hours. After cooling to room temperature, the resins were filtered, washed with a 1:1 mixture of DCM and methanol (1×1 ml), methanol (2×1 ml), and dried in desiccator under vacuum for 2 h. Reduction and cleavage were performed according to steps 5 and 6 in the original synthetic protocol. The product wells from the cleavage were analyzed by ESI-MS (Electro Spray Ionization Mass Spectroscopy) to ensure the identity of the actives, and were tested in the same Luc and MIC assays.

TABLE 4

Lay-Out of Representative 96-Well Filter Plate

| | | | | | | | | | | |
|---|---|---|---|---|---|---|---|---|---|---|
| A1 | A2 | A3 | A4 | A5 | A6 | A7 | A8 | A9 | A10 | Selected amine N2, Added to A1–A10 |
| B1 | B2 | B3 | B4 | B5 | B6 | B7 | B8 | B9 | B10 | Selected amine N2, Added to B1–B10 |
| C1 | C2 | C3 | C4 | C5 | C6 | C7 | C8 | C9 | C10 | Selected amine N2, Added to C1–C10 |
| D1 | D2 | D3 | D4 | D5 | D6 | D7 | D8 | D9 | D10 | Selected amine N2, Added to D1–D10 |
| E1 | E2 | E3 | E4 | E5 | E6 | E7 | E8 | E9 | E10 | Selected amine N2, Added to E1–E10 E1–E10 |
| F1 | F2 | F3 | F4 | F5 | F6 | F7 | F8 | F9 | F10 | Selected amine N2, Added to F1–F10 |
| G1 | G2 | G3 | G4 | G5 | G6 | G7 | G8 | G9 | G10 | Selected amine N2, Added to G1–G10 |
| H1 | H2 | H3 | H4 | H5 | H6 | H7 | H8 | H9 | H10 | Selected amine N2, Added to H1–H10 |

*X* selected Amines N2

TABLE 4-continued

Lay-Out of Representative 96-Well Filter Plate

| Resin #1 | Resin #2 | Resin #3 | Resin #4 | Resin #5 | Resin #6 | Resin #7 | Resin #8 | Resin #9 | Resin #10 | to be added on the step 4 Individual Resins #1–10, preloaded with proper amine N1. |
|---|---|---|---|---|---|---|---|---|---|---|

EXAMPLE III

Solid-Phase Synthesis of Selected Substituted Ethylenediamine Compounds Using the QUEST® 210 Synthesizer The solid-phase protocol described above in Example I was applied to the scaled-up synthesis of the selected substituted ethylene diamine compounds. Here, all reaction steps, from the activation of the Rink-acid resin to the cleavage of the final product, were carried out using the QUEST® instrument only, which allowed for the simultaneous syntheses of twenty parallel reactions. Purification of all crude samples was done by HPLC to yield desirable products in purity greater than 90%. Table 3 lists the scale-ups of substituted ethylene diamines. Here, the synthesis of one of the active compounds, N-Geranyl-N'-(2-adamanthyl)ethane-1,2-diamine is described below as an example.

Figure 12:
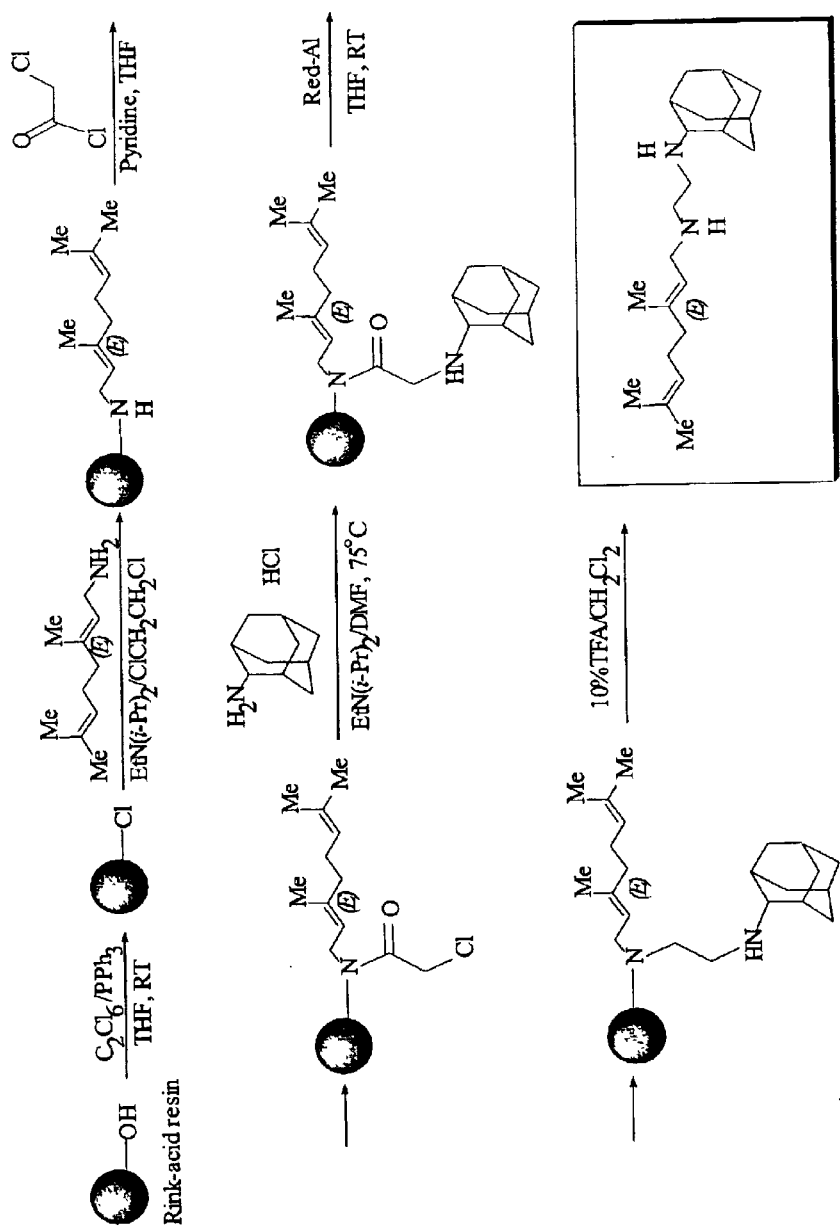
FIG. 12 represents a flow schematic showing a synthesis of N-Geranyl-N'-(2-adamanthyl)ethane-1,2-diamine (compound 109).

The Preparation of N-Geranyl-N'-(2-adamanthyl)ethane-1,2-diamine (compound 109) is set forth in FIG. 12.

Compound 109

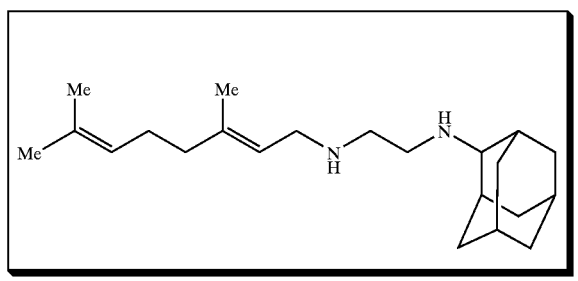

1. Activation of the Rink-acid resin. Synthesis of Rink-Cl resin. Rink-acid resin, coverage (linker) of 0.43 to 0.63 mmol/g (0.8 g, 0.5 mmol), was placed into one of the 10 ml tubes of QUEST® 210 Synthesizer, and washed twice with THF. A solution of triphenylphosphine (0.380 g, 1.45 mmol) in THF (3 ml) was added, followed by the addition of a solution of hexachloroethane (0.4 g, 1.43 mmol) in THF (3 ml). THF was added up to the volume of the tube (approximately 2 ml). After 6 hours, the resin was filtered, washed with THF (2×8 ml) and dichloromethane (2×8 ml).

2. Addition of the first amine. Synthesis of resin attached geranylamine. The tube with activated resin was charged with 3 ml of dichloroethane, EtN(iPr)$_2$, (0.3 ml, 1.74 mmol), and geranylamine (0.230 g, 1.5 mmol). Dichloroethane was added to a volume of 8 ml. The reaction was carried for 8 hours at 45° C., and for 6–8 hours at room temperature. Geranylamine loaded resin was filtered, washed with a 2:1 mixture of dichloromethane and methanol (1×8 ml), then with methanol (2×8 ml), and suck dried for 10 minutes under argon.

3. Acylation with chloroacetyl chloride. Synthesis of resin attached N-Geranyl-α-chloroacetamide. The resin was prewashed with THF (2×8 ml). The tube was charged with 8 ml of THF, pyridine (0.3 ml, 3.67 mmol), and chloroacetyl chloride (0.2 ml, 2.5 mmol), and allowed to stir for 8 h at 45° C., and 6–8 h at room temperature (RT). After the reaction was complete, the resin was filtered, washed with a 2:1 mixture of dichloromethane and methanol (1×8 ml), methanol (2×8 ml), and THF, and the acylation was repeated using the same loads of the reagents, but shorter reaction time: 4 hours at 45° C. and 2 hours at room temperature. At the end, the α-chloroacetamide loaded resin was filtered, washed with a 2:1 mixture of dichloromethane and methanol (1×8 ml), methanol (3×8 ml), and suck dried for 15 min under argon.

4. Addition of the second amine. Synthesis of resin attached N-Geranyl-N'-(2-adamantyl)acetamide. The tube with the resin was charged with DMF (3 ml) and EtN(iPr)$_2$ (0.6 ml, 4.4 mmol), followed by the addition of a suspension of 2-adamantamine hydrochloride (2.0 g, 1.1 mmol) in DMF (4 ml), and was allowed to stir at 70–75° C. for 16 hours. After cooling down to the room temperature, the resin was filtered, washed with a 1:1 mixture of DCM and methanol (1×8 ml), methanol (2×8 ml), and suck dried for 15 minutes under argon.

5. Reduction with Red-Al. Synthesis of resin attached N-Geranyl-N'-(2-adamantyl)ethane-1,2-diamine. The resultant resin was suspended in anhydrous THF (3 ml) in a tube, and stirred for 15 min. Commercially available Red-Al, 65+w % in toluene, was added (2.0 ml, 6.4 mmol), followed by addition of 2–3 ml of anhydrous THF (to fill up the volume of the tube). The mixture was allowed to react for 4 hours. After the reaction, the resin was filtered, washed with THF (1×8 ml), a 1:1 mixture of THF and methanol (1×8 ml) (addition of MeOH should proceed with caution), methanol (3×8 ml), and then dried.

6. Cleavage from the resin and purification. Synthesis of N-Geranyl-N'-(2-adamanthyl)ethane-1,2-diamine acetate. For this last step of the synthesis, the tube with the resin was charged with a 10:90 mixture of TFA and dichloromethane, and the formed bright red suspension was allowed to stir for 30 min. After addition of MeOH (0.5 ml), the colorless suspension was filtered, and the filtrate was collected into a proper tube. The procedure was repeated, and solvents were evaporated on a SPEED-VAC®. Half of the amount of crude N-Geranyl-N'-(2-adamanthyl)ethane-1,2-diamine (in a form of trifluoroacetate salt) was purified by HPLC using following conditions: column C18, flow 4 ml/min, 30 min run, gradient starting with 5% AcOH/MeOH (100%) finishing up with acetonitrile (100%). Obtained: 27 mg of N-Geranyl-N'-(2-adamanthyl)ethane-1,2-diamine diacetate, 24% yield, 98% purity by NMR.

EXAMPLE IV

Representative Solution Phase Synthesis of the Active Compounds

Figure 13:
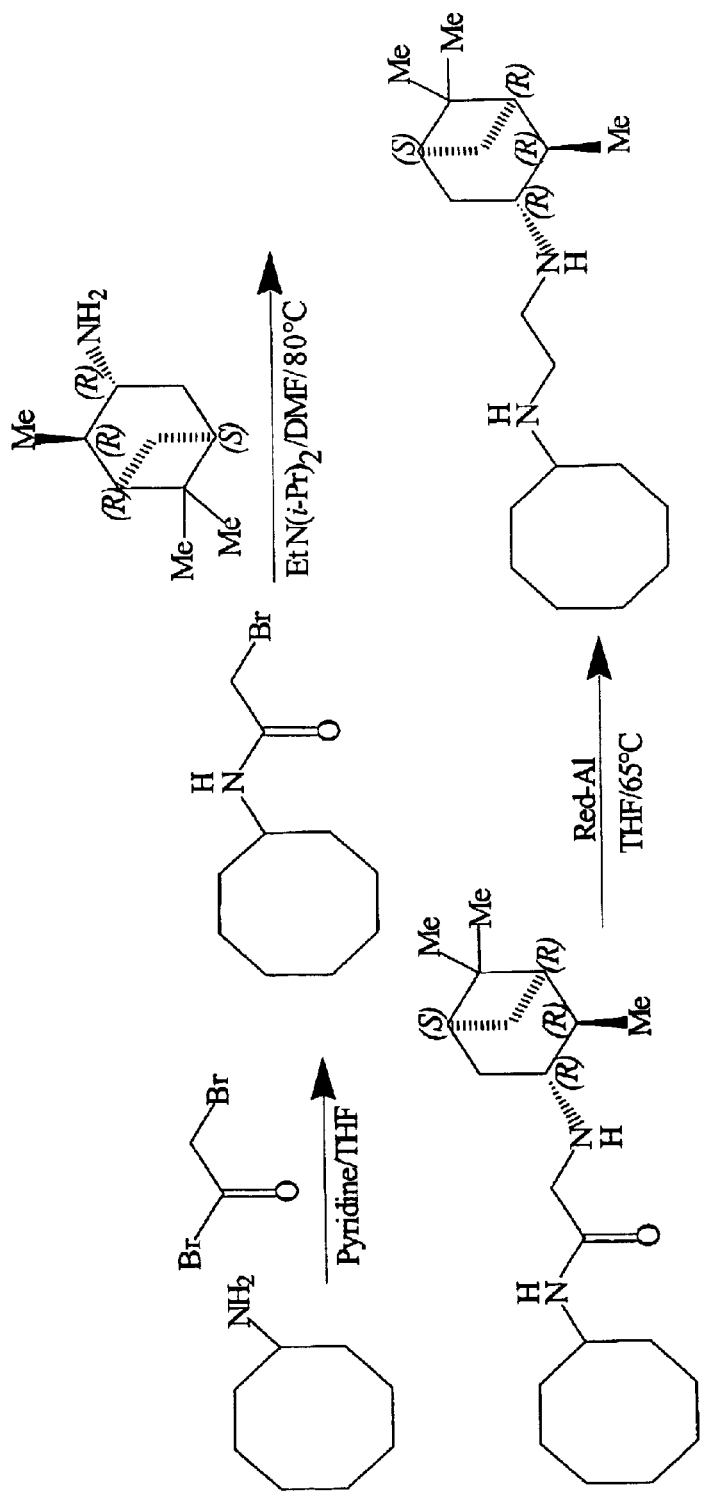
FIG. 13 is a flow schematic showing a synthesis of N-(Cyclooctyl)-N'-(1R,2R,3R,5S)-(−)-isopinocampheylethane-1,2-diamine as hydrochloride (compound 59).

Preparation of N-(Cyclooctyl)-N'-(1R,2R,3R,5S)-(−)-isopinocampheylethane-1,2-diamine as hydrochloride (compound 59) is set forth in FIG. 13.

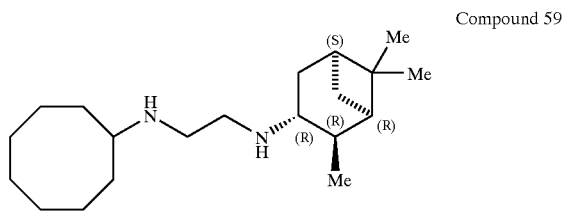

Compound 59

Bromocyclooctylacetylamide. To a mixture of cyclooctylamine (3.3 g, 0.026 mol) and pyridine (2.42 g, 0.031 mmol) in anhydrous THF (80 ml) at 0° C. was added dropwise, via syringe, bromoacetylbromide (5.78 g, 0.029 mol). The reaction temperature was maintained by an ice bath. The reaction mixture was allowed gradually to warm up to room temperature, and was stirred at room temperature for 1 hour. The precipitate was removed by filtration, washed with ethyl ether (1×30 ml), and the filtrate was concentrated to dryness on a rotory evaporator. Bromocyclooctylacetylamide was forwarded to the second step without additional purification.

N-(Cyclooctyl)-N'-(1R,2R,3R,5S)-(−)-isopinocampheyl-1-carbonylethane-1,2-diamine. To a solution of the bromocyclooctylacetylamide in DMF (60 ml) were added Hunig's base (4.64 g, 0.036 mol) and (1R,2R,3R,5S)-(−)-isopinocampheylamine (4.5 g, 0.029 mol), and the reaction mixture was stirred at 80° C. for 16 hours. After cooling off to the room temperature, the reaction mixture was diluted with 150 ml of ethyl ether, and washed with 1M NaOH solution (2×50 ml). The organic layer was washed with brine (1×50 ml), dried over MgSO$_4$, and concentrated to dryness on the rotory evaporator. The residue (11.04 g) as brown oil was purified on COMBIFLASK® (Isco, Lincoln, Nebr., USA), using Silicagel catridges commercially available from BIOTAGE® (Biotage, Inc. of Dyax Corp, Va, USA), and the following mobile phase gradient: 30 min run, starting with DCM, 100%, and finishing up with a mixture DCM:MeOH:NH$_4$OH (600:400:10). The final product (7.29 g) was obtained as a brown oil; 76% yield, purity 90%.

N-(Cyclooctyl)-N'- (1R,2R,3R,5S)-(−)- isopinocampheyl ethane-1,2-diamine. To a solution of the amide, from previous step, in anhydrous THF (160 ml), was added dropwise via syringe commercially available (SIGMA-ALDRICH®) Red-Al, as 65 wt % solution in THF (28 ml, 0.09 mol). The reaction mixture was stirred at reflux for 20 hours. After cooling down to the room temperature, the reaction mixture was poured into 1.5M NaOH (200 ml), and extracted with ethyl ether (2×100 ml). The organic layer was washed with brine (1×100 ml), dried over MgSO$_4$, and evaporated to dryness on the rotory evaporator to yield 7.2 g of a crude product, as a brown oil. Chromatographic purification of the crude using the same equipment and conditions as for the previous step, gave 3.5 g of the diamine. The diamine was treated with 2.0M solution of HCl in ethyl ether (25 ml), and kept in a refrigerator overnight. A dark yellow solid (4.2 g) formed, and was filtered off, and recrystallized from MeOH and ethyl ether to yield 1.5 g of the diamine as an HCl salt (of purity greater than 98%, NMR and MS are available), 19% overall yield.

EXAMPLE V

Mass Spectroscopy Analysis

Mass spectra data were obtained by Elecrospray Ionization technique on a PERKIN ELMER®/SCIEX®, API-300, TQMS with an autosampler, manufactured by SCIEX®, Toronto, Canada.

A. Library of Substituted Ethylenediamines

Mass spectroscopy served as a means for monitoring the reaction results of the library of ethylenediamines. Mass spectroscopy was done on two randomly selected rows (24 samples) per reaction plate, for roughly 28,000 compounds in pool of 10 or 30 compounds per well. Thus, if ten compounds per well were synthesized, the mass spectra for each well should contain ten signals, correlating with the proper molecular ions for each compound. The presence or absence of a particular signal indicated the feasibility of the particular synthesis. Based on the mass spectral data, and on a general analysis of the reactivity of the various amines, it is estimated that 67,000 compounds were formed out of 112,000 compounds.

Figure 14:
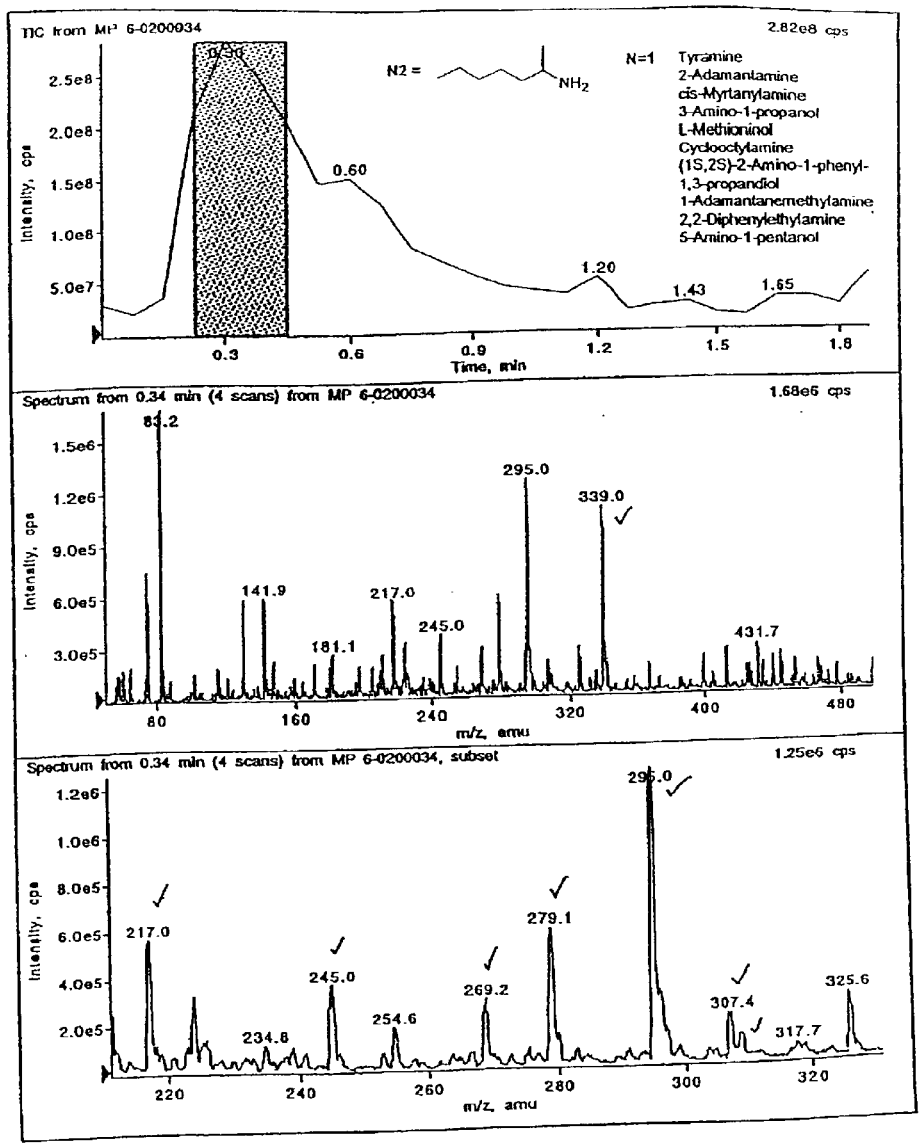
FIG. 14 is a mass spec profile for one representative sample well containing pooled substituted ethylene diamine compounds.
Figure 15:
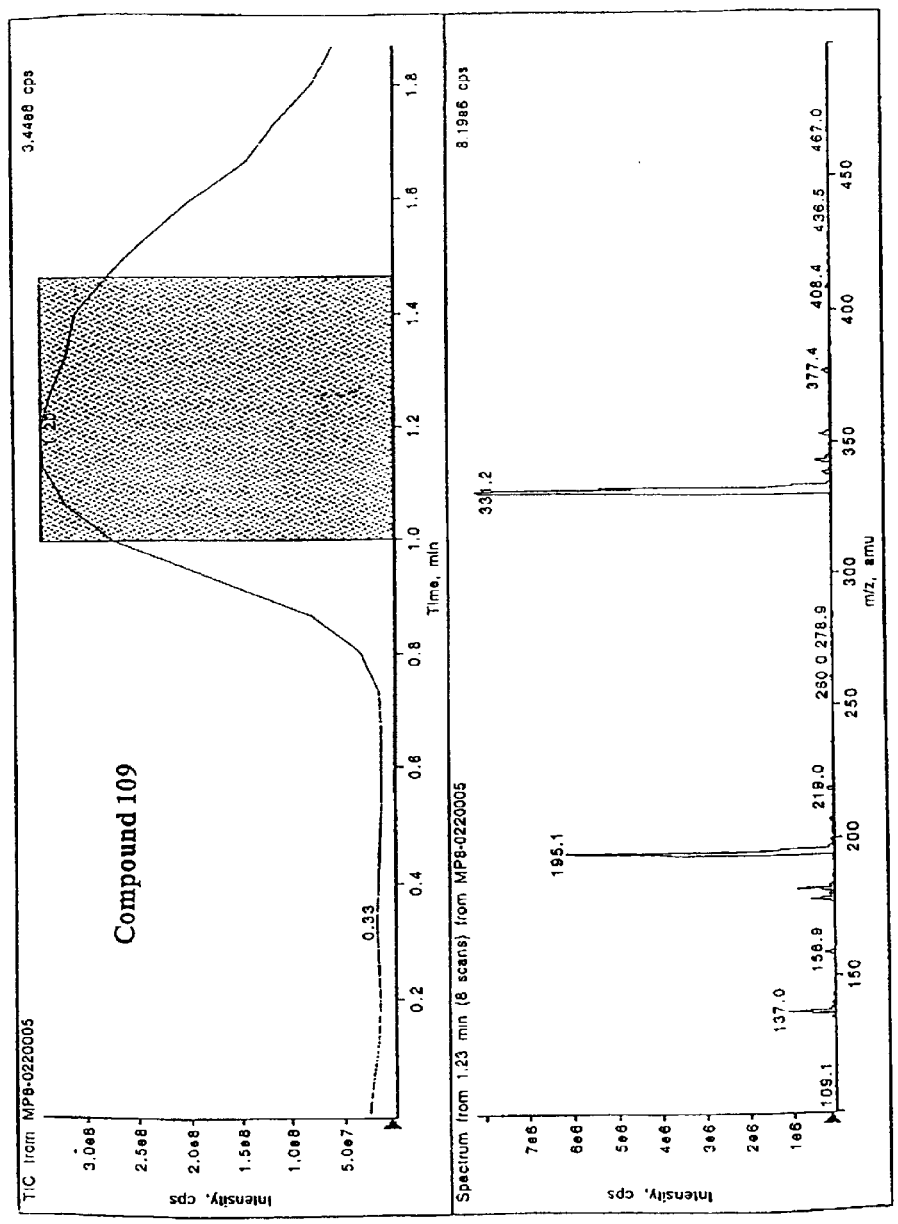
FIG. 15 is a mass spec profile for compound 109, N-Geranyl-$N^1$-(2-adamanthyl)ethane-1,2-diamine.

FIG. 14 is a representative mass spec profile for one sample well. Mass spectra for a representative ethylene diamine compound is shown in FIG. 15. Tables 5 to 8, below, list illustrative examples of mass spec data for representative reaction wells, with each well containing ten substituted ethylene diamines.

TABLE 5

ILLUSTRATIVE EXAMPLES OF MASS SPEC DATA FOR REPRESENTATIVE ETHYLENEDIAMINES (TEN COMPOUNDS PER WELL).

| $R_1NH_2$ in the 1$^{st}$ position (pool of 10 resins) | $R_2R_3NH$ in the 2$^{nd}$ position (from the master plate of the amines) | [M + 1]$^+$ of the product $R_1NHCH_2CH_2NR_2R_3$ |
|---|---|---|
| Plate #4-034-2, well D10 | | |
| 1-(2-Aminoethyl)piperidine | 2-Aminoheptane | 270 absent |
| Phenethylamine | | 263 |
| 4-(2-Aminoethyl)morpholine | | 272 absent |
| Tryptamine | | 302 |
| Cyclohexylamine | | 241 |
| Exo-2-Aminonorbomane | | 253 |
| Benzylamine | | 249 |
| 2-Fluorophenethylamine | | 281 |

TABLE 5-continued

ILLUSTRATIVE EXAMPLES OF MASS SPEC DATA FOR
REPRESENTATIVE ETHYLENEDIAMINES
(TEN COMPOUNDS PER WELL).

| $R_1NH_2$ in the 1$^{st}$ position (pool of 10 resins) | $R_2R_3NH$ in the 2$^{nd}$ position (from the master plate of the amines) | $[M + 1]^+$ of the product $R_1NHCH_2CH_2NR_2R_3$ |
|---|---|---|
| ? -Methylphenethylamine | | 277 |
| 4-Methoxyphenethylamine | | 293 |
| Plate #4-56-1, well C4 | | |
| 4-Methylbenzylamine | exo-2-Aminonorbornane | 259 |
| Cyclopentylamine | | 223 |
| 2-(Aminomethyl)piperidine | | 246 low intensity |
| Furfurylamine | | 235 |
| 3,4,5-Trimethoxybenzylamine | | 335 |
| 1-Methyl-3-phenylpropylamine | | 287 |
| Cylcobutylamine | | 209 |
| 1,2,3,4-Tetrahydro-1-naphthylamine | | 258 |
| 2,3-Dimethylcyclohexylamine | | 265 |
| 2-Amino-1-butanol | | 227 low intensity |
| Plate #4-44-2, well G1 | | |
| Veratrylamine | 4-Fluorophenethylamine | 333 |
| 2-(1-Cyclohexenyl)ethylamine | | 291 |
| 5-Aminoquinolone | | 310 absent |
| 1-(1-Naphthyl)ethylamine | | 337 absent |
| 1-Aminopiperidine | | 266 |
| 3-Fluorobenzylamine | | 291 |
| 2,4-Dimethoxybenzylamine | | 333 |
| 3-Amino-1,2,4-triazine | | 262 absent |
| 2-Ethoxybenzylamine | | 317 |
| 4-(3-Aminopropyl)morpholine | | 310 absent |

TABLE 6

Mass Spec Data for Synthesized Ethylenediamines

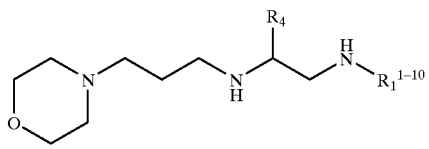

| $R_1NH_2$ in the 1$^{st}$ position | $[M + 1]^+$ of the products, $R_4 = H$ | $[M + 1]^+$ of the products, $R_4 = Ph$ | |
|---|---|---|---|
| | | Diamines, 1 | Amino alcohols, 13 |
| Tyramine | 308 | 384 | 258 formed |
| 2-Adamantamine | 321 absent | 398 absent | 272 formed |
| cis-Myrtanylamine | 324 | 400 | 274 formed |
| 3-Amino-1-propanol | 246 | 322 | 196 absent |
| L-Methioninol | 305 absent | 382 absent | 256 absent |
| Cyclooctylamine | 298 | 374 | 248 formed |
| (1S,2S)-2-Amino-1-phenyl-1,3-propandiol | 337 absent | 414 absent | 288 absent |
| 1-Adamantanemethylamine | 336 | 412 absent | 286 formed |
| 2,2-Diphenylethylamine | 368 | 444 | 318 formed |
| 5-Amino-1-pentanol | 274 | 350 | 224 formed |

TABLE 7

Mass Spec Data for Synthesized Ethylenediamines, $R_4$ = H and Me

| $R_1NH_2$ in the 1st position | [M + 1]+ of the products, $R_4$ = H | [M + 1]+ of the products, $R_4$ = Me Diamines, 1 | Amino alcohols, 13 |
|---|---|---|---|
| Tyramine | 278 | 293 | 196 absent |
| 2-Adamantamine | 293 absent | 307 absent | 210 low intensity |
| cis-Myrtanylamine | 293 | 309 | 212 formed |
| 3-Amino-1-propanol | 217 | 231 | 134 absent |
| L-Methioninol | 277 absent | 291 absent | 194 formed |
| Cyclooctylamine | 269 | 269 absent | 186 absent |
| (1S,2S)-2-Amino-1-phenyl-1,3-propandiol | 309 low intensity | 323 absent | 226 formed |
| 1-Adamantanemethylamine | 307 | 321 | 224 formed |
| 2,2-Diphenylethylamine | 339 | 353 | 256 formed |
| 5-Amino-1-pentanol | 245 | 259 | 162 absent |

TABLE 8

Mass Spec Data for Synthesized Ethylenediamines, $R_4$ = H and Me

| $R_1NH_2$ in the 1st position | [M + 1]+ of the products, $R_4$ = H | [M + 1]+ of the products, $R_4$ = Me Diamines, 1 | Amino alcohols, 13 |
|---|---|---|---|
| Tyramine | 278 | 292 absent | 196 absent |
| 2-Adamantamine | 292 absent | 306 absent | 210 formed |
| cis-Myrtanylamine | 294 | 308 absent | 212 formed |
| 3-Amino-1-propanol | 216 | 230 absent | 134 absent |
| L-Methioninol | 276 absent | 290 absent | 194 absent |
| Cyclooctylamine | 268 | 282 absent | 186 absent |
| (1S,2S)-2-Amino-1-phenyl-1,3-propandiol | 308 | 322 absent | 226 formed |
| 1-Adamantanemethylamine | 306 absent | 320 absent | 224 formed |
| 2,2-Diphenylethylamine | 338 | 352 absent | 256 formed |
| 5-Amino-1-pentanol | 244 | 258 absent | 162 absent |

EXAMPLE VI

1H NMR Spectroscopy

Proton NMR data was recorded on a VARIAN® Nuclear Magnetic Resonance Spectrometer (Palto Alto, Calif.) at 500 MHz.

Figure 16:
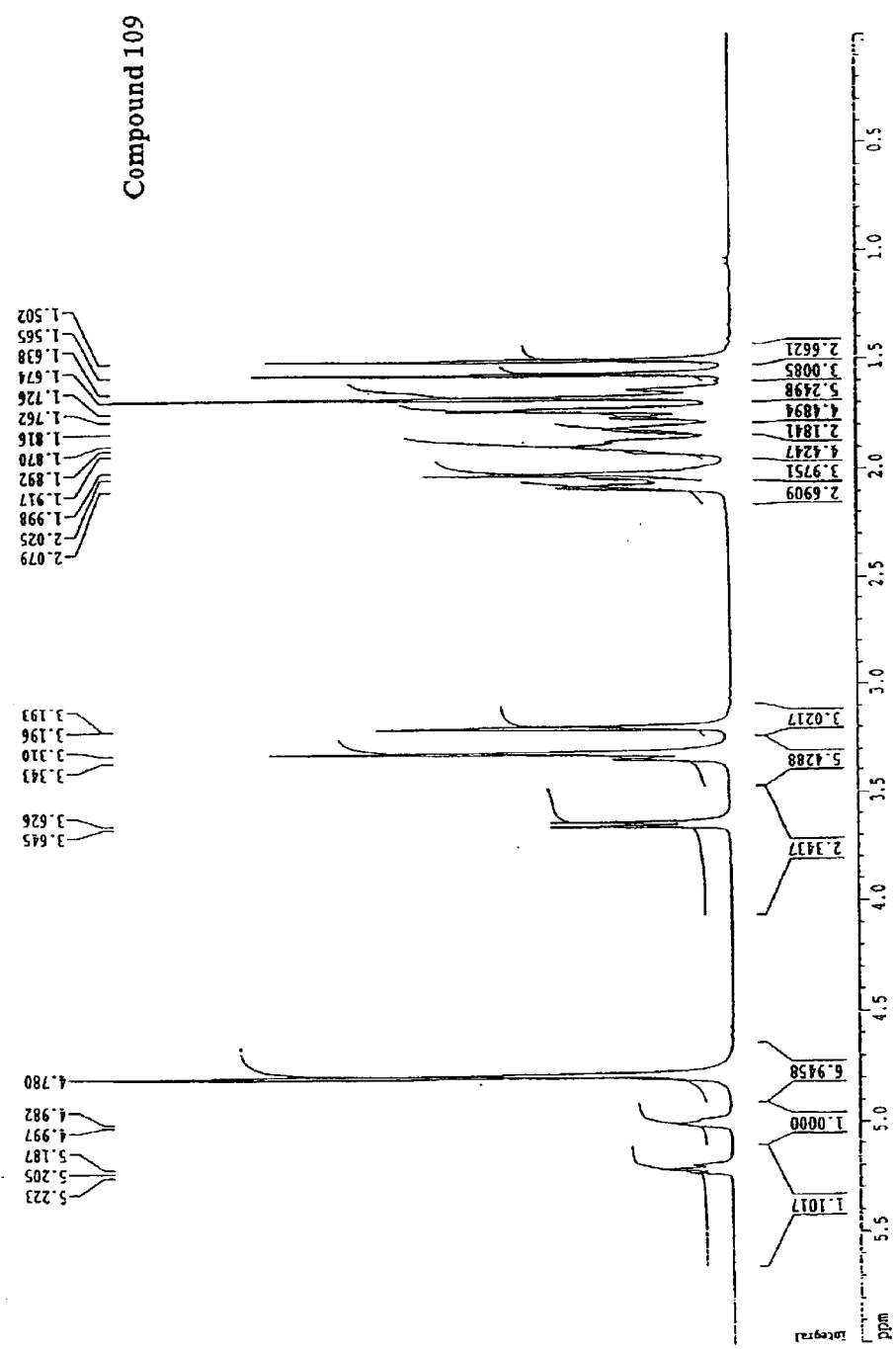
FIG. 16 is a proton NMR profile for compound 109, N-Geranyl-$N^1$-(2-adamanthyl)ethane-1,2-diamine.
Figure 17:
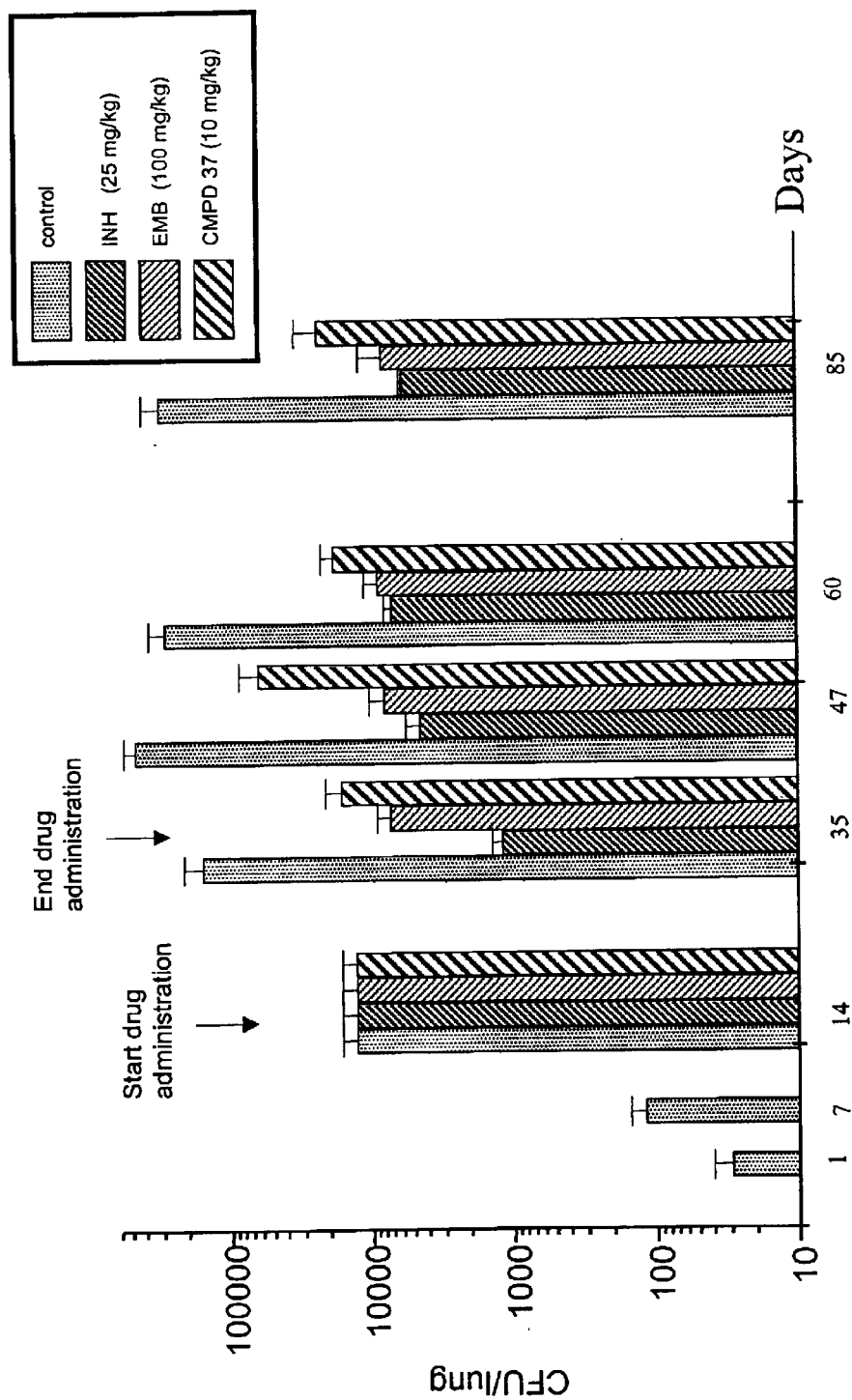
FIG. 17 is a bar graph of data from a Colony Forming Units/Lung (CFU/Lung) study showing CFU/Lung growth over time in days for various compounds.
Figure 18:
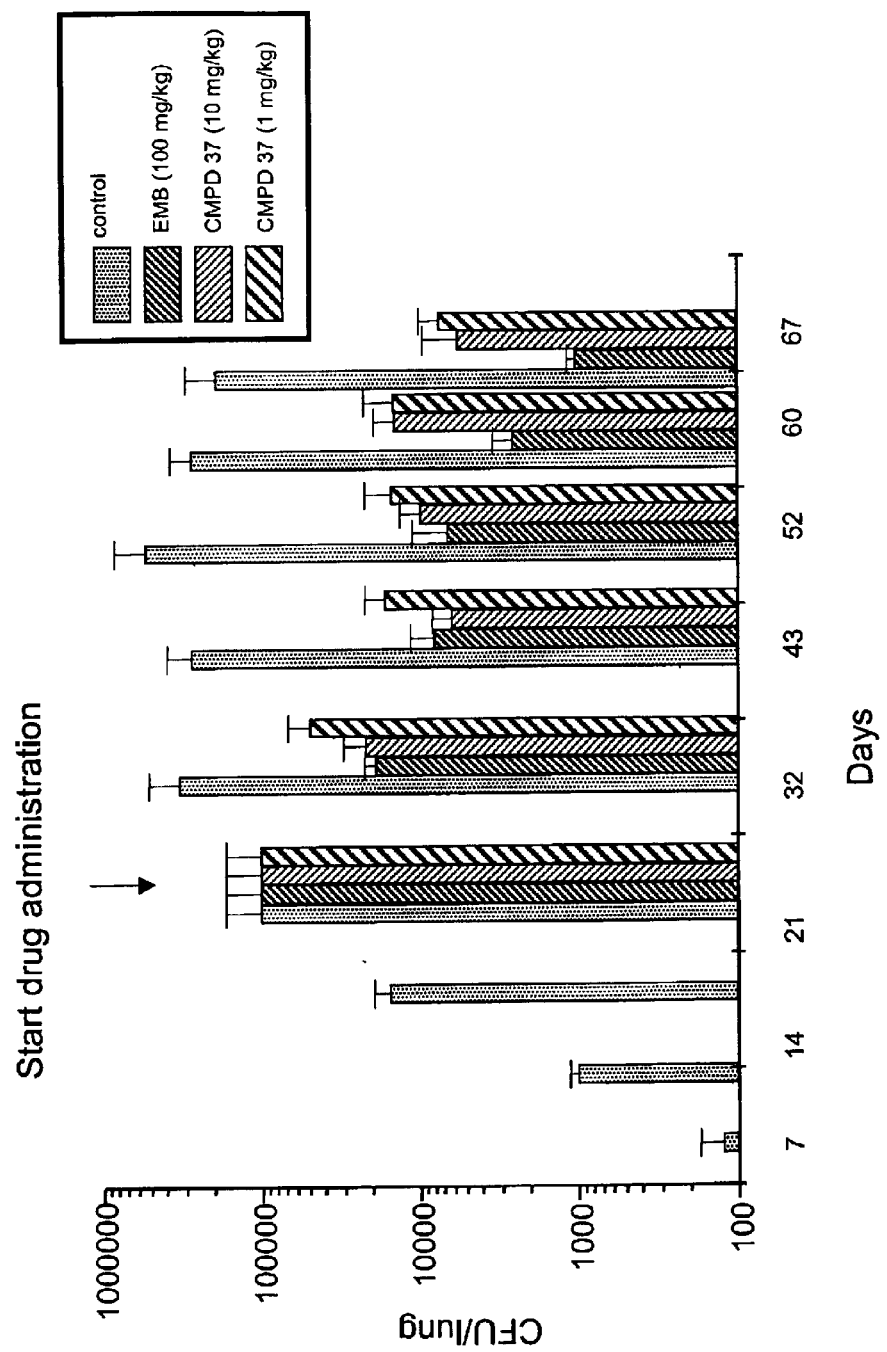
FIG. 18 is a bar graph of data from a CFU/Lung study showing CFU/Lung growth over time in days for various compounds.
Figure 19:
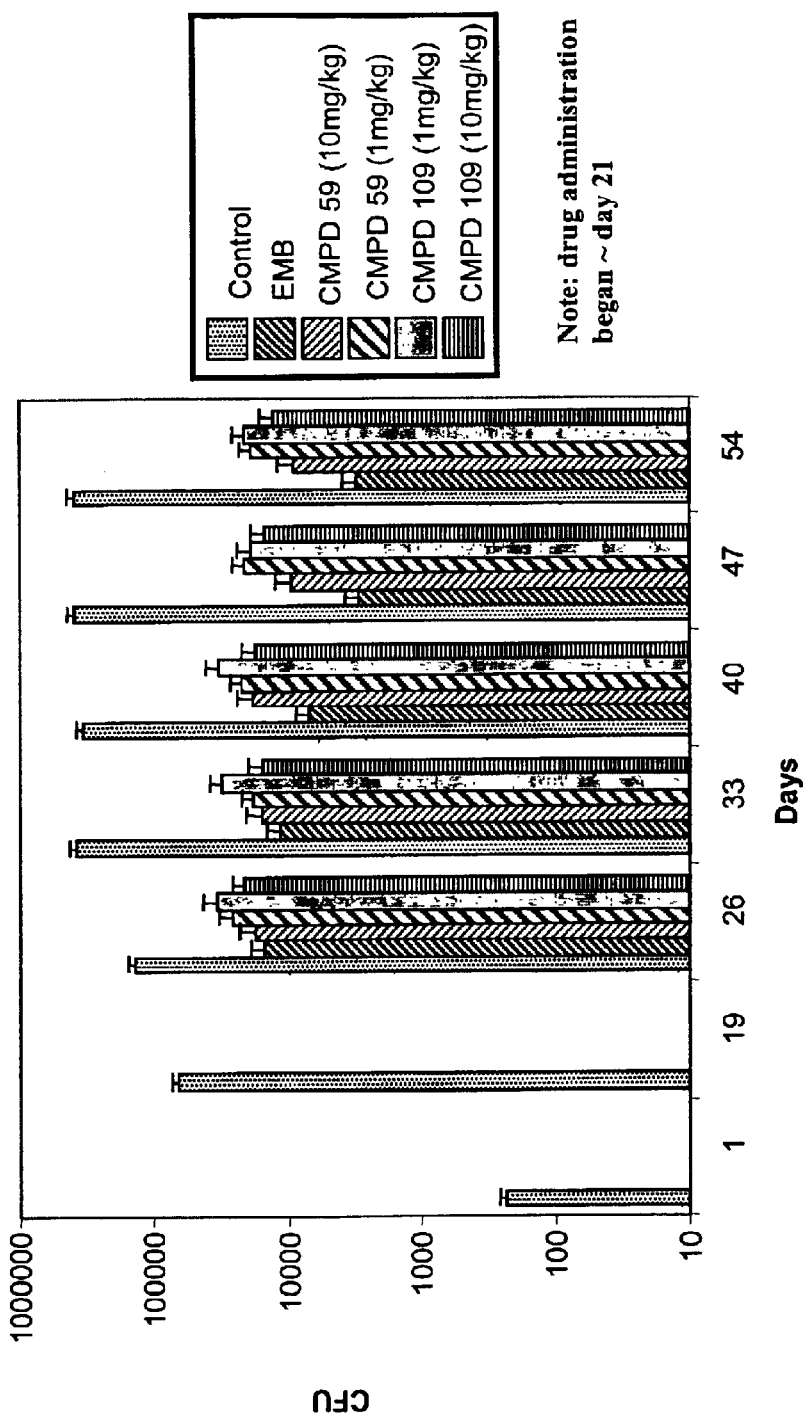
FIG. 19 is a bar graph of data from a CFU/Lung study showing CFU/Lung growth over time in days for various compounds.
Figure 20:
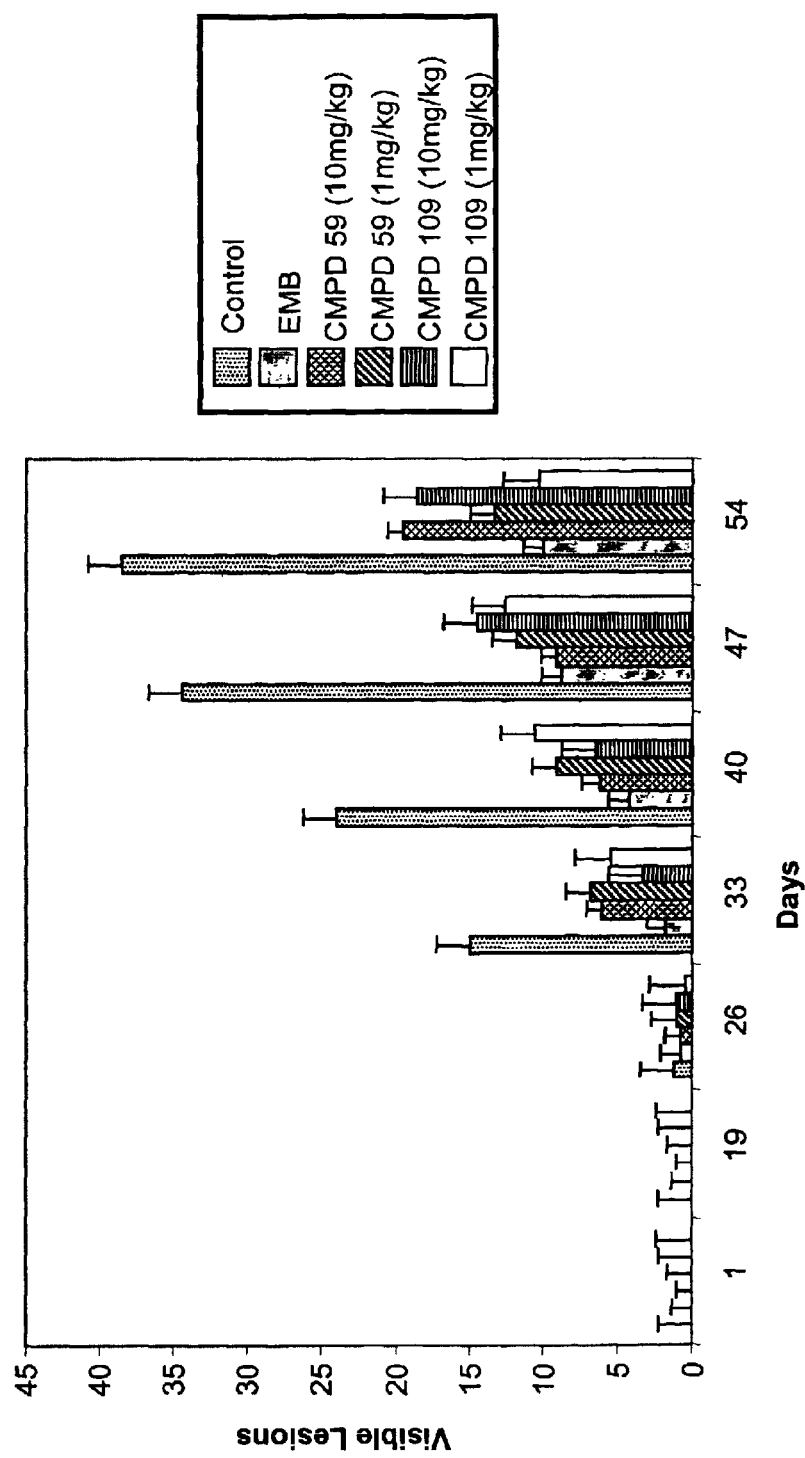
FIG. 20 is a bar graph of data from a lesion study showing visible lesions over time after treatment with various compounds.

Representative substituted ethylene diamines were purified by HPLC, and analyzed by proton NMR. A representative proton NMR profiles is shown in FIG. 16. NMR and MS data for some representative hit compounds are shown below.

Compound 6
$N^2$-(1-Adamantylmethyl)-$N^1$-(3,3-diphenylpropyl)propane-1,2-diamine. 55 mg, 36% yield. 1H NMR: δ 7.28–7.15 (m, 5H), 3.95 (t, J=7.9 Hz, 1H), 2.94 (br s 4H), 2.71 (dd, J=7.6, 9.8 Hz, 2H), 2.41 (s, 2H), 2.32 (dd, J=7.6, 7.9 Hz, 2H), 2.16 (s), 2.08–1.98 (m, 4H), 1.72 (m, 6H), 1.62 (m, 6H), 1.51 (d, J=2.4 Hz, 3H). Mass spectrum (ESI) m/z (MH)+ 417.

Compound 7
N-(3,3-Diphenylpropyl)-N'-(1-adamantylmethyl)ethane-1,2-diamine. 28 mg, 22% yield. 1H NMR (500 MHz) δ 7.30–7.12 (m, 10H); 3.95 (t, J=7.6 Hz, 1H); 2.91 (d, J=1.2 Hz, 4H); 2.70 (dd, J=7.6 and 1.2 Hz, 2H); 2.40 (d, J=1.3 Hz, 2H); 2.32 (q, J=8.0 Hz, 2H); 1.98 (br d, J=1.7 Hz, 4H); 1.72 (d, J=12.2 Hz, 4H); 1.62 (d, m? J=12.2 Hz, 4H); 1.51 (br s, 6H). Mass spectrum (ESI) m/z (MH)+ 403.6.

Compound 10
N-(−)-cis-Myrtanyl-N'-(3,3-diphenylpropyl)ethane-1,2-diamine. 14 mg, 11% yield. 1H NMR (500 MHz) δ 7.30–7.10 (m, 10H); 3.95 (m, 1H); 2.92–2.83 (m, 4H); AB: 2.80 (d, J=7 Hz, 1H); 2.76 (d, J=8 Hz, 1H); 2.65 (dd, J=9.6 and 7.6 Hz, 2H); 2.42–2.20 (m, 4H), 2.29 (d, J=8 Hz, 2H), 1.90 (m, 8H); 1.42 (m, 1H); 1.19 (m, 2H); 1.17 (s, 3H); 0.95 (s, 3H); 1.00–0.8 (m, 2H). Mass spectrum (ESI) m/z (MH)+ 391.3.

Compound 14
N-(3,3-Diphenylpropyl)-N'-exo-(2-norborny)ethane-1,2-diamine. 17 mg, 16% yield. 1H NMR (500 MHz) δ 7.30–7.15 (m, 10 H); 3.95 (t, J=7.9 Hz, 1H); 2.86 (dd, J=11.5 and 1.5 Hz, 4H); 2.73 (dd, J=8.0 and 3.3 Hz, 1H); 2.64 (t, J=7.6 Hz, 2H); 2.29 (t, J=7.5 Hz, 2H); 2.31–2.26 (m, 2H) 2.30 1.96 (s, 3H); 1.63 (ddd, J=13.1, 7.9 and 2.5

Hz, 1H); 1.60–1.50 (m, 1H); 1.50–1.43 (m, 2H); 1.30 (dq, J=4.0 and 13.5 Hz, 1H), (1H, m), 1.20 (dd, J=10.4 and 1.1 Hz, 1H), 1.11 (dd, J=2.0, and 8.5 Hz, 1H), 1.08 (dd, J=2.5, and 8.5 Hz, 1H), 1.10 (dq, J=8.3 and 2.1, 2H). Mass spectrum (ESI) m/z (MH)+ 349.1.

Compound 21
N-(3,3-Diphenylpropyl)-N'-(1S)-(1-ethylcyclohexane)ethane-1,2-diamine. 5 mg, 4% yield. Mass spectrum (ESI) m/z (MH)+ 365.5.

Compound 32
N-(2,2-Diphenylethyl)-N'-®-(+)-bornylethane-1,2-diamine. 58 mg, 48% yield. 1H NMR (500 MHz): δ 7.30–7.10 (m, 10H); 4.18 (t, J=6.8 Hz, 1H); 3.34 (d, J=7.6 Hz, 2H); 3.02 (m, 4H); 2.95–2.90 (m, 1H); 2.15–2.08 (m, 1H); 1.94 (m, 1H); 1.72–1.65 (m, 2H); 1.48–1.30 (m, 2H); 1.27–1.10 (m, 2H); 1.06 (dd, J=13.6 and 4.1 Hz, 1H); 0.82 (s, 3H); 0.81 (s, 3H); 0.78 (s, 3H). Mass spectrum (ESI) m/z (MH)+ 377.2

Compound 34
N-(2,2-Diphenylethyl)-N'-(1-adamanthylmethyl)ethane-1,2-diamine. 6.8 mg, 6% yield. 1H NMR (500 MHz) δ 7.30–7.15 □m, 10H); 4.15 (t, J=7.6 Hz, 1H); 3.24 (dd, J=7.9 and 1.2 Hz, 2H); 2.79 (t, J=6.5 Hz, 2H); 2.74 (t, J=6.0 Hz,m, 2H); 1.95 (m, 8H); 1.69 (d, J=12.5 Hz, 4H); 1.59 (d, J=11.9 Hz, 4H); 1.40 and 1.39 (br s, 3H); Mass spectrum (ESI) m/z (MH)+ 389.0.

Compound 37
N-(2,2-Diphenylethyl)-N'-(−)-cis-myrtanylethane-1,2-diamine. 54 mg, 38% yield. $^1$H NMR: δ 7.31–7.18 (m, 10H), 4.13 (t, J=7.6 Hz, 1H), 3.26 (d, J=7.6 Hz, 2H), 2.86 (dd, J=4.3, 8.0 Hz, 4H), 2.76 (dd, J=7.6, 12.2 Hz, 2H), 2.37 (ddd, J=1.8, 9.0, 12.5 Hz, 1H), 2.12 (dq, J=1.8, 7.6 Hz, 1H), 1.98 (br s, 2H), 1.98–1.84 (m, 4H), 1.39 (ddd, J=2.4, 4.0, 6.1 Hz, 1H), 1.18 (s, 3H), 0.95 (s, 3H), 0.91 (d, J=10.0 Hz, 1H) Mass spectrum (ESI) m/z (MH)+ 377.2.

Compound 38
N-(−)-cis-Myrtanyl-N'-(2,2-diphenylethyl)propane-1,2-diamine. 39 mg, 30% yield. 1H NMR (500 MHz) δ 7.30–7.15 (m, 10H); 4.13 (t, J=8.0 Hz, 1H); AB: 3.28 (d, J=7.5 Hz, 1H); 3.24 (d, J=7.5 Hz, 1H); 3.26 (d, J=6.1 Hz, 2H); 2.96 (m, 1H); 2.88–2.75 (m, 2H); 2.71 (ddd, J=4.5, 9.0, 13.0 Hz, 1H), 2.58 (ddd, J=7.0, 10.0, 14.0 Hz, 1H); 2.35 (m, 1H); 2.21 (m, 1H); 2.00–1.80 (m, 6H); 1.40–1.20 (m, 1H); 1.17 (s, 3H); 0.93 (s, 3H); 0.89 (dd, J=9.7 and 4.2 Hz, 1H). Mass spectrum (ESI) m/z (MH)+ 391.0.

Compound 40
N-(2,2-Diphenylethyl)-N'-(1R,2R,3R,5S)-(−)-isopinocampheylethane-1,2-diamine. 33 mg, 23% yield. $^1$H NMR: δ 7.31–7.18 (m, 10H), 4.13 (t, J=7.5 Hz, 1H), 3.27 (d, J=8.0 Hz, 2H), 3.14 (dt, J=6.0, 10 Hz, 1H), (4H), 2.36 (qd, J=2.0, 6.0 Hz, 1H), 2.34 (dt, J=2.0, 10 Hz, 1H), 2.07–1.96 (m, 3H), 1.82 (dt, J=2.0, 6.0 Hz, 1H), 1.71 (ddd, J=2.5, 5.5, 13.5 Hz, 1H), 1.22 (s, 3H), 1.09 (d, J=7.0 Hz, 3H), 0.96 (d, J=10.5 Hz, 1H), 0.91 (s, 3H). Mass spectrum (ESI) m/z (MH)+ 377.3.

Compound 47
N-(−)-cis-Myrtanyl-N'-(1R,2R,3R,5S)-(−)-isopinocampheylethane-1,2-diamine. 42 mg, 33% yield. $^1$H NMR: δ 3.35–3.20 (m, 6H), 2.93 (dd, J=4.6, 2.0 Hz, 2H), 2.45–2.33 (m, 4H), 2.17 (s, 3H), 2.06 (quint, J=7.0 Hz, 1H), 2.0–1.9 (m, 6H), 1.90 (dd, J=2.1, 5.2 Hz, 1H), 1.87 (dt, J=1.8, 4.6 Hz, 1H), 1.51 (ddd, J=4.6, 10.0, 13.0 Hz, 1H), 1.23 (s, 3H), 1.19 (s, 3H), 1.12 (d, J=8 Hz, 3H), 1.03 (d, J=10.3 Hz, 1H), 0.98 (s, 3H), 0.94 (d, J=9.8 Hz, 1H), 0.94 (s, 3H). Mass spectrum (ESI) m/z (MH)+ 333.6.

Compound 52
N-(3,3-Diphenylpropyl)-N'-cyclooctylethane-1,2-diamine. 20 mg, 18% yield. 1H NMR (500 MHz): δ 7.30–7.10 (m, 10H); 3.96 (t, J=7.9 Hz, 1H); 3.00 (m, 1H); 2.90 (dd, J$_1$=J$_2$=5.5 Hz, 2H); 2.84 (dd, J$_1$=J$_2$=5.0 Hz, 2H); 2.61 (t, J=7.3 Hz, 2H), 2.27 (q, J=7.6 Hz, 2H); 1.83 (m, 2H); 1.74 (m, 2H); 1.65–1.40 (m, 10H).

Compound 55
N-(1-Adamantylmethyl)-N'-cyclooctylethane-1,2-diamine. 6.7 mg, 6% yield. 1H NMR (500 MHz): δ 3.08–3.02 (m, 1H), 3.02–2.98 (m, 2H); 2.97–2.92 (m, 2H); 2.36 (s, 2H); 1.98 (m, 2H); 1.93–1.86 (m, 2H); 1.80–1.50 (m, 19H).

Compound 57
N-(−)-cis-Myrtanyl-N'-(cyclooctyl)ethane-1,2-diamine. 18 mg, 18% yield. 1H NMR (500 MHz) δ 3.05–2.95 (m, 4H); AB: 2.76 (d, J=7.5 Hz, 1H), 2.23 (d, J=8.0 Hz, 1H); 2.76 (dd, J=11.6 and 7.3 Hz, 1H); 2.73 (dd, J=11.9 and 8.2 Hz, 1H); 2.40–2.34 (m, 1H); 2.28 (quintet, J=8.0 Hz, 1H); 1.97 (s, 3H); 2.00–1.84 (m, 6H); 1.80–1.70 (m, 2H); 1.68–1.38 (m, 11H); 1.18 (s, 3H); 0.97 (s, 3H); 0.92 (d, J=9.8 Hz, 1H). Mass spectrum (ESI) m/z (MH)+ 307.5.

Compound 58
N-(2-Adamantyl)-N'-cyclooctylethane-1,2-diamine. 25 mg, 23% yield. $^1$H NMR: δ 3.06 (m, 1H), 3.00 (t, J=6.1 Hz, 2H), 2.93 (t, J=5,5 Hz, 2H), 2.83 (br s, 1H), 1.96 (s, 3H), 1.92–1.80 (m, 10H), 1.80–1.50 (m, 20H). Mass spectrum (ESI) m/z (MH)+ 305.1.

Compound 59
N-(Cyclooctyl)-N'-(1R,2R,3R,5S)-(−)-isopinocampheylethane-1,2-diamine. 15 mg, 14% yield. 1H NMR (400 MHz): δ 3.47 (dt, J=6.0, 10.0 Hz, 1H), 3.40–3.28 (m, 7H), 2.44 (tq, J=2.0, 10.0 Hz, 1H), 2.36 (dtd, J=2.0, 6.0, 10.0 Hz, 1H), 2.09 (dq, J=2.0, 7.2 Hz, 1H), 2.00–1.90 (m, 3H), 1.88–1.78 (m, 2H), 1.78–1.63 (m, 4H), 1.65–1.30 (m, 8H), 1.18 (d, J=6.0 Hz, 3H), 1.16 (s, 3H), 1.17 (d, J=7.2 Hz, 1H), 0.90 (s, 3H). Mass spectrum (ESI) m/z (MH)+ 307.4.

Compound 62
N-(−)-cis-Myrtanyl-N'-(1S)-(1-ethylcyclohexane)ethane-1,2-diamine. 48 mg, 46% yield. 1H NMR (500 MHz): δ 3.06–3.00 (m, 1H); 2.98–2.95 (m, 2H); 2.92–2.84 (m, 1H); 2.79 (dd, J=11.9 and 7.0 Hz, 1H); 2.75 (dd, J=11.9 and 7.9 Hz, 1H); 2.73 (m, 1H); 2.39 (m, 1H); 2.28 (quintet, J=8.5 Hz, 1H); 2.00–1.86 (m, 6H); 1.82–1.76 (m, 2H); 1.68 (m, 2H); 1.54–1.42 (m, 2H); 1.32–1.10 (m, 6H); 1.19 (s, 3H); 1.13 (d, J=6.7 Hz, 3H); 1.07 (dd, J=12 and 3 Hz, 2H); 1.02 (dd, J=12 and 3 Hz, 2H); 0.98 (s, 3H); 0.93 (d, J=9.7 Hz, 1H). Mass spectrum (ESI) m/z (MH)+ 306.9.

Compound 65
N-trans-(2-phenylcyclopropyl)-N'-(1-adamanthyl)ethane-1,2-diamine. 18 mg, 16% yield. Mass spectrum (ESI) m/z (MH)+ 311.3.

Compound 66
N-(3,3-Diphenylpropyl)-N'-(1R,2R,3R,5S)-(−)-isopinocampheylethane-1,2-diamine. 2 mg, 2% yield. 1H NMR (500 MHz) δ 7.26 (m, 10H); 3.96 (t, J=7.6 Hz, 1H); 3.09 (m, 1H); 2.92 (m, 1H); 2.84 (m, 2H); 2.62 (m, 2H); 2.35 (m, 4H); 1.97 (s, 3H); 1.82 (m, 1H); 1.68 (m, 1H); 1.21 (s, 3H); 1.12 (d, J=7.3 Hz; 3H); 1.01 (m, 1H); 0.92 (s, 3H). Mass spectrum (ESI) m/z (MH)+ 391.4.

Compound 73
N-(2-Adamantyl)-N'-[2-(2-methoxyphenyl)ethyl]ethane-1,2-diamine. 21 mg, 19% yield. $^1$H NMR: δ 7.22 (dd, J=8.2, 7.3 Hz, 1H), 7.14 (d, J=7.3 Hz, 1H), 6.89 (d, J=7.1, Hz, 1H), 6.87 (d, J=8.2, Hz, 1H), 3.81 (s, 3H), 3.06 (t, J=7.1 Hz, 2H), 3.06 (m, 2H), 3.01 (m, 2H), 2.93 (t, J=7.1, 2H), 1.95 (br s, 2H), 1.90–1.80 (m, 7H), 1.78–1.66 (m, 6H), 1.59 (d, J=2.5 Hz, 2H). Mass spectrum (ESI) m/z (MH)+ 329.4.

Compound 78

N-2-Adamantyl-N'-2,3-dihydro-1H-inden-2-yl-ethane-1,2-diamine. 4.3 mg, 3% yield. $^1$H NMR: δ 7.20 (dd, J=4.9, 8.5 Hz, 2H), 7.14 (dd, J=5.5, 2.1 Hz, 2H), 3.71 (quint, J=6.1 Hz, 2H), 3.19 (dd, J=5.8, 15.9 Hz, 2H), 3.13 (br.s, 1H), 3.05 (m, 4H), 2.86 (dd, J=4.8, 15.8 Hz, 2H), 2.08 (m, 2H), 2.00 (m, 6H), 1.96–1.88 (m, 4H), 1.88–1.80 (m, 3H), 1.74 (m, 4H), 1.68–1.60 (m, 2H). Mass spectrum (ESI) m/z (MH)$^+$ 303.4.

Compound 109

N-Geranyl-N'-(2-adamanthyl)ethane-1,2-diamine. 27 mg, 24% yield. 1H NMR (400 MHz): δ 5.40 (t, J=7.2 Hz, 1H), 4.78 (br s, 2H), 3.64 (d, J=7.6 Hz, 2H), 3.34 (m, 2H), 2.07 (m, 2H), 2.08–1.95 (m, 4H), 1.95–1.85 (m, 4H), 1.82 (m, 2H), 1.88–1.70 (m, 4H), 1.70–1.62 (m, 3H), 1.67 (s, 3H), 1.56 (s, 3H), 1.50 (s, 3H). Mass spectrum (ESI) m/z (MH)$^+$ 307.4.

Compound 111

N-Geranyl-N'-(2-ethylpiperidine)ethane-1,2-diamine. 44 mg, 42% yield. 1H NMR (500 MHz): δ 5.22 (t, J=6.1 Hz, 1H); 5.04 (m, 1H), 3.52 (d, J=7.3 Hz, 2H); 3.05–2.85 (m, 4H); 2.66 (m, 1H); 2.44 (m, 2H); 2.08 (m, 4H); 1.80–1.50 (m, 2H); 1.70(s, 3H); 1.65 (s, 3H); 1.58 (s, 3H); 1.50–1.35 (m, 2H), 0.89 (t, J=7.3, 3H). Mass spectrum (ESI) m/z (MH)$^+$ 293.4.

Compound 116

N-Geranyl-N'-allyl-N'-(cyclopentyl)ethane-1,2-diamine. 45 mg, 42% yield. $^1$H NMR: δ 5.86 (ddd, J=10.0, 16.1, 6.7 Hz, 1H), 5.28 (d, J=15.9 Hz, 1H), 5.25 (d, J=8.7 Hz, 1H), 5.23 (t, J=7.3 Hz, 1H), 5.30 (m, 1H), 3.59 (d, J=7.3 Hz, 2H), 3.28 (br d, J=6.4 Hz, 2H), 3.16 (quintet, J=8.2 Hz, 1H), 3.02 (m, 2H), 2.95–2.86 (m, 2H), 1.88–1.80 (m, 4H), 1.70 (s, 3H), 1.74–1.66 (m, 3H), 1.65 (s, 3H), 1.58 (s, 3H), 1.56–1.50 (2H), 1.50–1.40 (m, 2H). Mass spectrum (ESI) m/z (MH)$^+$ 305.3.

Compound 117

N-Geranyl-N'-diphenylmethylethane-1,2-diamine. 24 mg, 20% yield. 1H NMR (500 MHz): δ 7.40 (d, J=7.2 Hz, 4H); 7.29 (t, J=7.3 Hz, 4H); 7.21 (t, J=7.0 Hz, 2H); 5.15 (t, J=7.5, 1H); 5.01 (m, 1H); 4.89 (br s, 1H); 3.42 (d, J=7.0 Hz, 2H); 3.00–2.78 2.93 (m, 4H); 2.20–2.00 2.17 (m, 4H); 1.63 (s, 3H); 1.59 (s, 3H); 1.56 (s, 3H). Mass spectrum (ESI) m/z (MH)$^+$ 363.3.

Compound 125

N,N'-bis-(−)-cis-Myrtanylpropane-1,2-diamine. 82 mg, 70% yield. 1H NMR (500 MHz): δ 3.62 (m, 1H); 3.18 (dd, J=13.7 and 3.7 Hz, 1H); 3.05 (dt, J=11.5 and 7.5 Hz, 1H); 3.06–2.92 (m, 2H); 2.86 (dt, J=12.2 and 7.3 Hz, 1H); 2.40 (m, 4H); 2.06–1.84 (m, 10H); 1.56–1.46 (m, 2H); 1.37 and 1.36 (two d, J=6.7 and J=7.0 Hz, 3H); 1.20 (s, 3H); 1.19 (m, 3H), 0.99 and 0.98 (two s, 3H) Hz, H); 0.97 (s, 3H); 0.94 (two d, J=10.1 Hz, 2H). Mass spectrum (ESI) m/z (MH)$^+$ 346.9.

Compound 151

N-[2-(2-Methoxy)phenylethyl]-N'-(1R,2R,3R,5S)-(−)-isopinocampheyl-ethane-1,2-diamine. 67 mg, 60% yield. 1H NMR (500 MHz): δ 7.23 (t, J=5.8 Hz, 1H); 7.13 (dd, J=5.8 and 1.8 Hz, 1H); 6.88 (m, 2H); 3.81 (s, 3H); 3.13 (m, 1H); 3.1–3.0 (m, 3H); 3.01 (t, J=7.0 Hz, 2H); 2.89 (t, J=7.0 Hz, 2H); 2.42–2.35 (m, 2H); 2.00 (m, 3H); 1.82 (dt, J=6.0 and 2.0 Hz, 1H); 1.72 (ddd, J=2.5, 5.5, 13.5 Hz, 1H); 1.22 (s, 3H) 1.13 d, J=7.3 Hz, 3H). 0.99 (d, J=10.1 Hz, 1H); 0.93 (s, 3H). Mass spectrum (ESI) m/z (MH)$^+$ 331.5.

N-2-(2-Methoxyphenyl)ethyl-N'-allyl-N'-cyclopentyl-ethane-1,2-diamine. 8 mg, 7% yield. $^1$H NMR: δ 7.26 (dd, J=7.3, 8.5, 1H), 7.18 (d, J=7.2 Hz, 1H), 6.91 (m, 2H), 5.61 ddd, (J=6.7, 17.0, 9.4 Hz, 1H), 5.13 (d, J=15.3 Hz, 1H), 5.10 (d, J=9.2 Hz, 1H), 3.83 (s, 3H), 3.13 (dd, J=7.0, 6.7 Hz, 2H), 3.10 (d, J=6.7 Hz, 1H), 3.00 (d, J=7.3 Hz, 1H), 3.05–2.90 (m, 2H), 2.97 (dd, J=8.2, 6.1 Hz, 2H), 2.75 (t, J=6.1 Hz, 2H), 1.73 (m, 2H), 1.62 (m, 2H), 1.50 (m, 2H), 1.22 (m, 2H). Mass spectrum (ESI) m/z (MH)$^+$ 311.4.

N$^2$-(3-Phenylpropyl)-N$^1$-[2-(4-fluorophenyl)ethyl]-1-phenylethane-1,2-diamine. 23 mg, 19% yield. $^1$H NMR: δ 7.35 (d, J=7.6 Hz, 2H), 7.34 (quart, J=7. Hz, 1H), 7.26 (d, J=6.4 Hz, 3H), 7.23 (d, J=7.6 Hz, 2H), 7.17 (dd, J=7.3, 6.4 Hz, 1H), 7.12 (d, J=7.0 Hz, 2H), 3.21 (m, 1H), 3.03 (ddd, J=4.2, 8.0, 12.8 Hz, 4H), 2.86 (t, J=8.0 Hz, 2H), 2.85–2.79 (m, J=12. Hz, 2H), 2.74–2.64 (m, 4H), 2.61 (t, J=7.7 Hz, 2H), 1.96 (quint, J=7.6 Hz, 2H). Mass spectrum (ESI) m/z (MH)$^+$ 377.3.

EXAMPLE VII

*M. Tuberculosis* Rv0341p Lucs Drug Response

Substituted ethylene diamines, as described herein, were tested on *Mycobacterium tuberculosis* using high-throughput screening assay with recombinant mycobacterial containing promoter fusion of luciferase to Rv0341 EMB-inducible promoter. This assay quickly and reliably identifies antimycobacterial activity in compound mixtures and/or in individual compounds. In this assay, bioluminescence increases when the mycobacteria is tested against an active compound, or an active compound mixture. During this assay, a theoretical yield of 100% was assumed for every unpurified substituted ethylene diamine, and the activity of each sample was compared to commercially available ethambutol (99.0% purity). Results were reported in LCPS, and % Max. LCPS based on the activity of EMB at 3.1 μM.

The substituted ethylene diamines were analyzed according to the following procedure. The diamines were dried in a speed vacuum to an approximate concentration of 6.3 mmoles per well. Each diamine, or diamine mixture, was then resuspended or dissolved in 200 μl of methanol for a concentration of 31.5 mM diamine(s). The diamine(s) solution was diluted to a concentration of 200 μM in 7H9 broth medium (a 1:15.75 dilution of the 31.5 mM stock, followed by a 1:10 dilution; each dilution in 7H9 broth medium). Next, 50 μl of the diluted diamine(s) solution was added to the first well of a row of twelve in an opaque, 96-well plate. The 7H9 broth medium, 25 μl, was added to each of the remaining wells (#2–12) in the row. The diamine(s) solution in "well one" was serially diluted by transferring 25 μl from "well one" to "well two", and repeating a 25 μl transfer from "well two" to "well three", and so on, on through "well eleven". In "well eleven", the extra 25 μl of solution was discarded. "Well twelve" was used as a growth control to assess background activity of the reporter strain. The plate was then covered and incubated at 37° C. for 24 hours. Immediately prior to analysis, the following substrates were prepared: a buffer solution containing 50 mM HEPES at pH 7.0 and 0.4% Triton X-100. Then, 0.25 ml of 1M DTT, and 14 μl of 10 mg/ml luciferin in DMSO were added to 5 ml of the buffer solution. This final solution (50 μl) was added to each of the twelve wells, immediately after the incubation period had run. The luminescence from each well was measured 20 minutes after the luciferin substrate was added, using a TOPCOUNT® (Downers, Grove, Ill.) NXT luminometer (55/well).

Figure 6:
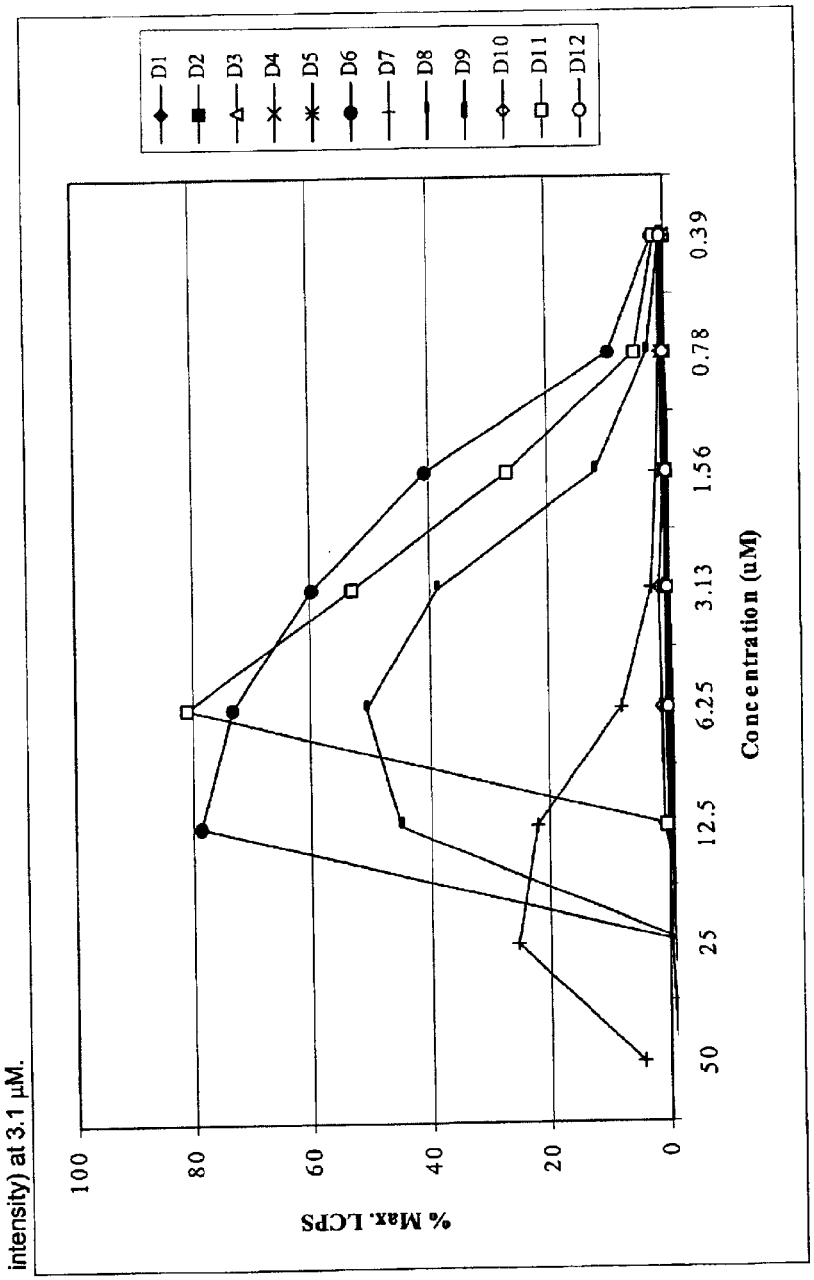
FIG. 6 is a graph of Luminescence Count per Second (LCPS) versus concentration showing HTS Luc assay results for pooled substituted ethylene diamine compounds.
Figure 7:
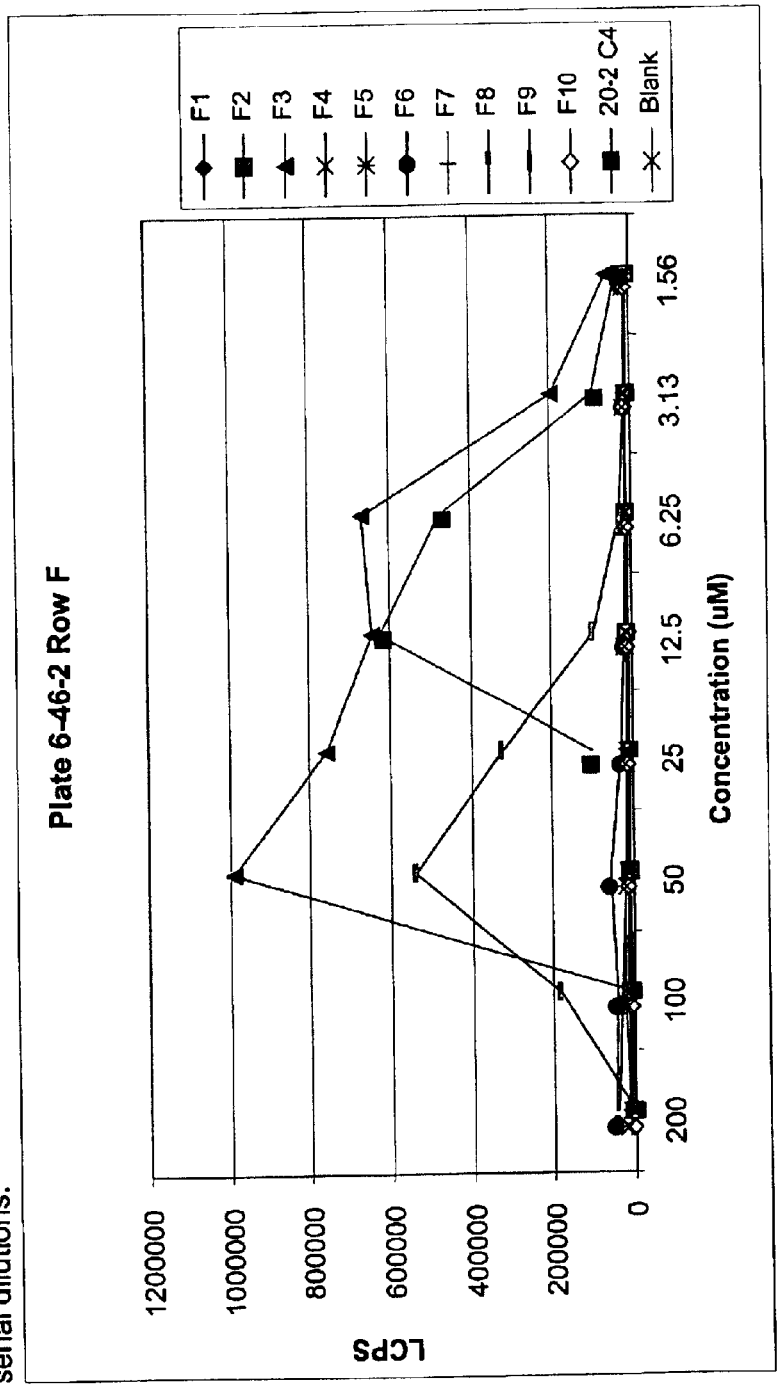
FIG. 7 is a graph of LCPS versus concentration showing HTS Luc assay results for individual substituted ethylene diamine compounds.
Figure 8:
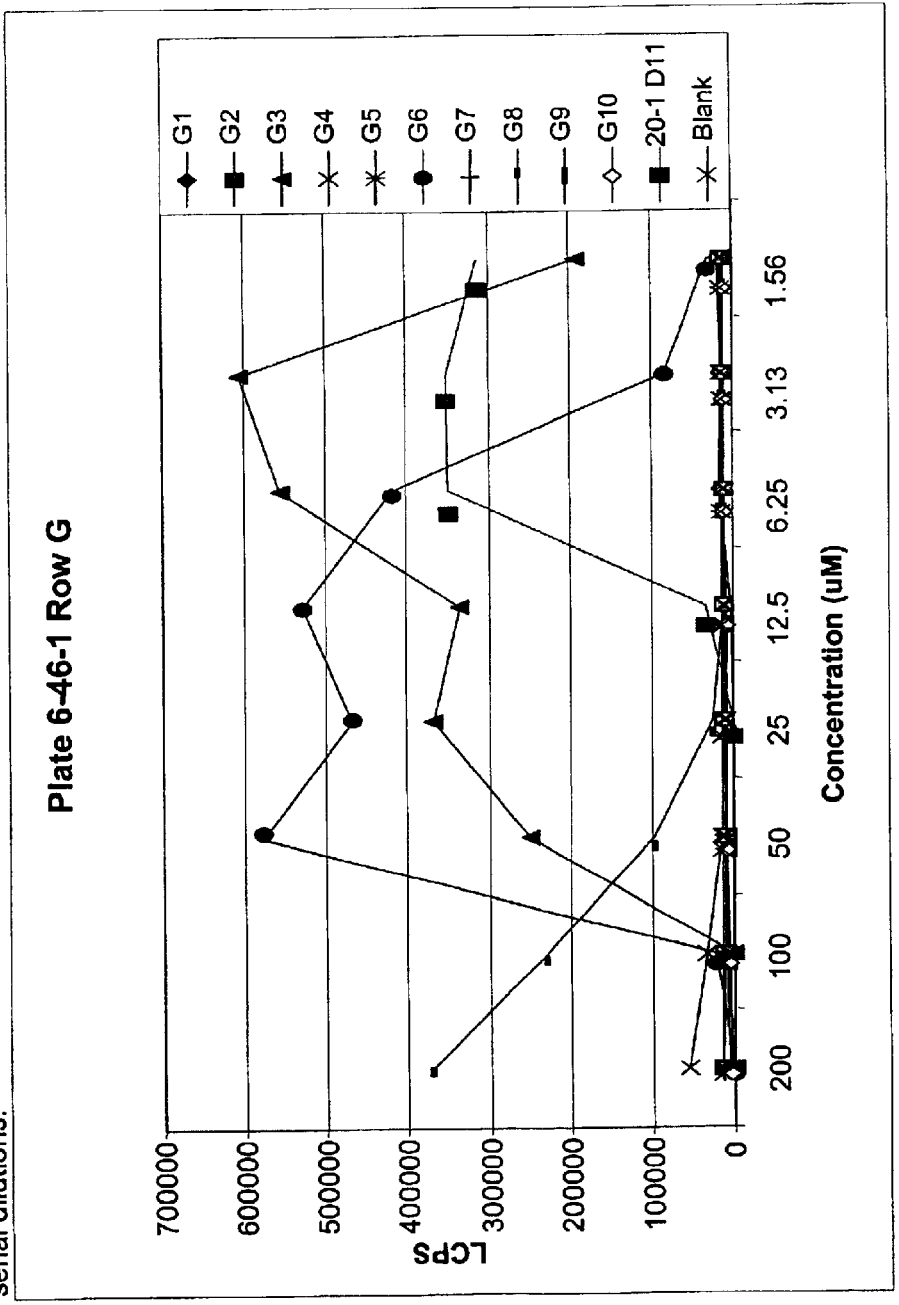
FIG. 8 is a graph of LCPS versus concentration showing HTS Luc assay results for individual substituted ethylene diamine compounds.
Figure 10:
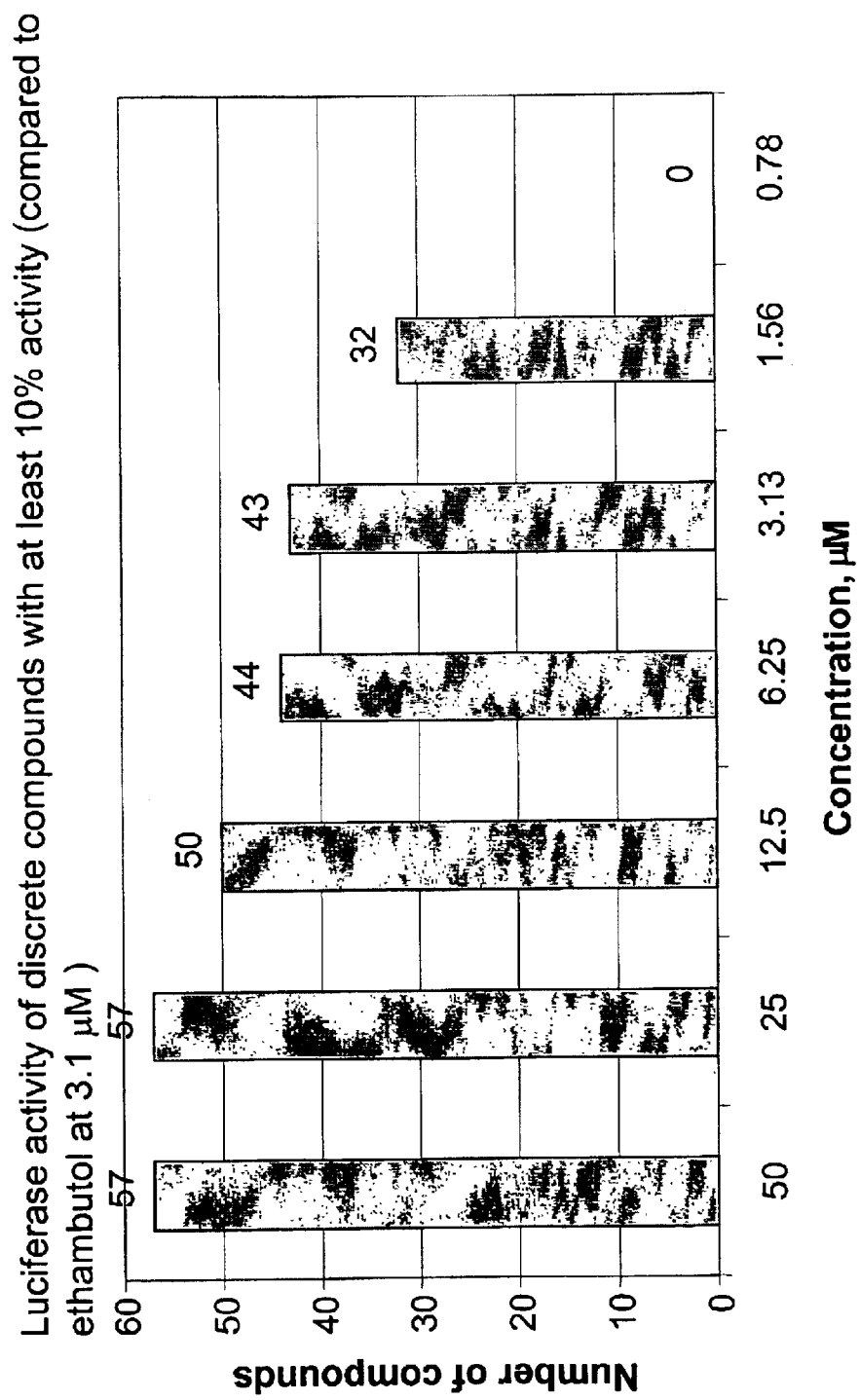
FIG. 10 is a bar graph providing a summary of Luciferase activity of discrete substituted ethylene diamines with at least 10% activity in reference to ethambutol at 3.1 $\mu$M.
Figure 11:
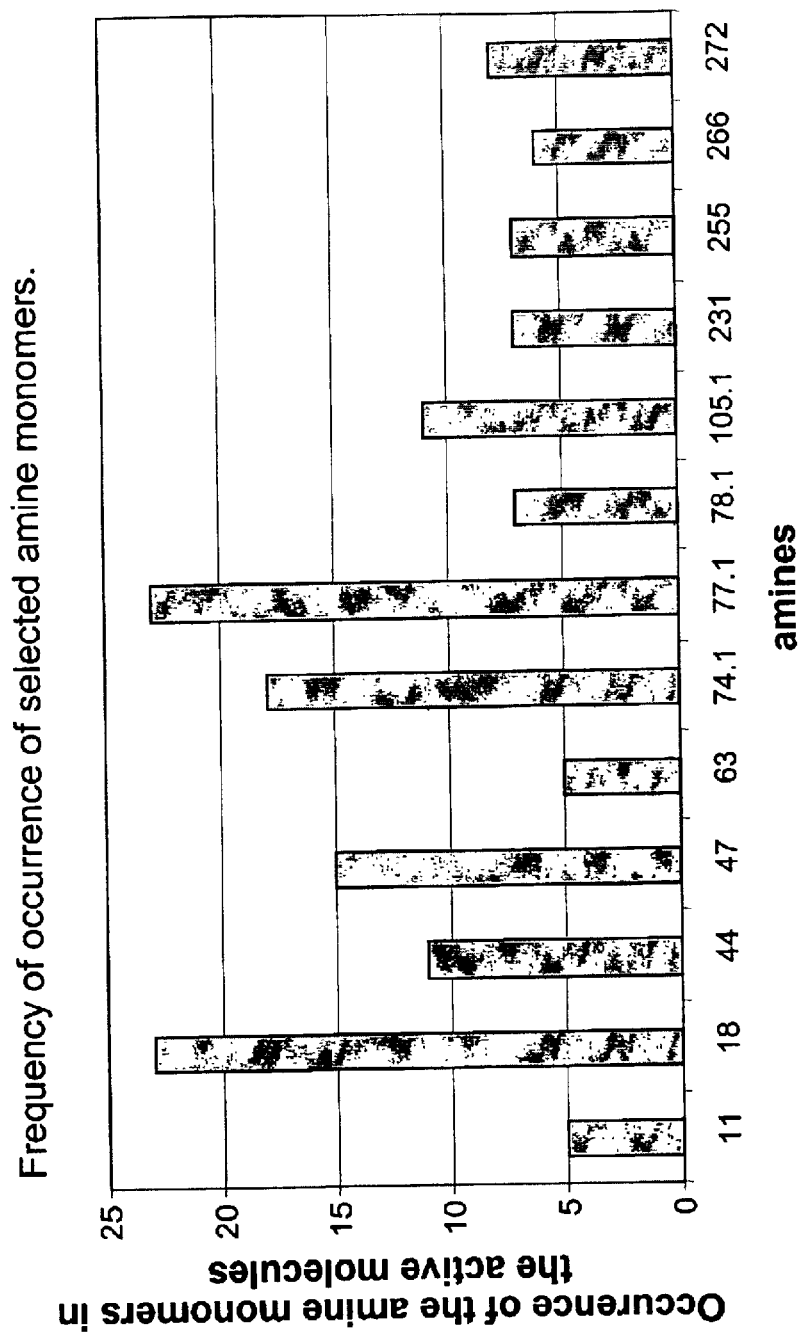
FIG. 11 is a bar graph showing the frequency of occurrences of the selected amine monomers in the substituted ethylene diamine compounds that were active against TB. Amine monomers are represented by their numerical designations.

FIGS. 6–8 show typical assay data for the luciferase reporter strain containing an Rv0341 EMB-inducible promoter with serial dilution of 12 wells (1 row) of a 96-well library plate. FIG. 10 shows the number of substituted ethylene diamines with at least 10% luciferase activity, based on the activity of ethambutol at 3.1 $\mu$M.

FIG. 6 represents typical assay data in the luciferase reporter strain containing an Rv0341 EMB-inducible promoter. The data represents values obtained from the HTS Luc assay for compound mixtures of one row (row D) in the 96-well library. Row D was subject to several serial dilutions. The effectiveness of the compound mixture in the assay was measured by the intensity of luminescence, and compared to ethambutol (100% intensity, 99% purity) at 3.1 $\mu$M. Each curve in FIG. 6 represents one well, or ten compounds. Results are reported in percent maximum Luminescence Count per Second (% Max. LCPS). During the screening, a theoretical 100% chemical yield was assumed for every unpurified compound. Concentrations are given for a single compound. Based on this initial screening, 300+ compound mixtures showed anti-TB activity.

EXAMPLE VIII

Representative MIC Experiment

The Minimum Inhibition Concentration (MIC) is the concentration of the growth inhibitor, here a substituted ethylene diamine, at which there is no multiplication of seeded cells. A microdilution method was used to determine the MIC of the substituted ethylene diamines, capable of inhibiting the growth of Mycobacterium tuberculosis in vitro. In a representative MIC experiment, bacteria, the H37Rv strain of Mycobacterium tuberculosis (M. tb), was cultivated in 7H9 medium to a density of 0.2 OD (optical density) at 600 nm. The bacterial culture was then diluted 1:100 in 7H9 broth medium. Stock solutions of isoniazid and ethambutol were each prepared at 32 $\mu$g/ml in 7H9 medium. A 3.2 mg/ml solution of isonizid and ethambutol were each prepared in water. The solutions were then filtered, and diluted 1:100 in 7H9 medium. Each drug, purchased from Sigma, was "laboratory use only" grade. A 10 mM solution of each substituted ethylene diamine was prepared in methanol. Next, 100 $\mu$l of the 7H9 medium was added to each well in a 96-well plate (rows (A through H) x columns (1 through 12)). To the first wells in rows C through H was added an additional 80 $\mu$l of the 7H9 medium. The isoniazid solution, 100 $\mu$l, was added to well A1, and the ethambutol solution, 100 $\mu$l, was added to well B1. Six substituted ethylene diamines, 20 $\mu$l each, were added to wells C1 through H1 (column 1), respectively. A serial dilution of each substituted ethylene diamine and the isoniazid and ethambutol controls, was performed across each row. For example, a serial dilution across row C1–C12 was done by mixing and transferring 100 $\mu$l of the previous well to the next consecutive well. In each well in "column 12," 100 $\mu$l of the final dilution was discarded. Next, 100 $\mu$l of the diluted H37Rv strain of M. tb was added to each well. The 96-well plate was then covered and incubated at 37° C. for 10 days. The plate was read for bacterial growth, or non-growth, using an inverted plate reader. The MIC was determined to be the lowest concentration of substituted ethylene diamine that inhibited visible growth of the M. tb.

Figure 9:
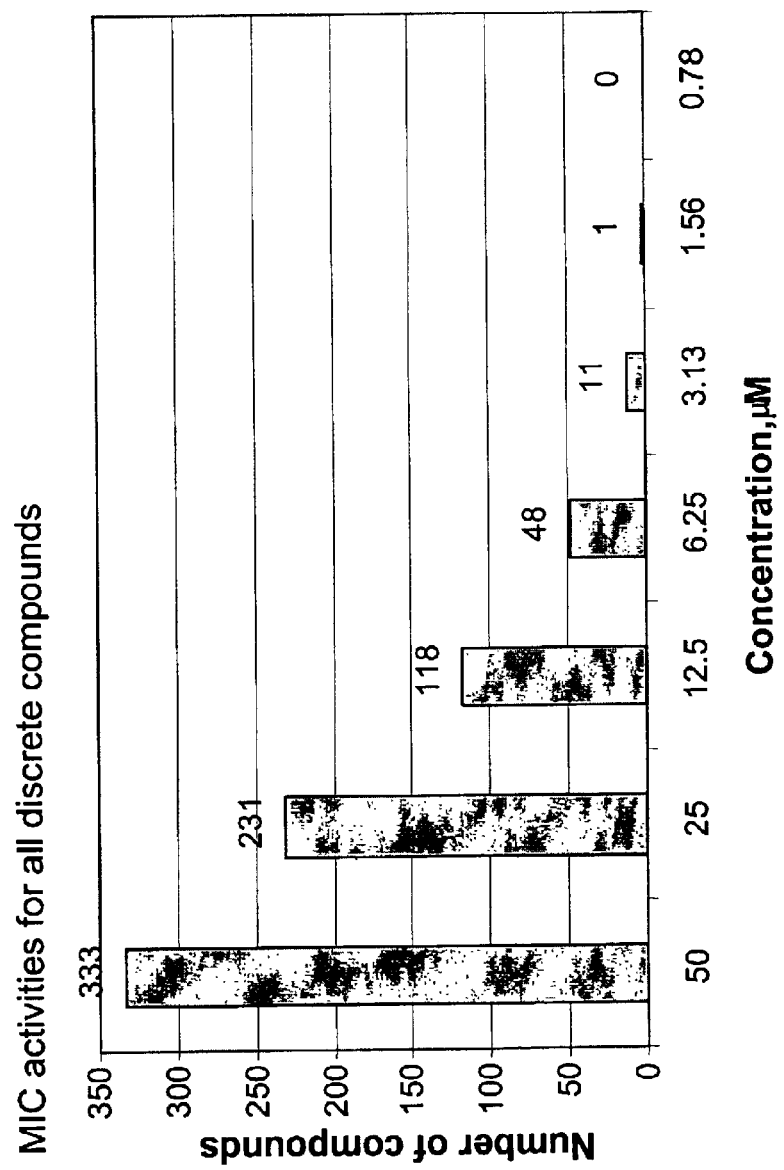
FIG. 9 is a bar graph providing a summary of MIC activities for discrete substituted ethylene diamines.

A representative plate layout, listing concentration in each well, is shown in Table 9. Table 10 lists MIC and LD50 data for selected compounds. The LD50 is the concentration of the substituted ethylene diamine at which 50% of the cells (H37Rv strain of M. tb) are killed. Table 11 lists MIC data for purified substituted ethylene diamines in comparison to ethambutol (EMB). FIG. 9 shows the number of substituted ethylene diamine compounds with MIC activity at various concentration levels.

TABLE 9

Concentration in Each Well (PM) Based on Columns 1–12

| DRUG | | | | | | | | | | | | |
|---|---|---|---|---|---|---|---|---|---|---|---|---|
| Isoniazid | 58.25 | 29.13 | 14.56 | 7.28 | 3.64 | 1.82 | 0.91 | 0.45 | 0.23 | 0.11 | 0.06 | 0.03 |
| Ethambutol | 28.75 | 14.38 | 7.19 | 3.60 | 1.80 | 0.90 | 0.45 | 0.22 | 0.11 | 0.06 | 0.03 | 0.01 |
| Subst. Ethylene Diamine | 500 | 250 | 125 | 62.5 | 31.25 | 15.63 | 7.81 | 3.91 | 1.96 | 0.98 | 0.49 | 0.24 |

TABLE 10

Selectivity Index for Selected Compounds

| Cmpd | MIC (uM) | LD50 (uM) | MW | MIC (ug/ml) | LD50 (ug/ml) | SI |
|---|---|---|---|---|---|---|
| 6 | 7.813 | 20 | 536 | 4.187768 | 10.72 | 2.559836 |
| 34 | 7.813 | 32 | 508 | 3.969004 | 16.256 | 4.095738 |
| 37 | 15.625 | 32 | 496 | 7.75 | 15.872 | 2.048 |
| 47 | 15.625 | 25 | 452 | 7.0625 | 11.3 | 1.6 |
| 57 | 15.625 | 18 | 426 | 6.65625 | 7.668 | 1.152 |
| 59 | 15.625 | 32 | 426 | 6.65625 | 13.632 | 2.048 |
| 65 | 15.625 | 60 | 430 | 6.71875 | 25.8 | 3.84 |
| 109 | 1.953 | 32 | 450 | 0.87885 | 14.4 | 16.38505 |
| 111 | 7.813 | 44 | 412 | 3.218956 | 18.128 | 5.63164 |
| 151 | 7.813 | 41 | 450 | 3.51585 | 18.45 | 5.247664 |

The above procedure was also used to examine batched compounds (10 compounds per well). Synthesized batches of substituted ethylene diamines were dried in speed vacuum and then resuspended in DMSO or sterile water to a concentration of 2.5 mg/ml.

TABLE 11

MIC Data for Purified Samples

Plate set-up

| INH | | | | | | | | |
|---|---|---|---|---|---|---|---|---|
| 58.25 | 29.125 | 14.56 | 7.28 | 3.64 | 1.82 | 0.91 | 0.45 | 0.23 |
| EMB | | | | | | | | |
| 28.75 | 14.375 | 7.1875 | 3.594 | 1.797 | 0.898 | 0.449 | 0.2245 | 0.1125 |
| CMPD | | | | | | | | |
| 500 | 250 | 125 | 62.5 | 31.25 | 15.625 | 7.813 | 3.9063 | 1.953 |

| Avg INH MIC (uM) 0.91 | Avg INH MIC (uM) 0.91 | | |
|---|---|---|---|
| Avg EMB MIC (uM) 7.1875 | Avg EMB MIC (uM) 8.37 | Avg EMB 7.25 | Avg EMB 7.25 |

| Cmpd | MIC (uM) | | | | BACTEC EMB: 2.5 UG/ML |
|---|---|---|---|---|---|
| 1 | 250 | 250 | 125 | 125 | |
| 2 | 250 | 250 | 250 | 250 | |
| 3 | 31.25 | 62.5 | 15.6 | 15.6 | |
| 4 | 125 | 62.5 | 62.5 | 62.5 | |
| 5 | >500 | 500 | 500 | 500 | |
| 6 | 7.813* | 7.813 | 3.9 | 3.9 | |
| 7 | 15.625* | 7.813 | 3.9 | 3.9 | |
| 8 | 125 | 125 | 31.25 | 31.25 | |
| 10 | 7.813* | 15.625 | 7.8 | 7.8 | |
| 11 | 31.25 | contaminated | 3.9 | 3.9 | |
| 13 | 31.25 | 31.25 | 15.6 | 15.6 | 15 |
| 14 | 15.625" | 15.625 | 7.8. | 7.8 | |
| 15 | >500 | >500 | 250 | 500 | |
| 17 | 62.5 | 62.5 | 15.6 | 15.6 | |
| 21 | 15.625* | 31.25 | 7.8 | 7.8 | |
| 22 | 31.25 | 31.25 | 7.8 | 15.6 | |
| 23 | 31.25 | 31.25 | 15.6 | 15.6 | |
| 24 | 125 | 125 | 31.25 | 31.25 | |
| 27 | 125 | 62.5 | 15.6 | 31.25 | |
| 28 | 125 | 62.5 | 31.25 | 31.25 | |
| 29 | 62.5 | 62.5 | 31.25 | 62.5 | |
| 31 | 31.25 | 61.25 | 15.6 | 15.6 | |
| 32 | 15.625* | 15.625 | 7.8 | 7.8 | |
| 33 | 62.5 | 62.5 | 31.25 | 31.25 | |
| 34 | 7.813* | 7.813 | 3.9 | 3.9 | |
| 35 | 62.5 | 62.5 | 15.6 | 31.25 | |
| 36 | 31.25 | 62.5 | 15.6 | 15.6 | |
| 37 | 15.625* | 15.625 | 3.9 | 7.8 | 1.25 |
| 38 | 7.813 | 7.813 | 3:9 | 7.8 | |
| 40 | 15.625* | 15.625 | 7.8 | 7.8 | |
| 41 | 31.25 | 15.625 | 15.6 | 15.6 | |
| 42 | 31.25 | 31.25 | 1.95 | 3.9 | |
| 43 | 31.25 | 31.25 | 3.9 | 7.8 | 12.5 |
| 47 | 15.625* | 15.625 | 1.95 | 7.8 | 5 |
| 51 | 31.25 | 250 | 31.25 | 31.25 | |
| 52 | 15.625* | 15.625 | 3:9 | 3.9 | |
| 53 | 31.25 | 31.25 | 31.25 | 31.25 | |
| 54 | 31.25 | 31.25 | 15.6 | 31.25 | |
| 55 | 15.625* | 15.625 | 15.6 | 15.6 | 25 |
| 56 | 500 | >500 | 500 | 500 | |
| 57 | 15.625* | 7.813 | 7.8 | 7.8 | |
| 58 | 15.625* | 15.625 | 7.8 | 7.8 | 5 |
| 59 | 15.625* | 31.25 | 15.6 | 15.6 | 12.5 |
| 61 | 62.5 | 62.5 | 31.25 | 31.25 | |
| 62 | 15.625* | 31.25 | 15.6 | 31.25 | |
| 63 | 62.5 | 62.5 | 31.25 | 62.5 | |
| 64 | 31.25 | 31.25 | 31.25 | 31.25 | |
| 65 | 15.625* | 31.25 | 31.25 | 31.25 | |
| 66 | 15.625* | 15.625 | 7.8 | 7.8 | |
| 68 | 500 | 500 | 500 | 500 | |
| 71 | 62.5 | 62.5 | 31.25 | 31.25 | |
| 73 | 62.5 | | 15.6 | 15.6 | |
| 76 | 62.5 | 62.5 | 31.25 | 31.25 | |
| 77 | 31.25 | 31.25 | 15.6 | 15.6 | |
| 78 | 15.625* | 31.25 | 15.6 | 15.6 | |
| 79 | 31.25 | 31.25 | 15.6 | 15.6 | |
| 103 | 31.25 | 31.25 | 62.5 | 62.5 | |
| 107 | 500 | 500 | 250 | 250 | |
| 109 | 1.953* | 1.953 | 1.95 | 1.95 | 0.63 |
| 111 | 7.813* | 7.813 | 7.8 | 7.8 | 5 |
| 116 | 15.625* | 15.625 | 7.8 | 15.6 | 12.5 |

TABLE 11-continued

MIC Data for Purified Samples

| 117 | 7.813* | 15.625 | 7.8 | 7.8 | |
|---|---|---|---|---|---|
| 118 | 31.25 | 62.5 | 31.25 | no data | |
| 119 | 125 contam | 62.5 | cont | no data | |
| 125 | 15.625* | 15.625 | cont | no data | 6.25 |
| 134 | >500 | >500 | 500 | no data | |
| 151 | 15.625* | 7813 | cont | no data | 6.25 |
| 164 | 62.5 | 125 | cont | no data | |
| 165 | 62.5 | 62.5 | 15.6 | 15.6 | |

EXAMPLE IX

Secondary Screening and Evaluation of Substituted Ethylene Diamines Against Drug Resistant Patient Isolates Secondary screening was performed on some of the substituted ethylene diamine compounds to examine their activity against three clinically resistant MDR patient isolates. MDR Strain TN576 is classified as a W1 strain ($STP^R$, $INH^R$, $RIF^R$, $EMB^R$, $ETH^R$, $KAN^R$, $CAP^R$) strain TN587 is classified as a W strain ($STP^R$, $INH^R$, $RIF^R$, $EMB^R$, $KAN^R$), and the third strain TN3086 is classified as a W1 strain ($STP^R$, $INH^R$, $RIF^R$, $EMB^R$, $KAN^R$). Each MDR strain is highly resistant to ethambutol with MIC values exceeding 12.5–25 μM. The MICs for the following substituted ethylene diamines, MP 116, MP 117, RL 241, compounds #59 and #109, were determined for all three patient isolates.

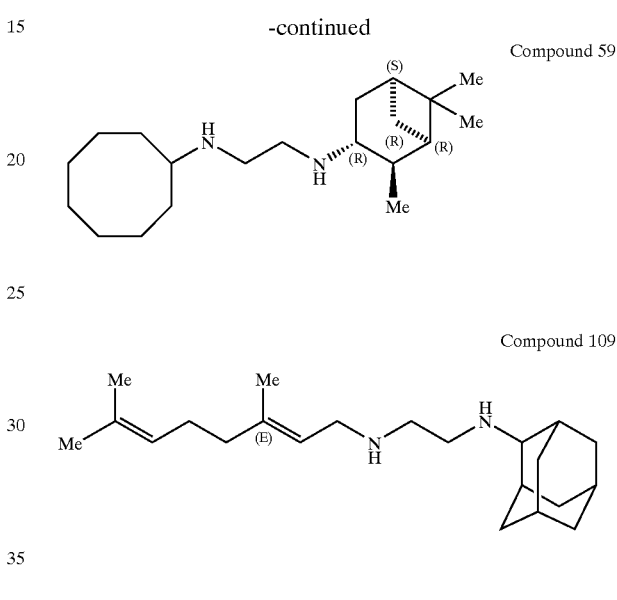

The results from this study are shown in Tables 12–13. Table 14 characterizes each MDR strain according to its resistance.

TABLE 12

Screening of Substituted Ethylene Diamines Against Drug Resistant Patient Isolates - (MIC values in ug/ml)

|  | WT | 576 | 587 | 3806 |
|---|---|---|---|---|
| EMB | 3.12 (or 11.1 uM) | 12.5–25 | 12.5–25 | 12.5–25 |
| MP 116 | 6.25 | 3.15 | 6.25 | 3.15 |
| MP 117 | 6.25 | 3.15 | 3.15 | 3.15 |
| RL 241 | 1.5 (or 3.34 uM) | 1.5 | 1.5 | 1.5 |

WT = wild type of M.tb
EMB as 2HCl salt
RL241 as 2HCl salt

TABLE 13

Screening of Substituted Ethylene Diamines Against Drug Resistant Patient Isolates - (MIC values in ug/ml)

|  | WT | 576 | 587 | 3806 |
|---|---|---|---|---|
| EMB | 1.6–1.8 | 50 | 50 | 50 |
| Cmpd#59 | 0.05 (or 0.13 uM) | 0.1 | 0.05 | 0.05 |
| Cmpd#109 | 0.10 (or 0.18 uM) | 0.2 | 0.2 | 0.1 |

Cmpd#59 as a 2HCl salt
Cmpd#109 as a 2CF$_3$COOH salt

TABLE 14

Drug Resistance of Each MDR Strain

| Strain  | STP | STP2 | INH1 | INH2 | Rif | Emb | Eth | Kan | Cip | Cap | Cyc |
|---------|-----|------|------|------|-----|-----|-----|-----|-----|-----|-----|
| 576 W1  | R   | R    | R    | R    | R   | R   | R   | R   | S   | R   | S   |
| 587 W   | R   | R    | R    | R    | R   | R   | S   | R   | S   | S   | S   |
| 3806 W1 |     | R    |      | R    | R   | R   | S   | R   |     |     |     |

R = resistant
S = susceptible
SIP = Streptomycin
INH = Isoniazid
Rif = Rifampicin
Emb = Ethambutol
Eth = Ethionamide
Kan = Kanamycin
Cip = Ciprofloxacin
Cap = Capreomycin
Cyc = Cycloserine

EXAMPLE X

In Vivo Animal Studies

Animal models were used in the final stages of the drug discovery cycle to assess the anti-microbial efficacy of some substituted ethylanediamine compounds in a representative system of human disease state. The in vivo testing approach involves the inoculation of four-six week old C57BL/6 mice via aerosol, containing approximately 200 colony forming units of M. tuberculosis H37R$_V$.

A. CFU Lung Study

Mice aerosolized with *M. tuberculosis* $H37R_V$ were examined for 10 to 12 weeks following inoculation. Drugs (substituted ethylene diamines) were administered via the esophageal cannula (gavage) 7 days/week, starting at either 14 or 21 days post infection. Bacterial load in the lungs of five mice per group were determined at approximately one-week intervals by viable colony counts. The drugs tested were directly compared to the front line anti-tuberculosis drug isoniazid, and to the second line drug, ethambutol. Isoniazid and ethambutol were tested at 25 mg/kg and 100 mg/kg, respectively. The substituted ethylene diamines, compound 37, compound 59 and compound 109, were each tested at 1 mg/kg and 10 mg/kg. FIGS. 17 to 19 represent data from three, independent CFU Lung studies. In each study, the number of colony forming units (CFU) that were recoverable and cultivatable, were determined during various time intervals (days).

B. Lesion Study

The ability of compound 59 and compound 109 to prevent the development of gross pathology due to bacterial burden was determined in conjunction with the CFU/Lung Study. The gross pathology was determined by visible quantitation of lesions on the surface of the lungs. Quantitation by inspection is a good surrogate for CFU determination, and directly correlates to the bacterial burden, as determined by the actual colony forming units. The lesions are first visibly examined, and then the lungs are processed and plated for CFU quantification. The lesion study demonstrates the ability of the drug to prevent the development of the disease pathology. FIG. 20 represents data from a lesion study. The corresponding CFU results are shown in FIG. 19.

C. Toxicity Study

Toxicity was assessed using a dose escalation study. This study was performed with ten C57BL/6 mice per candidate. Every two days, the mice were administered an increased concentration of the drug, and monitored for detrimental effects. The administration scheme was 50, 100, 200, 400, 600, 800 and 1000 mg/kg. The maximum limit of 1000 kg/mg was based on the goal of dose escalation, and the solubility of the drugs in the delivery vehicle. Compound 37 was toxic in mice at 100 kg/mg. Compound 59 and compound 109 were tolerated in mice at 1000 mg/kg and 800 mg/kg, respectively.

It should be understood that the foregoing relates only to preferred embodiments of the present invention, and that numerous modifications, or alterations, may be made therein without departing from the spirit and scope of the invention. The entire text of each reference mentioned herein is hereby incorporated, in its entirety, by reference.

REFERENCES

1. Dye, C.; Scheele, S.; Dolin, P.; Pathania, V.; Raviglione, M. C., "Consensus statement. Global Burden of Tuberculosis: Estimate Incidence, Prevalence, and Mortality By Country. WHO Global Survailance and Monitoring Project." *J. Am Med Association* 1999, 282, 677–686.
2. Bass, J. B.; Farer, L. S.; Hopewell, P. C.; O'Brein, R.; Jacobs, R. F.; Ruben, F.; Snider, D. E. Jr.; Thornton, G., "Treatment of Tuberculosis and Tuberculosis Infection in Adults and Children. The American Thoracic Society and the Canters for Disease Control and Prevention," *Am. J. Respir. Crit. Care Med.* 1994, 149, 1359–1374.
3. Farmer, P.; Bayona, J.; Becerra, M.; Furin, J.; Henry, C.; Hiatt, H.; Kim, J. Y.; Mitnick, C.; Nardell, E.; Shin, S., "The Dilemma of MDR-TB in the Global Era," *Int. J. Tuberc. Lung Dis.* 1998, 2, 869–876.
4. Pablos-Mendez, A.; Raviglione, M. C.; Laszlo, A.; Binkin, N.; Rieder, H. L.; Bustreo, F.; Cohn, D. L.; Lambregts van Weesenbeek, C. S.; Kim, S. J.; Chaulet, P.; Nunn, P., "Global Surveillance for Antituberculosis-drug Resistance," 1994–1997. *N. Engl. J. Med* 1998, 338, 1641–1649. [Erratum, *N. Engl. J. Med.* 1998, 339, 139].
5. Chan-Tack, K. M., "Antituberculosis-drug Resistance," *N. Engl. J. Med.* 1998, 339, 1079.
6. Cole, S. T.; Brosch, R.; Parkhill, J.; Garnier, T.; Churcher, C.; Harris, D.; Gordon, S. V.; Eiglmeier, K.; Gas, S.; Barry, C. E. $3^{RD}$; Tekaia; Badcock, K.; Basham, D.; Brown, D.; Chillingworth, T.; Connor, R.; Davies, R.; Devlin, K.; Feltwell, T.; Gentles, S.; Hamlin, N.; Holroyd, S.; Hornsby, T.; Jagels, K.; Barrell, B. G., "Deciphering the Biology of *Mycobacterium tuberculosis* From The Complete Genome Sequence," [published erratum appears in *Nature* 1998 Nov. 12 396, 190]; *Nature* 1998, 393, 537–544.

7. O'Brien, R. J., "Scientific Blueprint for Tuberculosis Drug Development," The Global Alliance for TB Drug Development, Inc. 2001.
8. Barry, C. E., III; Slayden, R. A.; Sampson, A. E.; Lee, R. E., "Use of Genomics and Combinatorial Chemistry in the Development of New Antimycobacterial Drugs," *Biochem. Pharmacol* 2000, 59, 221.
9. Cynamon, M. H.; Klemens, S. P.; Sharpe, C. A.; Chase, S., "Activities of Several Novel Oxazolidinones Against *Mycobacterium Tuberculosis* In A Murine Model," *Antimicrob Agents Chemother.* 1999, 43, 1189–91.
10. Shepard, R. G.; Baughn, C.; Cantrall, M. L.; Goodstein, B.; Thomas, J. P.; Wilkinson, R. G., "Structure-activity Studies Leading To Ethambutol, A New Type of Antituberculosis Compound," *Ann, N. Y. Acad. Sci* 1966, 135, 686.
11. Deng, L.; Mikusova, K.; Robuck, K. G.; Scherman, M.; Brennan, P. J., McNeil, M. R., "Recognition of Multiple Effects of Ethambutol on Metabolism of Mycobacterial Cell Envelope, "*Antimicrob. Agents Chemother.* 1995, 39, 694–701.
12. Lee, R. E.; Mikusova, K.; Brennan, P. J.; and Besra, G. S.; "Synthesis of the Mycobacterial Arabinose Donor β-D-Arabinofuranosyl-1-monophosphoryl-decaprenol, Development of a Basic Arabinosyl-transferase Assay, and Identification of Ethambutol As An Arabinosyl Transferase Inhibitor," *J. Am. Chem. Soc.* 1995, 117, 11829–11832.
13. Belanger, A. E.; Bestra, G. S.; Ford, M. E.; Mikusova, K.; Belisle, J. T.; Brennan, P. J.; Inamine, J. M, "The EmbAB Genes of *Mycobacterium avium* Encode An Arabinosyl Transferase Involved in Cell Wall Arabinan Biosynthesis That is The Target for The Antimycobacterial Drug Ethambutol," *Proc. Natl. Acad. Sci USA* 1996, 93, 11919.
14. Telenti, A.; Phillip, W. J.; Sreevatsan, S.; Bernasconi, C.; Stockbauer, K. E.; Wieles, B.; Musser, J. M.; Jacobs, W. R. Jr., "The Emb Operon, A Gene Cluster of *Mycobacterium Tuberculosis* Involved in Resistance to Ethambutol," *Nat. Med.* 1997, 3, 567.
15. Cuervo, J. H.; Weitl, F.; Ostretch, J. M.; Hamashin, V. T; Hannah, A. L.; Houghten, R. A. in *Peptides* 1994: *Proceedings of the European Peptide Symposium;* Maia HSL Ed., Esom: Leiden, 1995, 465–466.
16. Silen, J. L; Lu, A. T.; Solas, D. W.; Gore, M. A.; Maclean, D.; Shah, N. H.; Coffin, J. M.; Bhinderwala, N. S.; Wang, Y.; Tsutsui, K. T.; Look, G. C.; Campbell, D. A.; Hale, R. L.; Navre, M.; Deluca-Flaherty, C. R., "Screening For Novel Antimicrobials from Encoded Combinatorial Libraries by Using a Two-Dimensional Agar Format," *Antimicrob. Agents Chemother.* 1998, 42, 1147.
17. Gustafson, G. R.; Baldino, C. M.; O'Donnel, M.-M. E.; Sheldon, A.; Tarsa, R. J.; verni, C. J.; Coffen, D. L., "Incorporation of Carbohydrates and Peptides Into LargeTriazine-based Screening Libraries Using Automated Parallel Synthesis," *Tetrahedron* 1998, 54, 4067.
18. H. Rink *Tetrahedron Lett.* 1987, 28, 3787.
19. Garigipati, R. V., "Reagents for Combinatorial Organic Synthesis: Preparation and Uses of Rink-chloride," *Tetrahedron Lett.* 1997, 38, 6807.
20. Brown, D. S.; Revill, J. M.; Shute, R. E. Merrifield, "Alpha-Methoxyphenyl (MAMP) Resin; A New Versatile Solid Support for The Synthesis of Secondary Amines, "*Tetrahedron Lett.* 1998, 39, 8533.
21. Zuckermann, R. N.; Kerr, S. B. H.; Moos, W. H., "Efficient Method for The Preparation of Peptoids [oligo (N-substituted glycines)] by Submonomer Solid-phase Synthesis," *J. Am. Chem. Soc.* 1992, 114, 10646–10647.
22. Gordon, D. W.; Steele, J., "Reductive Alkylation on a Solid Phase: Synthesis of a Piperazidione Combinatorial Library, *Bioorg. Med. Chem. Lett.* 1995, 5, 47.
23. Liu, G.; Eliman J. A., "A General Solid-phase Synthesis Strategy for The Preparation of 2-Pyrrolidinemethanol Ligands," *J. Org. Chem.* 1995, 60, 7712.
24. March, J., "Advanced Organic Chemistry," $3^{rd}$ Ed., Wiley, New York, p. 916.
25. Luknitskii, Vovsi., *Russ. Chem. Rev.,* 1969, 38, 487–494.
26. Lee, M. H.; Pascopella, L.; Jacobs, W. R.; Hatfull, G. F., "Site Specific Integration of Mycobacteriophage L5: Integration-Proficient Vectors for *Mycobacterium smegmatis, Mycobacterium tuberculosis,* and *bacilli* Calmette-Guerin," *Proc. Matl Acad. Sci USA* 1991, 88, 3111.
27. Shawar, R. M.; Humble, D. J.; Van Dalfsen, J. M.; Stover, C. K.; Hickey, M. J.; Steele, S.; Mitscher, L. A.; Baker, W., "Rapid Screening of Natural Products for Antimycobacterial Activity By Using Luciferase-Expressing Strains of *Mycobacterium bovis* BCG and *Mycobacterium intracellulare,*" *Antimicrob. Agents Chemother.* 1997, 41, 570–574.
28. Arain, T. M.; Resconi, A. E.; Hickey, M. J.; Stover, C. K., "Bioluminesence Screening In Vitro (Bio-Siv) Assays for High-Volume Antimycobacterial Drug Discovery," *Antimicrob. Agents Chemother.* 1996, 40, 1536–1541.

We claim:

1. A composition comprising a substituted ethylene diamine compound of the formula

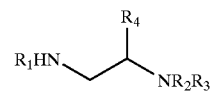

wherein $R_4$ is selected from H, alkyl, aryl, alkenyl, alkynyl, aralkyl, aralkynyl, cycloalkyl, cycloalkenyl;

and wherein $R_1$, $R_2$ and $R_3$ are independently selected from H, alkyl, aryl, alkenyl, alkynyl, aralkyl, aralkenyl, aralkynyl, cycloalkyl, cycloalkenyl, halide, alkoxy, aryloxy, alkylthio, arylthio, silyl, siloxy, or amino, including straight or branched chain derivative thereof, cyclic derivative thereof, substituted derivative thereof, functionalized derivative thereof, salts thereof, isomers thereof, a or combinations thereof;

and wherein when R4 is H, the substituted ethylene diamine compound does not comprise;

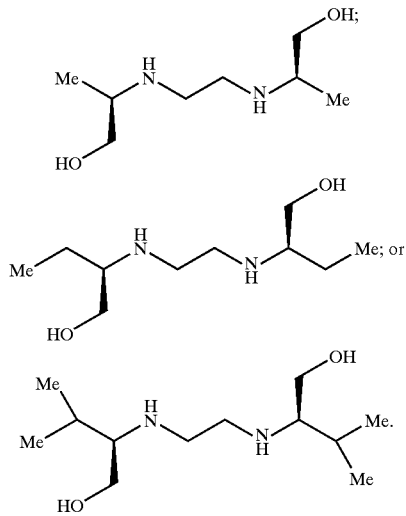

2. The composition of claim 1, wherein NHR$_1$ or NR$_2$R$_3$ of the substituted ethylene diamine has the chemical structure

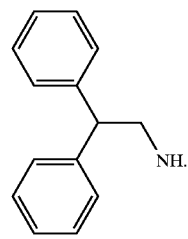

3. The composition of claim 2, wherein the substituted ethylene diamine compound is

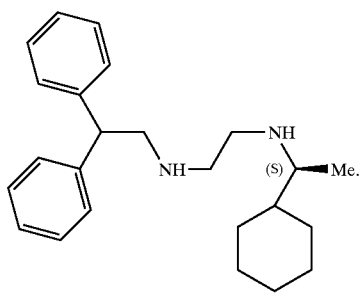

4. The composition of claim 2, wherein the substituted ethylene diamine compound is

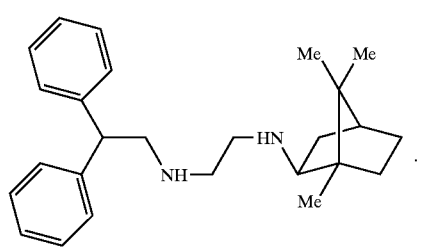

5. The composition of claim 2, wherein the substituted ethylene diamine compound is

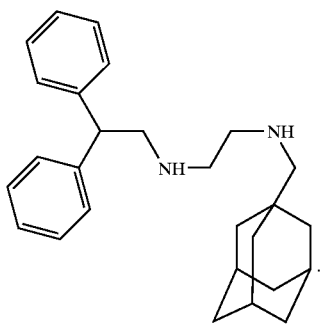

6. The composition of claim 2, wherein the substituted ethylene diamine compound is

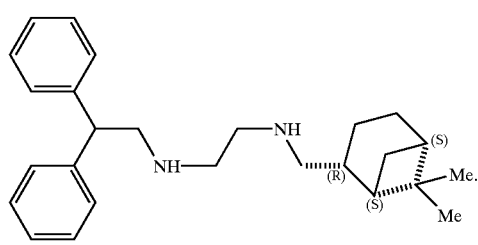

7. The composition of claim 2, wherein the substituted ethylene diamine compound is

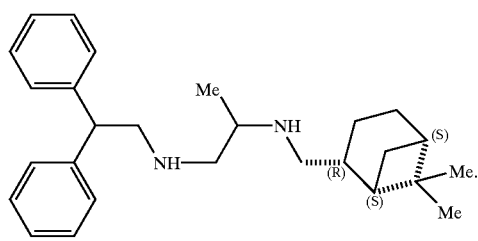

8. The composition of claim 2, wherein the substituted ethylene diamine compound is

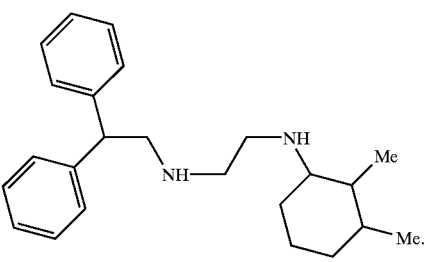

9. The composition of claim 2, wherein the substituted ethylene diamine compound is

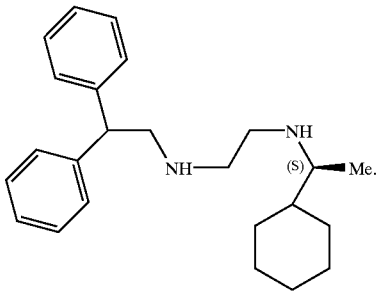

10. The composition of claim 2, wherein the substituted ethylene diamine compound is

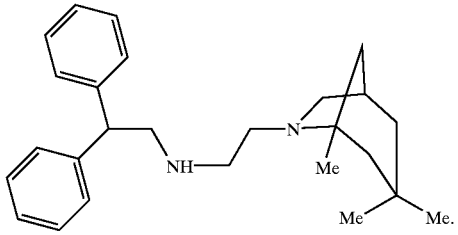

11. The composition of claim 2, wherein the substituted ethylene diamine compound is

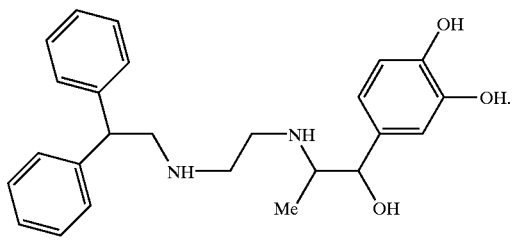

12. The composition of claim 2, wherein the substituted ethylene diamine compound is

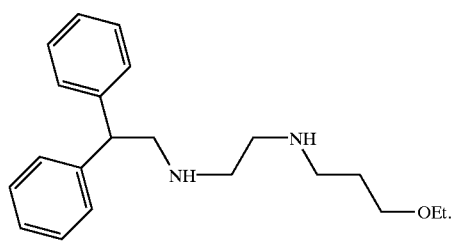

13. The composition of claim 2, wherein the substituted ethylene diamine compound is

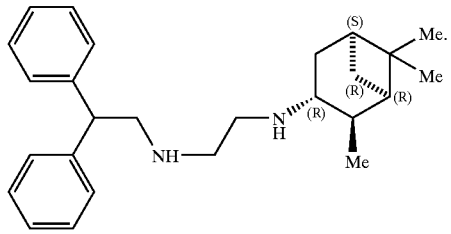

14. The composition of claim 1, wherein $NHR_1$ or $NR_2R_3$ of the substituted ethylene diamine has the chemical structure

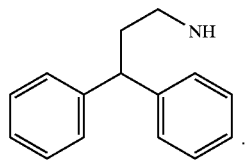

15. The composition of claim 14, wherein the substituted ethylene diamine compound is

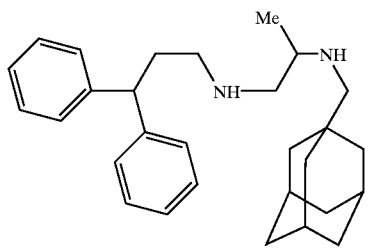

16. The composition of claim 14, wherein the substituted ethylene diamine compound is

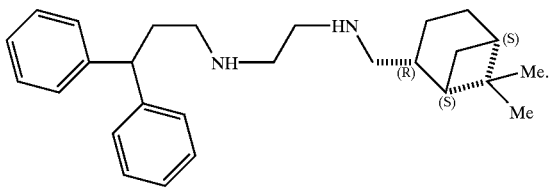

17. The composition of claim 14, wherein the substituted ethylene diamine compound is

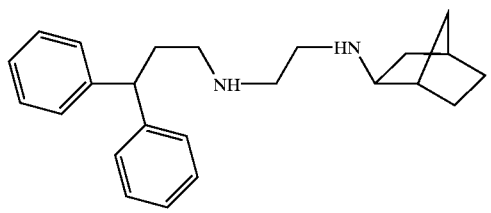

18. The composition of claim 14, wherein the substituted ethylene diamine compound is

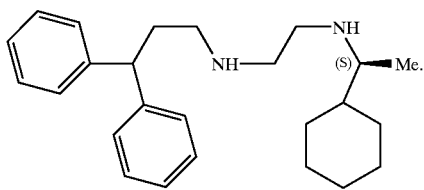

19. The composition of claim 14 wherein the substituted ethylene diamine compound is

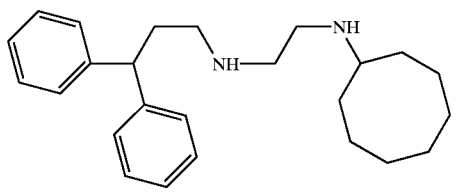

20. The composition of claim 14, wherein the substituted ethylene diamine compound is

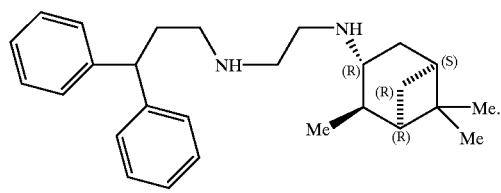

21. The composition of claim 14, wherein the substituted ethylene diamine compound is

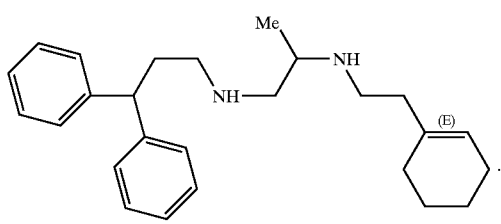

22. The composition of claim 14, wherein the substituted ethylene diamine compound is

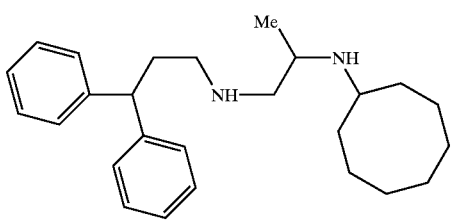

23. The composition of claim 14, wherein the substituted ethylene diamine compound is

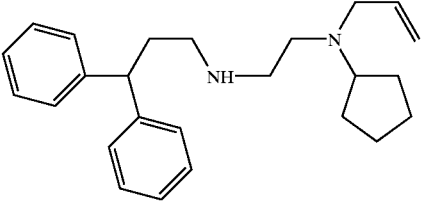

24. The composition of claim 14, wherein the substituted ethylene diamine compound is

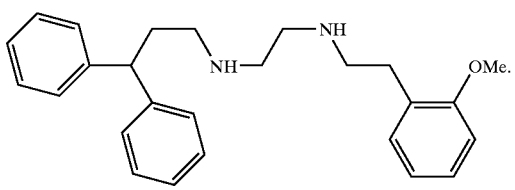

25. The composition of claim 14, wherein the substituted ethylene diamine compound is

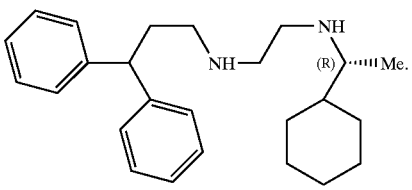

26. The composition of claim 14, wherein the substituted ethylene diamine compound is

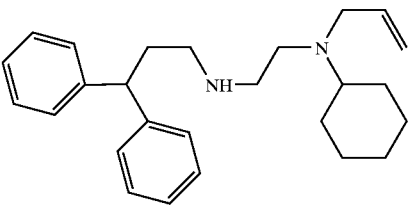

27. The composition of claim 14, wherein the substituted ethylene diamine compound is

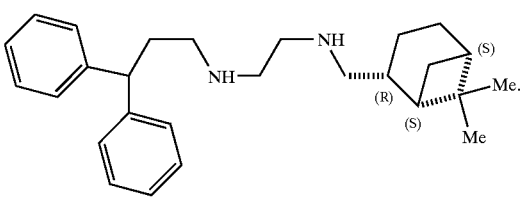

28. The composition of claim 1, wherein $NHR_1$ or $NR_2R_3$ of the substituted ethylene diamine has the chemical structure

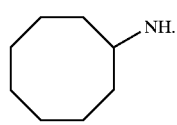

29. The composition of claim 28, wherein the substituted ethylene diamine compound is

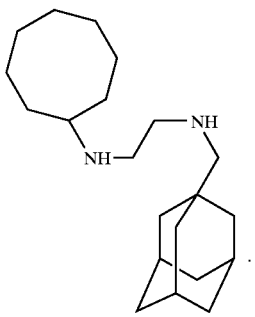

30. The composition of claim 28, wherein the substituted ethylene diamine compound is

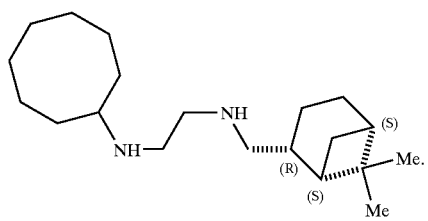

31. The composition of claim 28, wherein the substituted ethylene diamine compound is

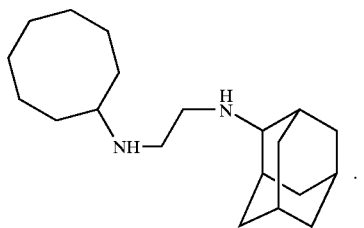

32. The composition of claim 28, wherein the substituted ethylene diamine compound is

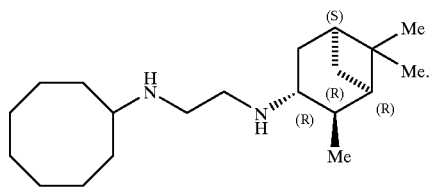

33. The composition of claim 28, wherein the substituted ethylene diamine compound is

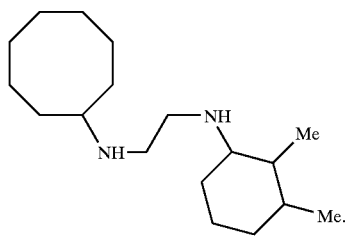

34. The composition of claim 28, wherein the substituted ethylene diamine compound is

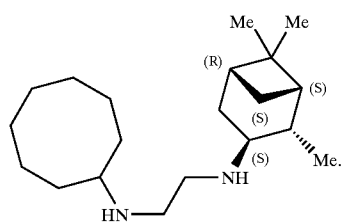

35. The composition of claim 28, wherein the substituted ethylene diamine compound is

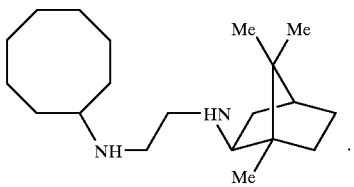

36. The composition of claim 28, wherein the substituted ethylene diamine compound is

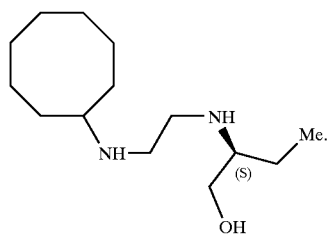

37. The composition of claim 28, wherein the substituted ethylene diamine compound is

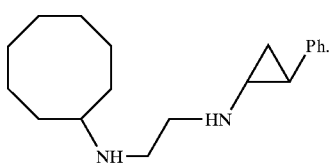

38. The composition of claim 28, wherein the substituted ethylene diamine compound is

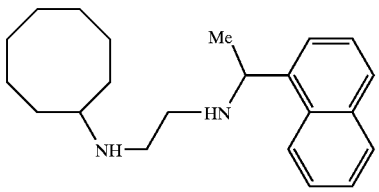

39. The composition of claim 28, wherein the substituted ethylene diamine compound is

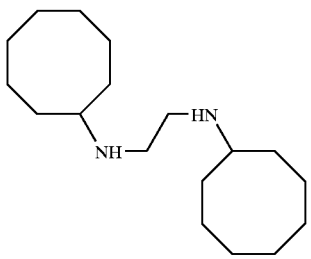

40. The composition of claim 1, wherein $NHR_1$ or $NR_2R_3$ of the substituted ethylene diamine has the chemical structure

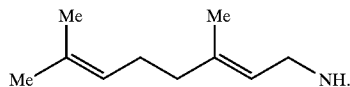

41. The composition of claim 40, wherein the substituted ethylene diamine compound is

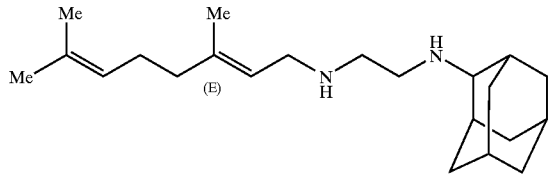

42. The composition of claim 40, wherein the substituted ethylene diamine compound is

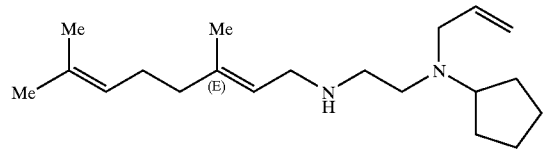

43. The composition of claim 40, wherein the substituted ethylene diamine compound is

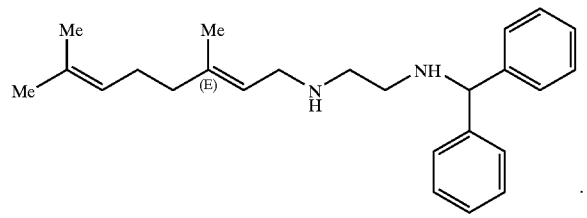

44. The composition of claim 1, wherein the substituted ethylene diamine compound is

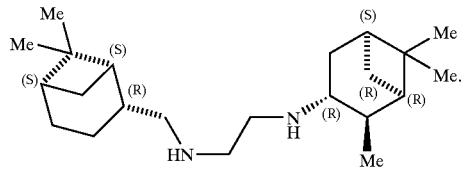

45. The composition of claim 1, wherein the substituted ethylene diamine compound is

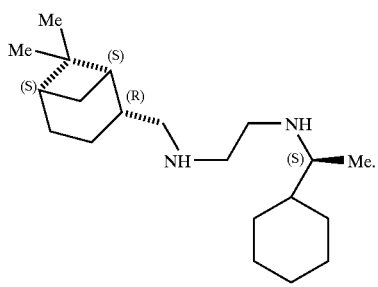

46. The composition of claim 1, wherein the substituted ethylene diamine compound is

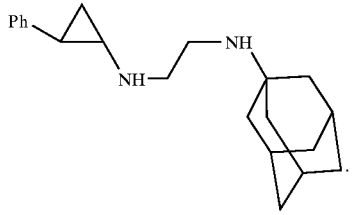

47. The composition of claim 1, wherein the substituted ethylene diamine compound is

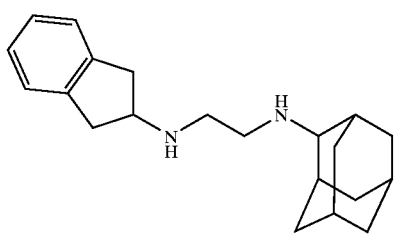

48. The composition of claim 1, wherein the substituted ethylene diamine compound is

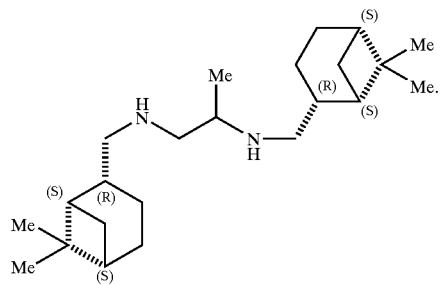

49. The composition of claim 1, wherein the substituted ethylene diamine compound is

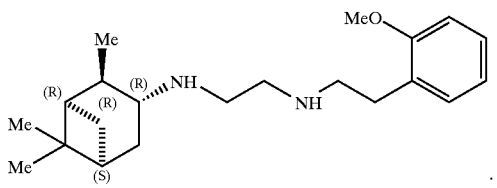

50. The composition of claim 1, wherein the substituted ethylene diamine compound is

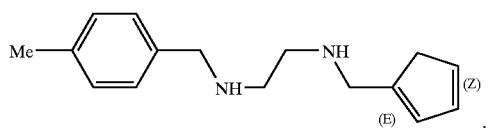

51. The composition of claim 1, wherein the substituted ethylene diamine compound is

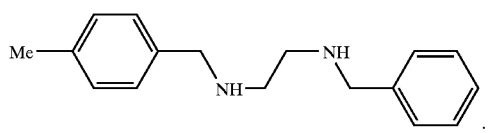

52. The composition of claim 1, wherein the substituted ethylene diamine compound is

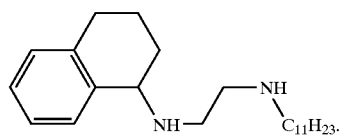

53. The composition of claim 1, wherein the substituted ethylene diamine compound is

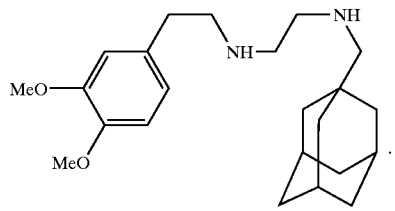

54. The composition of claim 1, wherein the substituted ethylene diamine compound is

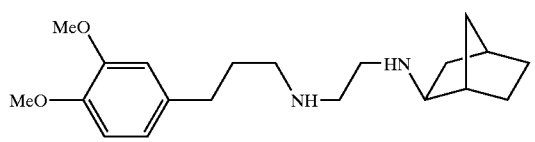

55. The composition of claim 1, wherein the substituted ethylene diamine compound is

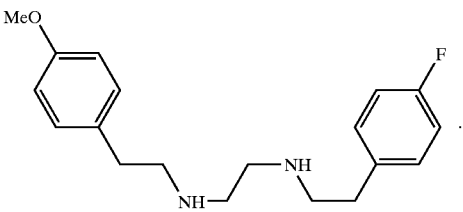

56. The composition of claim 1, wherein the substituted ethylene diamine compound is

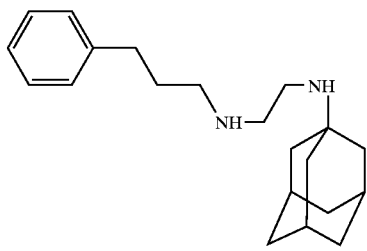

57. The composition of claim 1, wherein the substituted ethylene diamine compound is

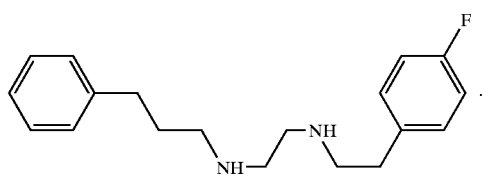

58. The composition of claim 1, wherein the substituted ethylene diamine compound is

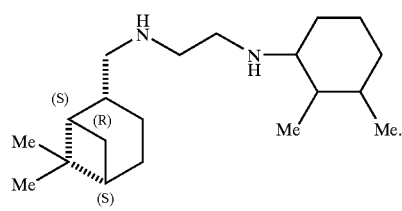

59. The composition of claim 1, wherein the substituted ethylene diamine compound is

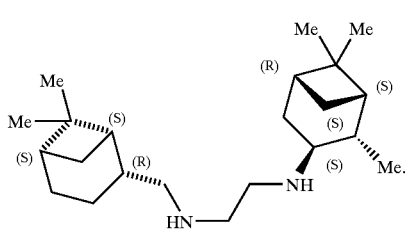

60. The composition of claim 1, wherein the substituted ethylene diamine compound is

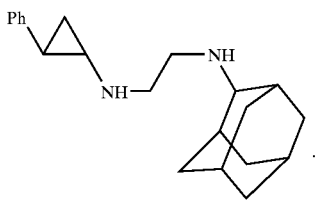

61. The composition of claim 1, wherein the substituted ethylene diamine compound is

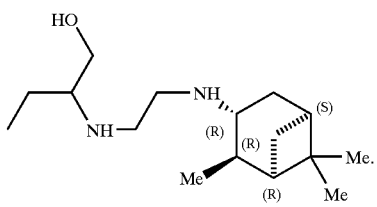

62. The composition of claim 1, wherein the substituted ethylene diamine compound is

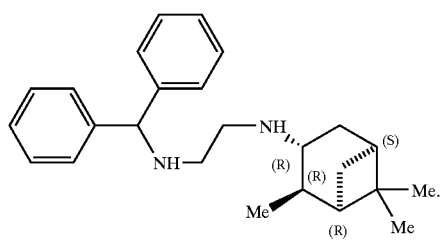

63. The composition of claim 1, wherein the substituted ethylene diamine compound is

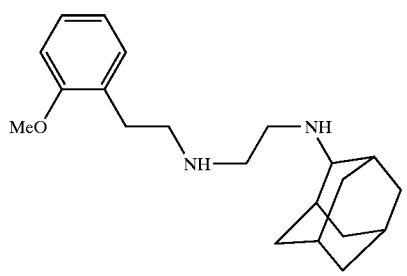

64. The composition of claim 1, wherein the substituted ethylene diamine compound is

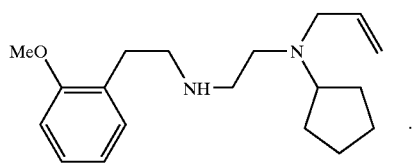

65. The composition of claim 1, wherein the substituted ethylene diamine compound is

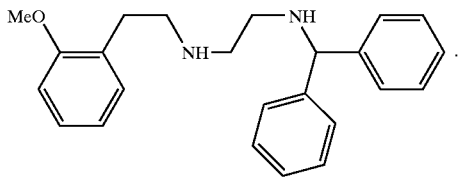

66. The composition of claim 1, wherein the substituted ethylene diamine compound is

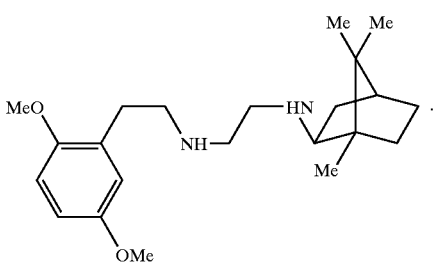

67. The composition of claim 1, wherein the substituted ethylene diamine compound is

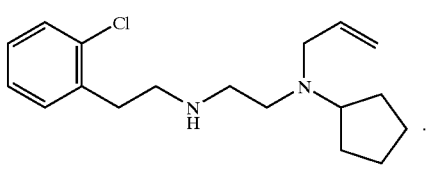

68. The composition of claim 1, wherein the substituted ethylene diamine compound is

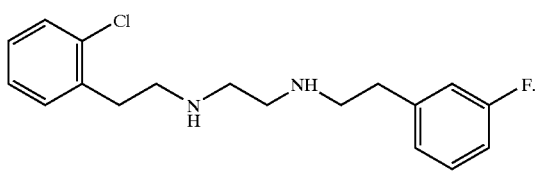

69. The composition of claim 1, wherein the substituted ethylene diamine compound is

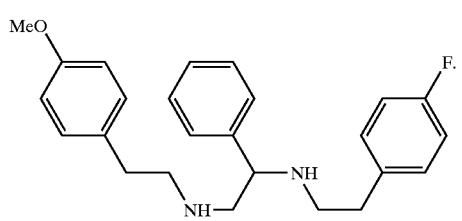

70. The composition of claim 1, wherein the substituted ethylene diamine compound is
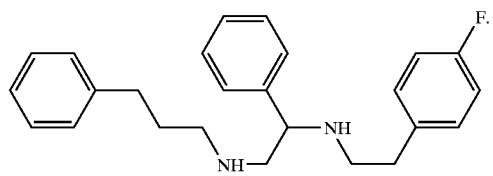
71. The composition of claim 2, wherein the substituted ethylene diamine compound is selected from
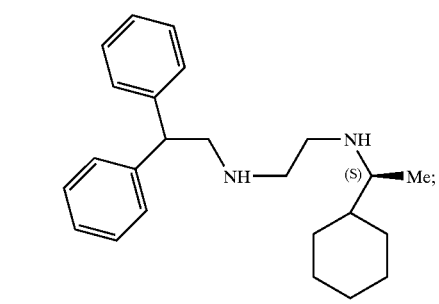
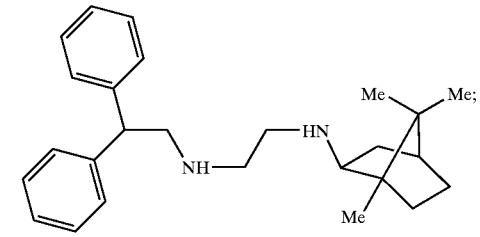
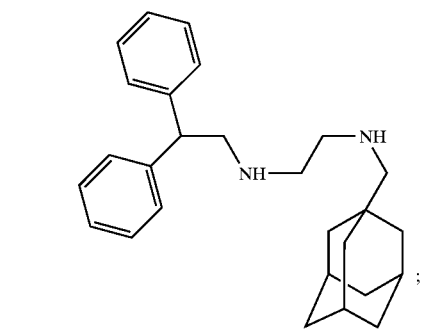
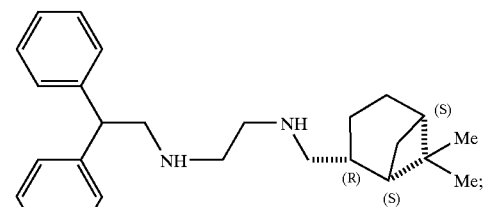
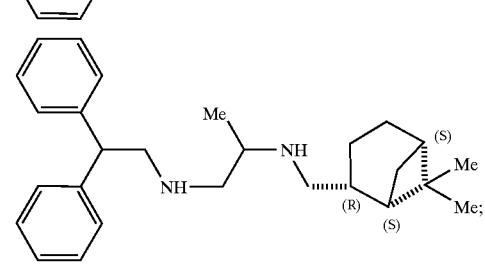
-continued
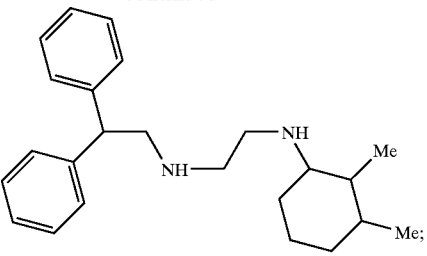
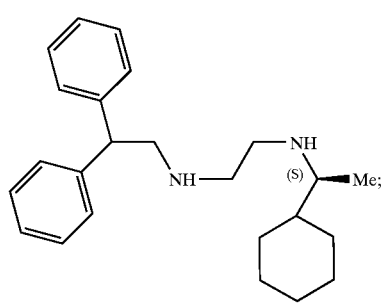
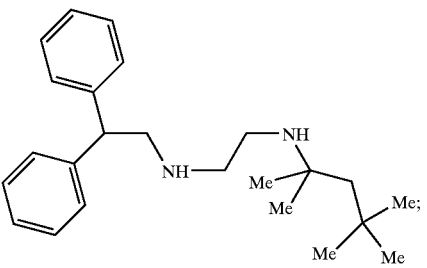
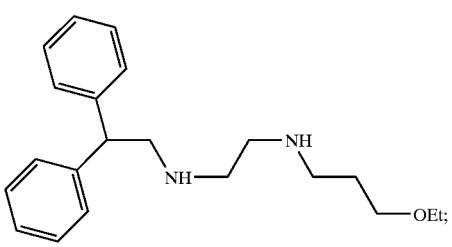
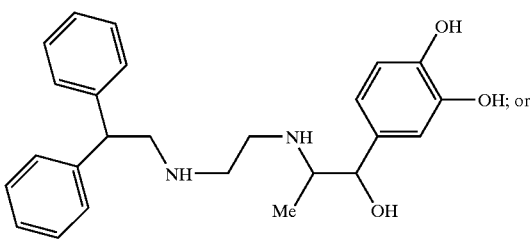
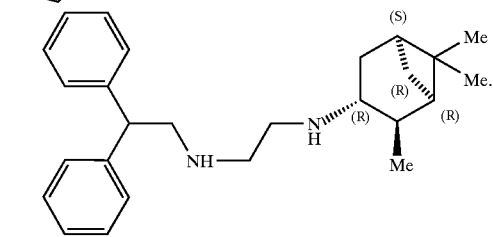

72. The composition of claim 14, wherein the substituted ethylene diamine compound is selected from
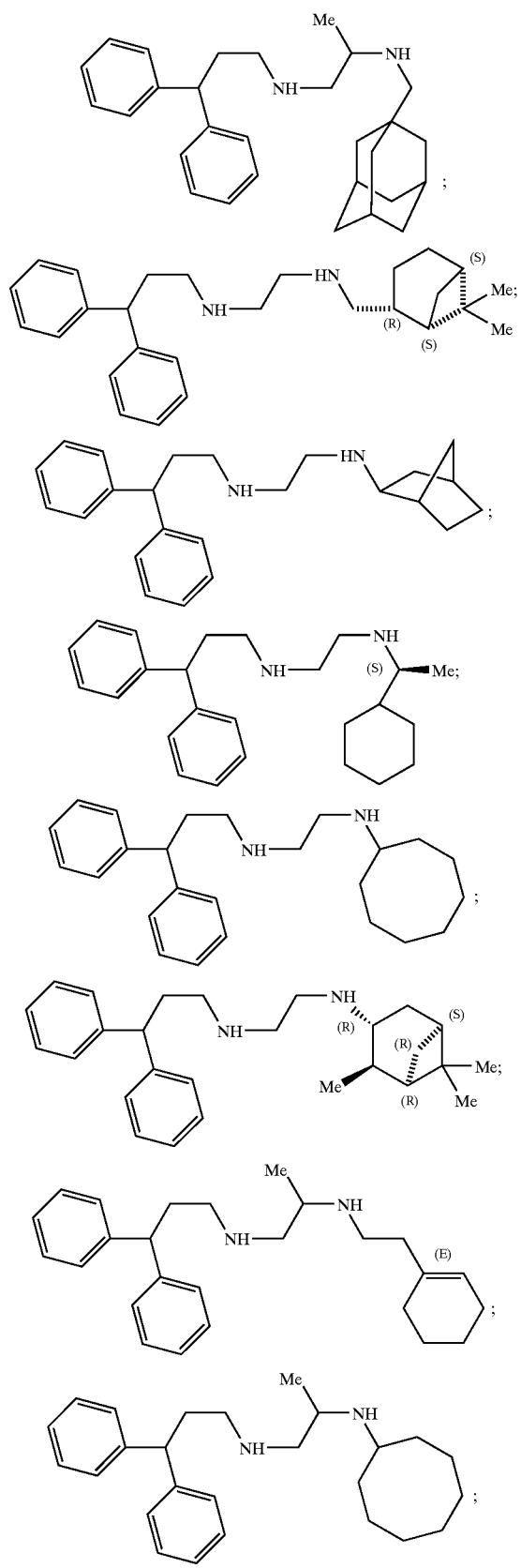
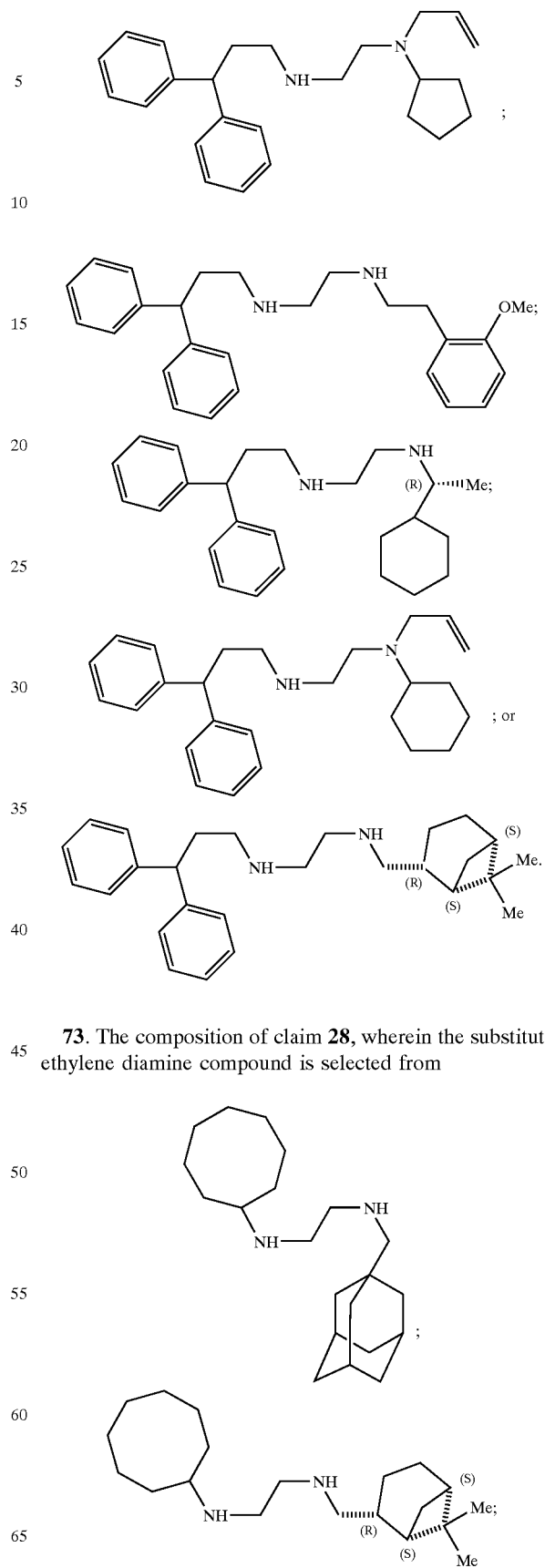
73. The composition of claim 28, wherein the substituted ethylene diamine compound is selected from

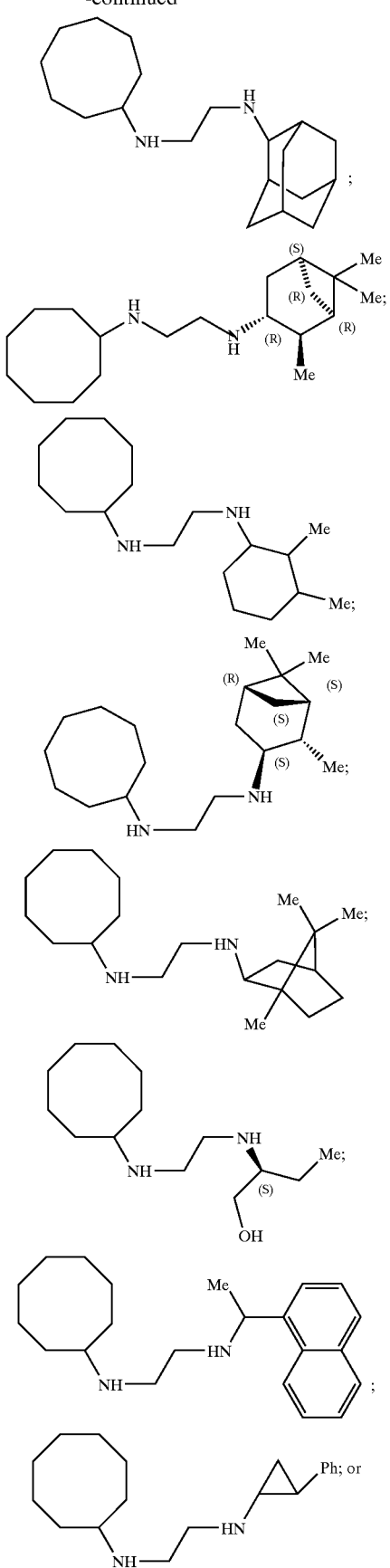
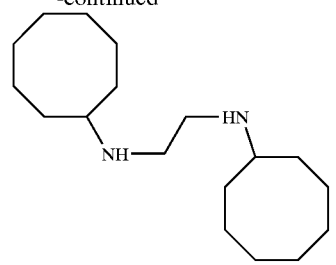
74. The composition of claim 40, wherein the substituted ethylene diamine compound is selected from
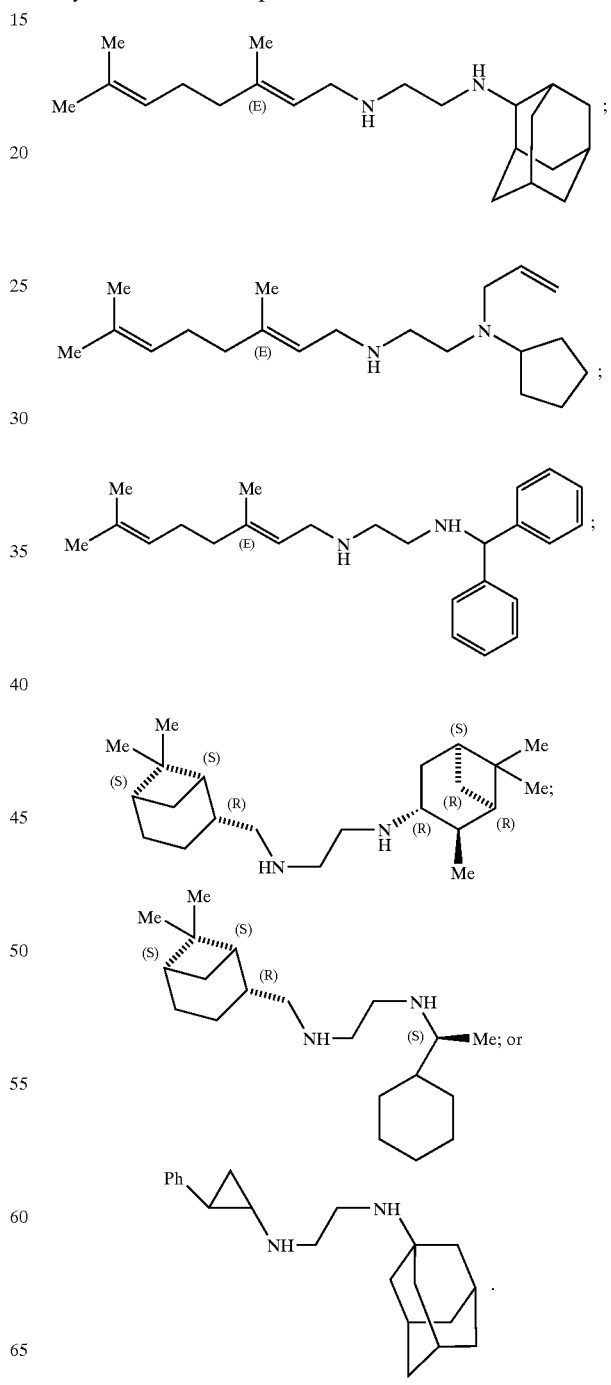

75. The composition of claim 74, wherein the substituted ethylene diamine compound is
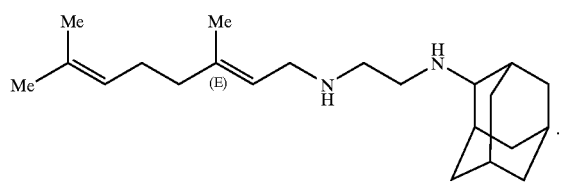
76. The composition of claim 1, wherein the substituted ethylene diamine compound is selected from
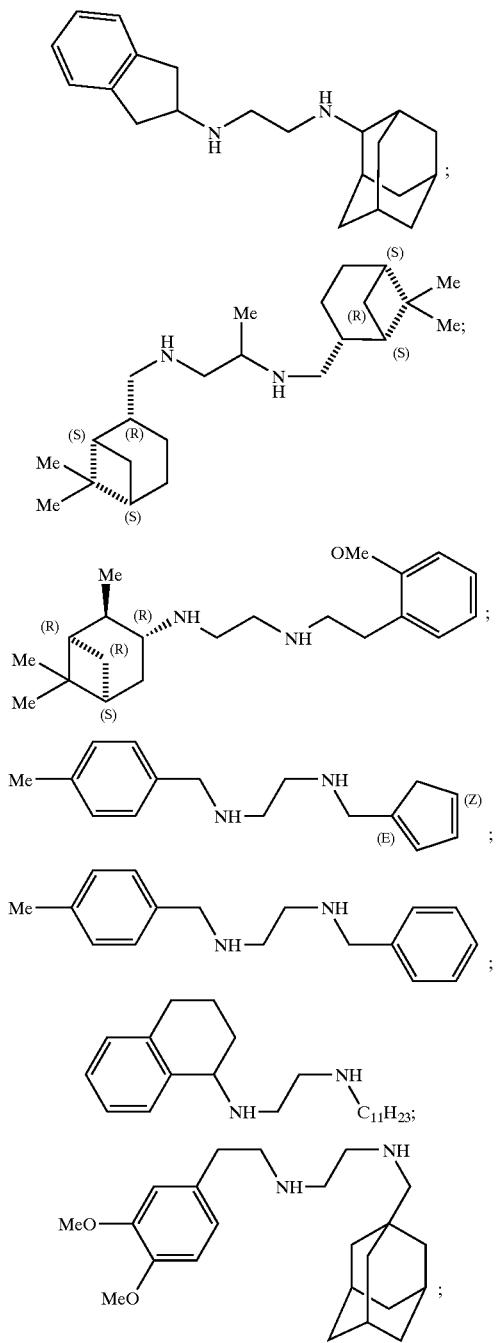
-continued
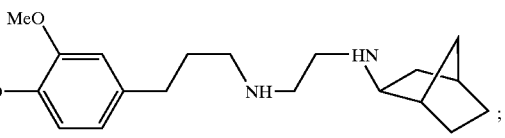
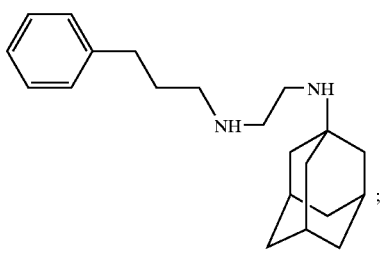
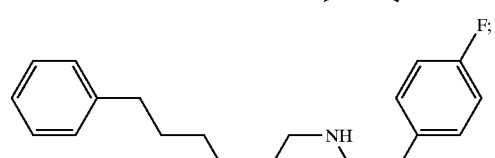
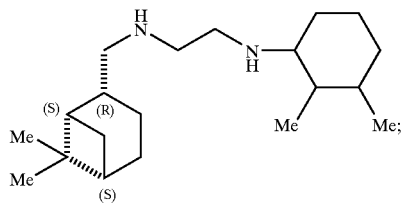
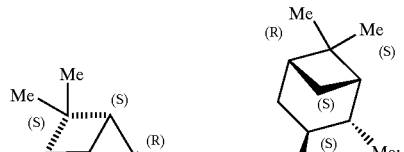
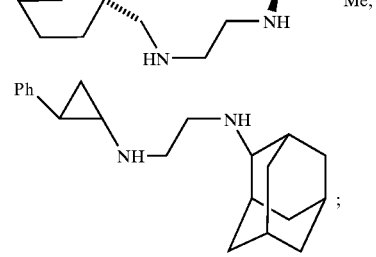
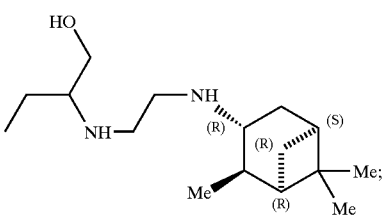

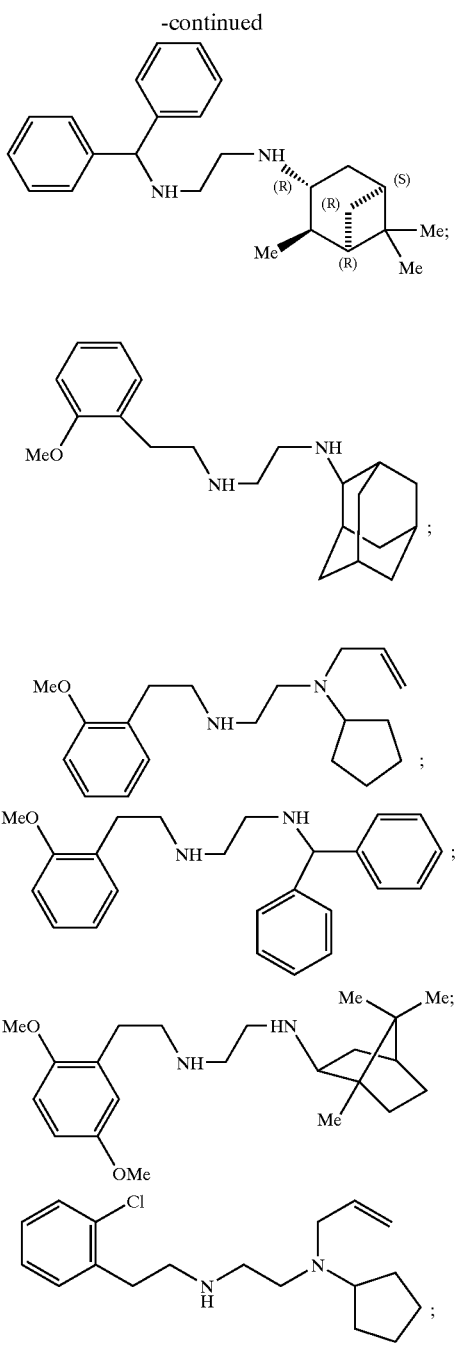

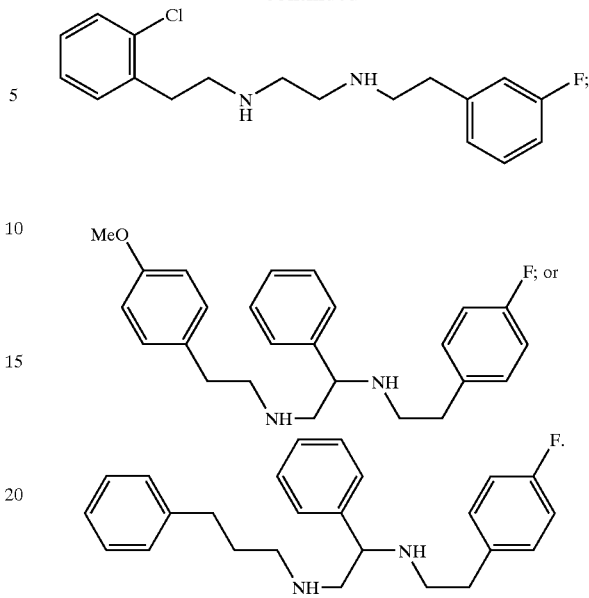

77. The composition of claim 1, wherein $R_1$ of the substituted ethylene diamine is selected from 1-adamantanemethylamine, 2,2,-diphenylethylanilne, 3,3-diphenyipropylamine, 2-amino-1-butanol, cis-(−)myrtanylamine, cyclooctylamine, 2-adamantanilne, (+)-bomylamine, cyclohexyethylamine, undecylamine, geranylamine, (+)-isopinocampheylamine (−)-isopinocampheylamine, or a combination thereof, or substituted derivatives thereof, or stereoisomers thereof.

78. The composition of claim 1, wherein $NR_2R_3$ of the substituted ethylene diamine is selected from 1-adamantanemethylamine, 2,2,-diphenylethylamine, 3,3-diphenylpropylamine, 2-amino-1-butanol, cis-(−)myrtanylamine, cyclooctylamine, 2-adamantamine, (+)-bornylamine, cyclohexyethylamine, undecylamine, geranylamine, (+)-isopinocampheylamine, (−)-isopinocampheylamine, or a combination thereof, or substituted derivatives thereof, or stereoisomers thereof.

79. The composition of claim 1, wherein $R_1$, $R_2$, and $R_3$ are selected from isopinocamphenyl; bornyl; norbornyl; adamantanetetyl; cis-(−)myrtanyl; adamantyl; noradamantyl; 6-azabicyclo[3.2.1]octane; or exo-norbornane.

\* \* \* \* \*